(12) United States Patent
Batten et al.

(10) Patent No.: US 9,788,849 B2
(45) Date of Patent: Oct. 17, 2017

(54) DEVICES AND METHODS FOR ARCHED ROOF CUTTERS

(71) Applicant: SPINE VIEW, INC., San Jose, CA (US)

(72) Inventors: David Batten, San Jose, CA (US); John To, Newark, CA (US); Hiep Nguyen, Milpitas, CA (US)

(73) Assignee: Spine View, Inc., Fremont, CA (US)

( * ) Notice: Subject to any disclaimer, the term of this patent is extended or adjusted under 35 U.S.C. 154(b) by 0 days.

(21) Appl. No.: 14/462,449

(22) Filed: Aug. 18, 2014

(65) Prior Publication Data

US 2015/0190162 A1 Jul. 9, 2015

Related U.S. Application Data

(63) Continuation of application No. 12/825,251, filed on Jun. 28, 2010, now Pat. No. 8,808,320, which is a
(Continued)

(51) Int. Cl.
*A61B 17/32* (2006.01)
*A61B 17/16* (2006.01)

(52) U.S. Cl.
CPC .... *A61B 17/32002* (2013.01); *A61B 17/1615* (2013.01); *A61B 17/1617* (2013.01);
(Continued)

(58) Field of Classification Search
CPC ............ A61B 17/1615; A61B 17/1617; A61B 17/1671; A61B 17/32002; A61B 2017/320064
See application file for complete search history.

(56) References Cited

U.S. PATENT DOCUMENTS

| 177,490 A | 5/1876 | Fones et al. |
| 4,061,146 A | 12/1977 | Baehr et al. |

(Continued)

FOREIGN PATENT DOCUMENTS

| WO | WO02/055146 A1 | 7/2002 |
| WO | WO02/098300 A3 | 12/2002 |

(Continued)

OTHER PUBLICATIONS

International Search Report dated Sep. 15, 2009, for PCT Patent Application No. D PCT/US2009/051736, filed Jul. 24, 2009, 2 pages.
(Continued)

*Primary Examiner* — Ashley Fishback
(74) *Attorney, Agent, or Firm* — Ross M. Carothers

(57) ABSTRACT

Disclosed herein are tissue-removal devices and methods for treating spinal diseases using such devices. The tissue-removal devices may comprise a cable and/or extendable elements with a retracted and a deployed configuration. The cable and/or extendable elements may be distally supported and restrained by a support element such that the support element may be pushed transversely away when the extendable element is distally extended into its deployed configuration. An annular cutting element may be provided about the distal end of the extendable element or the support element. Various configurations of the extendable and support elements are described herein, as well as methods of using tissue-removal devices with extendable and support elements coupled by an annular cutting element for treating spinal diseases.

23 Claims, 83 Drawing Sheets

Related U.S. Application Data continuation of application No. 12/761,311, filed on Apr. 15, 2010, now Pat. No. 8,801,739.

(60) Provisional application No. 61/243,986, filed on Sep. 18, 2009, provisional application No. 61/241,787, filed on Sep. 11, 2009, provisional application No. 61/170,507, filed on Apr. 17, 2009.

(52) U.S. Cl.
CPC ............... *A61B 17/1671* (2013.01); *A61B 2017/320064* (2013.01)

(56) References Cited

U.S. PATENT DOCUMENTS

| | | | |
|---|---|---|---|
| 4,466,429 A | | 8/1984 | Lascher et al. |
| 4,573,448 A | | 3/1986 | Kambin |
| 4,603,694 A | | 8/1986 | Wheeler |
| 4,646,738 A | | 3/1987 | Trott |
| 4,711,238 A | | 12/1987 | Cunningham |
| 4,711,607 A | | 12/1987 | Wynosky et al. |
| 4,857,046 A | | 8/1989 | Stevens et al. |
| 5,030,201 A | | 7/1991 | Palestrant |
| 5,078,723 A | | 1/1992 | Dance et al. |
| 5,100,423 A | | 3/1992 | Fearnot |
| 5,108,404 A | | 4/1992 | Scholten et al. |
| 5,217,474 A | | 6/1993 | Zacca et al. |
| 5,286,253 A | | 2/1994 | Fucci |
| 5,354,311 A | * | 10/1994 | Kambin et al. ............... 606/205 |
| 5,383,884 A | | 1/1995 | Summers |
| 5,411,514 A | | 5/1995 | Fucci et al. |
| 5,437,630 A | | 8/1995 | Daniel et al. |
| 5,529,580 A | | 6/1996 | Kusunoki et al. |
| 5,569,178 A | | 10/1996 | Henley |
| 5,591,187 A | | 1/1997 | Dekel |
| 5,669,926 A | | 9/1997 | Aust et al. |
| 5,695,513 A | | 12/1997 | Johnson et al. |
| 5,836,947 A | | 11/1998 | Fleischman et al. |
| 5,882,329 A | | 3/1999 | Patterson et al. |
| 5,885,258 A | | 3/1999 | Sachdeva et al. |
| 5,891,153 A | | 4/1999 | Patterson |
| 5,902,263 A | | 5/1999 | Patterson et al. |
| 5,941,869 A | | 8/1999 | Patterson et al. |
| 5,964,716 A | | 10/1999 | Gregoire et al. |
| 5,968,062 A | | 10/1999 | Thomas et al. |
| 6,053,907 A | | 4/2000 | Zirps |
| 6,068,642 A | | 5/2000 | Johnson et al. |
| 6,127,597 A | | 10/2000 | Beyar et al. |
| 6,217,509 B1 | | 4/2001 | Foley et al. |
| 6,319,242 B1 | | 11/2001 | Patterson et al. |
| 6,352,539 B1 | * | 3/2002 | Avellanet ............... 606/113 |
| 6,375,634 B1 | | 4/2002 | Carroll |
| RE38,018 E | | 3/2003 | Anctil et al. |
| 6,540,747 B1 | | 4/2003 | Marino |
| 6,554,799 B1 | | 4/2003 | Hatamura et al. |
| 6,666,891 B2 | | 12/2003 | Boehm, Jr. et al. |
| 6,673,023 B2 | | 1/2004 | Pflueger |
| 6,780,175 B1 | | 8/2004 | Sachdeva et al. |
| 6,857,943 B2 | | 2/2005 | Kapgan |
| 7,037,321 B2 | | 5/2006 | Sachdeva et al. |
| 7,108,705 B2 | | 9/2006 | Davison et al. |
| 7,273,468 B2 | | 9/2007 | Bedell |
| 7,338,495 B2 | | 3/2008 | Adams |
| 7,591,790 B2 | | 9/2009 | Pflueger |
| 7,621,950 B1 | | 11/2009 | Globerman et al. |
| 2002/0016624 A1 | | 2/2002 | Patterson et al. |
| 2002/0138091 A1 | | 9/2002 | Pflueger |
| 2003/0114875 A1 | * | 6/2003 | Sjostrom ............... 606/170 |
| 2003/0130673 A1 | | 7/2003 | Trerotola |
| 2004/0236328 A1 | | 11/2004 | Paul et al. |
| 2005/0267502 A1 | | 12/2005 | Hochman |
| 2006/0036273 A1 | | 2/2006 | Siegal |
| 2006/0206118 A1 | | 9/2006 | Kim et al. |
| 2006/0258951 A1 | | 11/2006 | Bleich et al. |
| 2006/0264957 A1 | * | 11/2006 | Cragg et al. ............... 606/80 |
| 2007/0055259 A1 | | 3/2007 | Norton et al. |
| 2007/0060935 A1 | | 3/2007 | Schwardt et al. |
| 2007/0106246 A1 | | 5/2007 | Modesitt |
| 2007/0149990 A1 | | 6/2007 | Palmer et al. |
| 2007/0162062 A1 | | 7/2007 | Norton et al. |
| 2007/0173939 A1 | | 7/2007 | Kim et al. |
| 2008/0033465 A1 | | 2/2008 | Schmitz et al. |
| 2008/0051812 A1 | | 2/2008 | Schmitz et al. |
| 2008/0058588 A1 | | 3/2008 | Emanuel |
| 2010/0076476 A1 | | 3/2010 | To |
| 2011/0054507 A1 | | 3/2011 | Batten et al. |
| 2011/0098711 A1 | | 4/2011 | Batten et al. |

FOREIGN PATENT DOCUMENTS

| | | | |
|---|---|---|---|
| WO | WO06/072941 A3 | | 7/2006 |
| WO | WO07008710 A3 | | 1/2007 |
| WO | WO07100591 A3 | | 9/2007 |
| WO | WO07124130 A3 | | 11/2007 |
| WO | WO08/060277 A3 | | 5/2008 |
| WO | WO 2008060277 A2 | * | 5/2008 |

OTHER PUBLICATIONS

International Search Report dated Jun. 16, 2010, for PCT Patent Application No. PCT/US2010/031448, filed Apr. 16, 2010, 2 pages.
Written Opinion dated Sep. 15, 2009, for PCT Patent Application No. PCT/US2009/051736, filed Jul. 24, 2009, 11 pages.
Written Opinion dated Jun. 16,2010, for PCT Patent Application No. PCT/US2010/031448, filed Apr. 16, 2010, 8 pages.

* cited by examiner

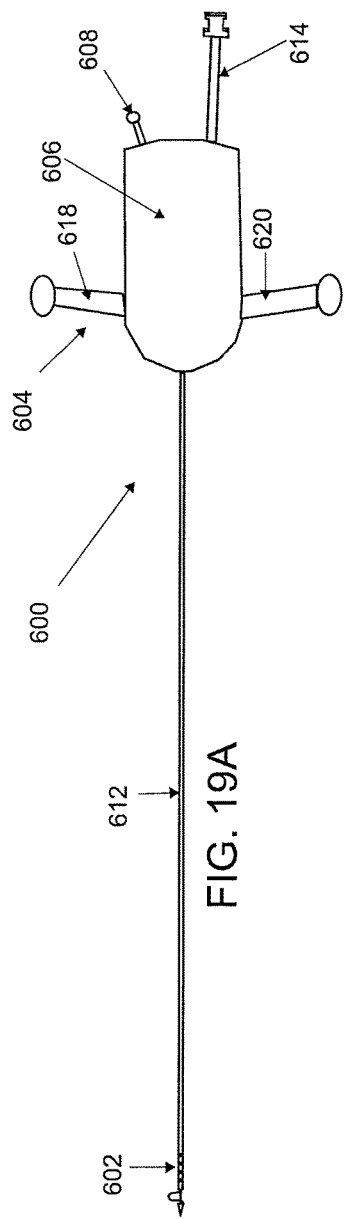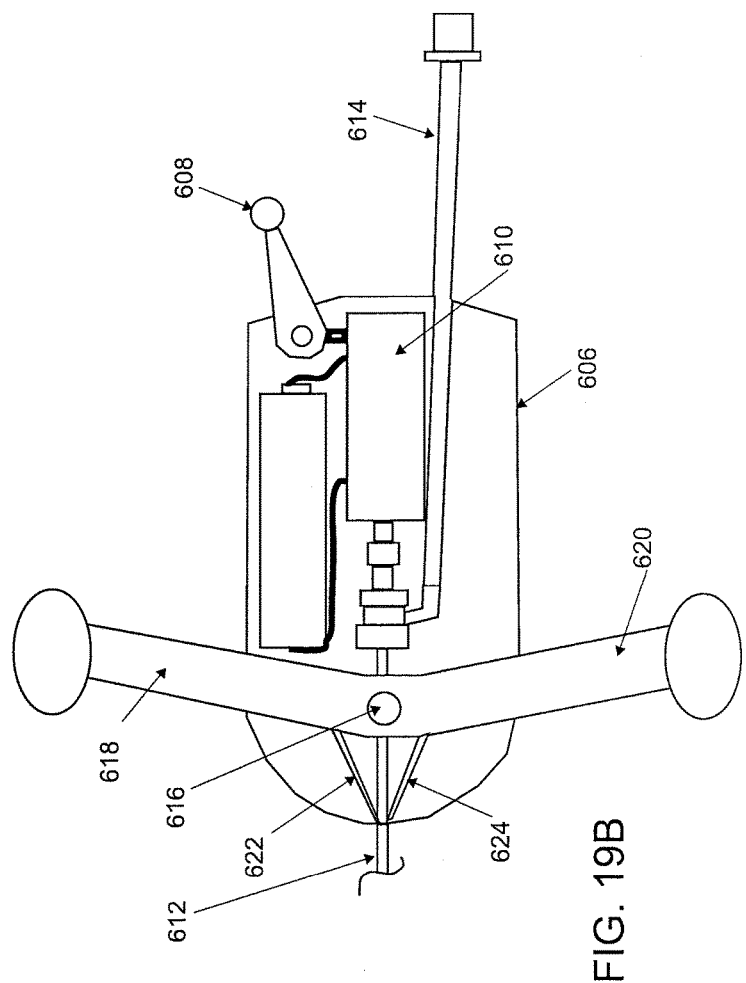
FIG. 19A
FIG. 19B

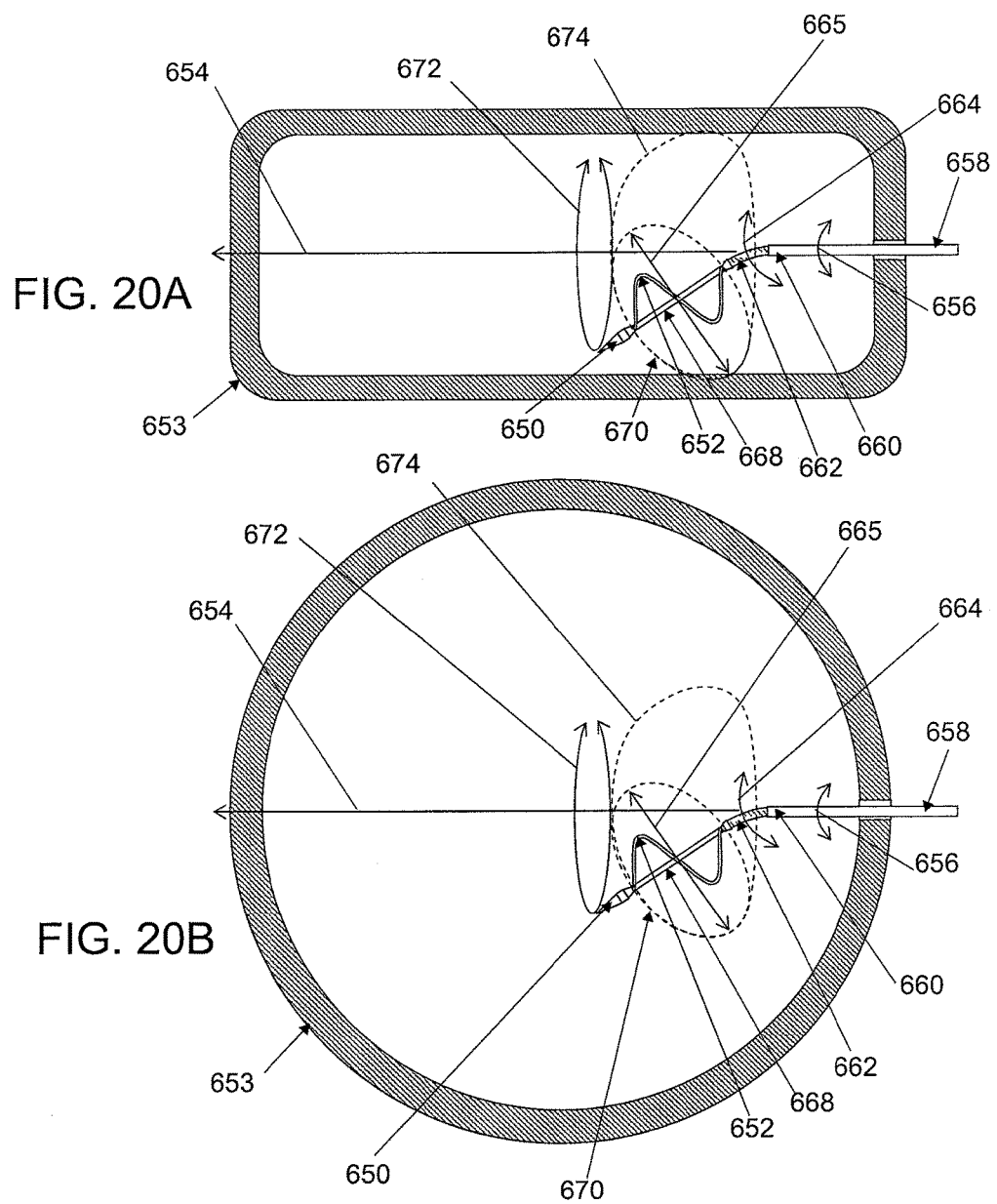

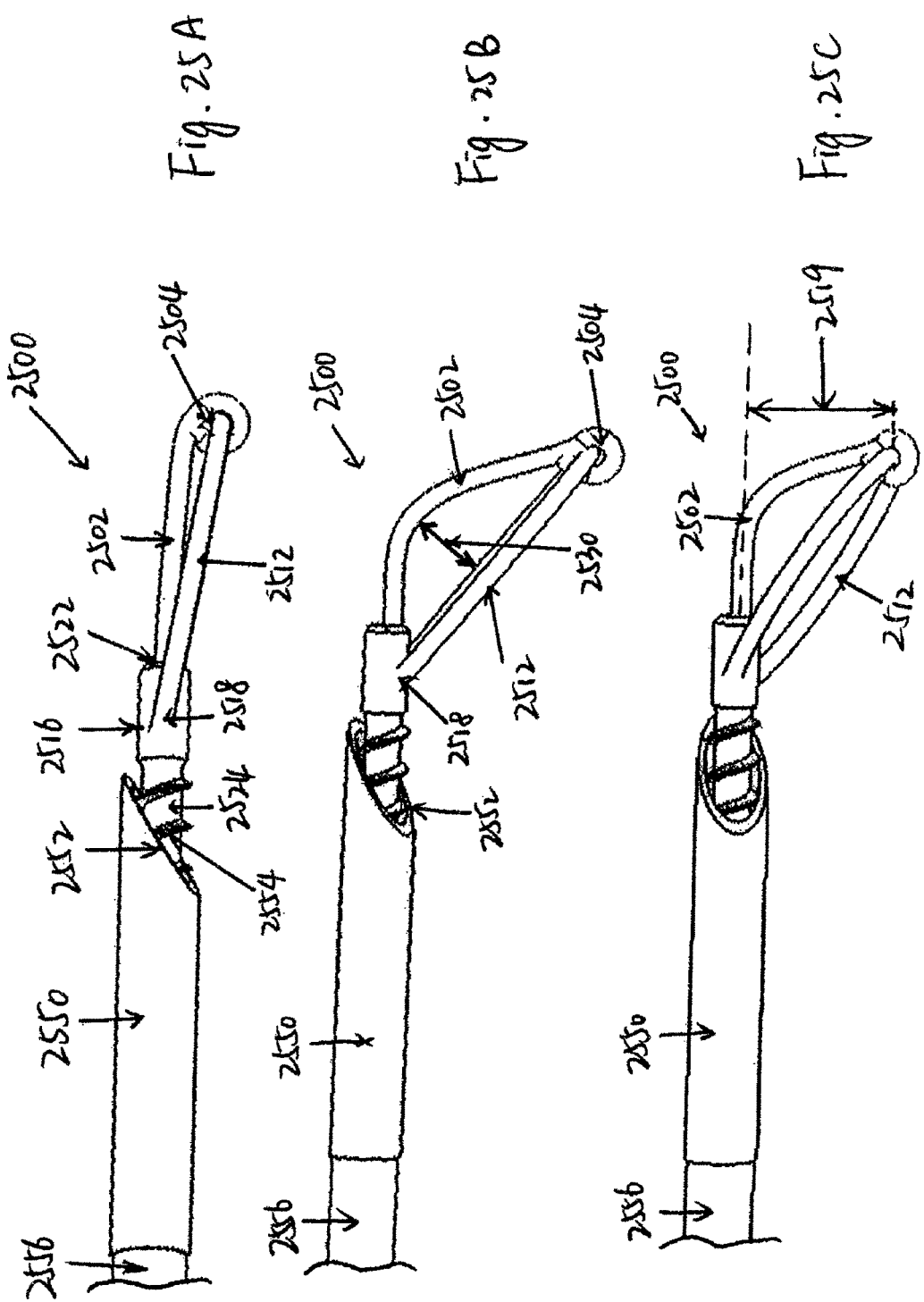

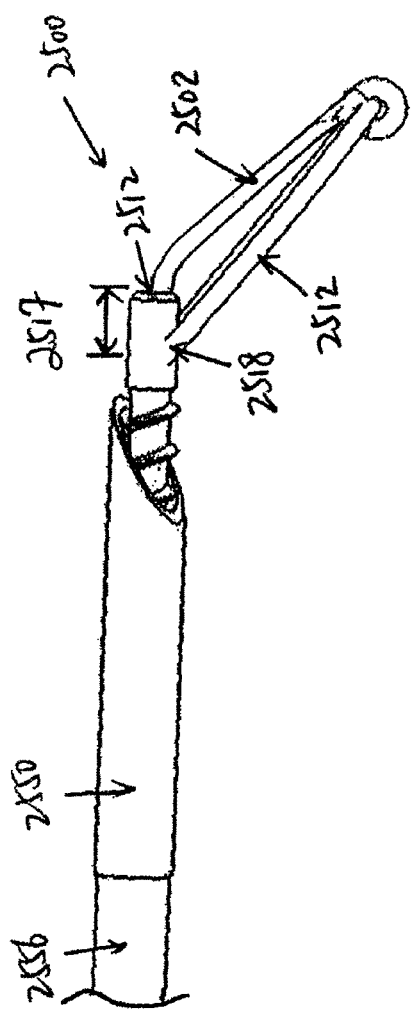
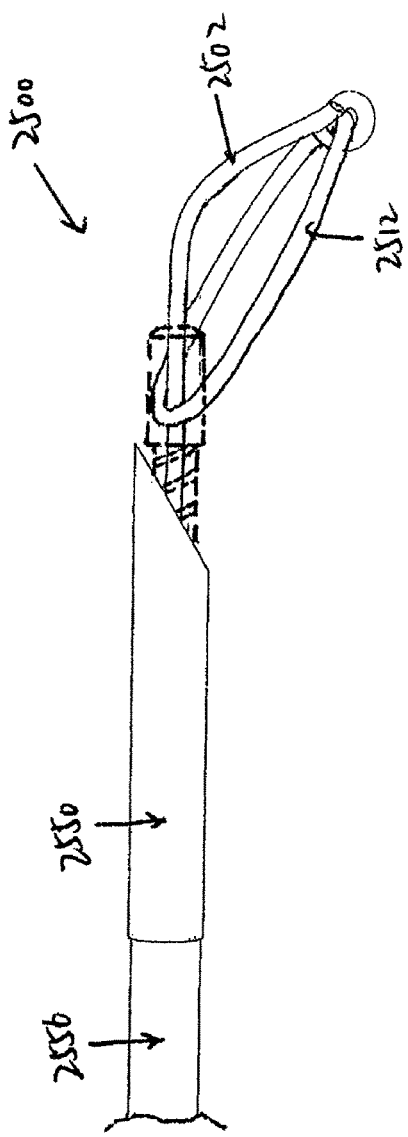

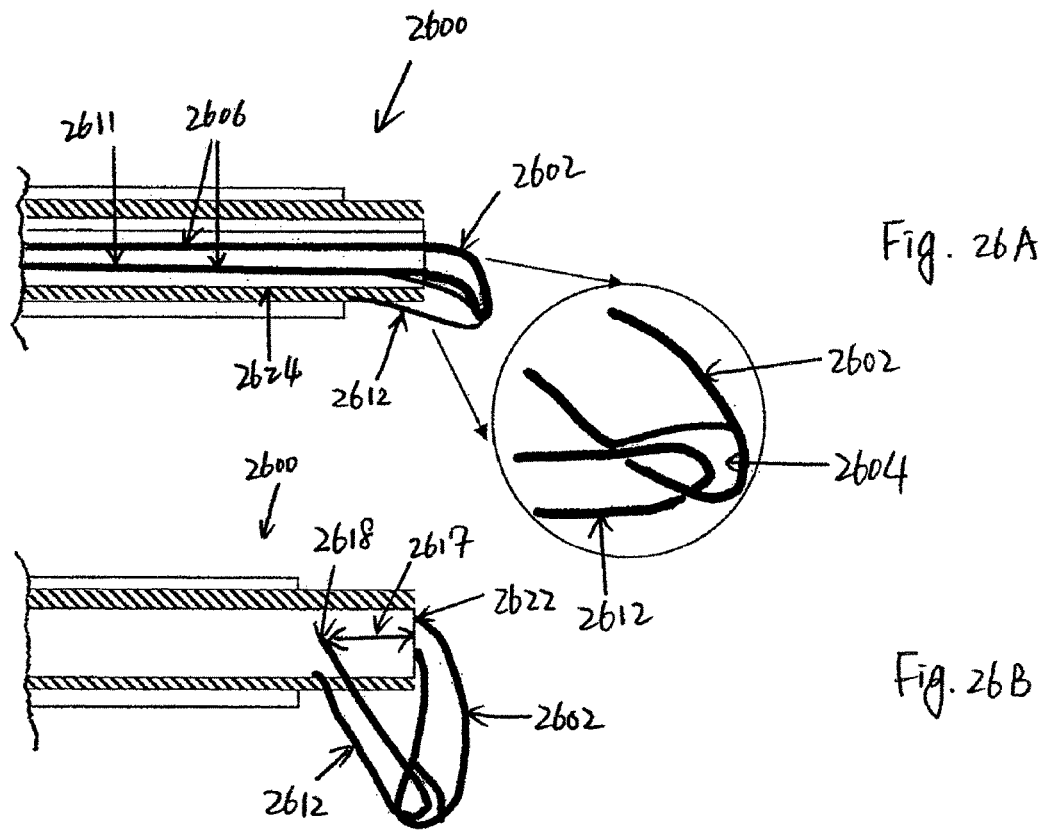
Fig. 26A
Fig. 26B
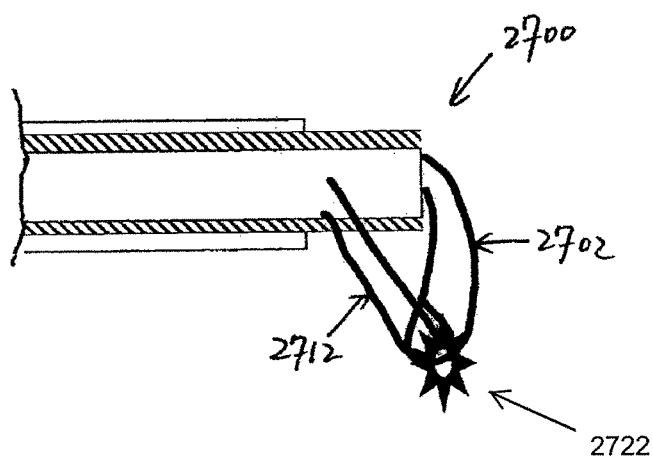
Fig. 27

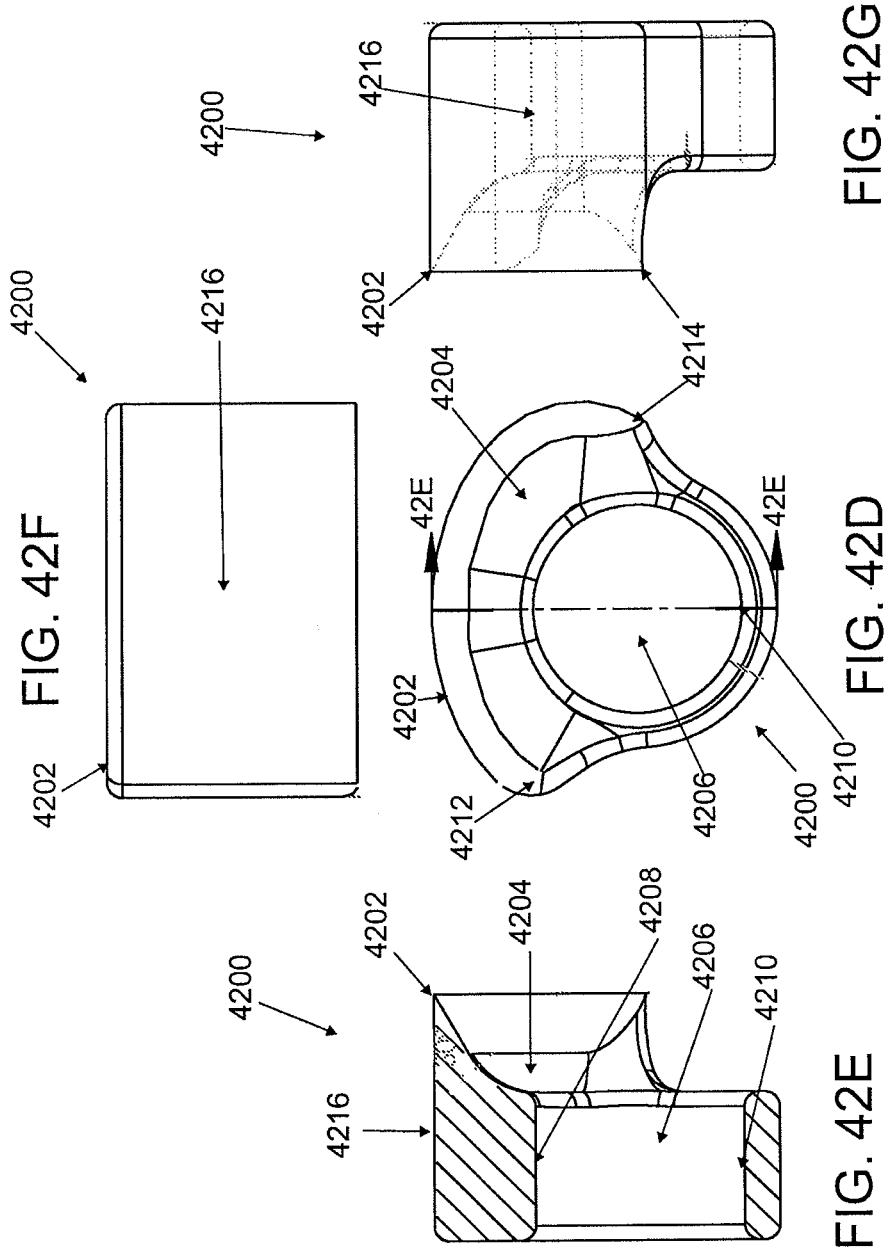

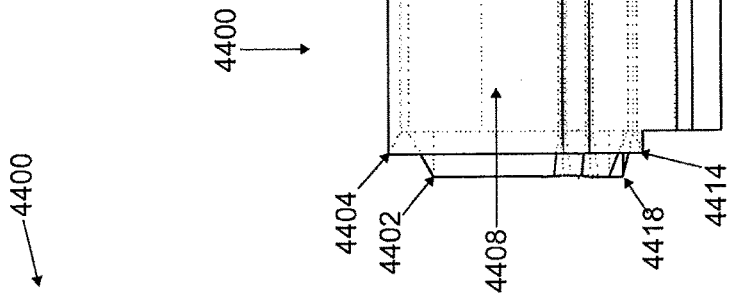
FIG. 44G
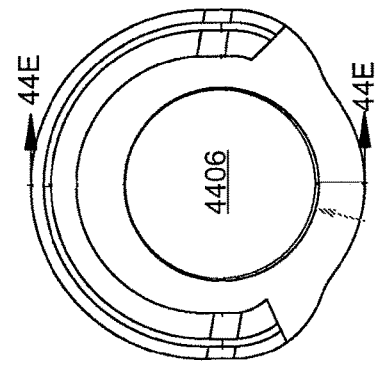
FIG. 44F  FIG. 44D
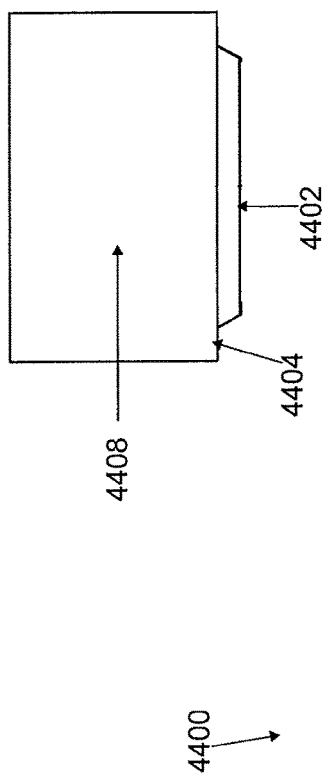
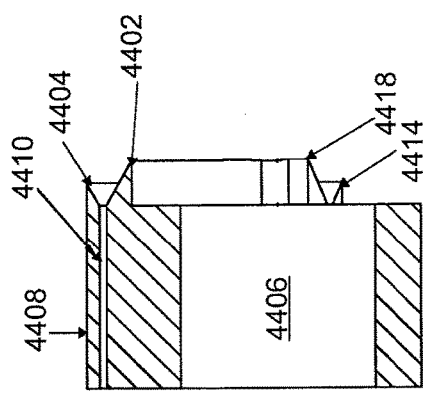
FIG. 44E

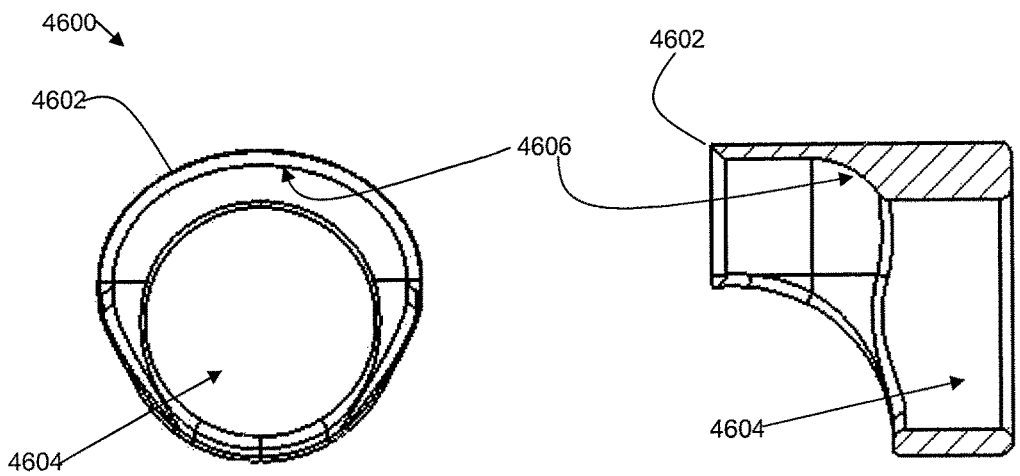
FIG. 46A   FIG. 46B
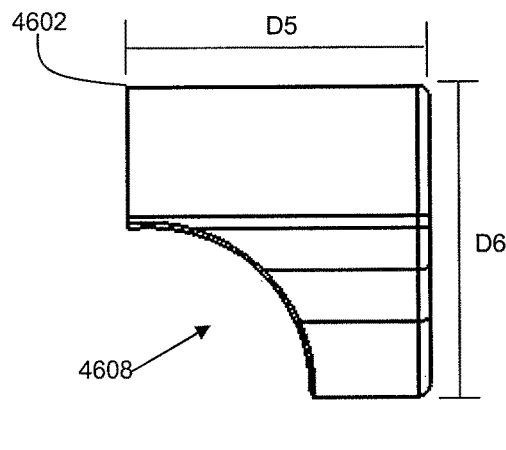 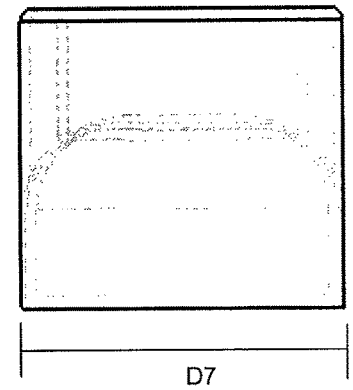
FIG. 46C   FIG. 46D

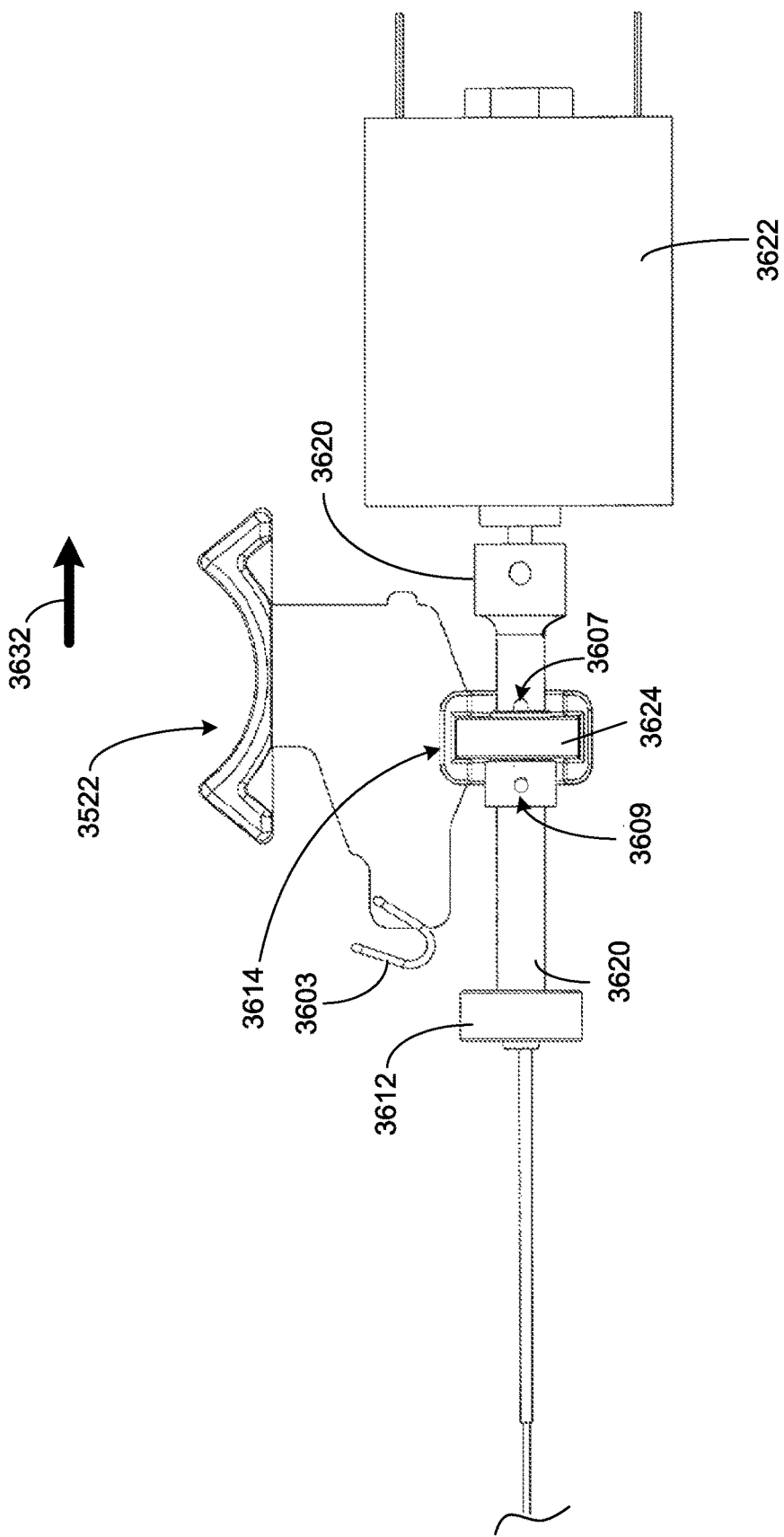

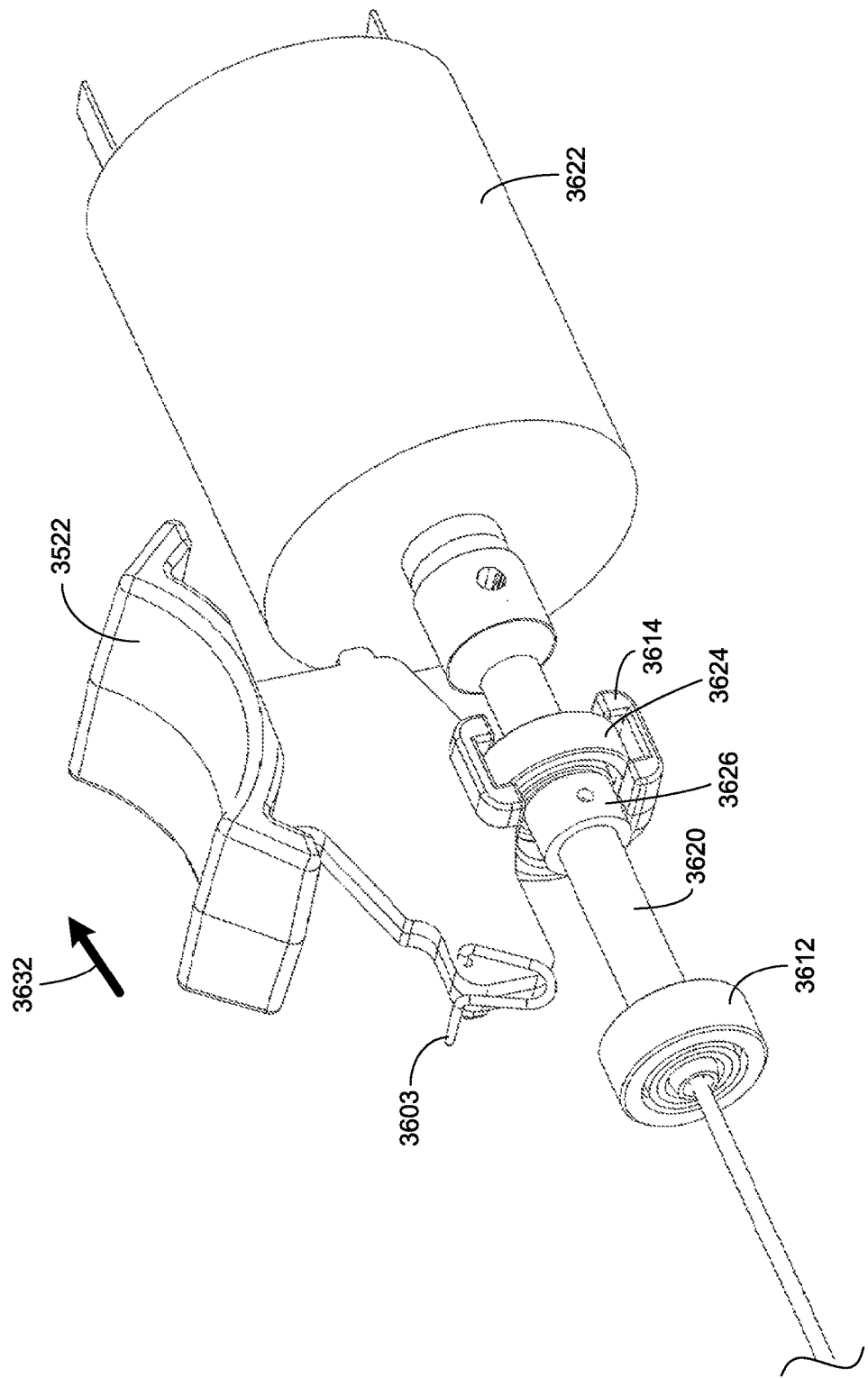

DEVICES AND METHODS FOR ARCHED ROOF CUTTERS

RELATED APPLICATIONS

This application is a continuation of U.S. patent application Ser. No. 12/825,251, filed Jun. 28, 2010, now U.S. Pat. No. 8,808,320, which is a continuation of U.S. patent application Ser. No. 12/761,311, filed Apr. 15, 2010, now U.S. Pat. No. 8,801,739, which claims benefit from a) U.S. Provisional Application Ser. No. 61/170,507, filed Apr. 17, 2009, b) U.S. Provisional Application Ser. No. 61/241,787, filed Sep. 11, 2009 and c) U.S. Provisional Application Ser. No. 61/243,986, filed Sep. 18, 2009, which are hereby incorporated by reference in their entirety. This application is also related to U.S. application Ser. No. 12/753,788, filed Apr. 2, 2010, which is also hereby incorporated by reference in its entirety.

BACKGROUND

Vertebral disc herniation is a common disorder where a portion of a vertebral disc, a cushion-like structure located between the bones of the spine, bulges out or extrudes beyond the usual margins of the disc and the spine. Disc herniation is believed to be the result of a loss of elasticity of the tissue comprising the disc, and is associated with increasing age. Disc herniation and other degenerative disc disease are also associated with spinal stenosis, a narrowing of the bony and ligamentous structures of the spine. Although disc herniation can occur anywhere along the perimeter of the disc, it occurs more frequently in the posterior and posterior-lateral regions of the disc, where the spinal cord and spinal nerve roots reside. Compression of these neural structures can lead to pain, parasthesias, weakness, urine and fecal incontinence and other neurological symptoms that can substantially impact basic daily activities and quality of life.

Temporary relief of the pain associated with disc herniation is often sought through conservative therapy, which includes positional therapy (e.g. sitting or bending forward to reduce pressure on spine), physical therapy, and drug therapy to reduce pain and inflammation. When conservative therapy fails to resolve a patient's symptoms, surgery may be considered to treat the structural source of the symptoms. Surgical treatments for disc herniation traditionally involve open procedures that require extensive dissection of muscle, connective tissue and bone along a patient's back to achieve adequate surgical exposure. These surgeries also expose the patient to a significant risk of complications, due to the presence of critical neurovascular structures near the surgical site. For example, a discectomy procedure may be used to decompress the herniation by accessing the affected disc and removing a portion of the disc and any loose disc fragments. To achieve sufficient access to the affected disc, a portion of the lamina or bony arch of the vertebrae may be removed, thereby increasing the invasiveness of the procedure. When discectomy fails to resolve a patient's symptoms, more drastic measures may include disc replacement surgery or vertebral fusion.

Fractures of the vertebrae bodies are another common disorder of the spinal column. When a vertebra fractures, the usual shape of the bone becomes compressed and distorted, which results in pain. These vertebral compression fractures (VCF), which may involve the collapse of one or more vertebrae in the spine, are a common finding and result of osteoporosis. Osteoporosis is a disorder that often becomes more severe with age and results in a loss of normal bone density, mass and strength. Osteoporosis often leads to a condition in which bones are increasingly porous or full of small holes and vulnerable to breaking. In addition to osteoporosis, vertebrae can also become weakened by cancer or infection.

In some instances, fractures of the vertebral bodies may be treated with surgical removal of the vertebral body and the implantation of a vertebral body replacement device. Other treatments may include vertebroplasty and kyphoplasty, which are minimally invasive procedures for treating vertebral compression fractures (VCF). In vertebroplasty, physicians use image guidance to inject a cement mixture through a hollow needle into the fractured bone. In kyphoplasty, a balloon is first inserted through the needle into the fractured vertebral body to restore at least some of the height and shape of the vertebral body, followed by removal of the balloon cement injection into the cavity formed by the balloon.

BRIEF SUMMARY

Systems and methods for treating disc herniation include surgical and endoscopic access and removal of disc tissue. The tissue removal devices that may be used include extendable elongate members, such as a cable, which may be inserted into a vertebral disc and rotated to pulverize the disc material and to facilitate its removal.

The tissue removal devices may comprise a cable with a refracted and a deployed configuration. The cable may be distally supported by a movable rigid element that restrains the distal end of the cable a fixed distance from the shaft of the tissue removal device.

Systems and methods for treating disc herniation include surgical and endoscopic access and removal of disc tissue. The tissue removal devices that may be used include extendable elongate members, such as a cable, which may be inserted into a vertebral disc and rotated to pulverize the disc material and to facilitate its removal.

The tissue removal devices may comprise a cable with a retracted and a deployed configuration. The cable may be distally supported by a movable rigid element that restrains the distal end of the cable a fixed distance from the shaft of the tissue removal device.

One variation of a tissue removal system described herein may comprise a handheld housing with a power connector, an adjustment assembly, and a motor configured to rotate at a speed of at least 8,000 rpm. The tissue removal system may also comprise an outer shaft with a beveled distal end and a proximal end attached to the handheld housing. The outer shaft my have a length of about 10 centimeters (cm) to about 30 cm, and an average diameter of less than about 3 millimeters (mm). The tissue removal system may additionally comprise an inner shaft with a blunt distal end may be located within the outer shaft and coupled to the motor, an elongate member distally extending through a distal opening of the inner shaft, and a support element coupled proximally to the inner shaft and distally to the elongate member. The elongate member may be joined to the support element by a hinge configuration. The hinge mechanism may be configured to generally limit relative movement between the elongate member and the support element to a plane that is generally formed by the elongate member and the support element. In some variations, the cutting edge may be further from the central axis of the device shaft than the outer surface of the cutter.

A tissue removal system, comprising a rotatable shaft comprising a proximal end, a distal end and a distal opening about the distal end, an extension mechanism configured to extend and retract in the distal opening of the rotatable shaft, a support mechanism comprising a proximal attachment to the rotatable shaft, a cutting mechanism attached to at least one of the extension mechanism and the support mechanism, and a control at the proximal end of the rotatable shaft, wherein the control is configured to manipulate the extension mechanism, wherein the support mechanism comprises a distal attachment to at least one of the extension mechanism and the support mechanism and wherein the support mechanism comprises a generally fixed length between its proximal attachment and distal attachment. The extension mechanism may comprise an elongate member with a resilient, non-linear extended configuration and a generally straightened retracted configuration. The elongate member may be a looped elongate member. The looped elongate member may be a fused looped elongate member. The proximal attachment of the support mechanism may comprise a first attachment and a second attachment. The first attachment and the second attachment may comprise pivot joint attachments. The distal attachment of the support mechanism may comprise a middle segment between the first attachment the second attachment. The cutting mechanism may comprise a first cutting edge. The first cutting edge may be an arcuate cutting edge. The cutting mechanism may further comprise a second cutting edge located between the first cutting edge and the rotatable shaft. The cutting mechanism may further comprise a second cutting edge located between the first cutting edge and the extension mechanism. The cutting mechanism may further comprise a first lumen located between the first cutting edge and the second cutting edge. The cutting mechanism may further comprise a second lumen in which at least one of the extension mechanism and the support mechanism resides. The cutting mechanism may further comprise a retaining lumen in which at least one of the extension mechanism and the support mechanism resides. The first cutting edge may be generally oriented in a first plane that is substantially transverse to a second plane that is transverse to a rotation axis of the rotatable tube. The rotatable shaft may further comprise a transport mechanism proximal to the proximal attachment of the support mechanism. The transport mechanism may be a helical transport mechanism. The rotatable shaft may comprise a multifilament cable. The rotatable shaft may comprise an extendable rotatable cable. The tissue removal system may further comprise a tube in which the rotatable shaft resides. The tube may comprise a curved segment. The tissue removal system may further comprise a travel limiter configured to slidably receive the tube.

In another example, a method for treating a patient is provided, comprising inserting an cutting element into a vertebral disc, wherein the cable is coupled to a rotatable shaft assembly, wherein the cutting element is asymmetrically located with respect to the rotatable shaft assembly, extending the cutting element from an opening of the rotatable shaft assembly, and rotating the cutting element around a rotation axis of the rotatable shaft assembly while supporting the cutting element from at least two or at least three locations on the rotatable shaft assembly. Supporting the cutting element may also comprise supporting the cutting element using a cable loop attached at two separate locations to the rotatable shaft assembly. Rotating the cutting element may place the cable loop in tension and compression. Extending the cutting element from the opening in the rotatable shaft assembly may comprise extending the cutting element from the opening in the rotatable shaft assembly using a resilient elongate member. The resilient elongate member may be a curved resilient elongate member. The resilient elongate member may also comprise a multifilament cable. The multifilament cable may be looped through the cutting element and non-adjacent portions of the multifilament cable are fused together. The method may further comprise transporting material proximally along the rotatable shaft assembly. Transporting material proximally along the rotatable shaft assembly may be performed by a helical structure located on the rotatable shaft assembly. Transporting material proximally along the rotatable shaft assembly may be performed along a curved pathway in a tube in which the rotatable shaft assembly resides. The material may be collected in a collection chamber through which at least a portion of the rotatable shaft assembly resides.

BRIEF DESCRIPTION OF THE DRAWINGS

FIG. 19A schematically depicts one embodiment of a flexible tissue removal device; FIG. 19B is a schematic side elevational view of the proximal end of the flexible tissue removal device of FIG. 19A with a portion of the housing removed; FIGS. 20A and 20B are schematic side and superior cross-sectional views of a steerable tissue removal device inserted into a vertebral disc, respectively.

FIGS. 25A to 25E depict an embodiment of a cable-based tissue removal device with a distally supported and restrained extendable element in various deployment configurations.

FIGS. 26A and 26B depict another embodiment of an extendable element tissue removal device.

FIG. 27 depicts an embodiment of an extendable element tissue removal device with a distally attached cutting element.

FIGS. 42D to 42G are an anterior elevational view, a side cross-sectional view, a side elevational view and a superior elevational view, respectively, of the cutting element in FIGS. 42A to 42C.

FIGS. 44D to 44G are an anterior elevational view, a side cross-sectional view, a side elevational view and a superior elevational view, respectively, of the cutting element in FIGS. 44A to 44C.

FIGS. 46A to 46D are an anterior elevational view, a side cross-sectional view, a side elevational view and a superior elevational view, respectively, of a cutting element with a curved cutting edge along a recessed sloped surface.

FIG. 52B is a side perspective view of the tissue-removal assembly shown in FIG. 52A; FIG. 52C is a side elevational view and FIG. 52D is a superior elevational view; FIGS. 52E and 52F depict the different configurations of the tissue-removal assembly during deployment and use.

FIGS. 57A to 57B are various perspective views of the travel limiter. FIGS. 57C to 57F depict examples of how the travel limiter may be used with one example of a tissue-removal device.

FIGS. 60A to 60D illustrate one example of a mechanism that enables a cable of a tissue removal assembly to be rotated by a motor and simultaneously axially translated by a slider.

DETAILED DESCRIPTION

Figure 1:
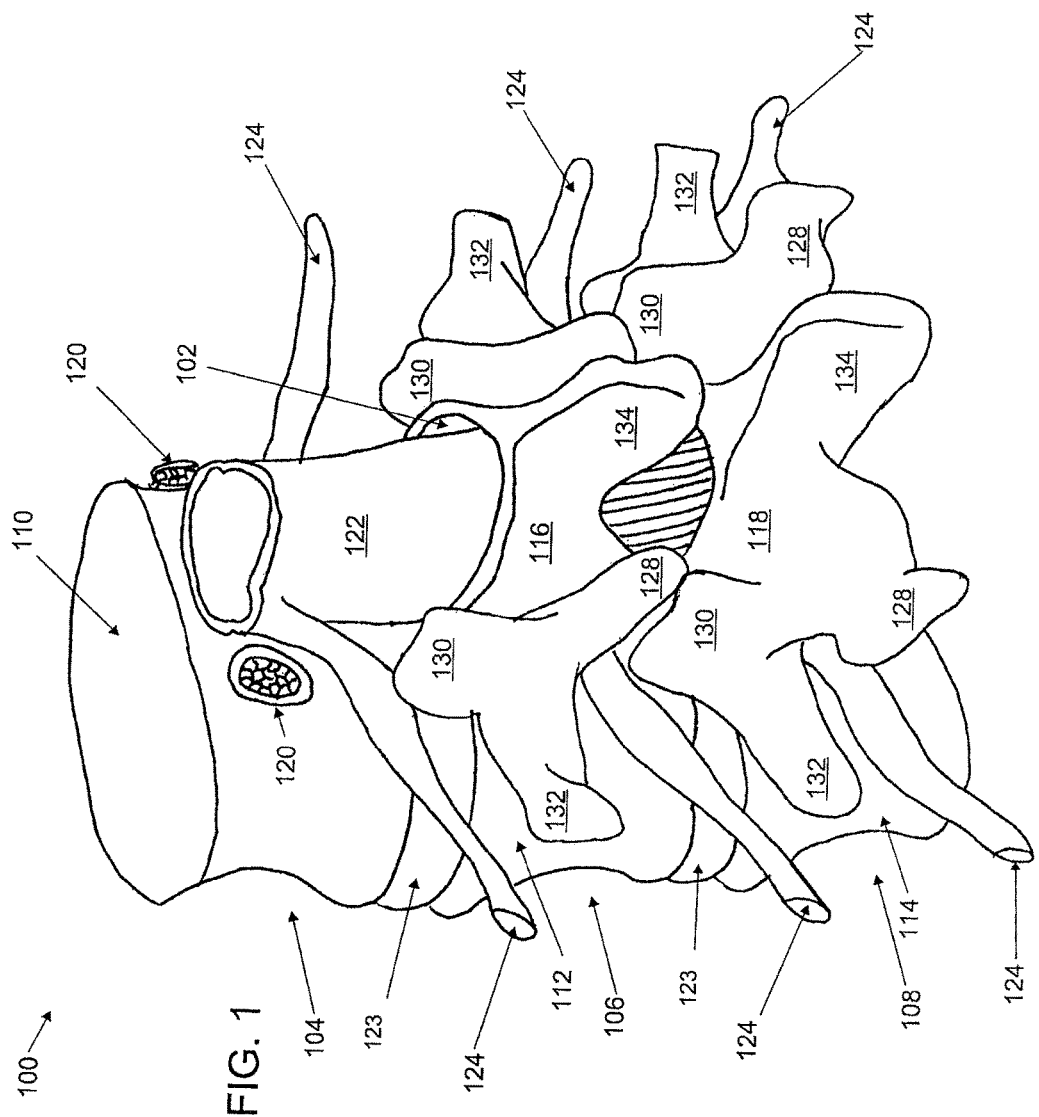
FIG. 1 is a schematic perspective view of a portion of a lumbar spine.
Figure 2:
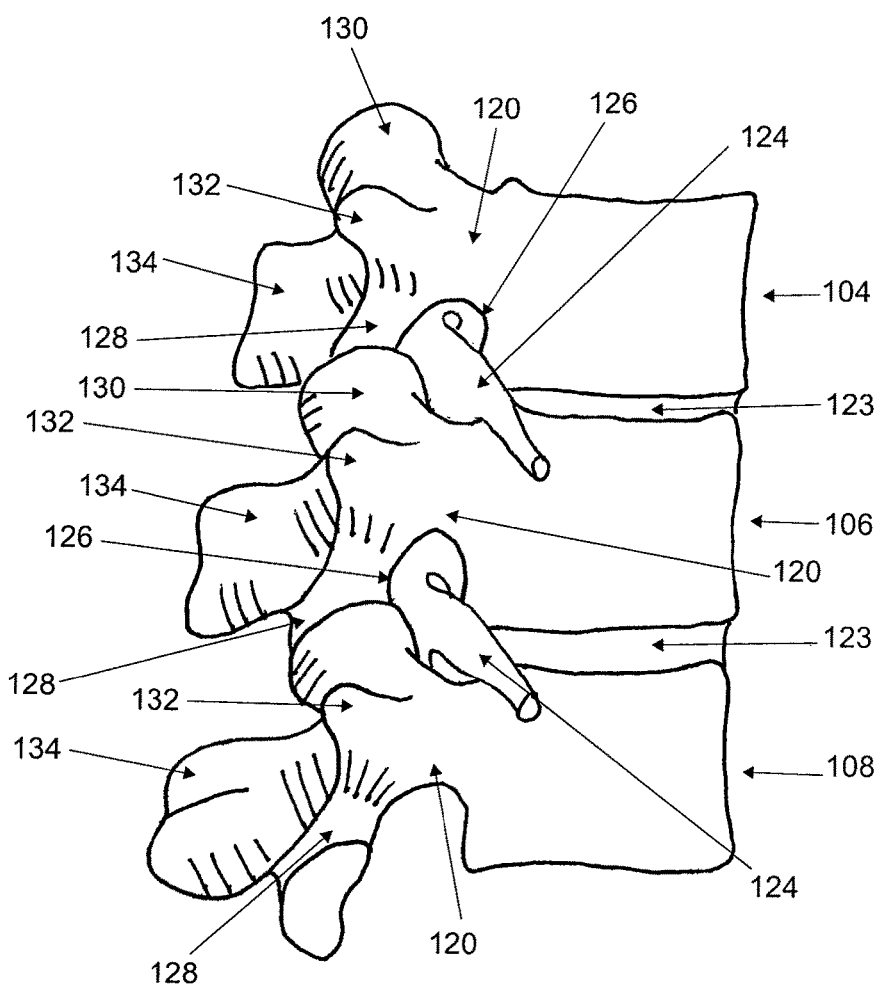
FIG. 2 is a schematic side elevational view of a portion of the lumbar spine.

FIGS. 1 and 2 are schematic views of a lumbar region of a spine 100. The vertebral canal 102 is formed by a plurality of vertebrae 104, 106, and 108, which comprise vertebral bodies 110, 112 and 114 anteriorly and vertebral arches 116 and 118 posteriorly. The vertebral arch and adjacent connective tissue of the superior vertebra 104 has been omitted in FIG. 1 to better illustrate the spinal cord 122 within the vertebral canal 102. Spinal nerves 124 branch from the spinal cord 122 bilaterally and exit the vertebral canal 102 through intervertebral foramina 126 (seen best in FIGS. 2 and 3) that are formed by the adjacent vertebra 104, 106 and 108. The intervertebral foramina 126 are typically bordered by the inferior surface of the pedicles 120, a portion of the vertebral bodies 104, 106 and 108, the inferior articular processes 128, and the superior articular processes 130 of the adjacent vertebrae. Also projecting from the vertebral arches 116 and 118 are the transverse processes 132 and the posterior spinous processes 134 of the vertebrae 106 and 108. Located between the vertebral bodies 110, 112 and 114 are the vertebral discs 123.

Figure 3:
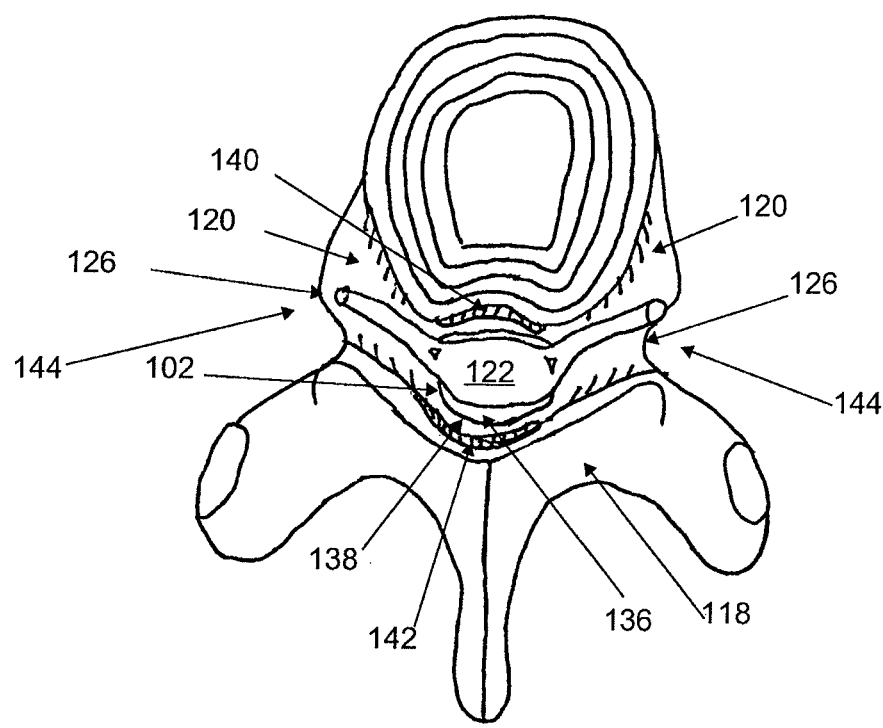
FIG. 3 is a schematic superior view of a portion of a lumbar vertebra and disc.

Referring to FIG. 3, the spinal cord 122 is covered by a thecal sac 136. The space between the thecal sac 136 and the borders of the vertebral canal 102 is known as the epidural space 138. The epidural space 138 is bound anteriorly and posteriorly by the longitudinal ligament 140 and the ligamentum flavum 142 of the vertebral canal 102, respectively, and laterally by the pedicles 120 of the vertebral arches 116 and 118 and the intervertebral foramina 126. The epidural space 138 is contiguous with the paravertebral space 144 via the intervertebral foramina 126.

Figure 4A:
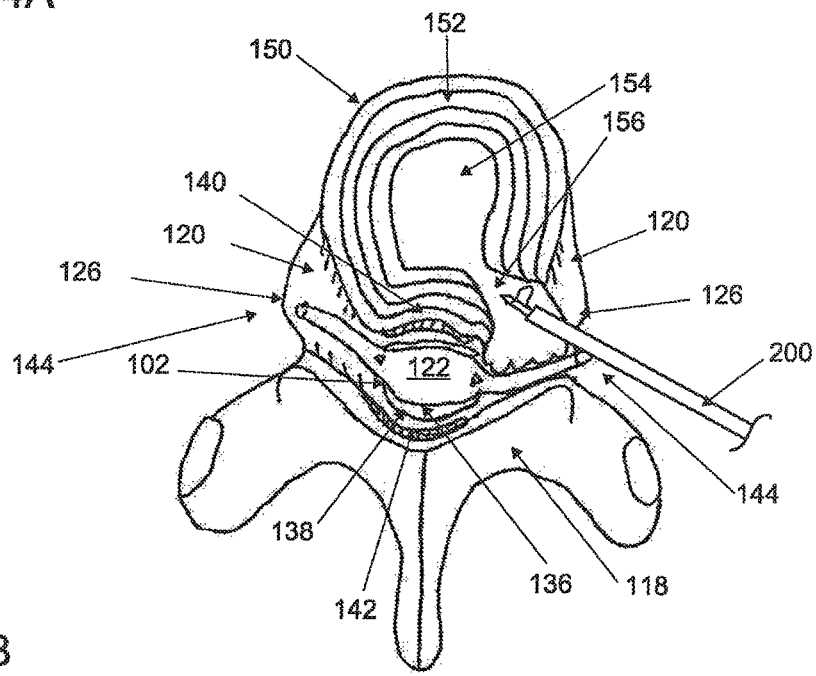
FIGS. 4A and 4B are schematic superior views of a herniated disc during and after treatment, respectively.

Referring to FIG. 4A, a vertebral disc 150 typically comprises an outer, multi-layer, annular band of connective tissue, known as the annulus fibrosus 152, which encases a gel-like resilient material known as the nucleus pulposus 154. The nucleus pulposus 154 acts as a shock-absorbing structure for the forces acting on the spine. Both the annulus fibrosus 152 and the nucleus pulposus 154 are elastic collagenous structures which, over time, may decrease in elasticity and cause the nucleus pulposus to bulge out at a weakened region of the annulus fibrosus 152, and even extrude through the annulus fibrosus 152. FIG. 4A schematically depicts an extrusion 156 of the nucleus pulposus 154, which has penetrated through the wall of the annulus fibrosus 152 within an intervertebral foramen 126 and compressed a nerve 124 exiting the spine. Although the extrusion 156 remains in continuity with the remaining nucleus pulposus 154, the extrusion 156 may sometimes pinch off or separate, resulting in the sequestration of a portion of the nucleus.

Figure 4B:
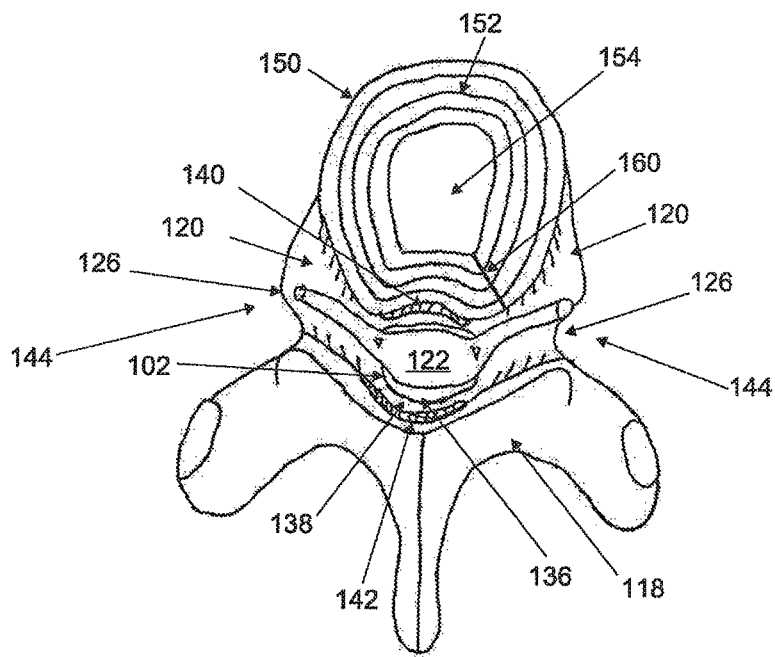

As mentioned previously, treatments of disc herniation may involve internal access to the affected disc with removal or volume reduction of the disc material. This may relieve the pressure causing the bulging or extrusion to at least partially restore the profile of the disc. In FIG. 4A, for example, a tissue removal device 200 has been inserted into the extrusion 156 extending out of the herniated disc 150. The tissue removal device 200 is then actuated to break up and remove the extruded material. In some embodiments, the tissue removal device 200 may be further inserted distally into the disc 150. Additional tissue with the disc 150 may then be removed. As shown in FIG. 4B, after removing a volume of the nucleus pulposus 154 and relieving some of the pressure causing the extrusion 156, the extrusion 156 was able to retract back into the disc 150, thereby reducing the extrusion pathway 160 and relieving compression of the spinal nerve 124. Although contralateral access of the herniated disc is depicted in FIG. 4A, ipsilateral access may also be used. Furthermore, direct tissue removal of the extruded herniated disc may also be performed.

Devices used to remove disc tissue for discectomy or nucleotomy may include lasers, discectomes, trephines, burrs, rongeurs, rasps, curettes and cutting forceps. Many of these devices have a substantial cross-sectional size, and when inserted into a disc, create an insertion channel which substantially compromises the integrity of the annulus fibrosus at the insertion site. Thus, any remaining nucleus pulposus material may extrude or herniate through the insertion site without taking measures to suture or otherwise close the insertion site, thereby adding complexity to the discectomy or nucleotomy procedure.

Figure 5A:
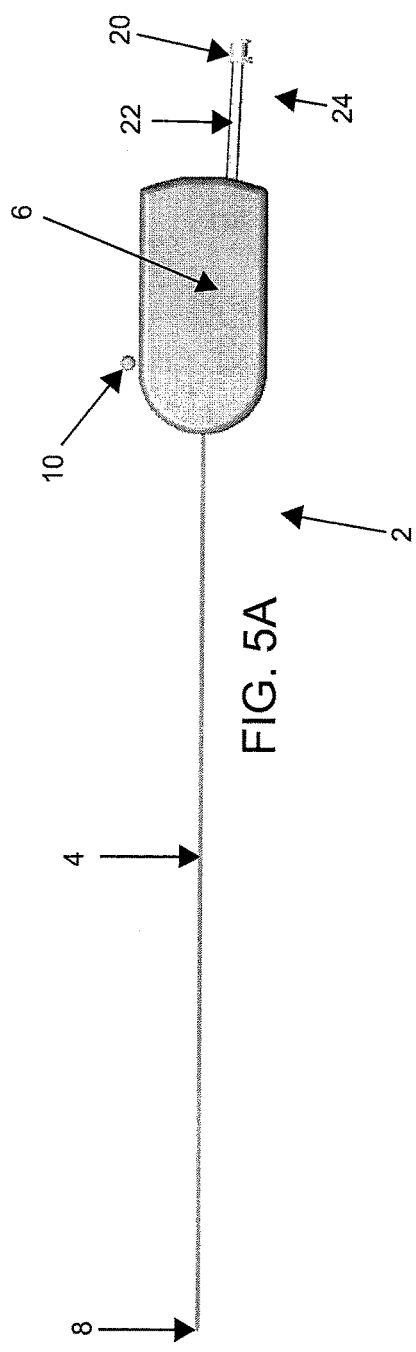
FIG. 5A is a side elevational view of an embodiment of a tissue removal device.

In contrast, a tissue removal device may be configured for minimally invasive insertion toward or into a vertebral disc without requiring suturing, gluing or other procedures to seal or close the access pathway into the disc. The tissue removal device may be used for any of a variety of procedures, including but not limited to discectomy, nucleotomy, lysis of adhesions, and other tissue removal procedures in the spine and throughout other regions of the body. FIG. 5A depicts one embodiment of a tissue removal device 2, comprising an outer tube 4 coupled to a housing 6. The static outer tube 4 covers a rotating drive shaft (not shown) that is attached to a tissue removal assembly 8. In other embodiments, the tissue removal device 2 may lack an outer tube and the drive shaft of the tissue removal device may be inserted into a lumen of a cannula or other access device. The housing 6 contains one or more components configured to control the tissue removal assembly 8 and other optional features of the tissue removal device 2. The tissue removal assembly 8, examples of which are described in greater detail below, may be configured to cut, chop, grind, burr, pulverize, debride, debulk, emulsify, disrupt or otherwise remove tissue when rotated at various speeds. Emulsification includes, for example, forming a suspension of tissue particles in a medium, which may be the existing liquid at the target site, liquid added through the tissue removal device, and/or liquid generated by the debulking of the tissue. Optional components may include, but are not limited to, a motor configured to rotate or move the tissue removal assembly, a power source or power interface, a motor controller, a tissue transport assembly, an energy delivery or cryotherapy assembly, a therapeutic agent delivery assembly, a light source, and one or more fluid seals. The optional tissue transport assembly may comprise a suction assembly and/or a mechanical aspiration assembly. One or more of these components may act through the outer tube 4 to manipulate the tissue removal assembly and/or other components located distal to the housing 6, or from the housing 6 directly. For example, the tissue removal device 2 further comprises an optional port 20 that may be attached to an aspiration or suction source to facilitate transport of tissue or fluid out of the target site or patient. The suction source may be a powered vacuum pump, a wall suction outlet, or a syringe, for example.

The housing 6 may further comprise a control interface 10 that may be used to control the power state of the tissue removal device 2, including but not limited to on and off states. In this particular embodiment, the control interface 10 comprises a lever or pivot member, but in other embodiments, control interface 10 may comprise a push button, a slide, a dial or knob. In some embodiments, the control interface 10 may also change the motor speed and/or movement direction of the tissue removal assembly 8. A bi-directional tissue removal device may be provided, for example, as a potential safety feature should the tissue removal assembly 8 get lodged in a body tissue or structure. The web-like connective tissue that may be found in the epidural space may get wound onto or caught up on the burr device or other tissue removal device. This connective tissue may be dislodged with a bi-directional tissue removal device by reversing the direction of rotation to unwind the tissue. The control interface 10 may be analog or digital, and may comprise one or more detent positions to facilitate selection of one or more pre-selected settings. In other embodiments, a separate motor control interface may be provided for one or more features of the motor. In still other embodiments, control interfaces for other features of the tissue removal device may be provided.

Figure 6A:
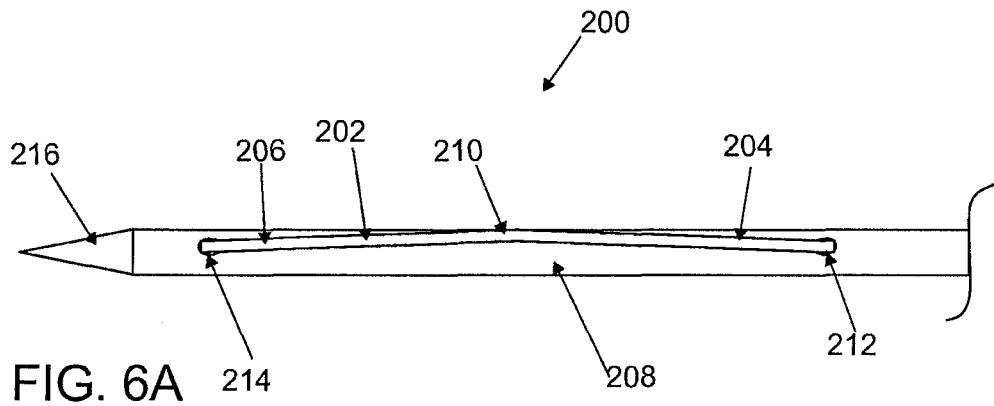
FIGS. 6A and 6B are side elevational views of an embodiment of tissue removal device with a rotatable elongate member in its retracted and extended configurations, respectively.
Figure 6B:
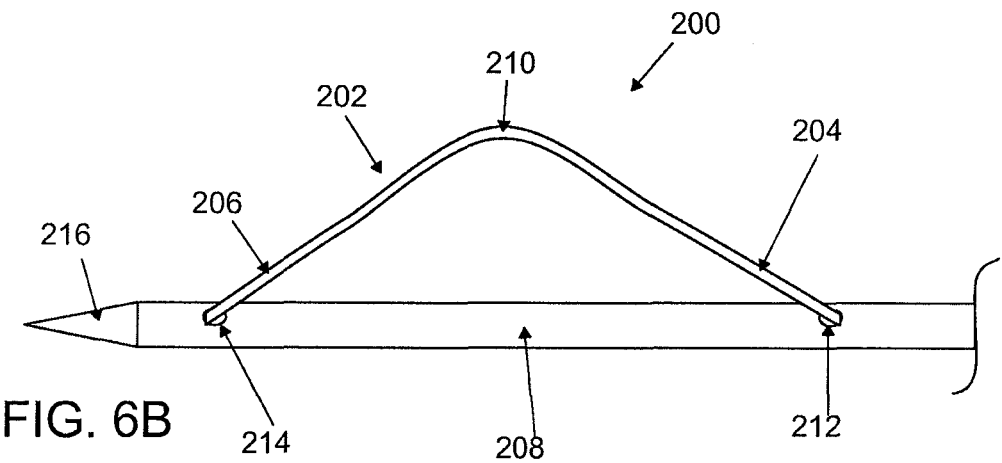

Referring to FIGS. 6A and 6B, the tissue removal assembly 200 may comprise at least one elongate member 202 having a proximal section 204 and distal section 206, with each section coupled to a rotatable shaft 208. The elongate member 202 has a retracted configuration, shown in FIG. 6A, and an extended configuration, shown in FIG. 6B. In the extended configuration, at least a portion 210 of the elongate member 202 is displaced farther away from the rotatable shaft 208 than the same portion 210 in the retracted configuration. To adjust the configuration of the elongate member 202, the proximal section 204 of the elongate member 202 may be slid in or out of a proximal opening 212 of the rotatable shaft 208 to alter the exposed length of the elongate member 208 between the proximal opening 212 and a distal opening 214 (or distal attachment of the distal section 206) of the elongate member 202. The percentage change in the length of the elongate member 202 from its retracted configuration to its extended configuration may be in the range of about 10% to about 60% or more, sometimes about 20% to about 40%, and other times about 15% to about 20%. In some embodiments, transformation of the elongate member 202 between configurations may include sliding its distal section 206 in or out of the distal opening 214, in addition to or in lieu of movement between the proximal section 204 and the proximal opening 212.

The tissue removal device 200 may further comprise a distal head 216 with a conical configuration, as depicted in FIGS. 6A and 6B. Other head configurations are also contemplated, including but not limited to an ovoid configuration, a dome configuration, a concave configuration, a cube configuration, etc. The head 216 may be configured to penetrate or dissect body tissue, such as the annular wall of a vertebral disc, and may be used while the rotatable shaft 208 is being rotated, or when the rotatable shaft 208 is not rotated. In other embodiments, the head may comprise multiple points or edges that may be used to cut, chop, grind, burr, pulverize, debride, debulk, emulsify, disrupt or otherwise remove tissue or body structures. In still other embodiments, the head may comprise surfaces with a grit that may be used as a burr mechanism. The grit number may range from about 60 to about 1200 or more, sometimes about 100 to about 600, and other times about 200 to about 500.

The head may optionally comprise a port or aperture which may be used to perform suction or aspiration at the target site and/or to perfuse saline or other biocompatible fluids or materials to the target site. Use of saline or other cooling materials or liquids, for example, may be used to limit any thermal effect that may occur from frictional or other forces applied to the target site during removal procedures. The saline or other materials may or may not be chilled. In other embodiments, one or more therapeutic agents may be provided in the saline or fluid for any of a variety of therapeutic effects. These effects may include anti-inflammatory effects, anti-infective effects, anti-neoplastic effects, anti-proliferative effects, hemostatic effects, etc.

Figure 7:
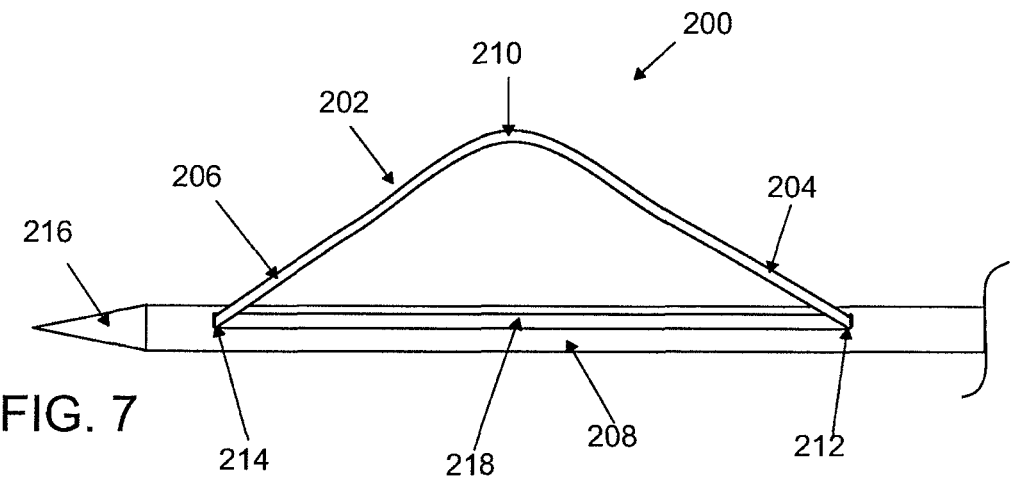
FIG. 7 depicts another embodiment of a tissue removal device with a recessed groove.

In some embodiments, the rotatable shaft may optionally comprise one or more recesses or grooves on its outer surface to receive the elongate member 202. For example, FIG. 7 depicts a single groove 218 between the proximal and distal openings 212 and 214 of the rotatable shaft 208. The depth and cross-sectional shape of the groove 218 may be configured to partially or fully receive the elongate member 202.

Figure 8:
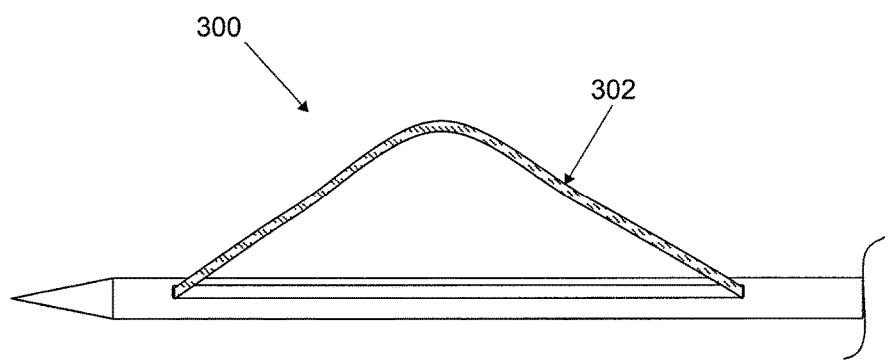
FIG. 8 depicts another embodiment of a tissue removal device with a multi-filament elongate member.

The elongate member 202 may comprise any of a variety of materials and structures. For example, the elongate member 202 may comprise titanium, a nickel-titanium alloy, stainless steel, a cobalt-chromium alloy, a polymer (e.g. nylon, polyester and polypropylene) or a combination thereof. The elongate member 202 may also have a monofilament or multi-filament structure. FIG. 8, for example depicts a tissue removal device 300 with an elongate member comprising a multi-filament cable 302. In some embodiments, a multi-filament elongate member may provide greater flexibility and/or stress tolerance than a monofilament elongate member. A multi-filament elongate member may comprise any number of filaments, from about 2 filaments to about 50 filaments or more, sometimes about 3 filaments to about 10 filaments, and other times about 5 filaments to about 7 filaments. In some embodiments, the elongate member has a flexural modulus that is less than the flexural modulus of bony tissue, such as the endplates of the vertebral bodies adjacent to a vertebral disc. In some instances, by providing a flexural modulus that is lower than certain body structures, damage to those body structures may be reduced or substantially eliminated. Thus, in some discectomy or nucleotomy procedures, a tissue removal device with an elongate member that has a flexural modulus that is less than the flexural modulus of both the bony tissue of the vertebral endplates and the flexural modulus of the annular fibrosus walls of the disc may be able to pulverize the inner tissue of a disc without damaging the adjacent walls of the disc or the vertebral bone. In some examples, the flexural modulus of the elongate member may be less than about half of the flexural modulus of intact bone or the annular fibrosis tissue, while in other embodiments, the flexural modulus of the elongate member is at least about 5 times lower, or even at least about 10 times or 20 times lower. In some embodiments, the flexural modulus of the elongate member is generally uniform along its exposed length or between its coupling sites on the rotatable shaft. For example, in some embodiments, the flexural modulus may not vary by more than about a 10× range along the length of the elongate member, while in other embodiments, the variation may be no greater than a range of about 5× or about 2×.

Although the elongate member 202 may have a retracted configuration and an extended configuration, the elongate member 202 may also have a native or base configuration in which the stress acting on the elongate member 202 is reduced compared to other configurations. This native configuration, if any, may be the refracted configuration, the extended configuration, or a configuration between the retracted configuration and the extended configuration. Thus, the stress exerted on the elongate member 202 in the native configuration may be lower in either the retracted configuration or the extended configuration, or a third configuration that is different from the retracted configuration or the extended configuration. In some embodiments, a native configuration that is similar to the extended configuration may be beneficial because a lower baseline stress acting on the elongate member 202 while in its extended configuration may provide greater stress tolerance from impacting tissues or bone before stressing the elongate member 202 beyond its fracture point. Although adjusting the elongate member 202 to its retracted configuration may result in greater stress acting on the elongate member 202, the stress may occur only during insertion and removal of tissue removal device 2, and without the impact stressed that act on the elongate member 202 during use. To produce the elongate member 202 with a particular native configuration, the manufacturing steps may vary depending upon the particular material or composition used. In embodiments where the elongate member 202 comprises stainless steel (e.g. 304L or 316L stainless steel) or nickel—titanium alloys, for example, a series of deformation steps and heat annealing steps may be used to form the elongate member 202 in a native, expanded configuration.

The elongate member 202 may have any of a variety of cross-sectional shapes, including but not limited to square, rectangular, trapezoidal, circular, elliptical, polygonal, and triangular shapes, for example. The cross-sectional shape and/or size may be uniform along its length, or may vary along one or more sections. In one example, the elongate member may have a tapered configuration, with a cross-sectional area that decreases from its proximal section to its distal section, or from its distal section to its proximal section. In some embodiments, the elongate member 202 may comprise a metallic wire or other elongate structure with a diameter or maximum cross-sectional dimension in the range of about 0.2 mm to about 1.5 mm or more, sometimes about 0.3 mm to about 1 mm, and other times about 0.3 mm to about 0.5 mm.

In some embodiments, the elongate member may be micropolished. Micropolishing may or may not reduce the risk of chipping or fragment formation when used to debride harder or denser body structures or tissues. In other embodiments, the elongate member may comprise a grit surface or a cutting edge along one or more portions of its length. For example, the elongate member may comprise a cutting edge with an edge angle in the range of about 90 degrees to about 10 degrees, sometimes about 75 degrees to about 15 degrees, and other times about 60 degrees to about 30 degrees, and still other times about 45 degrees to about 40 degrees. The configuration of the elongate member surface may be the same or different on opposing sides of the elongate member. For example, having different configuration on the leading surface compared to the trailing surface of the elongate member, may permit changes in the cutting, chopping, debriding, or emulsifying characteristics of the elongate member 202, depending upon its direction of rotation. In other embodiments, the leading and trailing surfaces may generally have the same features and may have similar performance in either rotation direction, but may also permit users to switch from one surface to the other if one surface has worn out. In still other embodiments, the rotation direction may be user-selected, depending upon the relative location of the tissue to be removed and any critical anatomical structures. For example, the rotation direction may be selected such that if the cutting edge 58 or 60 catches on the tissue or structure, tissue disrupting element 8 will be rotated away from the critical anatomical structure(s), if any.

Figure 9:
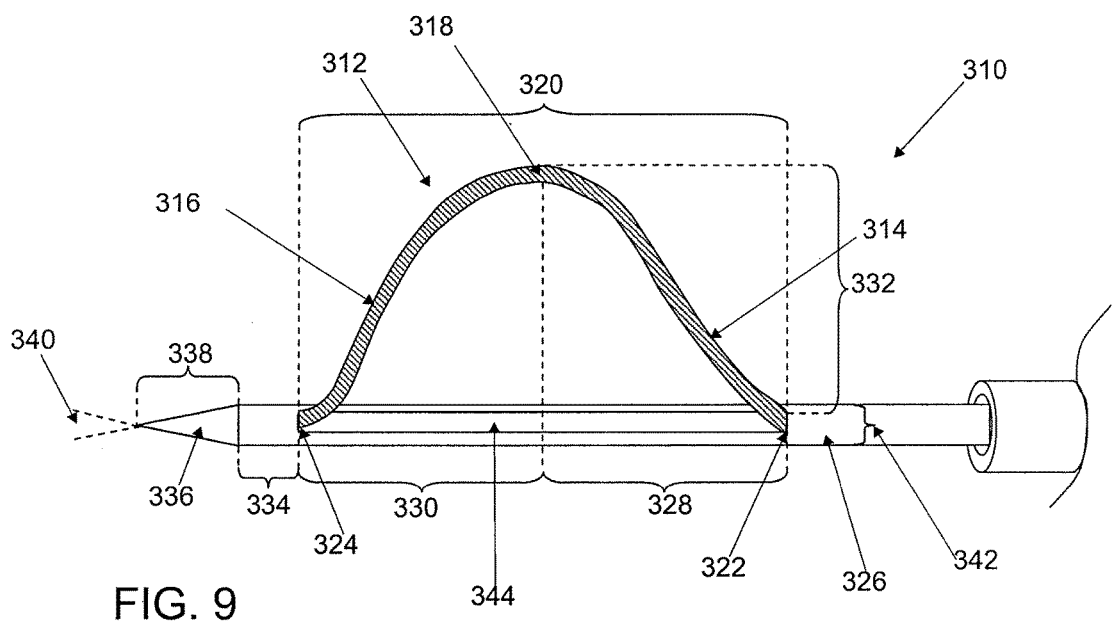
FIG. 9 depicts another embodiment of a tissue removal device.

As depicted in FIG. 6B, the elongate members 202 may have proximal and distal sections 204 and 206 with generally similar lengths and generally straight configurations, and a curved or angled middle portion 210 between them. FIG. 9, however, depicts another embodiment of a tissue removal device 310, comprising an elongate member 312 with proximal and distal sections 314 and 316 with concave configurations and a middle section 318 with a convex configuration. Other configurations are also contemplated, comprising any of a variety of linear, curved, or angled sections, and comprising symmetrical or asymmetrical configurations. In the embodiment depicted in FIG. 9, the longitudinal distance 320 between the proximal and distal openings 322 and 324 of the rotatable shaft 326 may be in the range of about 4 mm to about 30 mm or more, sometimes about 6 mm to about 15 mm, and other times about 9 mm to about 12 mm. The longitudinal distances 328 and 330 from the proximal and distal openings 322 and 324 to the peak displacement distance 332 of the elongate member 302, respectively, may be similar or different. In some embodiments, the distances 328 and 330 may be in the range of about 2 mm to about 20 mm or more, sometimes about 3 mm to about 10 mm, and other times about 4 mm to about 6 mm. The peak displacement distance 332 between the middle section 318 and the rotatable shaft 326 can vary, depending upon the particular configuration of the elongate member. The minimum displacement distance (not shown) of the middle section need not be zero, as in embodiments where the elongate member does not fully retract along its entire length against the rotatable shaft. In some embodiments, the displacement distance 318 may be in the range of about 2 mm to about 10 mm or more, sometimes about 3 mm to about 8 mm, and other times about 4 mm to about 6 mm. In some embodiments, the peak displacement distance 322 may be characterized relative to the longitudinal distance 320 or the proximal or distal distances 328 and 330 to the peak distance. For example, the ratio of the peak displacement distance to the longitudinal distance may be in the range of about 0.2 to about 1 or more, sometimes about 0.3 to about 0.8, and other times about 0.4 to about 0.5. The distance 334 between the distal opening 324 of the rotatable shaft and the distal head 336 may be in the range of about 0.5 mm to about 5 mm or more, sometimes about 1 mm to about 4 mm, and other times about 2 mm to about 3 mm. The length 338 of the head 336 may be in the range of about 2 mm to about 15 mm or more, sometimes about 3 mm to about 10 mm, and other times about 4 mm to about 5 mm. In embodiments comprising a conical or tapered head, the angle 340 of the head configuration may be in the range of about 10 degrees to about 90 degrees or more, sometimes about 20 degrees to about 60 degrees, and other times about 30 degrees to about 45 degrees.

The diameter 342 (or maximum transverse axial dimension) of the rotatable shaft 326 and/or head 336 may be in the range of about 0.5 mm to about 5 mm or more, sometimes about 1 mm to about 3 mm, and other times about 1.5 mm to about 2.5 mm. The diameter of the shaft 326 and the head 336 may be similar or different. The maximum cross-sectional dimension of the proximal and distal openings may be the same or different, and may be in the range of about 0.1 mm to about 1.5 mm or more, sometimes about 0.2 mm to about 1 mm, and other times about 0.4 mm to about 0.8 mm.

The width of the groove 344 of the rotatable shaft 326, if any, may be in the range of about 0.2 mm to about 1.5 mm or more, sometimes about 0.3 mm to about 1 mm, and other times about 0.4 mm to about 0.7 mm. The width of the groove 344 may also be characterized as a percentage of the diameter or width of the elongate member, which may be in the range of about 80% to about 400% or more, sometimes about 105% to about 300%, and other times about 150% to about 200%. As mentioned previously the depth of the groove 344 may be less than, similar to, or greater than the maximum transverse dimension of the elongate member 312. In some embodiments, the groove depth or average groove depth may be in the range of about 0.2 mm to about 2 mm or more, sometimes about 0.4 mm to about 1 mm, and other times about 0.6 mm to about 0.8 mm. In other embodiments, the depth of the groove may be a percentage of the depth of the elongate member, in the range of about 20% to about 200% or more, sometimes about 50% to about 125%, and other times about 40% to about 100%.

Although a single elongate member 202 is provided in the tissue removal device 200 depicted in FIG. 6A, other embodiments may comprise two or more elongate members. In some embodiments, however, a single elongate member may permit higher rotational speeds, due the reduced surface drag compared to tissue removal devices with multiple elongate members. In embodiments with multiple elongate members, the elongate members may be distributed uniformly or non-uniformly around the perimeter of the rotatable shaft. In some embodiments, each elongate member may have its own proximal and distal openings, but in other embodiments, two or more elongate members may share a proximal and/or distal opening. The proximal and/or distal openings may be located at the same or different longitudinal position on rotatable shaft, and each elongate member may have the same or different length or configuration. The elongate members may be independently adjustable or adjustable in groups.

Figure 10:
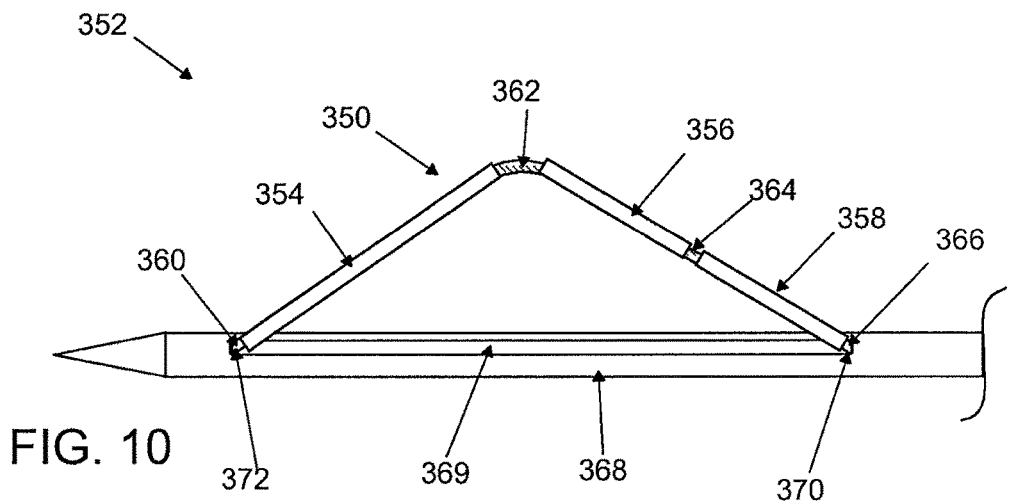
FIG. 10 depicts one embodiment of a tissue removal device with a plurality of rigid supports.

Referring to FIG. 10, in some embodiments, the elongate member 350 of the tissue removal device 352 may comprise other structures 354, 356 and 358 attached or coupled to the flexible elongate member 350. These structures may comprise any of a variety of structures, including tubes, rods, bars, cutting discs or other cutting members, beads or other structures. In the specific example depicted in FIG. 10, the elongate member 352 comprises rigid sections 354, 356 and 358 alternating between flexible segments 360, 362, 364 and 366. One or more flexible segments may also be substituted with a mechanical joint, such as a pin joint or a hinge joint. In some embodiments, the flexible elongate segments 360, 362, 364 and 366 are part of a single contiguous flexible elongate member that passes through a lumen of each rigid section 354, 356 and 358 or are otherwise coupled to each rigid section 354, 356 and 358. In other embodiments, one or more of the flexible segments 360, 362, 364 and 366 are separate and interconnect only two rigid sections 354, 356 and 358 or a rigid section and the rotatable shaft 368 or a structure therein. The particular number, shape, flexibility/rigidity, lengths and locations of the rigid segments and flexible segments may vary and need not be uniform or symmetrical. In some embodiments, the percentage of rigid section to flexible section along the length of the fully extended elongate member may in the range of about 0 to about 99%, sometimes about 50% to about 95%, and other times about 75 to about 90%. In some embodiments, the length of the flexible segment may be less than about 75% of the length of the adjacent rigid segments, sometimes less than about 50%, and other times less than about 20% or about 10%.

In the example shown in FIG. 10, the tissue removal device 352 comprises one rigid section 354 that is larger than the other rigid sections 356 and 358. The section located at the peak displacement distance of the elongate member 350 may be a flexible segment 362 as shown in FIG. 10, or a rigid section in other embodiments. The rigid sections 354, 356 and 358 are generally linear in shape, but may also be curved or angled or any combinations thereof. The elongate member 350 in FIG. 10 is also generally configured to lie in a single plane in both the retracted and extended configurations, but in other embodiments, one or more rigid or flexible sections may be oriented out of plane in the refracted and/or extended configurations. As further illustrated in FIG. 10, the shaft 368 may comprise a groove 369, or a region of the shaft with a narrow diameter or axial transverse dimension, which may reduce the overall cross-sectional area of the tissue removal device 352 by permitting the elongate member 352 to protrude less when in the refracted configuration.

Figure 11:
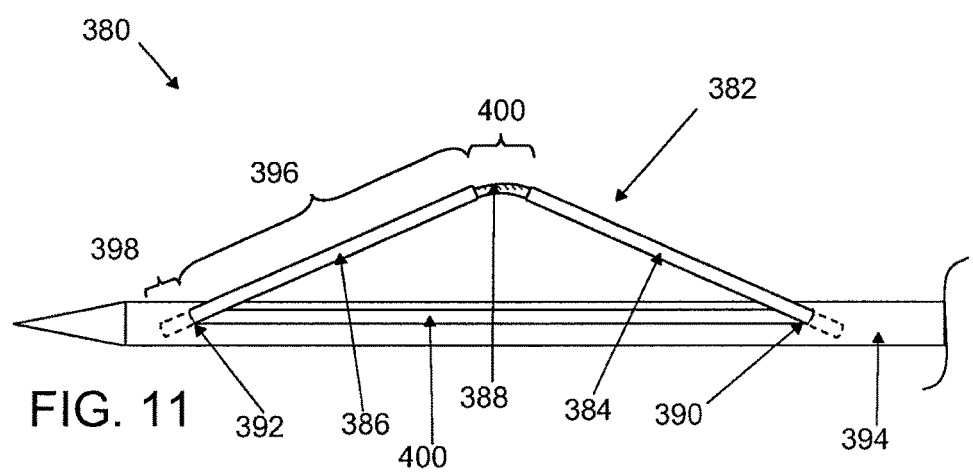
FIG. 11 depicts another embodiment of a tissue removal device with rigid supports.

As shown in FIG. 10, the elongate member 350 in the extended state may have flexible sections 366 and 360 located about its proximal and distal openings 370 and 372. In other embodiments, however, the elongate member may have a rigid section or other structure about the proximal or distal openings in the extended state. In FIG. 11, for example, the tissue removal device 380 comprises a generally symmetrical elongate member 382 with proximal and distal rigid members 384 and 386 interconnected by a flexible cable 388. In the extended configuration, the rigid members 384 and 386 are partially located or recessed within the proximal and distal openings 390 and 392 of the rotatable shaft 394. In some further embodiments, having rigid members 384 and 386 at the proximal and distal openings 390 and 392 may reduce the tilting or bending of the elongate member 382 with respect to the shaft 394. The degree with which the elongate member 382 is restricted may depend, for example, on the widths of the openings 390 and 392 and the rigid member 384 and 386, the lengths 396 and 398 of the rigid member 384 and 386 outside and inside the shaft 394, the lengths 400 of the flexible segment(s), and the overall diameter of the shaft 394, and the degree of rigidity of the rigid members 384 and 386. As further shown in FIG. 11, the shaft 394 may further comprise a groove 400 or other configuration with a reduced diameter or transverse axial dimension. At least a portion of the groove 400 or configuration is located between the proximal and distal openings 390 and 392, but the groove 400 or configuration may also be located proximal or distal to the openings 390 and 392, respectively.

Figure 12A:
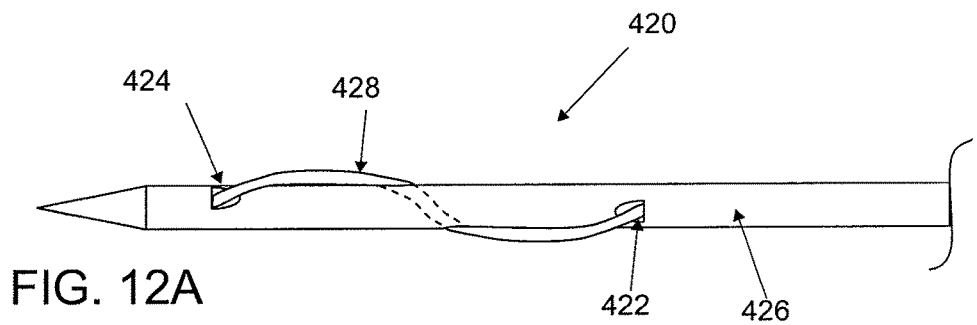
FIGS. 12A and 12B illustrate another embodiment of a tissue removal device with a helically-oriented elongate member in the refracted and extended states, respectively.
Figure 12B:
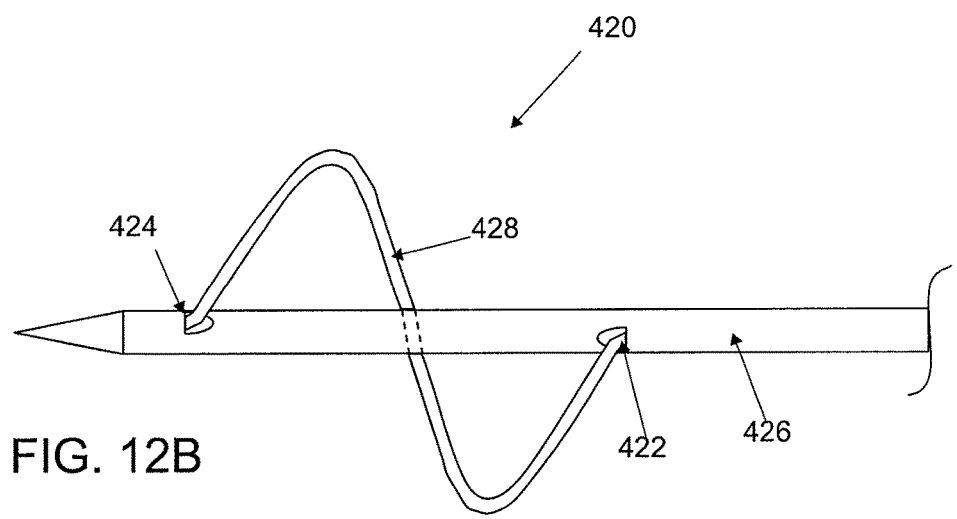

As shown in FIGS. 12A and 12B, in some embodiments, the tissue removal device 420 may have proximal and distal openings 422 and 424 which are located at different circumferential locations along the longitudinal length of the rotatable shaft 426, and/or where the elongate member 428 comprises at least one section having a helical, twisted or skewed configuration with respect to the rotatable shaft 426. FIG. 12A depicts the tissue removal device 420 in a retracted or collapsed configuration, while FIG. 12B depicts the tissue removal device 400 in an extended or expanded configurations. By extending the elongate member 408 through the proximal opening 422 of the shaft 426, the elongate member 426 may become axially compressed and expand radially outward from the shaft 426.

The configuration of the elongate member may vary in the direction of turning. For example, the elongate member may have a right or left-handed spiral orientation (i.e. a clockwise or counter-clockwise orientation). In FIGS. 12A and 12B, for example, the elongate member 428 has a left-handed or counter-clockwise spiral orientation (as viewed from the proximal end of the tissue removal device 420). The spiral orientation of the elongate member 428 may be in the same as the rotation direction of the shaft 426, or be the opposite of the rotation direction. The spiral configuration of the elongate member 428 may be characterized in any of a variety of ways. For example, the absolute number of turns may be the elongate member may be anywhere in the range from about zero (e.g. a linear elongate member) to about 4 turns or more, sometimes about a 1A turn to about 1V2 turns, and other times about V2 turn to about one turn. In other embodiments, the spiral configuration may be characterized by its rate of turning, which may be calculated as the number of turns per millimeter or centimeter. In some embodiments, the rate of turning may be in the range of about 0.3 turns/cm to about 2 turns/cm or more, sometimes about 0.7 turn/cm to about 1.5 turns/cm, and other times about 0.9 turns/cm to about 1 turn/cm. The elongate member 428 may also be characterized by its pitch angle, which may be in the range of about 0 degrees to about 90 degrees, sometimes about 5 degrees to about 90 degrees, and other times about 45 degrees to about 85 degrees. The spiral configuration of the elongate member may be generally curved along its length, but may also comprise multiple linear segments with angled or curved bends in between. The configuration of the spiral elongate member in the retracted and extended configuration may vary, depending upon the flexibility of the elongate member, the manner and angle with which one or more ends of the elongate member are attached or fixed to the rotatable shaft, and the native configuration of the elongate member.

Figure 13A:
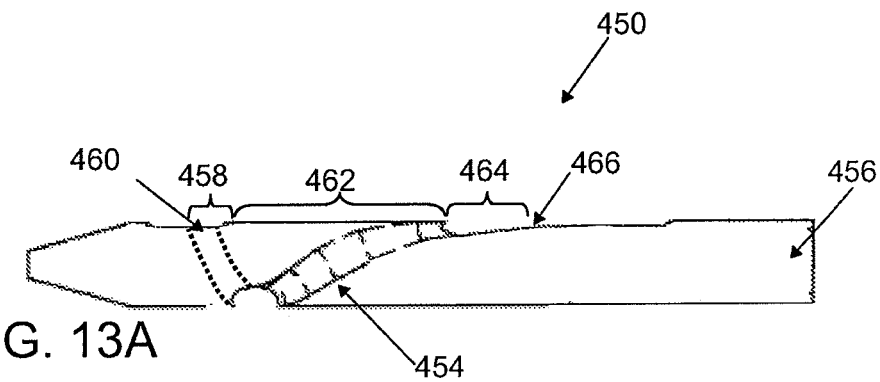
FIGS. 13A and 13B are side elevational and longitudinal cross-sectional views of another embodiment of a tissue removal device.
Figure 13B:
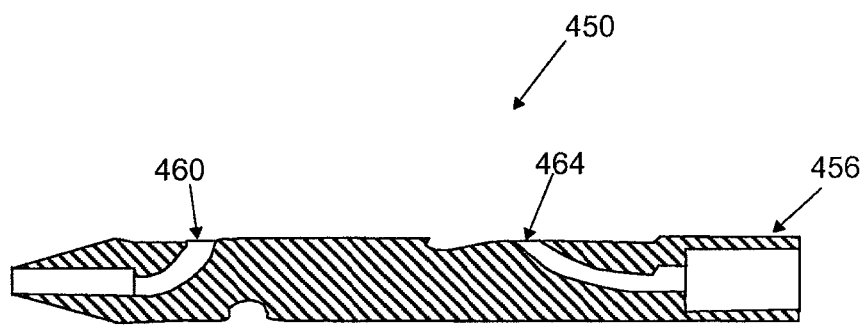
Figure 13C:
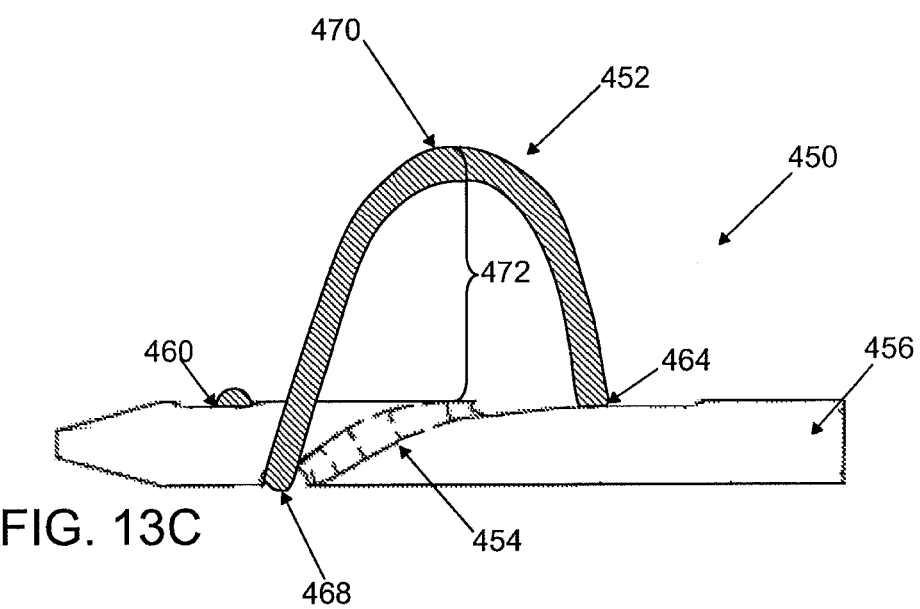
FIG. 13C is a side elevational view of the tissue removal device of FIG. 13A with a tissue-removing cable in an extended state.

As shown in FIGS. 13A to 13C, a tissue removal device 450 with a spiral elongate member 452 may also comprise one or more grooves 454 on the rotatable shaft 456. The groove 454 may facilitate seating and/or securing of the elongate member 452 in its retracted configuration. As can be seen in FIG. 13C, the spiral configuration of the elongate member 452 and the groove 454 may not be uniform along the length of the rotatable shaft 456. The distal groove 458 adjacent to the distal opening 460 comprises approximately a V2 turn along a longitudinal distance that is about 50% shorter than the V2 turn of the middle groove 462, while the proximal groove 464 between the middle groove 462 and the proximal opening 466 is generally linear. In some embodiments, the change in turn rate may be in the range of about zero to about 4 turns/cm or more, other times about zero to about 1 turn/cm, and other times about zero to about 0.5 turns/cm. In the particular embodiment depicted in FIGS. 13A to 13C, the distal portion 468 of the elongate member 452 remains generally wrapped around the shaft 456 in the distal groove 458 in the extended configuration, while the proximal portion 470 of the elongate member 452 bows radially outward. As can be seen in FIG. 13C, in this particular configuration, the peak displacement distance 472 of the elongate member 452 is located closer to the proximal opening 464 of the shaft 456 than the distal opening 460. The elongate member, however, may be configured with a peak displacement distance located anywhere between the proximal and distal openings, or even extending distal to the distal opening and/or proximal to the proximal opening. In other embodiments, the elongate member may even comprise multiple peak displacement distances (e.g. a multi-angle, undulating or sinusoidal elongate member in the extended configuration). In some embodiments, the peak displacement distance 472 is in the range of about 0.5 to about 10 times greater than the diameter or transverse axial dimension of the shaft 456, sometimes about 1 to about 5 times greater, and other times about 2 times to about 3 times greater. The longitudinal location of the peak distance may be characterized as a relative position from the proximal to distal openings, which may be about −20% or less, about −10%, about 0%, +10%, about +20%, about +30%, about +40%, about +50%, about +60%, about +70%, about +80%, about +90%, about +100%, about +110% or about +120% or more.

Figure 14A:
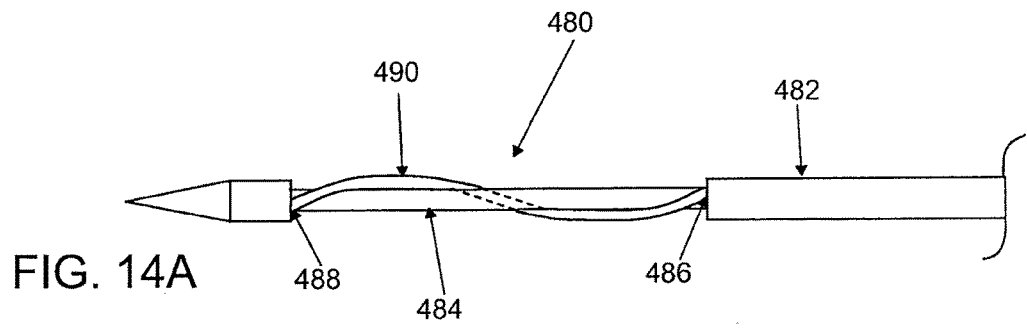
FIGS. 14A and 14B are side elevational views of another embodiment of tissue removal device in the retracted and extended configurations, respectively.
Figure 14B:
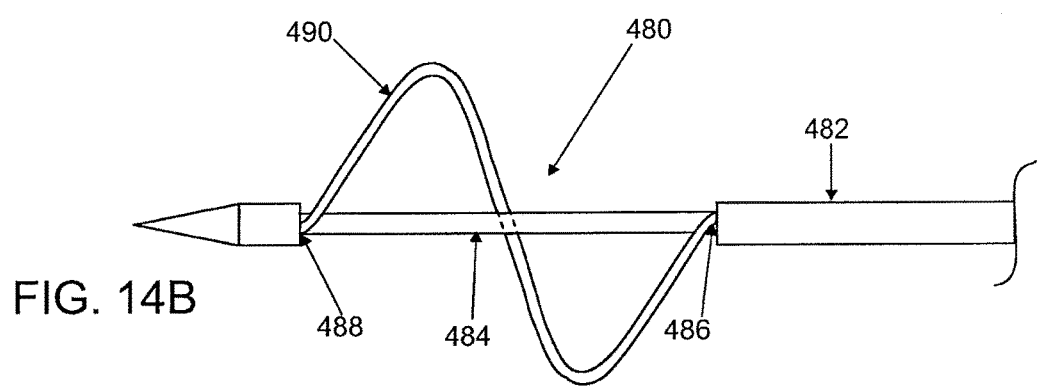

Referring now to FIGS. 14A and 14B, in some embodiments, the tissue removal device 480 may comprise a shaft 482 with a narrowed region 484. At least a portion of the narrowed portion 484 may be located between the proximal and distal attachments or openings 486 and 488 from which the elongate member 490 protrude, but in other embodiments, at least a portion of the narrowed portion 484 may be proximal or distal to the openings 486 and 488, respectively. As depicted in FIG. 14A, the narrowed portion 484 of the shaft 482 may facilitate a low profile retracted configuration, but may also provide additional space for snagged tissue or adhered biological material to occupy. This may occur, for example, when the elongate member 490 in FIG. 14B is retracted into its retracted configuration in FIG. 14A, or during a prolonged procedure. This additional space may be beneficial when withdrawing tissue removal device from an endoscopy instrument or cannula. As further illustrated in FIGS. 14A and 14B, the attachments or openings 486 and 488 may have a transverse axial orientation, rather than the surface orientation of the openings 422 and 424 of the tissue removal device 420 depicted in FIGS. 12A and 12B.

Figure 15:
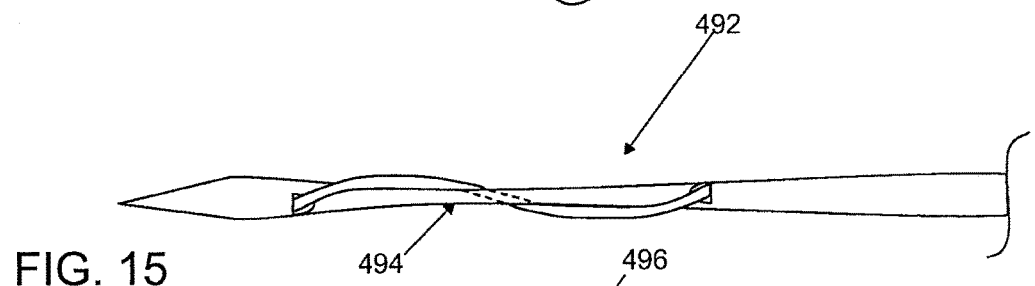
FIG. 15 is an embodiment of a tissue removal device with tapered central region.
Figure 16:
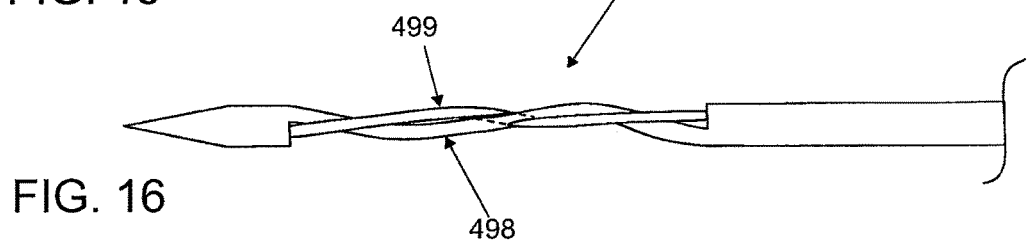
FIG. 16 is an embodiment of a tissue removal device with a narrow corkscrew region.

Although the narrowed portion 484 in FIGS. 14A and 14B has a uniform diameter and configuration, in other embodiments, such as the tissue removal device 492 in FIG. 15, the narrowed portion 494 may have a tapered configuration with a variable diameter or configuration. Referring back to FIGS. 14A and 14B, the longitudinal axis of the narrowed portion 494 may be co-axial with the axis of the rest of the shaft 482, but in some embodiments, the longitudinal axis may be different, e.g. eccentric or variable. In FIG. 16, for example, the tissue removal device 496 comprises a narrowed portion 498 with a non-linear longitudinal axis comprising a helical or corkscrew configuration. Also, although this example of the tissue removal device 496 has narrowed portion 498 and an elongate member 499 with the same helical orientation, in other example, the helical orientations may be different or opposite.

Figure 5B:
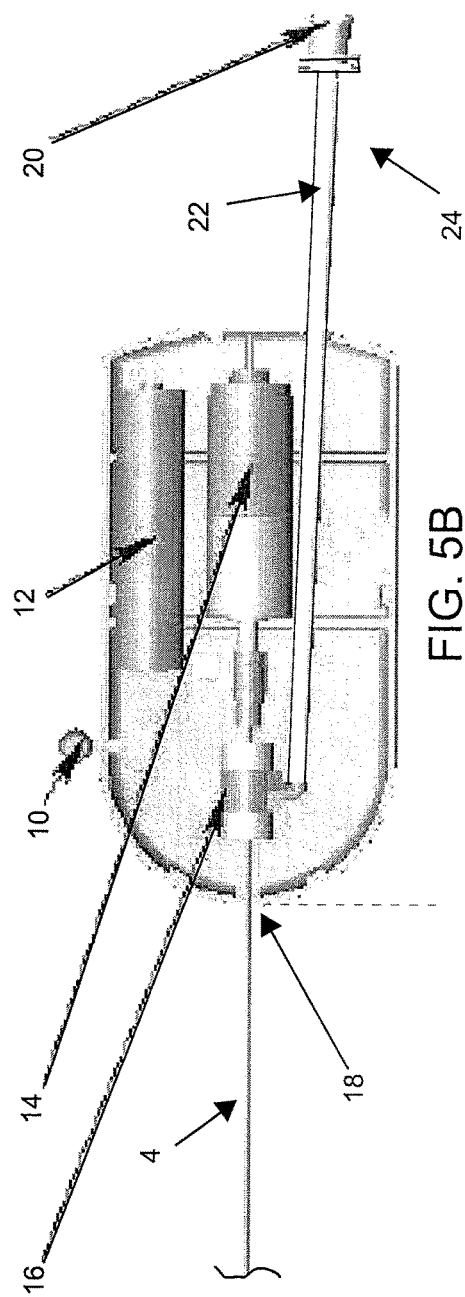
FIG. 5B is a detailed cutaway view of the device in FIG. 5A.

Referring now to FIG. 5B, the tissue removal device 2 in FIG. 5A is illustrated with a portion of the housing 6 removed to show various internal components. In this embodiment, the tissue removal device 2 further comprises a battery 12 to provide power to the motor 14 which drives the tissue removal assembly 8. In other embodiments, a connector to an external power source may be provided in addition to, or in lieu of, the battery 12. The type of battery and power provided may differ depending upon the particular power needs of the motor and/or other components of the tissue removal device 2.

In some embodiments, the motor 14 of the tissue removal device 2 is a DC motor, but in other embodiments, the motor 14 may have any of a variety of configurations, including but not limited to an AC or a universal motor. The motor 14 may be a torque, brushed, brushless or careless type of motor. In some embodiments, the motor 14 may be configured to provide a rotational speed of about 500 rpm to about 200,000 rpm or more, sometimes about 1,000 rpm to about 40,000 rpm, and at other times about 5,000 rpm to about 20,000 rpm. The motor 14 may act on the tissue removal assembly 8 via the outer tube 4, or a by drive member located within the outer tube 4. In some further embodiments, a fluid seal 16 may be used to protect the motor 14 and/or other components of the housing 6 from any fluids or other materials that may be transported through the outer tube 4, or through the housing aperture 18. In some embodiments, a connector or seal may be provided about the housing aperture 18 to permit coupling of the housing 6 to a trocar, an introducer, a cannula or other tubular member into which the tissue removal assembly 8 and the outer tube 4 are inserted. In some embodiments, the tissue removal device may be used with an introducer or cannula having an outer diameter of about 0.01 cm to about 1.5 cm or more, sometimes about 0.1 cm to about 1 cm, and other times about 2 mm to about 6 mm.

As shown in FIGS. 5A and 5B, the tissue removal device 2 may further comprise a conduit 24 which may be used to connect the tissue removal device 2 and an aspiration or suction source. An aspiration or suction source may be used, for example, to transport fluid or material through a lumen or conduit of the outer tube 4 or through a tubular member in which the outer tube 4 is inserted. In one particular embodiment, the conduit 24 comprises a port 20 which communicates with the fluid seal 16 via a length of tubing 22. The fluid seal 16 is configured to permit flow of fluid or material between the outer tube 4 and the tubing 22, while permitting movement of the outer tube 4 or a drive member therein coupled to the motor 14. In other embodiments, the conduit 24 may further comprise additional components, including but not limited to a fluid or material trap, which may be located within or attached to the housing 6, or attached to the port 20 or the tubing 22, or located anywhere else along the pathway from the tissue removal assembly 8 to the suction source. In some embodiments, a separate port may be provided for infusing or injecting substances into target site using the tissue removal device 2. In other embodiments, the conduit 24 may be used for both withdrawal and infusion of materials and/or fluids, or for infusion only. Depending upon the configuration of the tissue removal device, withdrawal and/or infusion may occur at the distal end of the outer tube 4, and/or through one or more openings of the tissue removal assembly 8. In other embodiments, a port may be used to insert a coagulation catheter, an ablation catheter or other energy delivery device to the target site.

In some embodiments, the outer tube comprises an outer tubular member with at least one lumen, and an elongate drive member configured to mechanically couple the motor to the tissue removal assembly. In other embodiments, the outer tube may contain additional members, for example, to adjust or control the configuration of the tissue removal assembly. In some embodiments, the outer tube 4 may comprise one or more lumens containing control wires, which may be used to manipulate the deflections of the distal end of the outer tube. The outer tube and optional drive members may be rigid or flexible. The outer tube may be pre-shaped with a linear or a non-linear configuration. In some embodiments, the outer tube and the components is configured to be user-deformable, which may facilitate access to particular target sites, or may be user-steerable using a steering mechanism comprising one or more pull wires or tension elements. In some embodiments, a stiffening wire or element may be inserted into the outer tube to provide additional stiffness to the tissue removal device. The length of the outer tube between the tissue removal element and the motor or housing may vary from about 0 cm to about 30 cm or more in some embodiments, sometimes about 4 cm to about 20 cm, and other times about 10 cm to about 14 cm.

In other embodiments, the tissue removal device may comprise a tissue removal assembly that may be detachably attachable to the shaft of a motor or coupled to a motor. In still other embodiments, the tissue removal device may comprise a tissue removal assembly coupled to a shaft, wherein the shaft may be detachably attachable to a motor or a shaft coupled to a motor.

In some embodiments, the housing 6 is configured with a size and/or shape that permits handheld use of the tissue removal device 2. In other embodiments, the tissue removal device 2 may comprise a grip or structure located about the outer tube 4 to facilitate handling by the user, while the proximal end of the outer tube 4 is attached to a benchtop or cart-based machine, for example, or a mounted or fixed machine. In these embodiments, the grip may or may not contain any other components of the tissue removal device, such as a motor, while the machinery at the proximal end of the outer tube 4 may contain one or more other components, such as a suction system or various radiofrequency ablation components, for example. In some embodiments, the housing 6 may have a length of about 1 cm to about 12 cm or more, sometimes about 2 cm to about 8 cm, and other times about 3 cm to about 5 cm. The average diameter of the housing (or other transverse dimension to the longitudinal axis of the housing) may be about 1 cm to about 6 cm or more, sometimes about 2 cm to about 3 cm, and other times about 1.5 cm to about 2.5 cm. The housing 6 may further comprise one or more ridges, recesses or sections of textured or frictional surfaces, including but not limited to styrenic block copolymers or other polymer surfaces.

Figure 17:
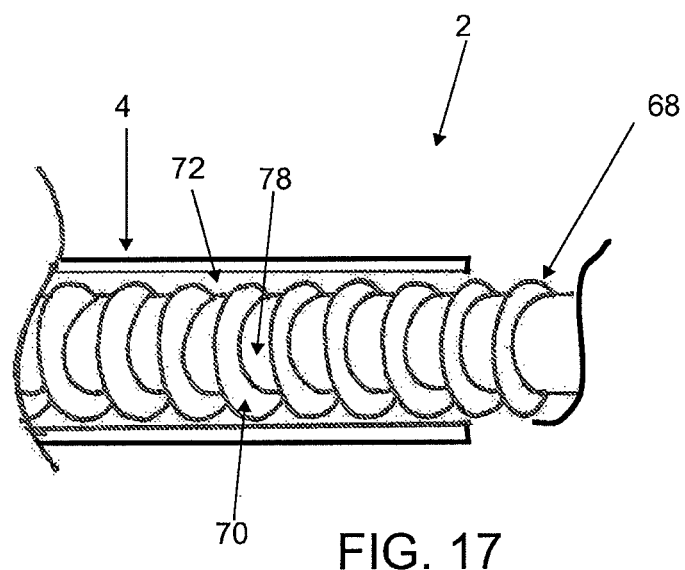
FIG. 17 is a detailed view of one embodiment of an optional tissue transport mechanism.

As illustrated in FIG. 17, a tissue removal device may optionally comprise a tissue transport assembly 68, which may be used to facilitate transport or removal of tissue within or along the outer tube 4. In the particular embodiment depicted, the tissue transport assembly 68 comprises a helical member 70 mounted on a drive member 78 that may be rotated. Actuation of the drive member 78 may mechanically facilitate proximal movement of tissue or other materials within the channel or the lumen 72 of the outer tube 4 by rotating the helical member 70. The actuated drive member 78 will also rotate the distal burr element or other tissue removal assembly 8. In some embodiments, use of the tissue transport assembly 68 may be performed at lower rotational speeds when tissue debulking is not concomitantly performed. When rotated in the opposite direction, the helical member 70 may be used expel or distally transport tissue, fluid or other materials or agents from the outer tube 4 or supplied to an infusion port of the housing 6.

In some embodiments, the helical member 70 may have a longitudinal dimension of about 2 mm to about 10 cm or more, sometimes about 3 mm to about 6 cm, and other times about 4 mm to about 1 cm. In other embodiments, the longitudinal dimension of the helical member 70 may be characterized as a percentage of the longitudinal dimension of the outer tube 4, and may range from about 5% to about 100% of the longitudinal dimension of outer tube 4, sometimes about 10% to about 50%, and other times about 15% to about 25%, and still other times is about 5% to about 15%. Although the helical member 70 depicted in FIG. 17 rotates at the same rate as the tissue removal assembly, due to their mounting or coupling onto common structure, drive member 78, in other embodiments, the helical member may also be configured to rotate separately from drive member. For example, a helical member may comprise a helical coil located along at least a proximal portion of the lumen of the outer tube but is not mounted on the drive member. In this particular example, the helical member may rotate independently of the drive member. In still other embodiments, the helical member 70 may be mounted on the surface of the lumen 72 and can be used to transport tissue or substances along the lumen 72 by rotation of the outer tube 4, independent of the drive member 78 or a tissue removal assembly.

Although the helical member 70 is depicted as a continuous structure, in some embodiments, the helical member 70 may be interrupted at one or more locations. Also, the degree or angle of tightness of the helical member 70 may vary, from about 0.5 turns/mm to about 2 turns/mm, sometimes about 0.75 turns/mm to about 1.5 turns/mm, and other times about 1 turn/mm to about 1.3 turns/mm. The cross-sectional shape of the helical member 70 may be generally rounded as depicted in FIG. 17, but in other embodiments, may have one or more edges. The general cross-sectional shape of the helical member 70 may be circular, elliptical, triangular, trapezoidal, squared, rectangular or any other shape. The turn tightness and cross-sectional shape or area of the helical member 70 may be uniform or may vary along its length. In some embodiments, multiple the helical members 70 may be provided in parallel or serially within the outer tube 4.

In some embodiments, the drive member 78 may be configured to extend distally and retract from the outer tube 4 by a length of about 0.01 cm to about 2 cm or more, sometimes about 0.02 cm to about 1.5 cm and other times about 0.05 to about 1 cm. In some embodiments, the helical member 70 is located proximal to the tissue removal assembly at a distance of about 0.01 cm to about 2 cm or more, sometimes about 0.02 cm to about 1.5 cm and other times about 0.05 cm to about 1 cm. In some embodiments, when drive member 78 is maximally extended from outer tube 4, helical member 70 may protrude from outer tube 4 by a longitudinal dimension of about 0.01 cm to about 2 cm or more, sometimes about 0.1 cm to about 1 cm, and other times about 0.25 cm to about 0.5 cm. In some embodiments, the degree of extension of the drive member 78 and/or the helical member 70 may affect the degree of tissue transport by the tissue transport assembly.

Figure 18A:
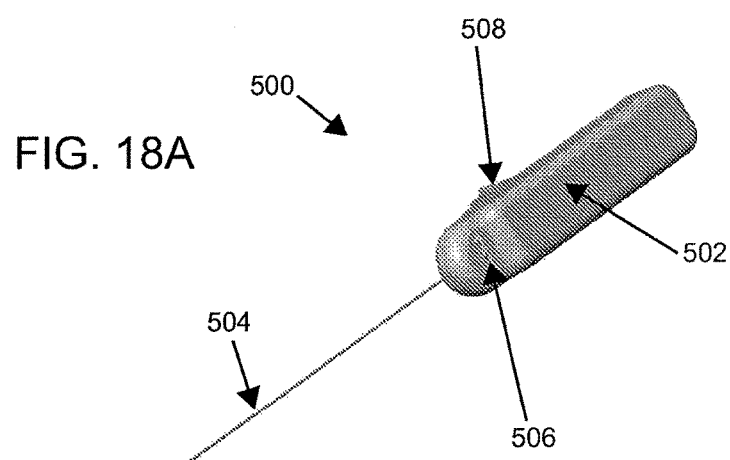
FIGS. 18A and 18B are perspective and side elevational views of another embodiment of a tissue removal device.
Figure 18B:
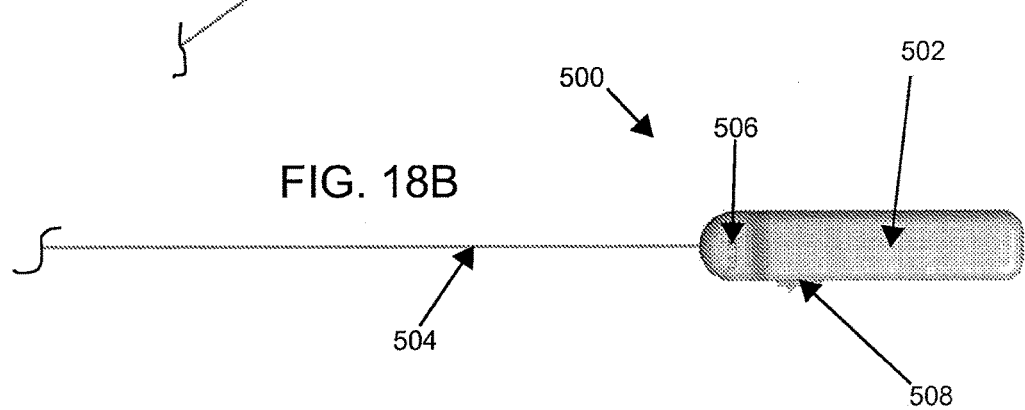

Referring to FIGS. 18A and 18B, in another embodiment, a tissue removal device 500 comprises a housing 502 and an outer shaft 504. The housing 502 may include an adjustment mechanism with a thumbwheel 506 configured to adjust the retraction and extension of extendable tissue removal assembly (not shown). The thumbwheel 506 may provide a continuous range of change to extendable tissue removal assembly, but in other embodiments, the turning of thumbwheel 506 may be configured with clicks or detents that provide one or more preset positions. As mentioned previously, any of a variety of other control mechanisms and interfaces may be used. The adjustment mechanism may comprise one or more blocking elements or other adjustment limiting configurations to resist or prevent overextension of extendable tissue removal assembly. For example, limit structures may be provided in housing 502 to resist overextension of extendable tissue removal assembly (not shown). In this particular embodiment, tissue removal device 500 is configured to rotate the tissue removal assembly at a fixed rotational speed, controllable by a rocker-type power switch 508. As mentioned previously, however, any of a variety of power and/or speed control mechanisms may be used.

Figure 18C:
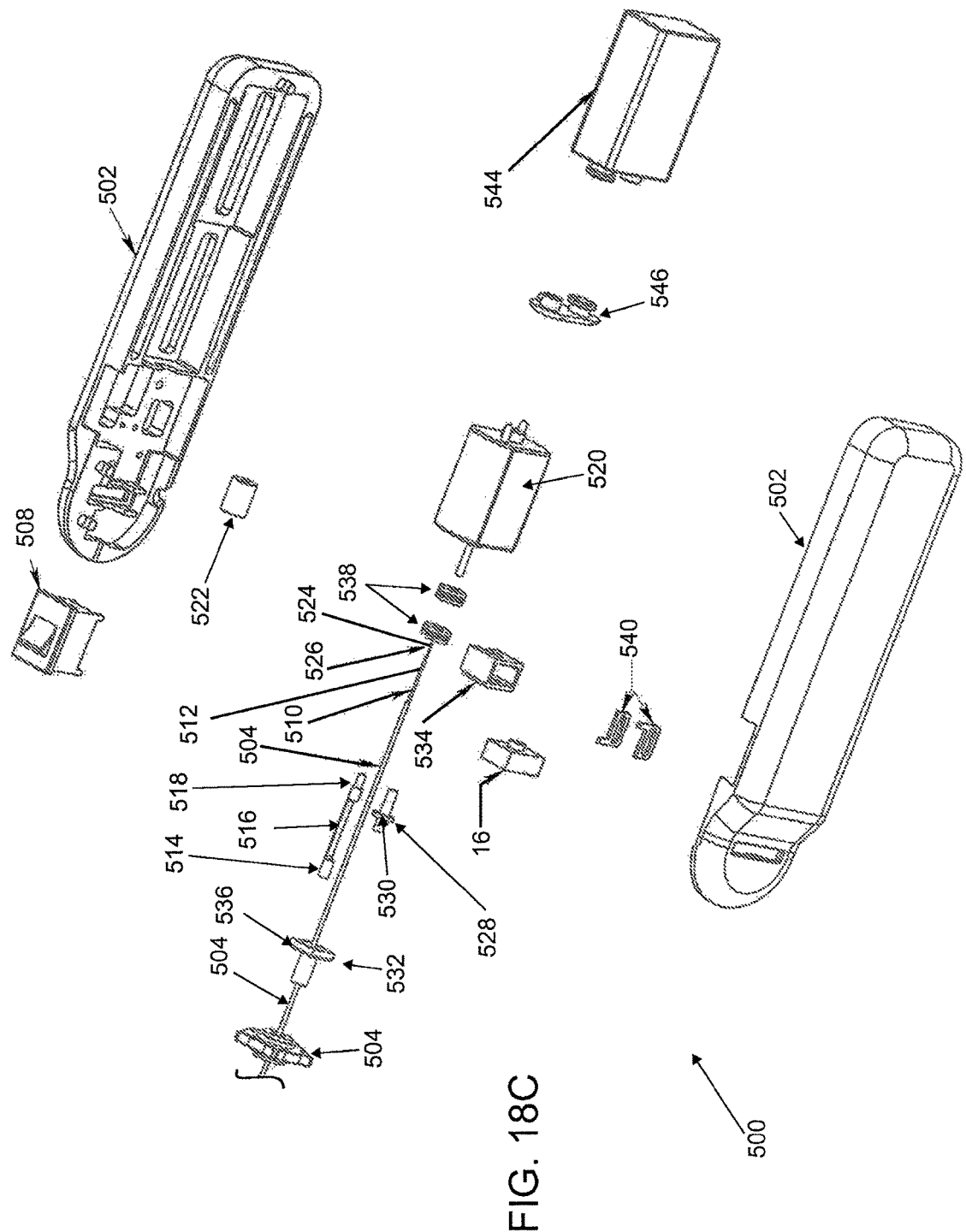
FIG. 18C is a component view of the tissue removal device in FIGS. 18A and 18B.
Figure 18D:
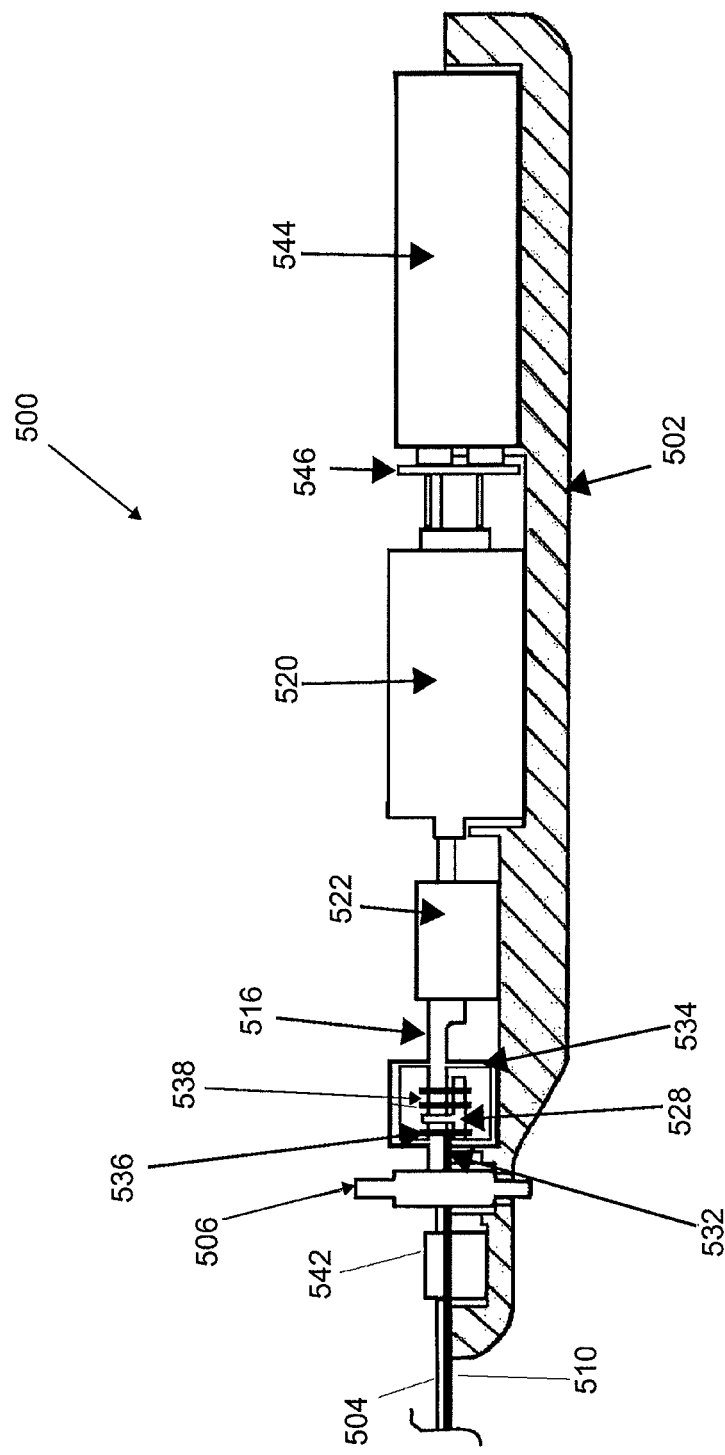
FIG. 18D is a cross-sectional view of the tissue removal device in 18A and 18B with a portion of the housing removed.

Referring to FIGS. 18C and 18D, FIG. 18C is a component view of the internal components within housing 502, while FIG. 18D is a schematic cross-sectional view of the internal components with a portion of housing 502 removed. As shown in FIG. 18C, a drive member 510 rotatably resides within the outer shaft 504 of the tissue removal device 500. The distal end (not shown) of the drive member 510 is coupled to the tissue removal assembly (not shown), while the proximal end 512 of the drive member 510 is coupled to the distal end 514 of a driveshaft 516. The proximal end 518 of the driveshaft 516 may be coupled to a motor 520, either directly or through a coupler 522. The coupler 522 may be configured to permit some axial movement of driveshaft 526. The proximal end 524 of an adjustment member 526 protrudes from the proximal end 512 of drive member 510 and is attached to a drive key 528.

The drive key 528 may comprise a flange 530 that is slidably located between the proximal and distal ends 518 and 514 of the driveshaft 516. The thumbwheel 506 may be movably coupled to a thrust member 532 so that the rotation of the thumbwheel 506 results in the axial movement of thrust member 532. In some embodiments, the thrust member 532 may be configured with helical threads that are complementary to a threaded lumen of the thumbwheel 506. In other embodiments, however, the thrust member may comprise a slide member, a pivot member or other coupling structure. The thrust member 532 may be configured to axially slide the drive key 528 through a retaining structure 534 which movably couples the thrust member 532 to the drive key 528. The retaining structure 534 permits the rotation of the driveshaft 516 by the motor 520 while also coupling the axial movements of the thrust member 532 to the drive key 528, thereby permitting adjustment of the tissue removal assembly located at the distal end of the shaft 504 while maintaining the ability of the drive member 510 to rotate. The thrust member 532 may comprise a flange 536 to facilitate retention of the thrust member 532 within the retaining structure 534. The flange 536 may comprise one or more bearings to facilitate rotational movement of the drive key 528 against the non-rotating flange 536. The retaining structure 534 may also contain one or more retaining bearings 538 to facilitate the rotation of the driveshaft 516 against the drive key 528 while transmitting any axial forces to the drive key 528. The retaining structure 534 is optionally provided with one or more limiters 540, which may be used to restrict overextension or retraction of the tissue removal assembly. A seal 542 may be provided around the outer shaft 504 to protect the contents of the housing 502.

Figure 60A:
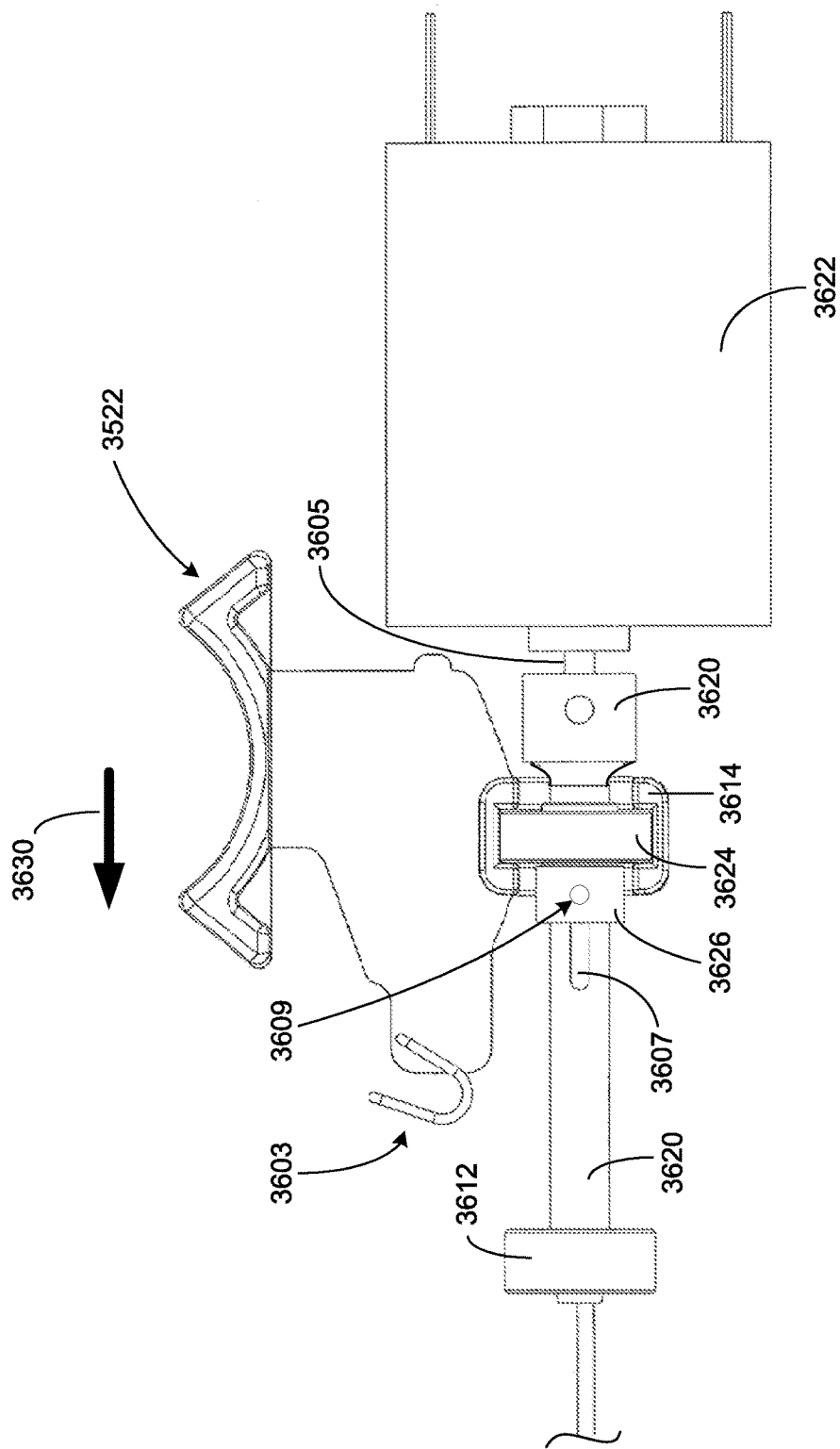

Another variation of such a mechanism is depicted in FIGS. 60A to 60D and described below. FIG. 60A illustrates a rotatable shaft 3620 that is coupled to a motor 3622 that is configured to rotate the tissue removal assembly at rotational speeds previously described. The motor 3622 may be powered by a battery, e.g., a 9 volt battery, or may be coupled to an external power source. The operating range of the motor 3622 may be between 1.5 to 4.5 volts, nominally with a 3 volt constant.

The tissue removal device may be configured to provide a rotatable shaft with an axially extendable and retractable mechanism to alter the configuration of the elongate member 3511 located distally. For example, a rotatable shaft 3620 may be rotatably maintained in the handle with a first ball bearing 3624 and a second ball bearing 3612. The ball bearings may be configured to facilitate rotation of the rotatable shaft 3620. The second ball bearing 3612 is retained within a retaining structure that is affixed to the handle housing, while the first ball bearing 3624 may be movably retained in a retaining structure 3614 that is affixed to the slide actuator 3522. A coupler 3626 may be provided along the rotatable shaft 3620, where the coupler 3626 is configured to slide along the length of the rotatable shaft 3620 and interfaces with the movable first ball bearing 3624. The displacement of the coupler 3626 along the shaft 3620 by the first ball bearing 3624 provides movement of structures within the rotatable shaft while also permitting rotation of the coupler 3626 and the shaft 3620 within the first ball bearing 3624. Together, this configuration permits axial translation of the elongate member within the rotatable shaft 3620 during rotation. In some variations, the coupler 3626 may be attached to the proximal section of an elongate member of the tissue removal assembly, whereby manipulation of the slide actuator 3522 results in reconfiguration of the elongate member between a retracted state and an extended state while rotating.

Figure 60B:
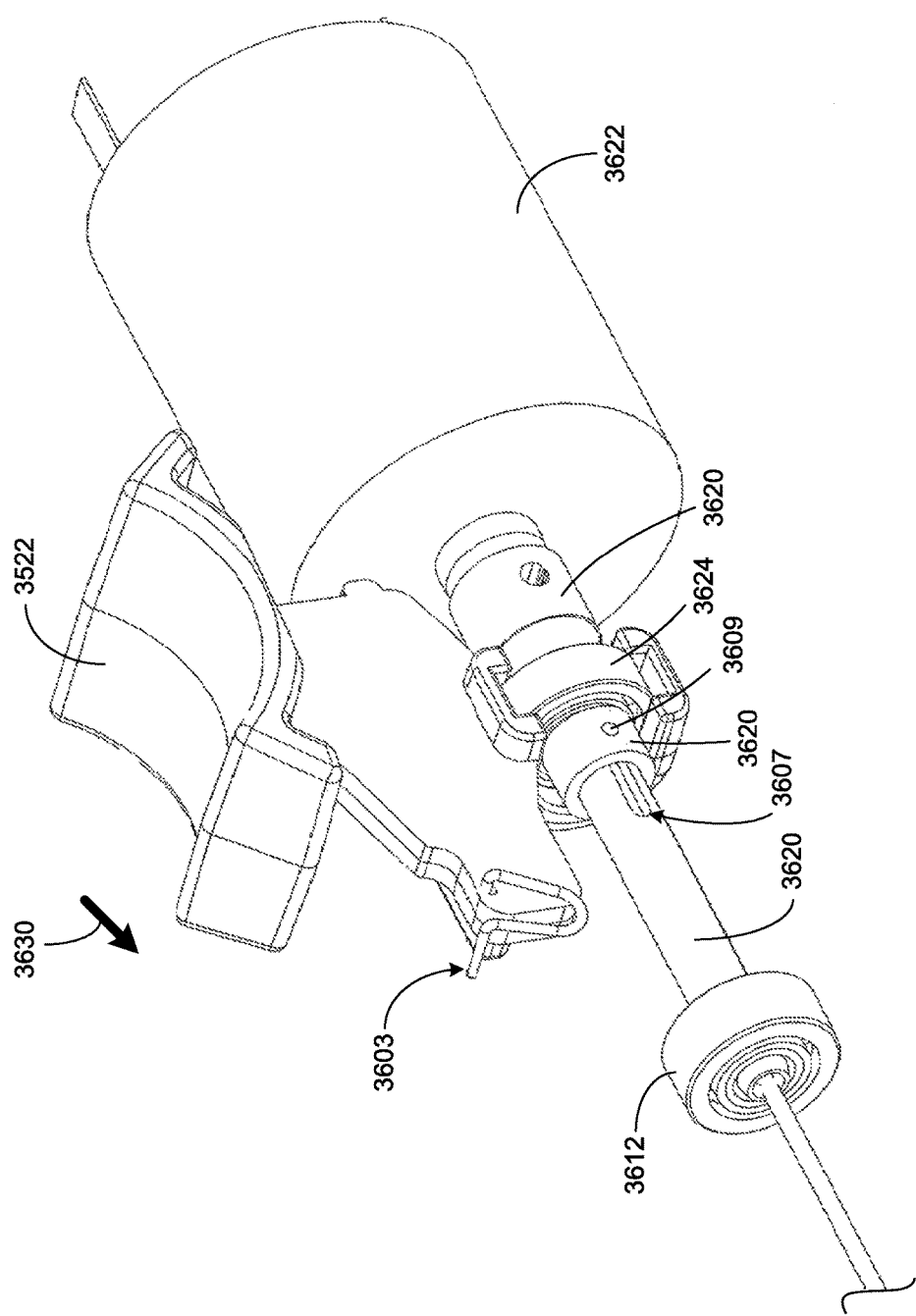

FIGS. 60A-60D provide additional details of the mechanism by which an elongate member that is housed within the rotatable shaft 3620 may be transitioned between an extended and refracted configuration during rotation. FIGS. 60A and 60B depict a side view and a side perspective view of the mechanism when the elongate member is in a retracted configuration. The rotatable shaft 3620 extends from the second ball bearing 3612 through the first ball bearing 3624 and is connected proximally to the motor 3622 via a motor connector 3605. The rotatable shaft 3620 may be soldered, welded, brazed, heat bonded, chemically bonded, snap fit, mechanically attached (e.g. set screw, press fit, swaged, crimped, etc.) or otherwise securely and fixedly attached to the motor connector 3605. As described previously, the coupler 3626 may be slidable along the rotatable shaft 3620, and may couple an elongate member within the shaft (not shown) to the shaft with a pin 3609 such that the elongate member may rotate as the rotatable shaft is rotated by the motor. For example, an elongate member within the shaft may be coupled to the pin 3609 via a metal lug that is slidably disposed within the rotatable shaft 3620. The rotatable shaft 3620 may comprise a longitudinal slot 3607 that extends along a length of the shaft. The length of the slot 3607 provides a range of movement for the coupler 3626, and may be from about 0.25 inch to about 2 inches, for example, 0.6 inch. Sliding the slider 3522 in the direction of arrow 3630 pushes the first ball bearing 3624 retained by the retaining structure 3614 in the same direction. The first ball bearing 3624 then pushes against the slidable coupler 3626, which is also urged in the direction of the arrow 3630 along the slot 3607. Displacement of the slidable coupler 3626 distally (as illustrated by arrow 3630), results in the distal displacement of the elongate member within the rotatable shaft 3620. FIGS. 60C and 60D depicts the coupler 3626 in a distal most position of the slot 3607 after maximum distal actuation of the slider 3522. The slider 3522 may also be moved proximally (as illustrated by arrow 3632) to transition the elongate member back to the retracted configuration. An optional spring member 3603 that may be attached to the handle housing may bias the slider 3522 to a distal or proximal location, and/or may help the slider 3522 snap into position as the slider is urged according to the arrow 3630.

In the various examples described herein, the outer tube and the driveshaft of the tissue removal device may comprise a rigid structure and material, but may also optionally comprise at least one flexible region which may bend while still permitting rotation of the driveshaft. Examples of flexible driveshafts that may be used are disclosed in U.S. Pat. Nos. 5,669,926 and 6,053,907, which are hereby incorporated by reference in their entirety. In some examples, the flexible region(s) may comprise a substantial portion or all of the length of the driveshaft and outer tube. A tissue removal device with a flexible region may facilitate access to certain regions of the body, such as the central spinal canal through an intervertebral foramen. In some examples, the flexible tissue removal device may comprise a steering assembly that uses one or more steering wires that are attached distal to the flexible region and manipulated by a steering member in the proximal housing. Other steering mechanisms used with catheters and other elongate instruments may also be used. In other examples, an active steering mechanism is not provided on the flexible tissue removal device, but the flexible tissue removal device may be steered by an endoscopic instrument into which the tissue removal device has been inserted. Some examples of steerable endoscopic instruments are disclosed in Application No. 61/045,919, which is hereby incorporated by reference in its entirety.

Figure 19C:
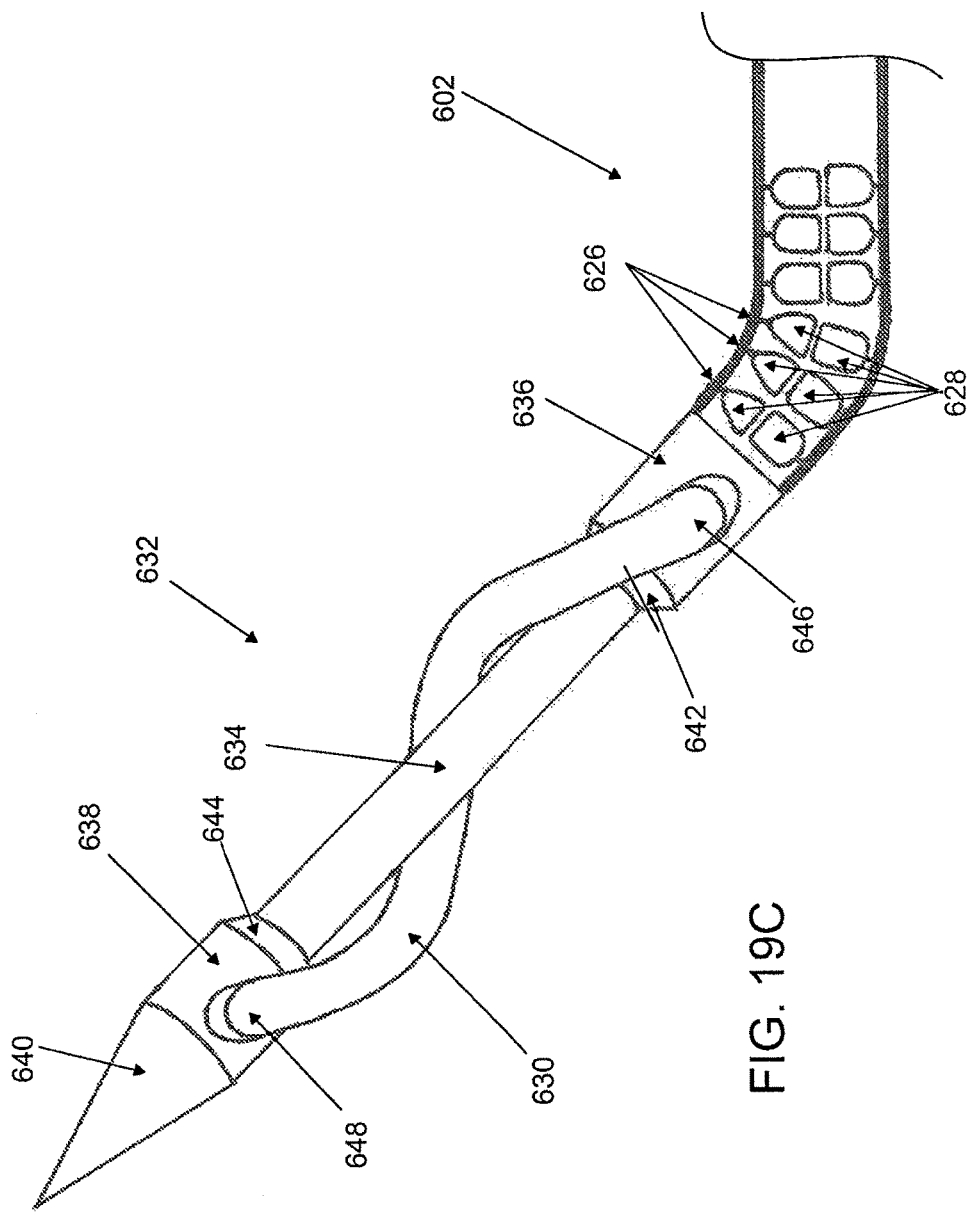
FIG. 19C is a detailed view of the distal end of the flexible tissue removal device of FIG. 19A in a bent configuration.

FIGS. 19A to 19C depict one embodiment of a tissue removal device 600 with a flexible region 602 and a steering assembly 604 located in the housing 606 of the tissue removal device 600. In addition, the housing 606 includes a power switch 608 which actuates the motor 610 that rotates the driveshaft (not shown) located in the outer tube 612, and an irrigation tube 614 which may be used infuse fluid or provide suction about the distal end of the device 600. As shown in FIG. 19B, the steering assembly 604 comprises a pivoting lever 616 with two arms 618 and 620 protruding from the housing 606. In other embodiments, the steering assembly 604 may comprise a single arm lever, a slider, knob or other type of actuator. The steering assembly 604 may optionally comprise one or more springs or bias structures, which may facilitate springback of the lever 616 once released. The steering assembly 604 may also optionally comprise a releasable locking mechanism to maintain the steering assembly in a particular configuration. The locking mechanism may be a frictional interfit or an interlocking mechanism, for example.

Coupled to the lever 616 are two steering elements or wires 622 and 624, which are slidably movable within the outer tube 614 and are distally coupled to a distal site of the flexible region 602. The steering wires 622 and 624 may be separate wires, or two segments of the same wire looped through the lever 616. When a steering wire 622 or 624 is tensioned by actuating one of the lever arms 618 and 620, the flexible region 602 will curve or bend. The flexible region may comprise any of a variety of flexible materials and/or flexible structures, including any of a variety of polymeric or metallic structures. In the depicted embodiment, the flexible region 602 comprise a plurality of optional slots 626, which may augment the bending characteristics, but in other embodiments, an accordion-like configuration or other type of bending configuration may be provided. The ends 628 of the slots 626 depicted in FIG. 19C have optional enlarged arcuate configurations, which may redistribute at least some of the bending forces that may act of the flexible region 602 and may resist tearing or reduce any resulting damage to the flexible region. The length of the flexible region may be in the range of about 1 mm to about 200 mm or more, sometimes about 5 mm to about 50 mm, and other times about 8 mm to about 20 mm. The width of the ends 628 of the slots 626, as measured in the unbent configuration along the longitudinal axis of the tissue removal device, may be in the range of about 0.5 mm to about 4 mm or more, sometimes about 1 mm to about 3 mm, and other times about 1 mm to about 2 mm. In still other embodiments, the flexible region may lack a particular configuration but comprises a flexible material that has a lower durometer than the other portions of the outer tube. The maximum degree of bending may vary from about 5 degrees up to about 10 degrees or more, sometimes about 15 degrees up to 25 degrees or more, and other times about 45 degrees to about 75 degrees or more, and even about 90 degrees to about 105 degrees or more in certain embodiments. In embodiments of the tissue removal device having bi-direction steering from its neutral axis, the maximum degree of bending in each direction may be the same or may be different.

As illustrated in FIG. 19C, a flexible elongate member 630 is coupled to a rotatable shaft assembly 632 comprising a reduced diameter core 634 located between a proximal and distal sections 636 and 638. A piercing element 640 may be attached to the distal end of the rotatable shaft assembly 632. The proximal and distal sections 636 and 638 each comprise optional taper regions 642 and 644. In some embodiments, the taper regions 642 and 644 may reduce or eliminate the potential snagging of the elongate member 630 during retraction, or snagging of the rotatable shaft assembly 632 during its insertion or withdrawal with respect to the vertebral disc, the epidural space, or the cannula or endoscopic device in which it was placed. In the refracted configuration illustrated in FIG. 19C, the elongate member 630 has a helical orientation about the reduced diameter core 634, but may or may not be contacting the core 634.

As depicted in FIG. 19C, the exposed proximal and distal ends 646 and 648 of the flexible elongate member 630 may be coupled to the rotatable shaft assembly 632 through either openings or attachment sites located on the circumferential surfaces of the proximal and distal ends 646 and 648. Other sites where one or both ends of the flexible elongate member 630 may be coupled include but are not limited to the taper regions 642 and 644, if any, or any other transversely surface have at least some degree of transverse orientation with respect to the longitudinal axis of the rotatable shaft assembly 632. Still other coupling sites may include the reduce diameter core 634 and the piercing element 640.

In another example, depicted in FIGS. 21A to 21D and FIG. 22, the tissue removal system 700 may comprise an extendable spiral cable 702 with a blunt distal tip 704. In some instances, a blunt distal tip 704 may be used when a passageway or channel has been previously formed, or when blunt dissection is sufficient. For example, during a discectomy or a vertebroplasty procedure, a cannula 706 containing a removable obturator with sharp distal end 708, as shown in FIG. 23, may be used to form a passageway or channel through the tissue surrounding the spine and/or through the surface of a vertebra. The obturator may be removed from the cannula 706 to insert the tissue removal system 700. In other examples, a trocar with a sharp distal end may be used to form a passageway and then removed to permit insertion of the tissue removal system 700. Alternatively, a trephine or bone burr, which may be either motorized or manually activated, may be used with the cannula 706, in addition to or in lieu of the obturator. The cannula 706 may comprise an optional proximal connector 709, such as Luer lock, to releasably couple the obturator and/or the tissue removal system 700. Additional variations of cannulas and stylets that may be used to create a passageway through the tissue to the spine and/or through the surface of a vertebra will be described later.

Figure 21A:
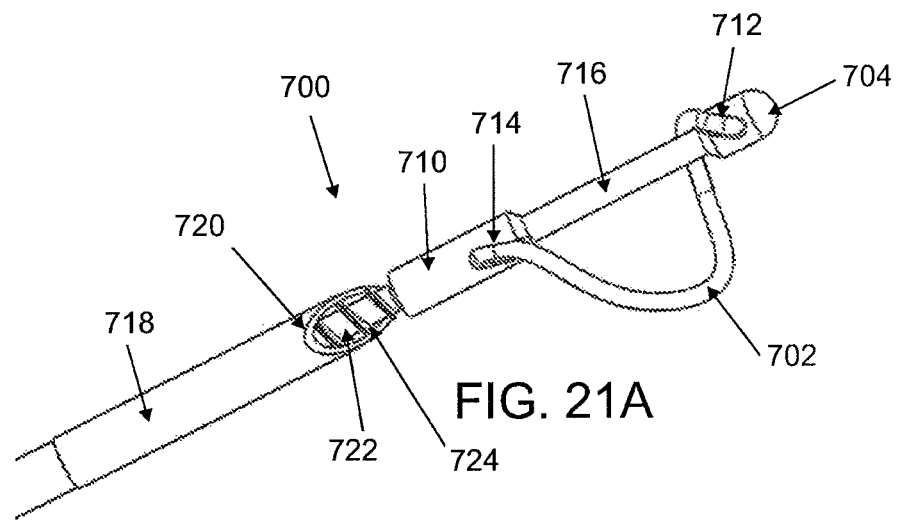
FIG. 21A depicts the distal end of another embodiment of a tissue removal device with a blunt tip and in an extended configuration.
Figure 21B:
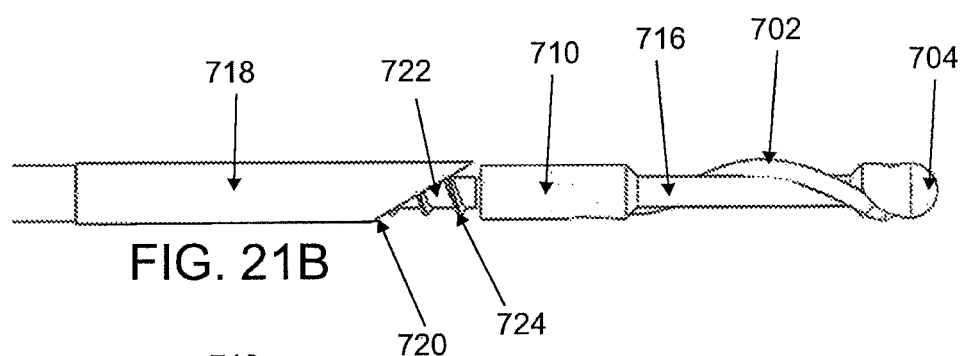
FIGS. 21B to 21D depict various views of the tissue removal device in FIG. 21A in the retracted configuration.
Figure 21C:
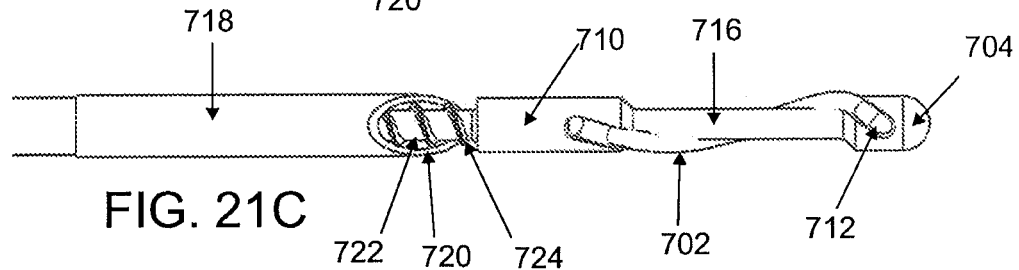
Figure 21D:
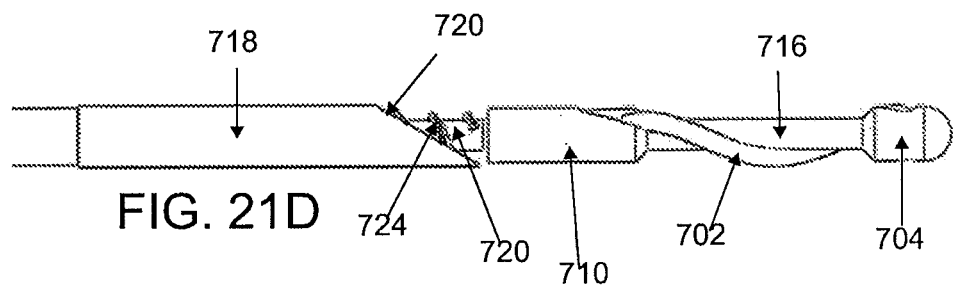

Referring to FIG. 21A, which depicts the spiral cable 702 in an extended position, and to FIGS. 21B to 21D, which depicts the spiral cable 702 in a retracted position, the cable 702 is attached distally to the blunt distal tip 704 and proximally to a base 710. The cable 702 may be partially recessed in channels 712 and 714 of the tip 704 and base 710. Between the tip 704 and base 710 is a cable shaft 716 with a cross-sectional size that is smaller than the tip 704 and/or base 710. In other embodiments, the cable shaft may have a cross-sectional size that is similar to or greater then the tip 704 or base 710. The cable shaft may also comprise an optional groove or recess to at least partially retain the cable 704 when in a retracted position.

Figure 49A:
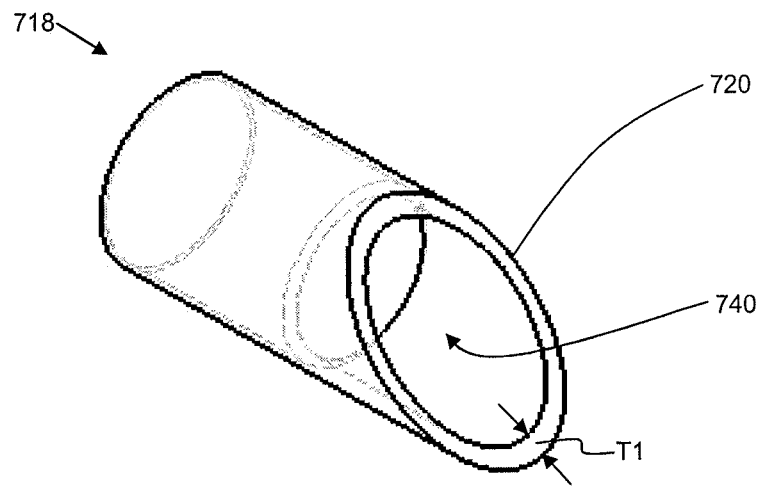
FIGS. 49A to 49B depict one variation of an outer tubular shaft with a beveled cutting edge.
Figure 49B:
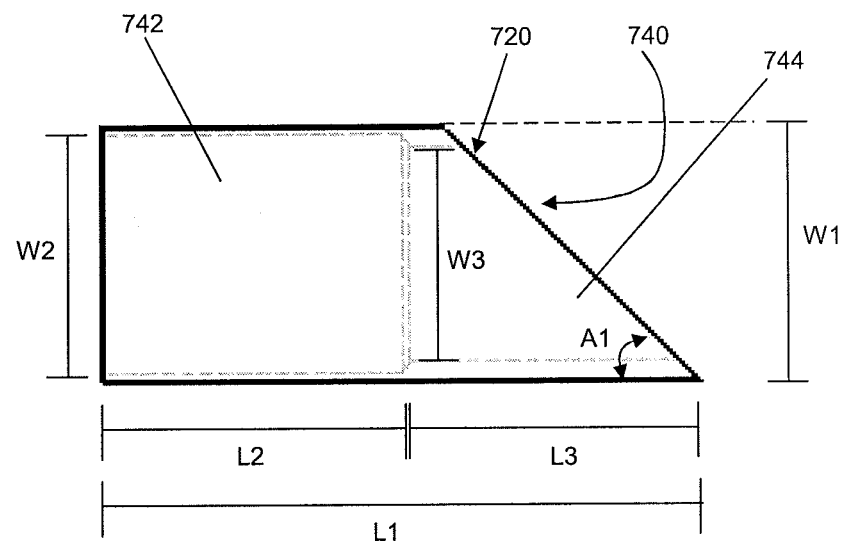
Figure 50A:
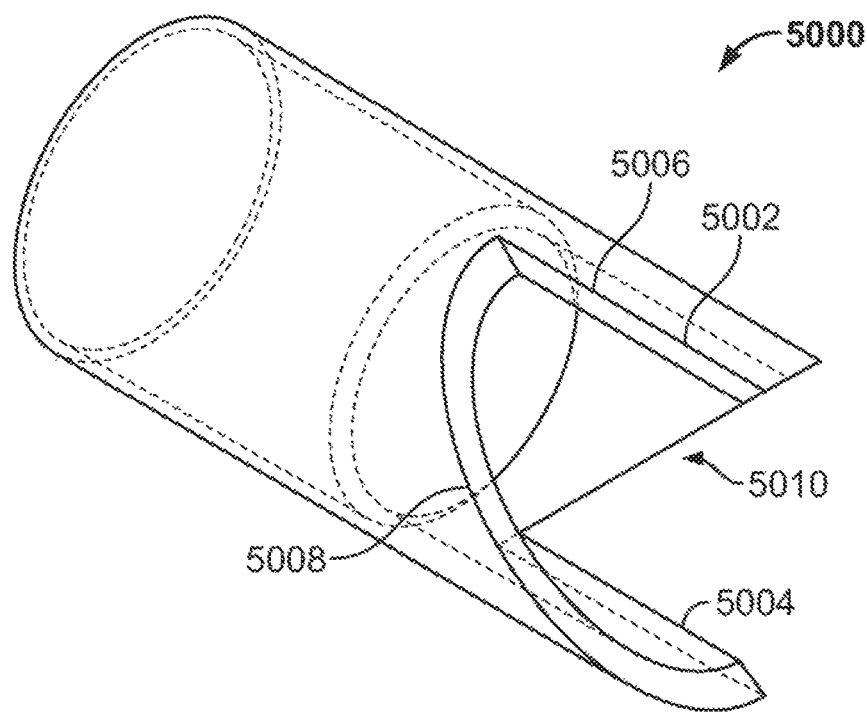
FIGS. 50A to 50B depict another variation of an outer tubular shaft with multiple cutting edges, comprising straight and curved edges.
Figure 50B:
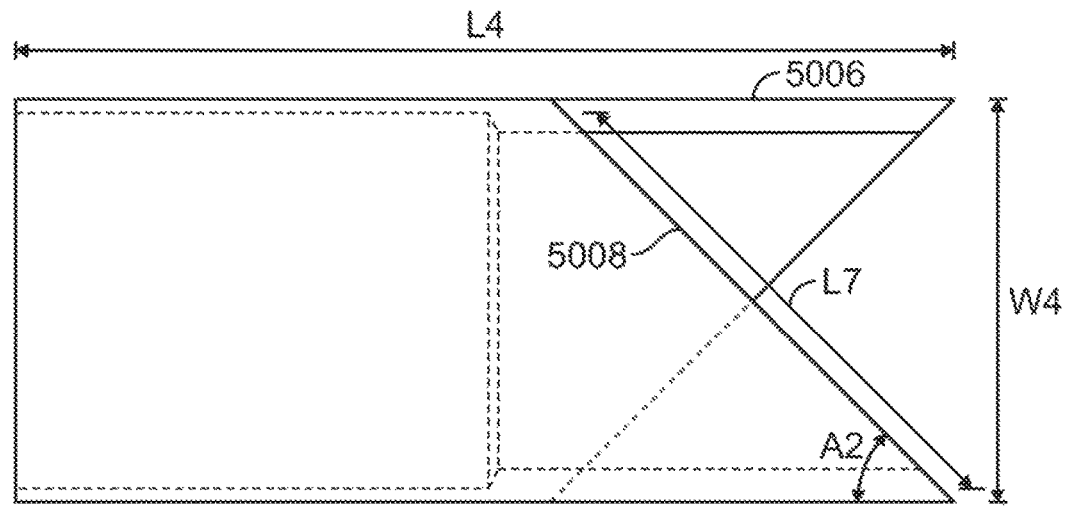

FIGS. 21A to 21D further depict an optional feature of the tissue removal system 700 comprising an outer tubular shaft 718 with a cutting edge 720. In this particular example, the cutting edge 720 is a beveled edge, which may or may not be at least partially sharpened. In other examples, the cutting edge may be sharpened but not beveled. As further depicted in FIGS. 21A to 21D, the inner shaft 722 located in the outer tubular shaft 718 may comprise at least one optional thread structure 724 which is configured to draw fluids and/or other materials into the outer tubular shaft 718 for removal from the target site. A beveled or sharpened edge may further shear or break-up materials pulled into the outer tubular shaft 718 by the thread structure 724. In some examples, the rotational sense of the thread structure 724 may be the same as the spiral cable 702, but in other examples, the thread structure 724 and the spiral cable 702 may be opposite rotational senses. A perspective and side view of the outer tubular shaft 718 is also depicted in FIGS. 49A and 49B. The cutting edge 720 may be beveled to have an angle A1 and a thickness T1. The angle A1 may be in a range from about 30° to about 90°, for example, about 35° or 50°. The thickness T1 may be in a range from about 0.002 inch to about 0.025 inch; for example, about 0.017 inch. The diameter or widest portion of the outer tubular shaft 718 may have a width W1, where W1 may be from about 0.085 inch to about 0.15 inch, for example, 0.102 inch, and the longest portion of the outer shaft may have a length L1, where L1 may be from about 0.2 inch to about 0.3 inch, for example, 0.236 inch. The outer tubular shaft 718 may have a lumen 740 therethrough, where the size and shape of the lumen cross-section may vary along the length of the outer tubular shaft. For example, as illustrated in FIG. 49B, a proximal portion 742 of the outer tubular shaft may have a rectangular cross-section, while a distal portion 744 may have a trapezoidal cross-section. The proximal portion 742 may have a width W2 and a length L2. The width W2 may less than W1, and may be from about 0.084 inch to about 0.14 inch, for example, 0.096 inch, and the length L2 may be from about 0.09 inch to about 0.12 inch, for example, 0.118 inch. The distal portion 744 may have a width W3 and a length L3. The width W3 may be less than W1, and in the example depicted in FIG. 49B, the width W3 may be less than W2. For example, the width W3 may be from about 0.083 inch to about 0.139 inch, e.g., 0.08S inch. The length L3 may be from about 0.08 inch to about 0.21 inch, for example, 0.118 inch. The outer tubular shaft may be made of stainless steel (e.g., 440F SE stainless steel, 17-4), and may be heat treated to RC 33-60, with a bright finish that may be passivated per ASTM-A967 standards. The outer tubular shaft may also be made of a variety of materials, such as other metallic materials (e.g., nickel titanium alloys, cobalt chromium, tungsten, etc.) and/or polymeric materials (e.g., PEEK, polyaramides, polyethylene, etc.), as appropriate.

Some variations of an outer tubular shaft may have one or more sharpened edges that may be used with a tissue removal system. The additional sharpened edges may help to further scrape or break up tissue. One example of an outer tubular shaft SOOO with additional sharpened edges is depicted in FIGS. SOA and SOB. The outer tubular shaft SOOO may comprise a first cutting edge S002 along the surface of the shaft, and a second cutting edge S004 that is opposite to the first cutting edge. The first cutting edge S002 may comprise a straight edge S006 that may be parallel to the longitudinal axis of the outer tubular shaft, and a curved edge S008 that may be at least partially transverse to the longitudinal axis of the outer tubular shaft. The second cutting edge S004 may have the same arrangement of edges, or may have different arrangements of edges. The contour of the curved edge may partially circumscribe the curved surface of the outer tubular shaft, and may also extend along the longitudinal axis of the shaft. FIG. SOB depicts a side view of the outer tubular shaft SOOO. The angle A2 between the curved edge S008 and the surface of the outer tubular shaft SOOO may be about 30° to about 90°, e.g., about 4S°. The length L7 of the projection of the curved edge S008 in the side view of FIG. SOB may be from about 0.1 inch to about 0.2 inch, e.g., 0.144 inch. The length L4 of the outer tubular shaft SOOO may be from about 0.2 inch to about 0.3 inch, e.g., 0.236 inch. The width W4 of the outer tubular shaft may be from about 0.08S inch to about O.1S inch, for example, 0.102 inch. The size and shape of a lumen S010 may vary, as described above.

Figure 21E:
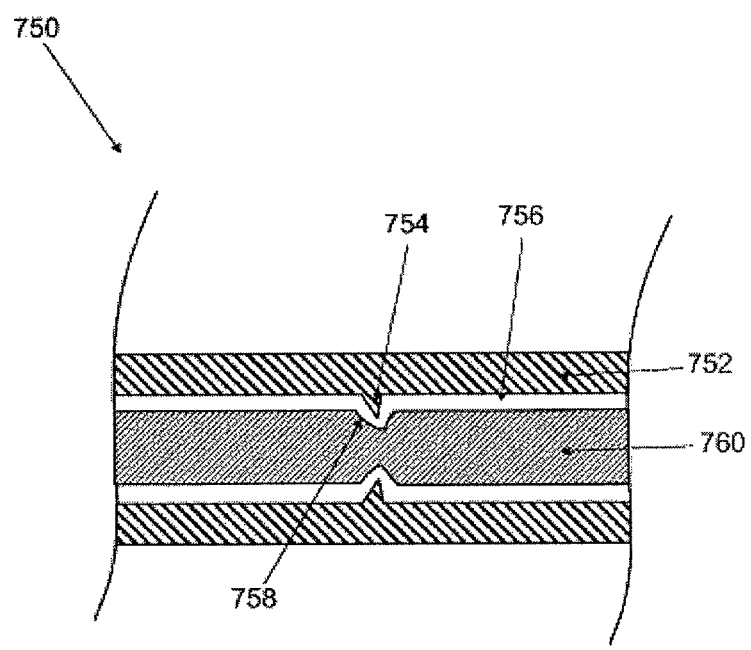
FIG. 21E is a schematic longitudinal cross-sectional view of another tissue removal device with an internal cutting mechanism.

FIG. 21E schematically depicts another example of a cutting mechanism where instead of a cutting edge 720 located at the distal opening of the outer tubular shaft 718 as depicted in FIGS. 21A to 21D, the tissue removal system may comprise an internal cutting or grinding mechanism 7SO. This mechanism comprises an outer tubular shaft 7S2 with an inner cutting or grinding structure 7S4 that protrudes into the inner lumen 7S6 of the outer tubular shaft 7S2 and cooperates with a circumferential groove or recess 7S8 on the inner tubular shaft 760 to morcellize, cut or otherwise breakdown any larger tissue fragments that may enter the outer tubular shaft 752. The inner cutting structure 754 may have any of a variety of configurations, including different rake angles and/or surface configurations. The configuration of the recess 758 on the inner tubular shaft 760 may vary in width and cross-sectional shape. Although only a single internal mechanism 750 is depicted, in other examples, multiple mechanisms may be provided along the shafts 752 and 760. In some further examples, an internal mechanism 750 may be used with the tip-based mechanism illustrated in FIGS. 21A to 21D.

Figure 22:
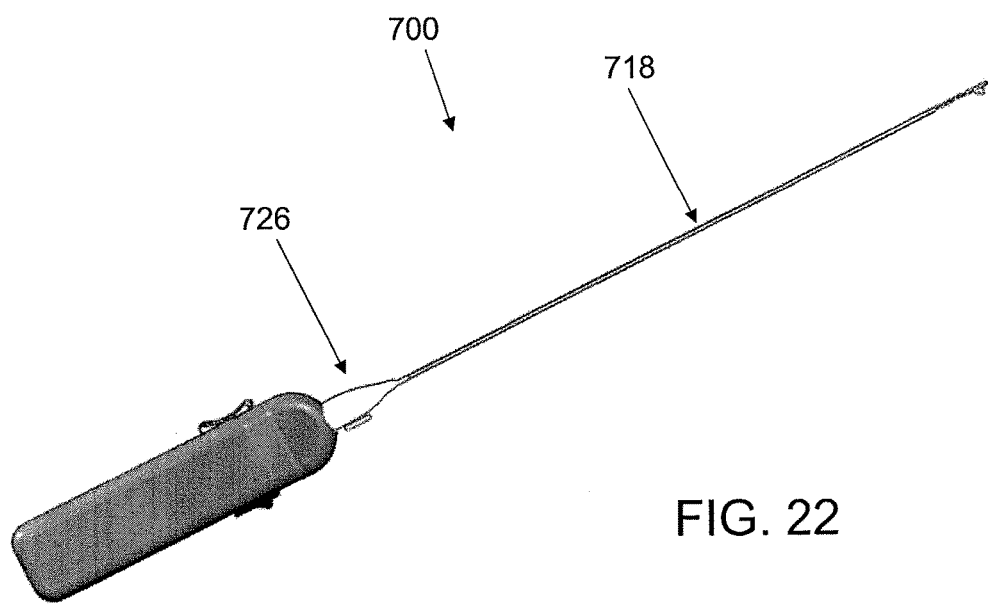
FIG. 22 illustrates the tissue removal device of FIG. 21A with an optional viewing chamber.
Figure 23:
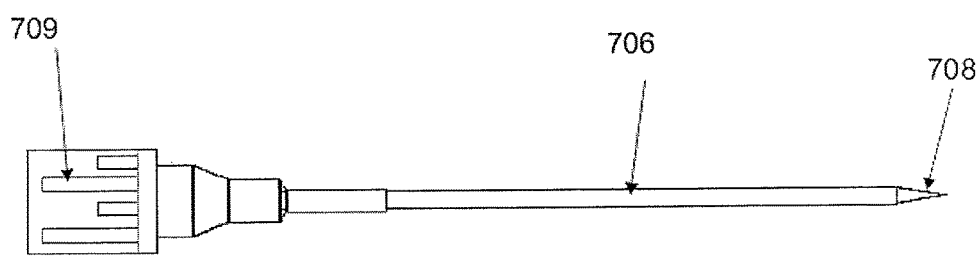
FIG. 23 illustrates an embodiment of a cannula and obturator device usable with various access systems.

FIG. 22 further depicts another optional feature of a tissue removal system 700, comprising an optically transparent chamber 726. Although the optically transparent chamber section 726 in FIG. 22 is located distally at the attachment of the outer tubular shaft 718, in other examples, the optically transparent housing chamber 726 may be located at a more proximal location. The optically transparent housing section 726 comprises an optically clear passageway or cavity in communication with the lumen of the outer tubular shaft 718 so that any fluid and/or materials either injected distally or removed proximally may be viewed by the user. In some instances, the passageway or cavity may have a volume of at least about 0.5 cubic centimeters, sometimes about 1 cubic centimeter, and other times about 2 cubic centimeters or 15 cubic centimeters or more. The quantity of fluid or tissue that may be contained within the optically transparent chamber may be less than or equal to the total volume of the chamber. For example, the total volume of an optically transparent chamber may be about 15 cubic centimeters, but may be configured to collect up to about 10, about 12, or about 14 cubic centimeters of material. The optically transparent housing chamber 726 may also comprise markings to identify the volume of material that has aspirated or prepared for infusion or irrigation, for example. The optically transparent chamber 726 may also feature a port with a removable cap to empty the contents of the chamber 726, to reduce clogging or to collect a diagnostic tissue sample. In some examples, the tissue removal system may have one or more infusion lumens with one or more openings at the base, cable shaft, and/or distal tip of the tissue removal system, which may be used in addition to or in lieu distal end of the outer tubular shaft 718. In other examples, the tissue removal system may be removed from the vertebral body and a separate infusion instrument may be used to deliver therapeutic agents or materials.

In use, the tissue removal system 700 depicted in FIGS. 21A to 22 may be used for with a variety of tissue removal procedures, including discectomy, vertebroplasty and interbody fusion, for example. In some examples, the particular configuration used may be tailored to the specific procedure.

A steerable tissue removal device may be used during some procedures to increase the region or amount of tissue removed, compared to a rigid tissue removal device, for example. In some instances, anatomical restrictions or increased risks of injury may limit the range with which a rigid tissue removal device may be manipulated. FIGS. 20A and 20B, for example, schematically depict some of the movement axes and the potential tissue removal zones that may be achieved with a steerable tissue removal device 650. Here, a steerable tissue removal device 650 with an extendable cable 652 may be inserted into a vertebral disc 653. While the steerable tissue removal device 650 and a rigid linear tissue removal device may translate and rotate with respect to its longitudinal axis 654, the pivoting range 656 of the rigid portion of the outer tube 658 of the tissue removal device 650 (and the corresponding structure on a rigid tissue removal device) may be substantially limited because even small angular movements of the outer tube 658 may result in substantial absolute displacement of the more proximal portions of the outer tube 658. This displacement, however, will be limited by the amount, the location and/or the compliance of the body tissues and structures between the proximal end (not shown) and the distal end 660 of the rigid portion of the outer tube 658. In contrast, a tissue removal device 650 with a flexible segment 662 located distally permits a range of angulation or bending 664 from the longitudinal axis 654 of the tissue removal device 650 without requiring substantial displacement or leveraging of the rigid portion of the outer tube 658. Thus, the flexible segment 662 may be able to reach tissue that is spaced apart from the longitudinal axis 654 with less physical effort, and may be even be able to reach tissue that cannot be reached by pivoting a rigid portion of the outer tube 658.

In addition to the bending of the flexible segment 662, the steerable tissue removal device 650 may also access tissues located away from the longitudinal axis 654 by increasing the extension of the extendable cable 652 along its extension range 665. The extension range 665 may be characterized as a dimension that is perpendicular to the longitudinal orientation of the core section 668 to which the extendable cable 652 is coupled. For example, a tissue removal device with a 1 mm diameter core and configured with an extendable cable that may be adjusted to a perpendicular distance of 3 mm away from the core can remove tissue in a zone that is 7 mm in at its maximum diameter (i.e. 1 mm shaft plus 2 times 3 mm of the rotated elongate member). In embodiments where the extendable cable is extended to a greater degree, even greater volumes or zones of tissue removal may be achieved. Thus, by manipulating the degree of cable extension, the volume or range of tissue removal that may be performed may be adjusted without requiring repositioning the tissue removal device, either by torqueing its shaft or using its steering mechanism (if any).

Because the particular tissue removal device 650 in FIGS. 20A and 20B permits the actuation of the extendable cable 652 while the flexible segment 662 is bent by providing a flexible or bendable driveshaft (not shown), the tissue removal zone 670 may be displaced away from the longitudinal axis 654. Furthermore, because each of the movement described above may be synergistically combined with one or more other movements, even greater larger tissue removal zones may be achieved. For example, rotation 672 of the bent tissue removal device 650 around the longitudinal axis 654 by torqueing the rigid portion of the outer tube 658, may achieve an even larger tissue removal zone 674. The rotation 672 of the bent tissue removal device 650 may occur while the extendable cable 652 is being rotated, or when the cable 652 is not rotating. The amount of rotation 672 may be anywhere in the range of about 1 degree to about 360 degrees or more. Any of a variety of combinations of cable extension, flexible zone bending, and outer tube rotation and translation may be used to achieve the desired tissue removal.

While various flexible, steerable and rigid embodiments of the tissue removal device may be used to remove larger volumes of tissue as described above, in other embodiments, a tissue removal device may be used to perform focal debulking of tissue. For example, by utilizing the small profile and/or the steerable features of certain embodiments of the tissue removal device, the tissue removal device may be more accurately positioned or navigated to a specific target site in a body structure. In some instances, the removal of lower volumes of tissue at a specific target location may be used to achieve a desired result, in comparison to the removal of a larger volume of tissue from a general target location. Furthermore, by adjusting the cable or tissue removal element relative to the shaft of the tissue removal device, the volume of mechanical tissue removal may be adjusted relative to the shaft without requiring repositioning of the shaft. By removing less disc tissue to reduce a herniation, for example, a larger amount of non-pathologic disc tissue and structural integrity of the disc may be preserved. In some instance, relatively greater preservation of the disc tissue which may slow the rate of further disc degeneration and reherniation compared to lesser degrees of tissue preservation.

In one example, a herniated disc may be accessed and visualized endoscopically. A steerable tissue removal device may be inserted into the disc and steered toward the region of herniation, rather than to the center of the disc, for example. The extendable cable or other adjustable tissue removal element is actuated to pulverize an initial amount of tissue at the region of herniation and removed by the auger. In some embodiments, to facilitate controlled volume tissue pulverization, the distance between the couplings of the extendable cable to its rotatable shaft may be less than about 10 mm, sometimes less than about 7 mm, and other times less than about 5 mm. To facilitate precise removal of the pulverized tissue, the distal suction opening of the tissue removal device may be located less than about 10 mm from the proximal coupling of the extendable cable, sometimes less than about 7 mm, and other times less than about 5 mm or about 3 mm. After the initial actuation of the extendable cable, the herniation is reevaluated endoscopically and the degree of cable extension may be adjusted higher in a stepwise manner and reevaluated until the desired reduction in the herniation is achieved.

In some uses of the tissue removal device, in both steerable and non-steerable configurations, the tissue removal zones may positioned whereby structures such as the annulus fibrosus and the vertebral body endplates may be unintentionally damaged or contacted. In embodiments where the tissue removal device has been configured as described previously to limit or avoid significant damage to these structures, greater tissue removal may be safely achieved even when the distal tip of the tissue removal device cannot be directly visualized, e.g. when the endoscope is located in the epidural space while the tissue removal device is located inside the vertebral disc.

In some instances, embodiments of the tissue removal device may be characterized by the ratio of the maximum diameter or cross-sectional area of tissue removal of a rotating extended elongate member, and the diameter or cross-sectional area of the outer tube of the tissue removal device or the tissue pathway formed by the tissue removal device. In the example described above, the diameter of the elongate member in its rotating deployed configuration to the diameter of the outer tube is a ratio of about 7:1. In some embodiments, this ratio is at least about 3:1 or higher, but in other embodiments, the ratio is at least about 5:1 or higher, or even about 10:1 or about 20:1 or higher in certain embodiments. In other examples, the tissue removal device may be characterized by the maximum perpendicular distance that the elongate member may be extended, or by the ratio of this distance to the diameter (or an axial transverse dimension) of the outer tube. In some examples, this ratio is at least about 3:1 or more, sometimes about 5:1 or more, or even about 7:1 or about 10:1 or more.

Examples of procedures that may be used to access the spine are disclosed in U.S. Pat. Nos. 7,108,705, 4,573,448, 6,217,509, and 7,273,468, which are hereby incorporated by reference in their entirety. The various embodiments of the tissue removal device disclosed herein may be used to perform a discectomy or nucleotomy, but may also be used to perform any of a variety of tissue removal procedures in the spine and outside of the spine. In one particular embodiment, a patient may be placed into a prone position with a pillow or other structure below the abdomen to limit lumbar lordosis. The patient is prepped and draped in the usual sterile fashion and anesthesia is achieved using general, regional or local anesthesia. Under fluoroscopic guidance, a sharp tipped guidewire, or a needle with a guidewire may be inserted into the paravertebral space or epidural space from a posterior or postero-lateral location of the patient's back at a location in the range of about 5 cm to about 15 cm lateral to the midline. In some instances, guidewire insertion may be facilitated by inserting a needle into the tissue first. In alternate embodiments, an anterior procedure through the abdominal cavity or anterior neck region may be performed. Once access to the target location is confirmed, a dilator may be used with the guidewire to enlarge the insertion pathway. Then, an introducer or cannula may be inserted over the guidewire, followed by subsequent guidewire removal and insertion of an endoscope into the introducer or cannula. Alternatively, an endoscope may be inserted over the guidewire. The endoscope may be manipulated or steered to directly visualize and identify the relevant structures such as the disc, the nerve or other adjacent structures and site(s) of tissue removal. In some embodiments where the patient is under local or regional anesthesia, the suspected nerve impingement may be confirmed by contacting or manipulating the suspected nerve with the endoscope, or other device inserted through the endoscope, and assessing the patient's response or symptoms. One embodiment of an endoscope that may be used is described in U.S. Application No. 61/045,919, which has been hereby incorporated by reference in its entirety. Once the target region has been evaluated, a tissue removal device may be inserted through the spinal access device or endoscope and to pierce through the annular wall of a herniated disc. Once inserted, the tissue removal device is manipulated the elongate member to its extended or deployed configuration and actuated to emulsify or pulverize the tissue of the nucleus fibrosus. In some embodiments, the tissue removal device may be actuated for a duration in the range of about 5 seconds to about 90 seconds or more, sometimes about 15 seconds to about 60 seconds, and other times about 30 seconds to about 60 seconds. The pulverized material may then be suctioned through the device and then the effect of the tissue removal may be re-evaluated by the endoscope or other visualization mechanisms. The actuation of the tissue removal device may be repeated as desired to remove disc material. In some embodiments, the tissue removal device may be withdrawn from the disc and reinserted directly into or against the extruded disc material and actuated. Once the tissue removal is completed, the tissue removal device may be withdrawn. The puncture site in the annular wall may have a cross-sectional area of less than about 2 mm2 or less, sometimes about 1 mm2 or less, and other times about 0.9 mm2 or less, and thus may self-seal without requiring treatment of the puncture location with an adhesive, a suture or coagulation probe. The body location may be rechecked with the endoscope or spinal access device to verify that no bleeding or comprise of the integrity of the disc or spinal nerves has occurred, and then the endoscope or spinal access device is removed from the body and the skin access site is bandaged.

While the embodiments described above may be used to remove soft tissue without substantially removing calcified or bony tissue, in other embodiments, the tissue removal device may be configured to remove bone. In some examples, this may include configuring the tissue removal device various bone-removing coatings and/or a higher rotational speed. The coatings may comprise coarser grit structures made from materials including, but not limited to titanium nitride, chrome alloy coating, tungsten carbide, diamond grits, silicon carbide grits, ceramics, or other suitable materials. The spiral cable may be spun at high speed (e.g. about 10,000 rpm to about 30,000 rpm or more) to grind the bone to smaller pieces that can be aspirated by the auger. Saline irrigation may be used to clean and/or cool the spiral cable and/or the surround tissue. In some further configurations, the tissue removal device may be further configured to differentially removing cancellous bone while generally preserving compact bone. Such a tissue removal device may be used, for example, to form a passageway or cavity within a vertebral body or a long bone without disrupting the integrity of the outer surface of the bony structure.

In one example, a hollow needle or trocar may be passed through the spinal muscles until its tip is precisely positioned within the fractured vertebra. This may be performed under external imaging guidance (e.g. fluoroscopy, CT or ultrasound) or using an endoscopy system. In other examples, intraosseous venography may be performed in conjunction with other visualization modalities. In some instances, intraosseous venography may be used to visualize the basivertebral venous plexus or a paravertebral vein and to possibly avoid inadvertent entry into these structures.

Upon reaching the outer surface of the vertebral body, the distal tip of the tissue removal device (e.g. the distal head 336 of the tissue removal device 300 in FIG. 8) may be used to penetrate the compact bone of the vertebral body to provide access to its interior. In other embodiments, a bone penetration device, such as a trephine or a burr, may be used to form a channel or passageway into the vertebral body. The bone penetration device is then removed and the cable-based tissue removal device may be inserted into the passageway and into the vertebral body. In other embodiments, the tissue removal device may be provided with a distal burr or drill head rather than a conical head. In some examples, the spiral cable is displaced radially outward before the rotating is initiated, while in other examples, rotation is initiated first before the spiral cable it let out. In some examples of vertebroplasty, the spiral cable may have a maximum radial displacement of about 4 mm, about 5 mm, about 6 mm, about 7 mm, or about 10 mm or more. In some examples, the volume of space formed by the tissue removal device may be further augmented similar to the range of tissue removal disclosed for removal of annular tissue depicted in FIGS. 20A and 20B. As mentioned previously, the spiral cable may be rotated in the directional sense as the spiral configuration, but may also be rotated in the opposite direction.

The spiral cable may be as a single filament or a multi-filament cable. Each filament may comprise the same or a different material or configuration. In some examples, each filament comprises stainless steel (e.g. 304, 316 or 17-4 stainless steel) which is wound into a cable. The stiffness of the cable may be altered by the changing the tightness of the winding, the number of filaments, and/or the thickness of the filaments. One or more of these characteristics, in combination with an optional grit surface may be used to adjust the preferential grinding features of the tissue removal device. In some procedures, by preferentially cutting the cancellous bone while preserving the compact bone, the compact bone shell or structure of the vertebrae or other bone may protect the soft tissue structures located outside the shell or surface. The compact bone shell or structure may also restrict flow of any bone cement injected into the target site. In some examples, contrast dye or other visualization agents may be injected into the target site to assess the integrity of the target site prior to cement injection or other treatments.

Figure 24A:
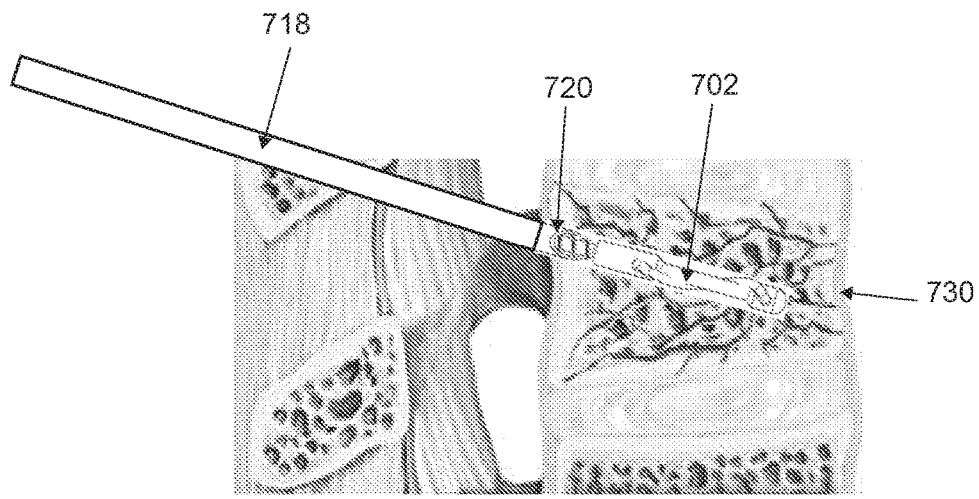
FIGS. 24A to 24C depicts one embodiment for performing Vertebroplasty.
Figure 24B:
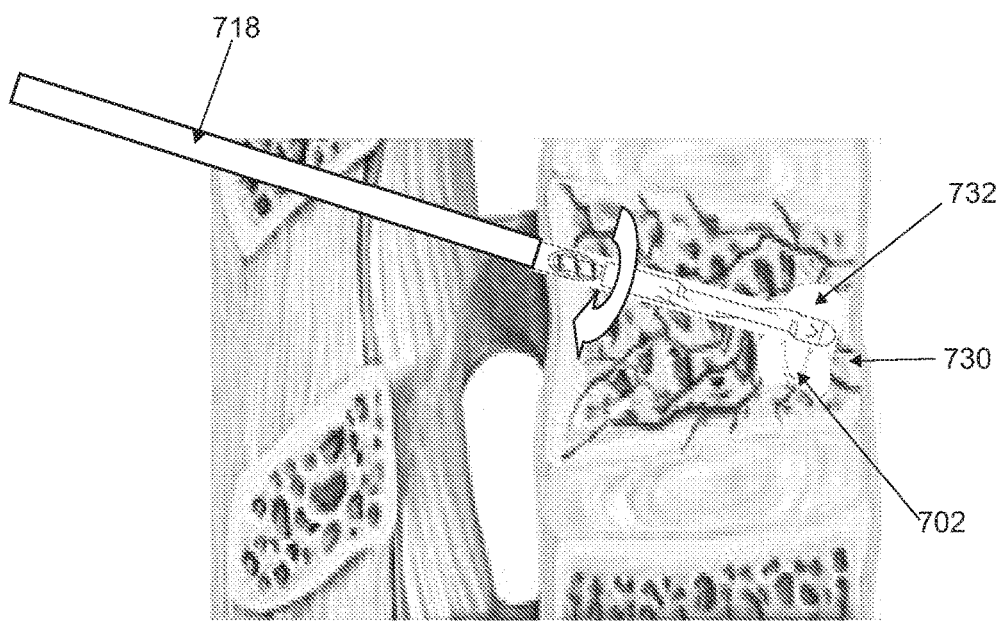
Figure 24C:
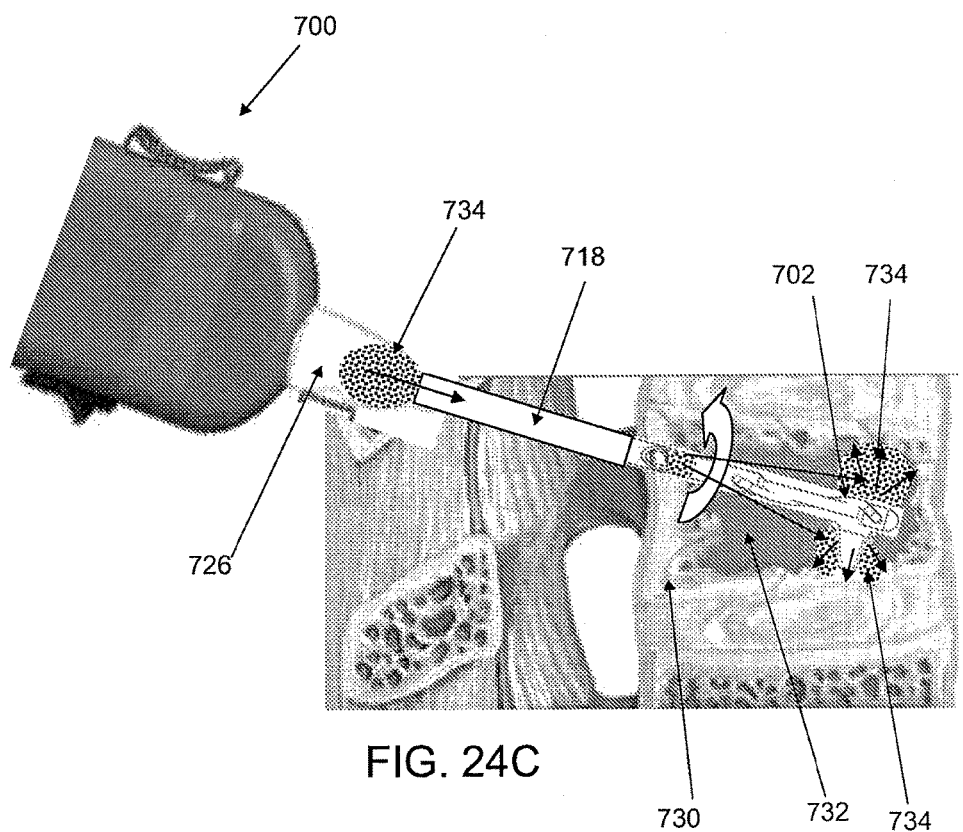

Referring to FIG. 24A and to 24C, a vertebral body 730 may be accessed for vertebroplasty by any of a variety of access procedures described herein. A tissue removal system 700 (with a shaft 718—not drawn to scale) may be inserted into the interior of the vertebral body (FIG. 24A) and then rotated with the cable 702 extended to form a cavity 732 in the vertebral body 730 (FIG. 24B). The tissue removal system 700 may be further manipulated until adequate removal of cancellous bone is achieved. As shown in FIG. 24C, the tissue removal system 700 may be loaded with a bone cement 734 which is then delivered to the cavity 732. In some examples, the bone cement 734 may comprise a material such as polymethyl methacrylate hydroxyapatite, or any of a variety of other bone cements or other hardenable or curable substances can be injected through the trocar to fill the cavity created by the by the tissue removal system 700. The cable 702 of the tissue removal system 700 may be retracted or extended during delivery of therapeutic agents. In some instances, the extended cable 702 may redistribute the therapeutic agents against the cavity walls, which may reduce the risk of leakage out of the cavity.

In some of the procedures described above, the cavity in the vertebral body is formed before the delivery of therapeutic agents, but in other procedures, the delivery of therapeutic agents may occur simultaneously. In procedure where the cavity is first formed, filling of the empty cavity may reduce initial filling pressures. In some instances, lower filling pressures may reduce the risk of leakage. In some examples, the tissue removal system may comprise a pressure sensor which may be used by the user or may be configured automatically to shut off delivery or pressurization of the therapeutic agents upon reaching a particular pressure limit.

Although some of the examples described herein are directed to treatment of vertebral disc fractures, in other examples, the tissue removal systems may be used to treat or diagnose bone lesions located in the vertebrae or other bones of the body. Diagnosis of bone lesions may include biopsy of bone. These bone lesions may include but are not limited to potentially cancerous bone lesions, including osteomas, osteosarcomas and metastatic lesions, as well as potentially infectious bone lesions, including tuberculosis. Bone cement, with or without other therapeutic agents such as anti-neoplastic and anti-infective agents, may or may not be injected into the cavity.

FIGS. 25A to 25E depict another embodiment of a cable-based tissue-removal device 2500, comprising a flexible or semi-rigid extendable element 2502 connected distally to the distal end of a movable support element 2512 with a generally fixed length between the rotatable shaft 2524 and the extendable element 2502. The extendable element 2502 and the support element 2512 may be flexible in bending but semi-rigid or rigid with respect to columnar compression or tension. The extendable element 2502 has a retracted configuration, as shown in FIG. 25A, and an extended or deployed configuration, as illustrated in FIGS. 25B to 25D. The extendable element 2502 may comprise an elongate, curved shape that is configured to extend and retract from a distal opening 2522 of a rotatable shaft 2524. The proximal end of the extendable element 2502 may be connected to an actuation mechanism to retract and extend the extendable element 2502. In some embodiments, the edge of the distal opening 2522 is round or otherwise blunt, which may reduce damage to the extendable element 2502.

The support element 2512 is distally attached to the distal region of the extendable element 2502 and proximally attached to a base 2516 located at the distal end of the rotatable shaft 2524. The support element 2512 may comprise a loop that extends from a base 2516 and couples or passes through an eyelet 2504 at the distal region of the extendable element 2502. In other examples, the support element 2512 may have a non-loop configuration, such as a strut. The extendable element 2502 and the support element 2512 may also be coupled at their distal ends by any suitable attachment methods that permit relative change of angle between the extendable element 2502 and the support element 2512 within the plane approximately parallel to that formed by the extendable element and support element. For example, they may be coupled with a hinge interface. In still other examples, the extendable element 2502 and the support element 2512 may have a fixed configuration, e.g. a weld. In some embodiments, the distance between the support element attachment point(s) 2518 on the base 2516 and the distal opening 2522 of the shaft 2524 may be about 2 mm to about 8 mm, sometimes about 3 mm to about 7 mm, and other times about 4 mm to about 6 mm. The proximal end of the support element 2512 may be attached to the base 2516 by any type of suitable attachment methods, such as welding, soldering, brazing, gluing, crimping, and/or mechanical locking. The support element may also be coupled to the base 2516 by a hinge or pivot joint. As illustrated in FIG. 25E, the support element 2512 may be a closed loop that is coupled to the base through two holes on the base 2516 and around the extendable element 2502. The support element 2512 the base 2516 may be configured to permit rotation of the support element 2512 within the two holes, and/or a sliding motion through the holes.

The tissue removal device 2500 may further comprise a sheath 2550 with a beveled or otherwise sharpened cutting edge 2552. The rotatable shaft 2524 extending through the sheath 2550 may comprise at least one optional thread structure 2554 configured to draw removed tissues from the target site into the sheath lumen, which is in fluid communication with a proximal shaft 2556. The removed tissues may be collected and/or examined at the proximal end of the device 2500 through the proximal shaft 2556. This lumen may be used as irrigation and/or aspiration channel for other suitable purposes. The proximal end of the proximal shaft 2556 may be further attached to a housing, where components and mechanisms (e.g., the actuation mechanism to distally deploy the extendable element 2502) used to manipulate the distal extendable element tissue removal device may be located. Various embodiments of housings are described elsewhere herein.

In its retracted configuration as illustrated in FIG. 25A, the proximal end of the extendable element 2502 inside the shaft 2524 may be pulled until the distal portion of extendable element 2502 is substantially straight, or when the rigid support element 2512 restricts further retraction of the extendable element 2502. When the extendable element 2502 is in its refracted configuration, the distal tip of the tissue removal device 2500 comprises a reduced profile that allows the device 2500 to be introduced though a cannula or other types of introducer into a target site.

When the extendable element 2502 is extended distally, the exposed portion of the extendable element 2502 is moved away from the distal end of the shaft 2524. The length of the support element 2512 restrains the degree of extension of the distal end of the extendable element 2502, which results in the exposed region of the extendable element 2502 proximal to its distal end to bow or curve away from the central axis 2517 or rotation axis of the device. In some instances, the extension forces may also cause pivoting or rotation of the support element 2512 with respect to the base 2516 where configured to do so. The degree of displacement of the extendable element 2502 from the central axis 2517 of the device may be characterized as the transverse displacement distance 2519 (e.g., the perpendicular distance between the distal end of the extendable element 2502 and the central axis 2517 of the shaft 2524), as illustrated in FIG. 25B. The particular configuration of the extendable element 2502 may vary, depending upon the mechanical properties (e.g., stiffness) of the material of the extendable element 2502 and/or the support element 2512, the length of the extendable element 2502 protruding from the distal opening 2502 of the shaft 2524, and/or the location of the support element 2512 attachment point 2518 on the shaft 2524. In the specific embodiment in FIG. 25B, the extendable element 2502 in a fully extended configuration comprises a generally fusiform shape with a tapered portion towards the distal end of the extendable element 2502. In some embodiments as shown in FIG. 25D, a distal portion of the extendable element 2502 may be made from relatively rigid or semi-rigid material, which may resist deformation when this portion of the extendable element 2502 is distally extended. As a result, the degree of displacement of the extendable element 2502 from the central axis 2517 of the device may be small.

In some embodiments, a fully extended tissue removal device may comprise a sweep diameter, which is defined as two times the transverse displacement 2519 of the extendable element 2502 (e.g., the perpendicular distance between the distal end of the extendable element 2502 and the central axis 2517 of the shaft 2524), from about 5 mm to about 15 mm, sometimes from about 6 mm to about 14 mm, sometimes from about 8 mm to about 12 mm, and other times from about 9 mm to about 11 mm. In some embodiments where the extendable element 2502 is transversely displaced from the support element 2512 when in its extended configuration, as illustrated in FIG. 25B, the sweep range of the tissue removal device 2500 may be further enlarged. The area of the sweep region may be adjusted by the length of the extendable element 2502 protruding from the distal opening 2512 of the shaft 2524. Therefore, the sweep diameter may be proximally controlled by the degree in which the extendable element 2502 is distally extended. In some embodiments, a tissue removal process may begin with the spinning of the shaft 2524 with a smaller sweep diameter. The extendable element 2502 may then be distally deployed to increase its lateral expansion, thereby enlarging the tissue removal region. In some embodiments, the initial tissue removal may be performed with a low motor speed and the spinning speed may be slowly increased as the extendable element 2502 is progressively extended.

Both the extendable element 2502 and the support element 2512 may comprise any of a variety of materials and structures. In some embodiments, the extendable element 2502 may be made from a flexible or semi-flexible material that may be bent but not stretched. The flexural stiffness of an extendable element may be greater than the flexural stiffness of a support element, e.g., may be 1.5, 2, 3, 5, 10 times greater. The support element may be made from a semi-flexible or rigid material that may bend but resists stretching or elongation. In this fashion, when the extendable element 2502 is extended, the support element 2512 is pushed away from the central axis 2517 of the shaft 2524 but is configured to resist elongation. Further, because neither of the two support elements are stretchable, the transverse displacement 2519 of the support element 2512 may be accurately controlled by the length the extendable element 2502 protruding beyond the distal opening 2512 of the shaft 2524. Each leg of the extendable element may have a diameter of about 0.006 inch to about 0.018 inch, e.g., 0.010 inch to about 0.014 inch, or 0.012 inch. The support element may have a diameter of about 0.006 inch to about 0.018 inch, e.g., 0.008 inch to about 0.014 inch, or 0.01 inch. In some embodiments, the extendable element 2502 and the support element 2512 may comprise a multifilament cable with any number of filaments (e.g., 2, 3, 4, 5, or more) twisted, braided, woven or otherwise bundled together. The multifilament cable may comprise multiple filaments twisted around a core filament at a pitch of about 0.01 inch to about 0.25 inch, e.g., from about 0.03 inch to about 0.12 inch, or from about 0.030 inch to about 0.040 inch, or 0.035 inch. The individual filaments of the cable may have a thickness of about 0.001 inch to about 0.007 inch, and a thickness of about 0.0005 inch to about 0.0050 inch, e.g., 0.004 inch. A multifilament extendable element may have a diameter that is from about 2 to 200 times greater than the diameter of an individual filament, e.g., may be about 2, about 3, about 4, about 8, about 10, about 12, about 50, about 100, about 125, about 150, about 185, or about 200 times greater. For example, a metallic multifilament cable may have a diameter that is about 2 to about 12 times, or about 2 to about 4 times, greater than the diameter of the individual metallic filaments. A polymeric multifilament cable may have a diameter that is about 10 to about 25 times, or more than about 100 times, greater than the diameter of the individual polymeric filaments. In other embodiments, the extendable element 2502 and the support element 2512 may comprise a monofilament cable or structure. Filaments may be made from any of a variety of materials. Non-limiting examples may include metallic materials such as stainless steel (e.g., 304 stainless steel), titanium alloys, tungsten alloys, cobalt chromium, platinum, etc., and/or polymeric materials such as carbon fiber, Kevlar™, polyethylene (e.g., high density molecular weight polyethylene), nylon, urethane, polyester, and polyaramide etc. Cables (e.g., multifilament or monofilament) may be sheathed in one or more coating materials that may enhance one or more aspects of the tissue removing capability. For example, cables may be coated with polyimide, parylene, silicone, or urethane to improve the rigidity and/or strength of the tissue removal device. In still other embodiments, the extendable element 2502 and the support element 2512 may be made from metal, metal alloy (e.g., shape memory metal alloys), polymer or a combination thereof. The extendable element 2502 and the support element 2512 may or may not be made from the same material. In certain variations, the extendable element and/or support element may be encased in a sheath, where the sheath may have a tensile modulus of about 2500 megapascals (MPa) to about 4500 MPa, and tensile strength greater than 60 MPa. The sheath may be made of a polymeric material, e.g., polyimide, provides the desired tensile modulus and/or strength to the extendable element and/or support element. For example, a sheath that may cover a support element may be about 0.003 inch thick.

FIGS. 26A to 26C depict another embodiment of a tissue removal device 2600 with an extendable element comprising a cable 2606 that extends out of the inner lumen 2611 of a rotatable shaft 2624 and forms a distal loop 2602 looped around the support element 2612 and back into the inner lumen 2611. The loop 2602 may comprise one or more coils, and in some examples, adjacent coils may be reinforced by welding or bonding to adjacent coils. In this specific embodiment, the support element 2612 comprises a loop that extends through the distal loop 2602 of the cable 2606. FIG. 26B depicts the device 2600 in its deployed configuration of the extended distal loop 2602, the support element 2612 and a portion of the shaft 2617 between the support element attachment point(s) 2618 and the distal end 2622 of the shaft 2624.

FIG. 27 depicts another embodiment of a tissue removal device 2700 comprising an extendable extendable element 2702 distally supported and restrained by a support element 2712. A cutting element 2722 is attached to the intersection of the extendable element 2702 and the support element 2712, or to either the extendable element 2702 or the support element 2712. The cutting element may have a fixed attachment to the extendable element 2702 and/or the support element 2712, or may be configured to permit some relative movement with the extendable element 2702 and/or the support element 2712. The relative movement may involve rotation, pivoting, sliding and the like. The cutting element 2722 may be of any of a variety of devices that may be used to cut, chop, grind, burr, pulverize, debride, debulk, emulsify, scrape, dissect or otherwise remove tissues or bones. The cutting element 2722 may have a spur-like configuration as shown in FIG. 27, but may also comprise a burr, rasp or serrated configuration. Cutting elements with cutting edges may have edges oriented anywhere from about 0 to about 180 degrees relative to the direction of rotation. In some examples, angled edges or ridges may be oriented with a leading distal end and a trailing end, which in some instances, may facilitate movement of disrupted tissue proximally toward the auger or distal lumen. The cutting element 2722 may facilitate removal of the intradiscal material, but may also facilitate removal of tissue located at the endplates of the vertebral bodies. For example, disc material is typically fully removed from both superior and inferior vertebral endplates to facilitate fusion in spinal fusion surgeries.

Figure 28A:
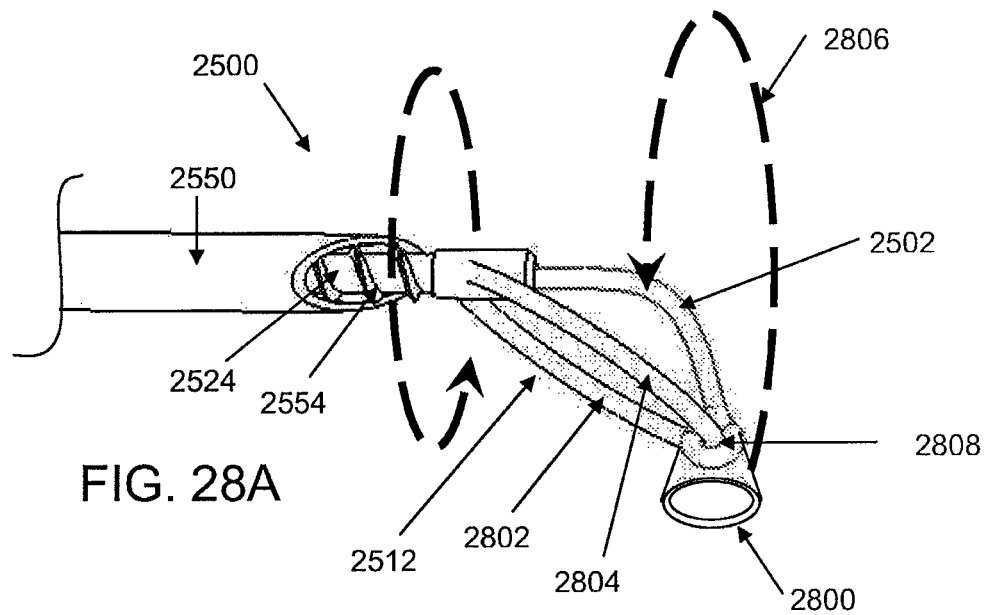
FIG. 28A depicts another embodiment of a cutting element attached to a cable-based tissue removal device.

Other variations of cutting elements that may be used with the devices depicted in are depicted in FIGS. 28A to 42, and 45-47. FIG. 28A, for example, schematically depicts a cutting element 2800 attached to the cable-based tissue-removal device 2500 in FIGS. 25A to 25E, but the cutting element 2800 may also be attached to any of a variety of cable-based tissue removal devices herein. In this particular example, the cutting element 2800 is attached to the leading arm 2802 of the support element 2512, e.g. the arm 2802 that first impacts tissue with respect to the direction of rotation 2806 that the device 2500 is configured to rotate during tissue removal, in contrast to the trailing arm 2804. The distal end 2808 of the extendable element 2502 may facilitate pushing or other force transfer from the rotational shaft 2524 to the cutting element 2800. The direction of rotation 2806 may correspond to the directionality as provided by the thread structure 2554 that transports disrupted material proximally down the sheath 2550 of the device 2500. In other examples, the cutting element may be attached to the distal end 2808 of the extendable element 2502 of the device 2500.

Figure 28B:
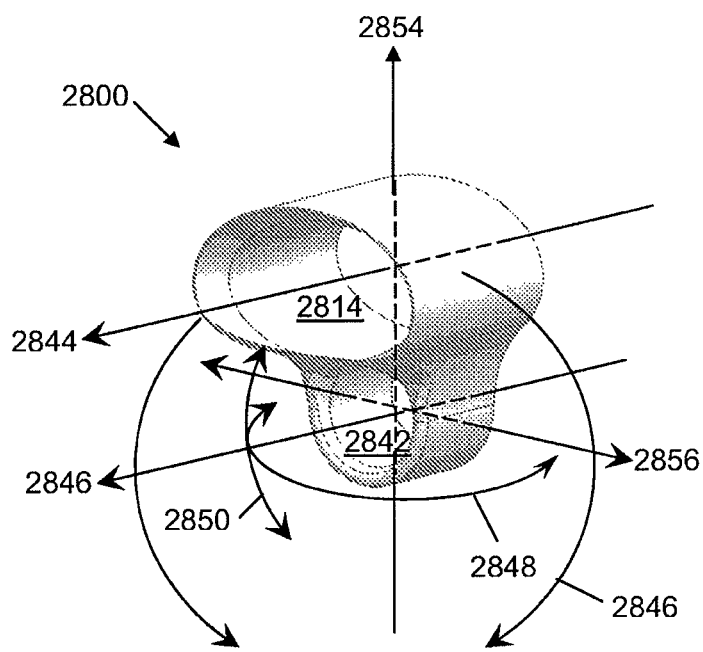
FIG. 28B is a schematic illustration of the relative movement range and orientation of the cutting element relative to its attachment site.
Figures 28C, 28D:
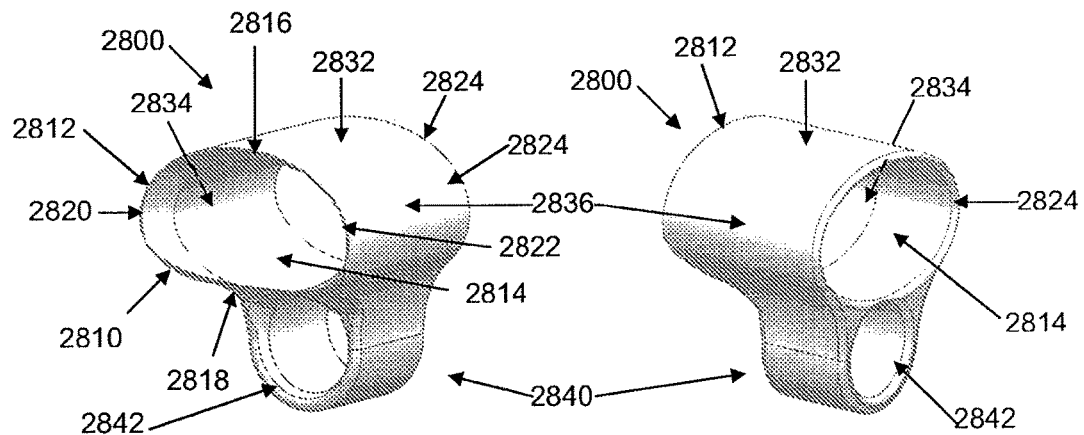
FIGS. 28C and 28D are anterior and posterior perspective views of the cutting element in FIG. 28A.
Figures 28E, 28F:
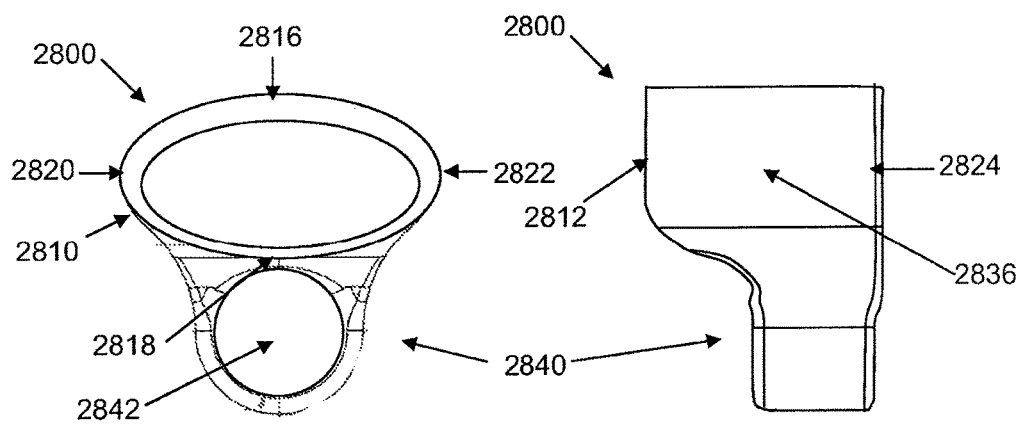
FIGS. 28E and 28F are anterior and side elevational views of the cutting element in FIG. 28A
Figure 28G:
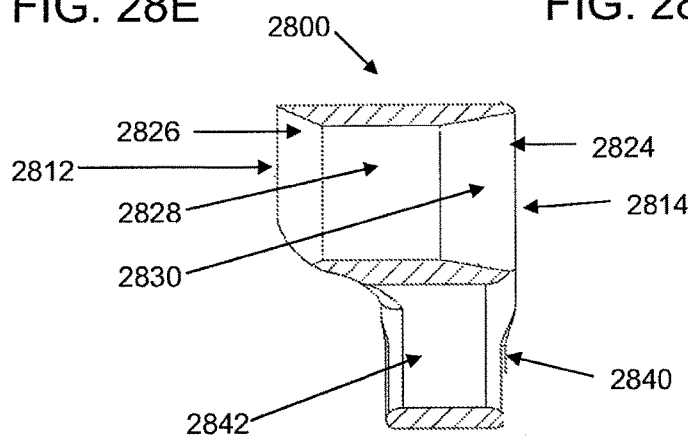
FIG. 28G is a cross-sectional sectional view of the cutting element in FIG. 28F.

As shown in FIG. 28C, the cutting element 2800 may comprise an annular cutting edge or blade 2810 located around the leading opening 2812 of a cutting lumen 2814. As the device 2500 is rotated, the cutting blade 2810 slices through tissue, separating the tissue into smaller fragments. The cutting blade 2810 may comprise a radially outward portion 2816, a radially inward portion 2818, a distal portion 2820 and a proximal portion 2822 with respect to the overall orientation of the device 2500. In use, the radially outward portion 2816 of the cutting blade 2810 may contact the vertebral body endplate and scrape or cut soft tissue away from the bone. As shown in FIGS. 28F and 28G, the cutting blade 2810 may comprise a non-planar configuration, wherein the outer, distal and proximal portions 2816, 2820 and 2822 of the blade 2810 protrudes farther than the radially inward portion 2818 with respect to the leading opening 2812 of the cutting element 2800. In other examples, however, the cutting blade may comprise a generally planar configuration, or any other non-planar configuration wherein the one or more of the outer, inner, distal or inner portions may protrude more than another portion or portions. As further depicted in FIGS. 28F and 28G, the cutting blade 2810 may have a generally orthogonal orientation with respect to its attachment structure 2840, but in other examples, the cutting blade or leading opening may be angled differently between about 0 to about 180 degrees. In still other examples, the blade or opening may be generally oriented about 5, 10, 15, 20, 25, 30, 35, 40, 45, 50, 55, 60, 65, 70, 75, 80, 85, 90, 95, 100, 105, 110, 115, 120, 125, 130, 140, 145, 150, 155, 160, 165, 170, 175, 180 or 185 degrees, or between any range of any two angles recited above.

As shown in FIGS. 28C and 28D, the cutting blade 2810 may surround a cutting lumen 2814 through which disrupted tissue may be passed. The cutting lumen 2814 is located between leading opening 2812 and a trailing opening 2824. The lumen may comprise a fixed or variable cross-sectional shape and/or size with respect to the longitudinal axis 2850 of the cutting lumen 2814, as illustrated in FIG. 28B. Referring back to FIG. 28G, the lumen 2814 may comprise a leading section 2826 which comprises an inwardly tapered cross-sectional configuration, a middle section 2828 which may have a fixed cross-sectional configuration, and a trailing section 2830 that may comprise a outwardly tapered cross-sectional configuration to the trailing opening 2824. In other examples, the lumen may comprise a fewer number or greater number of sections (e.g. 1, 2, 4, 5, 6 or more sections), and where each section may be characterized as having an inwardly tapered, outwardly tapered or fixed configuration. The tapered configuration, if any, may be a constant taper as depicted in FIG. 28G or may be a variable taper. The taper angle (as measured from the acute angle formed between the zero line and the tapered surface) may be about 5, 10, 15, 20, 25, 30, 35, 40, 45, 50, 55, 60, 65, 70, 75, 80, or 85, degrees, or in a range between any two of the angles. The trailing opening 2824 and each lumen section 2826, 2828 and 2830 depicted in FIG. 28G may have a generally orthogonal orientation with respect to the attachment structure 2840, but in other examples may be angled differently between about 0 to about 180 degrees. In still other examples, the trailing opening and/or each lumen section may be generally oriented about 5, 10, 15, 20, 25, 30, 35, 40, 45, 50, 55, 60, 65, 70, 75, 80, 85, 90, 95, 100, 105, 110, 115, 120, 125, 130, 140, 145, 150, 155, 160, 165, 170, 175, 180 or 185 degrees, or between any range of any two angles recited above.

The lumen may have any of a variety of cross-sectional shapes which may be the same or may change along the length of the lumen. FIG. 28E illustrates the oval configuration of the lumen 2814 of the device 2500, but in other examples, one or more sections of the lumen may have different oval size and/or orientation, or may have a circular, square, rectangular, triangular, polygonal or other shape. In other examples, the lumen may also comprise one or more cutting edges that protrude into the lumen or span across the lumen. The luminal cutting structures, if any, may span the entire length of one or more sections of the lumen and may have any of a variety of angles, orientations, spacings, and locations within the lumen, and in some further examples, may also protrude from out of the lumen.

The outer surface of the cutting element may have the same general configuration as the lumen, or may have a different configuration. In the example depicted in FIGS. 28C to 28G, the radially outward, distal and proximal outer surfaces 2832, 2834 and 2836 of the cutting element adjacent to the lumen 2814 have a fixed, smooth configuration, but in other examples, one or more of these surfaces may be tapered or may comprise recesses or projections.

The attachment structure of the cutting element may comprise any of shapes and a variety of fixed or movable interfaces with respect to the flexible and/or support elements 2502, 2512. In some examples, the attachment structure may be integrally formed with either the flexible and/or support elements 2502, 2512. In the examples in FIGS. 28A to 34, the attachment structure 2840 comprises a generally cylindrical configuration with attachment lumen 3842 that also has a generally cylindrical configuration with a lumen axis that is oriented tangential or otherwise along the orbital or rotational path the distalmost region or tip of the flexible and support elements 2502, 2512. In other examples, the attachment structure may comprise a non-cylindrical shape, including a frusto-conical shape, box shape, ovoid shape, spherical shape or other shape. The attachment lumen may also comprise a non-cylindrical configuration. In other examples, the attachment lumen may have square, rectangular, triangular, oval or polygonal shape, and the shape of the lumen and/or the cross-sectional size of the lumen may vary along its longitudinal length. In some examples, the non-cylindrical shape of the attachment lumen may form a complementary interfit with the configuration of the flexible and/or support elements. Additionally or alternatively, the attachment structure of the cutting element may be soldered, brazed, and/or glued to the flexible and/or support elements. Depending upon the configurations and/or tolerances between the attachment lumen and the flexible and/or support elements, or other attachment site to a tissue removal device, relative rotation and/or translational motion between the cutting element and rest of the tissue removal device may be restricted or provided.

Referring to FIG. 28B, the longitudinal axis 2844 of the cutting lumen 2814 and the longitudinal axis 2846 of the attachment lumen 2842 may be generally parallel, but in other examples, the two axes may be oriented with an angle of about 5, 10, 15, 20, 25, 30, 35, 40, 45, 50, 55, 60, 65, 70, 75, 80, 85, 90 degrees or more along the horizontal plane 2848 and/or sagittal plane 2850, or in a range between any two of the angles. In some variations, the amount of translational motion between the attachment lumen (or cutting element in general) and the rest of the tissue removal device may be substantially zero, or may be configured to provide up to about 0.01 inches, 0.02 inches, 0.03 inches, 0.04 inches, 0.05 inches, 0.08 inches, 0.1 inches, 0.2 inches, 0.3 inches, 0.5 inches, 0.7 inches or more. The orientation of the translational motion may be along the longitudinal axis 2846 of the attachment lumen 2842, or along the radial axis 2854 and/or, distal-proximal axis 2856. In some variations, the amount of angular displacement between the attachment lumen (or cutting element in general) and the rest of the tissue removal device may be substantially zero, or may be configured to provide up to about 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360 degrees, or in a range between any two of the angles. The angular displacement may occur in the horizontal plane 2848, sagittal plane 2850 and/or frontal plane 2852.

The cutting element may comprise a variety of dimensions. The maximum transverse dimension between the distal-proximal axis of the cutting lumen 2814 may be in the range of about 0.02 inches to about 0.5 inches, in some variations about 0.04 inches to about 0.2 inches, and in other variations about 0.08 inches to about 0.1 inches. The transverse dimension between the outer and inner surfaces of the lumen 2814 may be in the range of about 0.01 inches to about 1.2 inches, in some variations about 0.02 inches to about 0.1 inches, and in other variations about 1.3 inches to about 0.06 inches. The longitudinal length of the lumen 2814 may be in the range of about 0.02 inches to about 0.3 inches, in some variations about 0.04 inches to about 0.2 inches, and in other variations about 0.08 inches to about 0.1 inches. In some variations, the longitudinal length of the lumen 2814 is shorter than either or both of the transverse dimensions of the lumen 2814 described above.

The transverse dimension between the two opposing surfaces of the attachment lumen 2842 may be in the range of about 0.01 inches to about 0.2 inches, in some variations about 0.02 inches to about 0.1 inches, and in other variations about 0.04 inches to about 0.6 inches. The longitudinal length of the lumen 2842 may be in the range of about 0.01 inches to about 0.2 inches, in some variations about 0.02 inches to about 0.1 inches, and in other variations about 0.04 inches to about 0.6 inches. In some variations, the longitudinal length of the attachment lumen 2842 is shorter than longitudinal length of the cutting lumen 2814, but in other variations, the attachment lumen may have the same or greater length as the cutting lumen. The ratio of the lengths of the attachment lumen 2842 to the cutting lumen 2812 may be in the range of about 0.5 to 5 or more, in some variations about 0.75 to about 3, and in other variations about 1 to about 2. The relative position of the attachment structure and the cutting structure may vary. In the example shown in FIGS. 28F and 28G, the leading opening of the cutting lumen protrudes farther in the direction of rotation relative to the attachment structure, which may or may not reduce interference between disrupted tissue and the attachment structure. As also shown in FIGS. 28F and 28G, the cutting structure and the attachment structure are generally flush or aligned with respect to the trailing surface of the cutting element, but in other examples, either the cutting structure or the attachment structure may protrude relative to the other structure with respect to the trailing surface of the cutting element. The dimensions and configurations described herein for this embodiment of the cutting element are similar to the dimensions and/or configuration of other cutting elements described herein, where applicable.

Figures 29A, 29B:
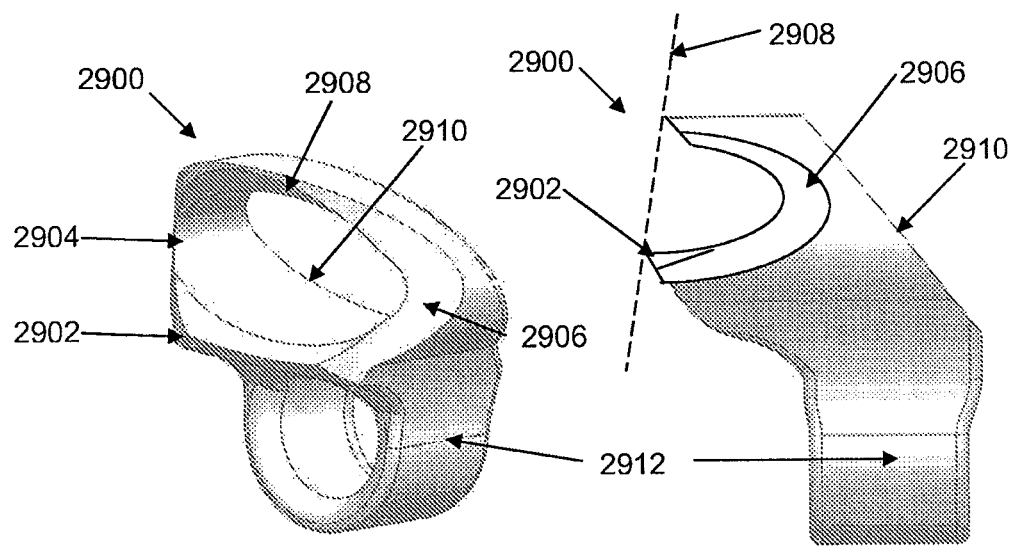
FIGS. 29A and 29B depict anterior perspective and side elevational views of another embodiment of a cutting element.

FIGS. 29A and 29B depict another example of a cutting element 2900 comprising a contoured cutting blade 2902 wherein the distal and proximal portions 2904 and 2906 of the blade 2902 comprise non-orthogonal or obtuse angles with respect to the non-planar leading face 2908 of the cutting element 2900. The trailing face 2910 of the cutting element 2900 also comprises a non-orthogonal angle, obtuse angle with respect to the attachment structure 2912. Here, the trailing face 2910 is angle but otherwise comprises a generally planar configuration, but in other examples, the trailing face may be non-planar.

Figures 45A, 45B:
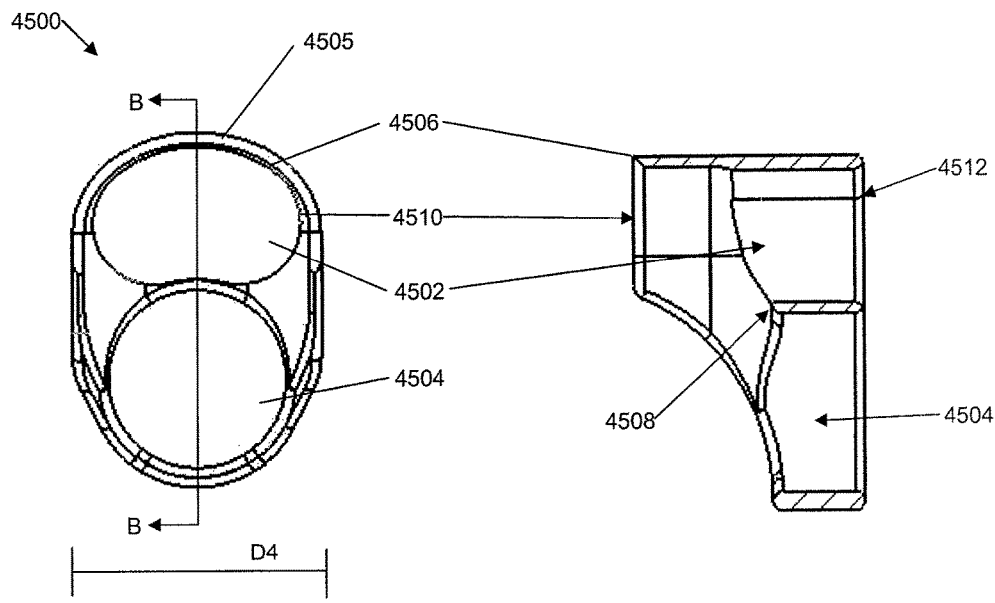
FIGS. 45A to 45D are an anterior elevational view, a side cross-sectional view, a side elevational view and an inferior elevational view, respectively, of a cutting element with ovoid-shaped cutting edges.
Figures 45C, 45D:
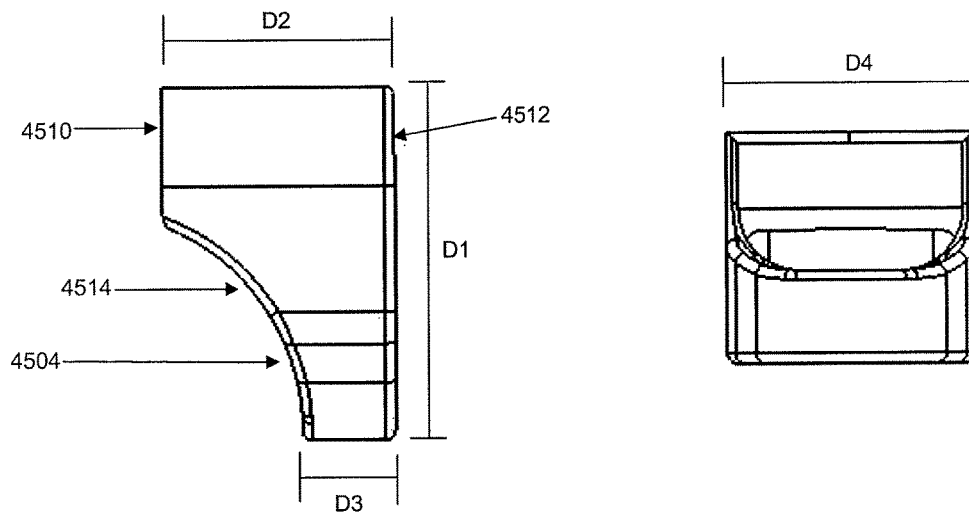
Figure 47A:
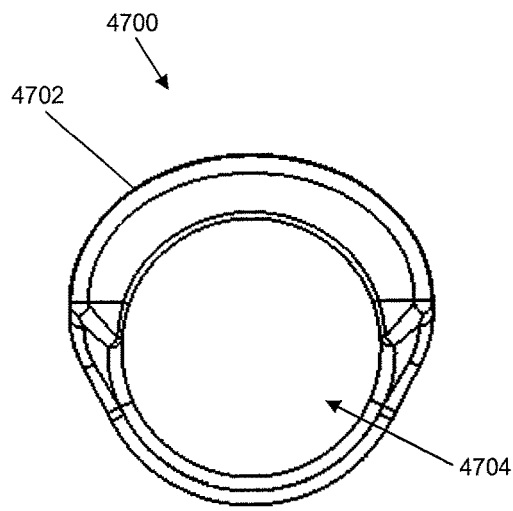
FIGS. 47A to 47D are an anterior elevational view, a side cross-sectional view, a side elevational view and a superior elevational view, respectively, a curved cutting edge with a different radius of curvature than the cutting element in FIGS. 46A to 46D.
Figure 47B:
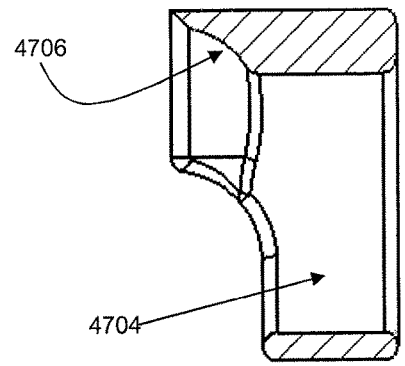
Figure 47C:
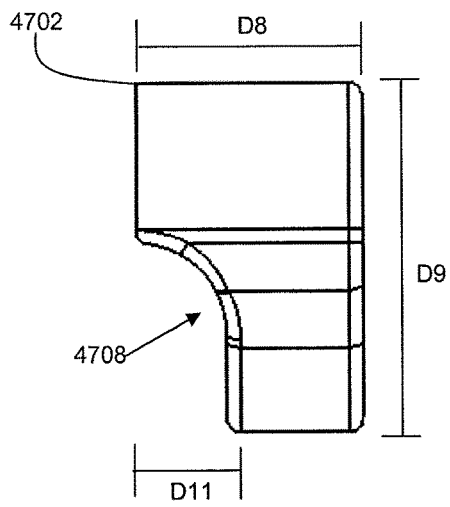
Figure 47D:
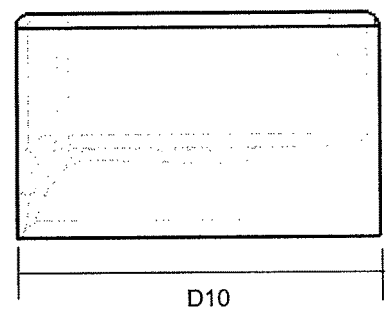

Another variation of a cutting element 4500 with one or more cutting edges is depicted in FIGS. 45A to 45D. The cutting element 4500 may comprise a first contoured blade 4506 on the edge of a leading opening 4510 of a cutting lumen 4502, and a second contoured blade 4508 on the edge of an attachment lumen 4504 that is located below the cutting lumen 4502. The second contoured blade 4508 may be recessed relative to the first contoured blade 4506, as depicted in FIG. 45B. The cutting lumen may have an ovoid geometry that may have contours of different radii of curvature. For example, the cutting lumen 4502 depicted in FIG. 45A may have one or more curves with a radius of curvature in the range of about 0.016 inch to about 0.033 inch, for example. A radially outward portion 4505 of the first blade 4506 may have a radius of curvature of about 0.033 inch. The second blade 4508 may be located on the edge of the attachment lumen 4504 that is in closest proximity to the cutting lumen 4502. FIG. 45B depicts a cross-section of the cutting element 4500 taken along the line B-B. As illustrated there, the second blade 4508 is set within an interior portion of the cutting element, i.e., recessed within the cutting element, while the first blade 4506 is located towards the periphery of the cutting element 4500. FIG. 45C depicts a side view of the cutting element 4500. The second blade 4508 may be set within a curved recessed portion 4514. The radius of curvature of the recessed portion 4514 may be about 0.045 inch to about 0.06 inch, e.g., 0.056 inch. During use, as the cutting element 4500 is rotated, the first blade 4506 contacts the tissue before the second blade 4508 contacts the tissue. In some variations, the configuration of the first blade with respect to the second blade in the cutting element 4500 may help reduce cutting resistance and/or to more finely cut or macerate the tissue. The dimensions of the cutting element 4500 may be varied according to the geometry and size of the target tissue region. For example, the cutting element 4500 may have a dimension D1, e.g., height, a dimension D2, e.g., depth of a first portion, a dimension D3, e.g., depth of a second portion, and a dimension D4, e.g., width. The dimension D1 may be from about 0.085 inch to about 0.1 inch, e.g., 0.092 inch. The dimension D2 may be from about 0.05 inch to about 0.07 inch, e.g., 0.06 inch. The dimension D3 may be from about 0.015 inch to about 0.03 inch, e.g., 0.024 inch. The dimension D4 may be from about 0.06 inch to about 0.07 inch, e.g., 0064 inch. The attachment lumen 4504 may have a diameter of about 0.045 inch to about 0.048 inch, e.g., 0.0465 inch.

While the cutting element 4500 only has a blade on the leading opening 4510 of the cutting lumen 4502, in other variations, the trailing opening 4512 may also comprise a sharpened edge. In some procedures, tissues with distinct geometries may need to be removed. A tissue removal device with a first sharpened edge on the leading opening rotated in a first direction may be suitable for removing tissue of a first geometry. The tissue removal device with a second sharpened edge on the trailing opening rotated in a second direction (e.g., opposite the first direction) may be suitable for removing tissue of a second geometry.

Figure 30:
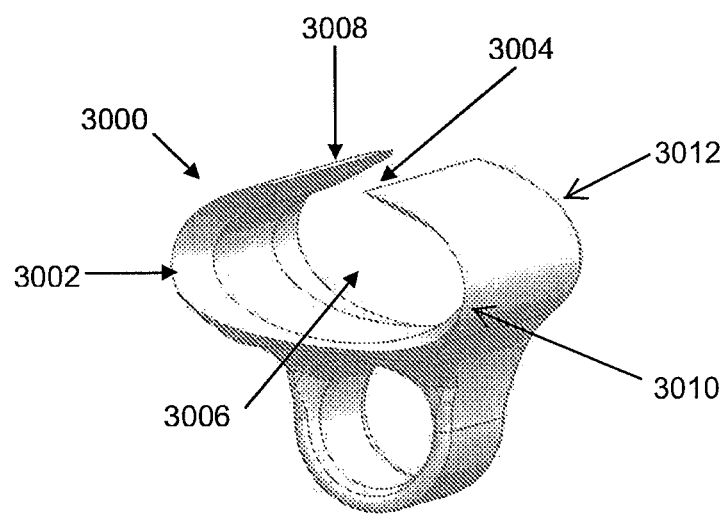
FIG. 30 depicts an open-configuration annular cutting element.

FIG. 30 depicts another example of a cutting element 3000 wherein the cutting blade 3002 comprises an open configuration with a gap 3004 along the entire length of the lumen 3006 and located along the radially outward surface 3008 of the cutting element 3000. In other examples, the gap 3004 may be located on the distal or proximal surfaces 3010, 3012, and/or may be less than the full length of the lumen 3006, and may further comprise multiple partial gaps. The average width of the gap 3004 may be in the range of about 0.005 inches to about 0.1 inches, in some other variations about 0.008 inches to about 0.05 inches, or about 0.01 inches to about 0.02 inches, for example.

Figure 31:
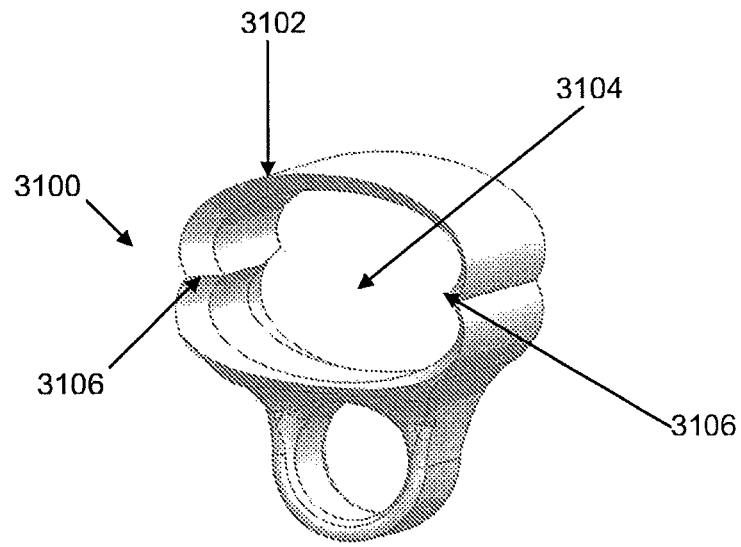
FIG. 31 depicts a double-ellipse cutting element.
Figure 32:
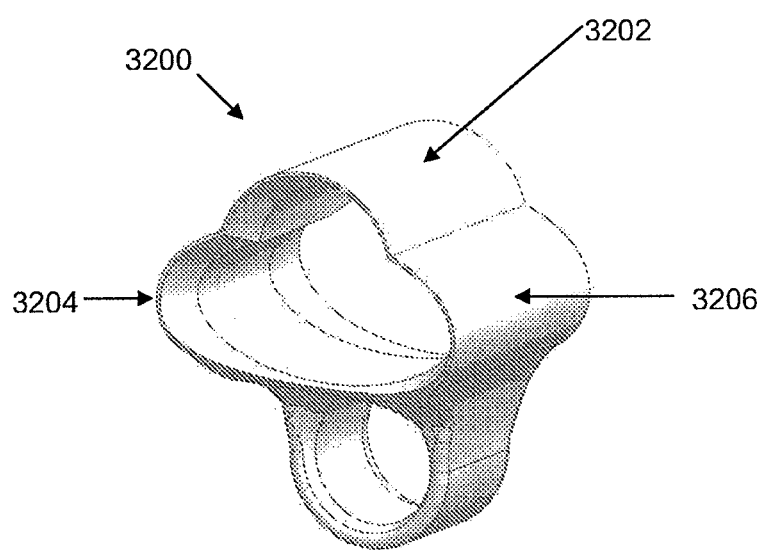
FIG. 32 depicts a tri-lobe cutting element.
Figure 33:
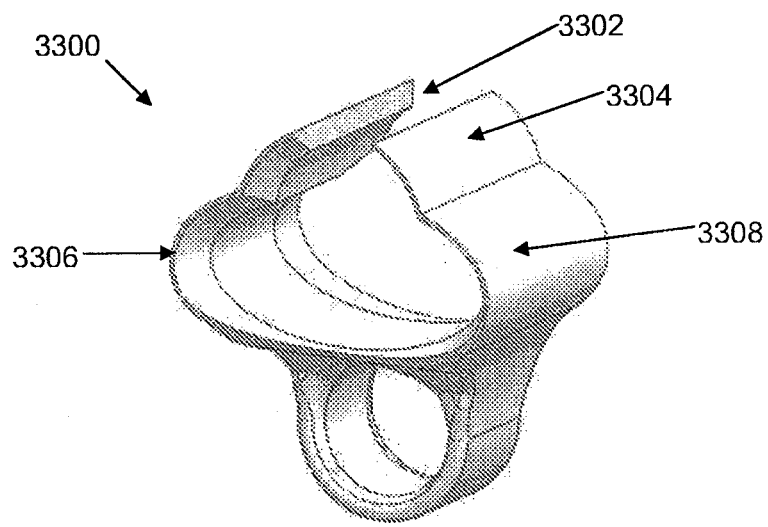
FIG. 33 depicts an open-configuration tri-lobe cutting element.

FIG. 31 depicts another example of a cutting element 3100 wherein the cutting blade 3102 and the cutting lumen 3104 comprises a configuration that may be characterized as double-overlapping ovals with acutely angled blade regions 3106 located at the intersections of the oval shapes. Here, the acutely angled blade regions 3106 are located at the distal and proximal regions of the lumen, but in other examples, the acutely angled blade regions may be located elsewhere and/or need not be located at polar opposite sides of the cutting element 3100. In still other examples, the cutting lumen may comprise a configuration comprising overlapping ovals of different sizes, overlapping other shapes with each shape having a different shape and/or size, or overlapping configurations of three, four or more shapes. FIG. 32, for example, is a cutting element 3200 that may be characterized as having a tri-lobe configuration or an overlapping small circle and larger oval configuration. In some variations, the smaller radius of the radially outward lobe 3202 (or circle shape) may facilitate more aggressive tissue removal. Although the radially outward lobe 3202 depicted in FIG. 32 is symmetrically located with respect to the other lobes 3204, 3206, in other examples, the location of the radially outward lobe may be more distally or more proximally located, and/or may have a different longitudinal length than the other lobes 3204, 3206. FIG. 33 depicts another example of a cutting element 3300 comprising the tri-lobe configuration with a gap 3302 along the radially outward lobe 3304, but in other examples, the gap may be located along either the distal or the proximal lobes 3306, 3308.

Figure 34:
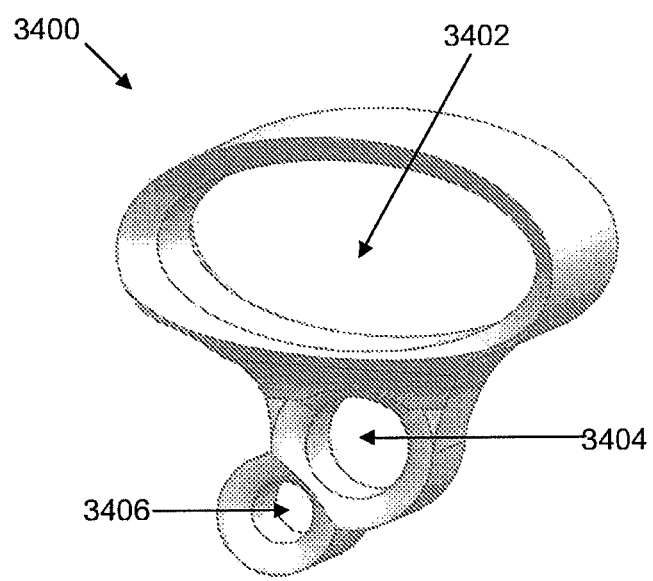
FIG. 34 depicts a closed-configuration annular cutting element with an exchange lumen.

FIG. 34 depicts another example of a cutting element 3400 wherein in addition to the cutting lumen 3402 and the attachment lumen 3404 (or other attachment structure), an auxiliary opening or lumen 3406 is provided. In some procedures, the auxiliary opening 3406 may be used with a guidewire or cannula to facilitate insertion and/or withdrawal of the tissue removal device. In other examples, the auxiliary opening 3406 may provide an additional attachment site for the cutting element to the flexible or support element, which may facilitate maintaining or providing a particular orientation to the cutting element as the length or configuration of the extendable element is changed. Although the auxiliary opening 3406 in the FIG. 34 has a similar orientation as the cutting lumen 3402 and the attachment lumen 3404, in other examples, the auxiliary opening 3406 may comprise a longitudinal axis that is oriented along the distal-proximal axis and/or the radial axis of the device shaft. In other examples, one or more projections and/or recesses may be provided to attach a control wire or other manipulatable element attached to the rotatable shaft and that can adjust the orientation of the cutting element In other variations, the cutting lumen may also be used as an attachment site to the cable or other displaceable structure of the cutting instrument. In still other variations, multiple cutting lumens may be provided. Also, in some variations of the cutting element, the cutting edge may comprise an arcuate configuration that occupies less than a full perimeter around the cutting lumen. In some examples, the degree with which the cutting edge surrounds the cutting lumen may be characterized by the degree or percentage of the perimeter that the cutting edge occupies with respect to the cutting lumen. The degree may be about 5 degrees, about 10 degrees, about 15 degrees, about 20 degrees, about 25 degrees, about 30 degrees, about 35 degrees, about 45 degrees, about 60 degrees, about 75 degrees, about 90 degrees, about 105 degrees, about 120 degrees, about 135 degrees, about 150 degrees, about 165 degrees, about 180 degrees, about 195 degrees, about 210 degrees, about 225 degrees, about 240 degrees, about 255 degrees, about 270 degrees or about 285 degrees about 300 degrees, about 315 degrees, about 330 degrees, about 345 degrees, about 360 degrees or greater (e.g. spiral variations about 450 degrees, about 540 degrees, about 630 degrees or about 720 degrees or more, as measured from the center of the cutting lumen, cutting element, or other relative location. In other variations, the configuration of the cutting edge may be in a range of any two of the above configurations. The percentage may be about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 100%, about 125%, about 150%, about 175%, or about 200% or greater. In other variations, the configuration of the cutting edge may be in a range of any two of the above degree or percentage configurations. In some instances, a larger cutting edge configuration may permit cutting across a larger range of deployment positions when used with an expandable or variable diameter cutting instrument.

FIGS. 42A to 42G depict another example of a cutting element 4200, comprising a cutting edge 4202 with a sloped surface 4204 that leads into a cutting lumen 4206 which is also used to attach the cutting element 4200 to the cable or support element of the cutting instrument. In the example depicted in FIG. 42A, the cutting edge 4202 surrounds the cutting lumen 4206 and has a configuration that occupies about 135 degrees of the perimeter of the cutting lumen 4206. When attached to the cutting instrument, the cutting edge 4202 will generally lie in a plane that may also be generally co-planar with the rotational axis of the cutting instrument, but in other variations, the plane of the cutting edge 4202 may be angled with respect the plane of the rotational axis. This angle may be positive (e.g. facing radially inward) or negative (e.g. facing radially outward) at an angle of about 5%, about 10%, about 15%, about 20%, about 25%, about 30%, about 35%, about 40%, about 45% or greater. Where the cutting lumen 4206 is also used as an attachment site of the cutting element 4200, the cross-sectional area of the cable or support structure may occupy less than about 75%, about 60%, about 50%, about 40%, about 30%, about 20%, or about 10% or less than cross-sectional area of the cutting lumen. The cable or support structure may be welded, glued or otherwise attached anywhere along the internal surface 4208 of the cutting lumen 4206, including but not limited to the attachment site 4210 of the internal surface 4208 that is opposite the cutting edge 4202.

Figure 42A:
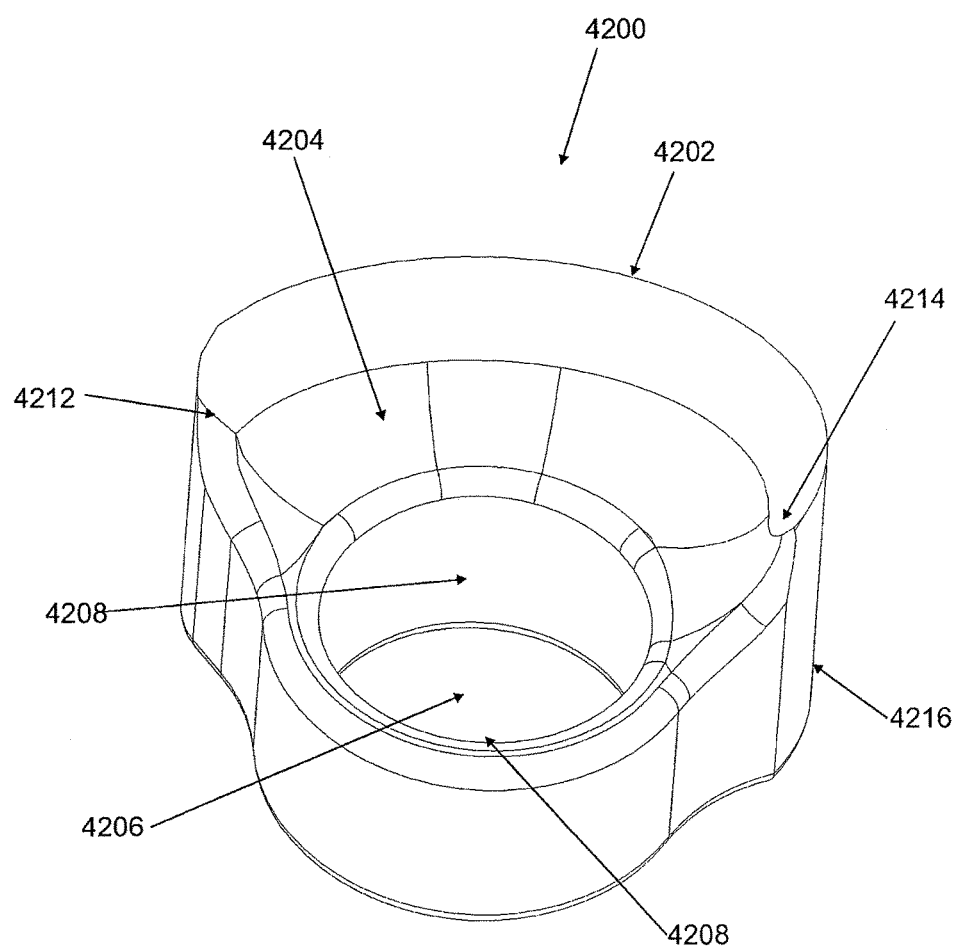
FIGS. 42A to 42C are various perspective views of cutting element with an arcuate cutting edge.
Figure 42B:
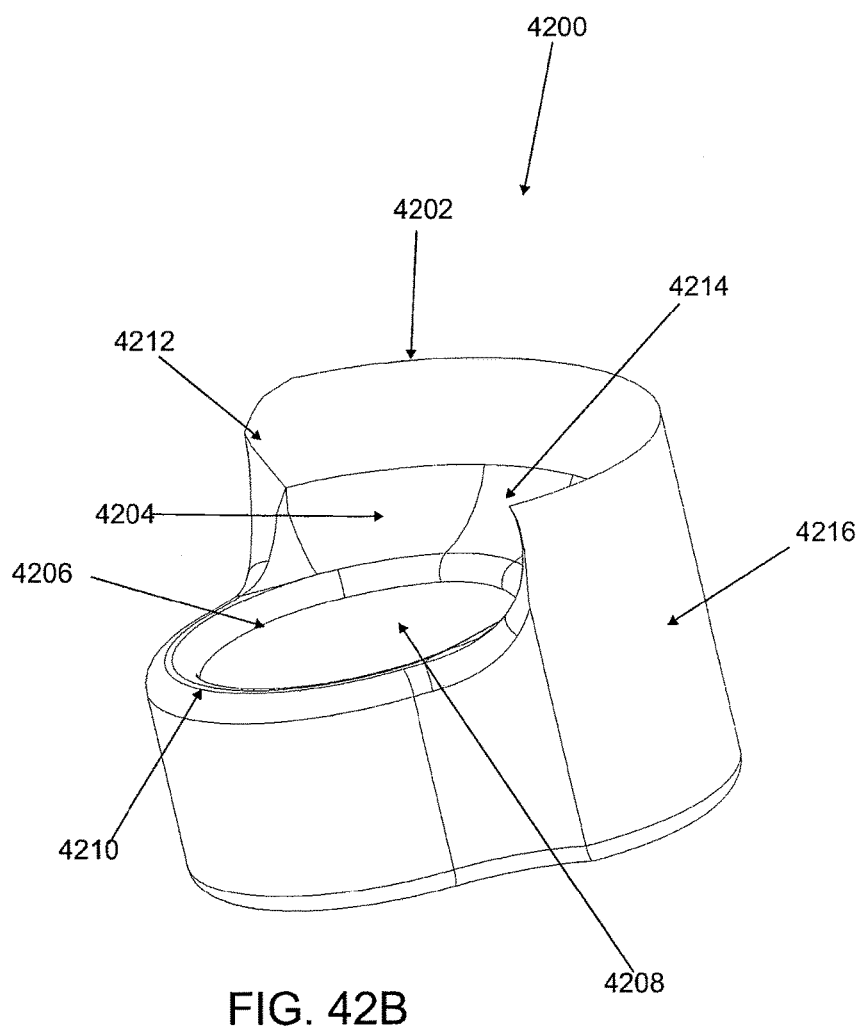
Figure 42C:
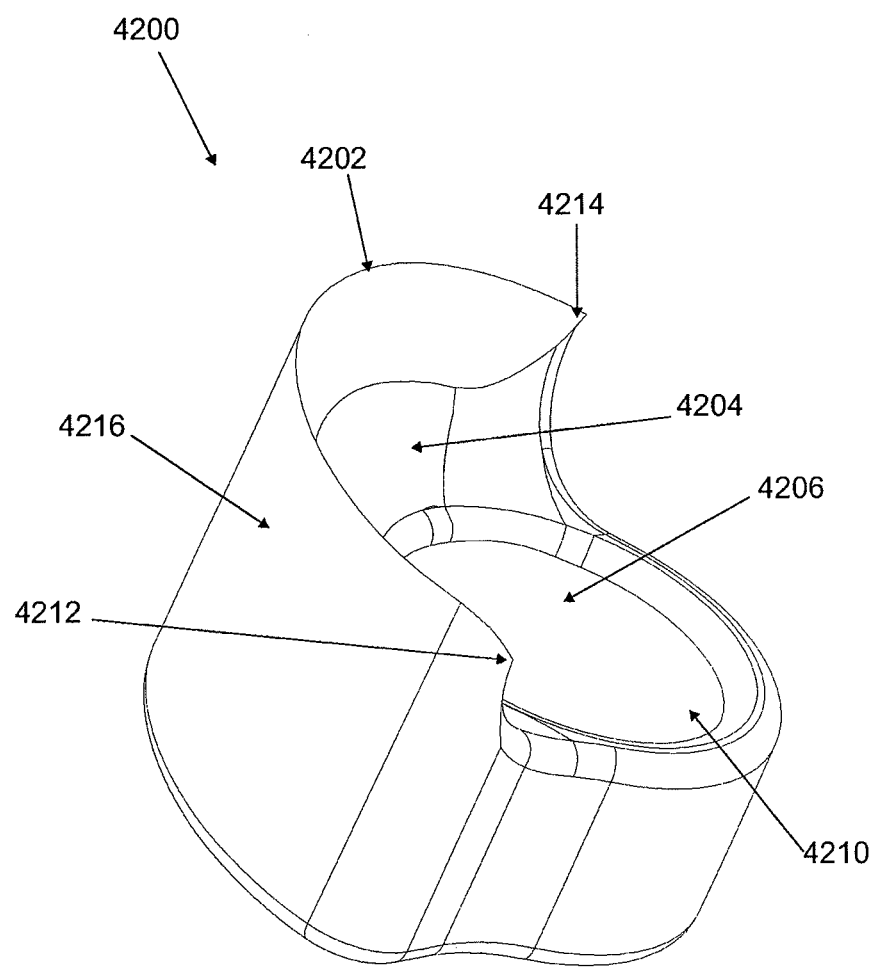
Figure 43A:
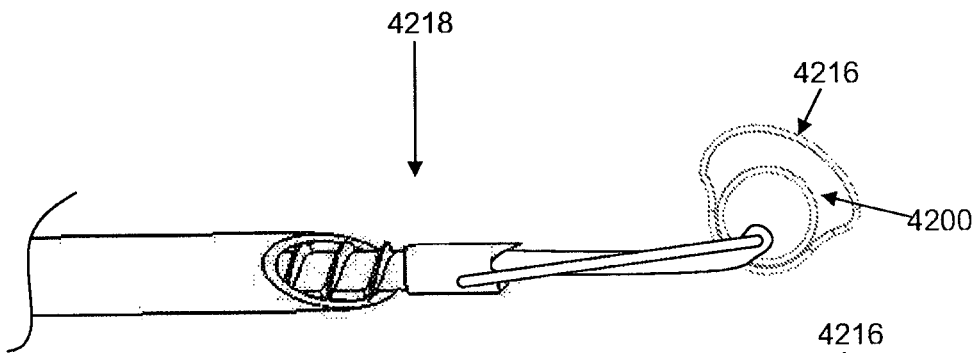
FIGS. 43A to 43C are schematic views of the cutting element of FIGS. 42A to 42G at different deployment positions of the cutting instrument.
Figure 43B:
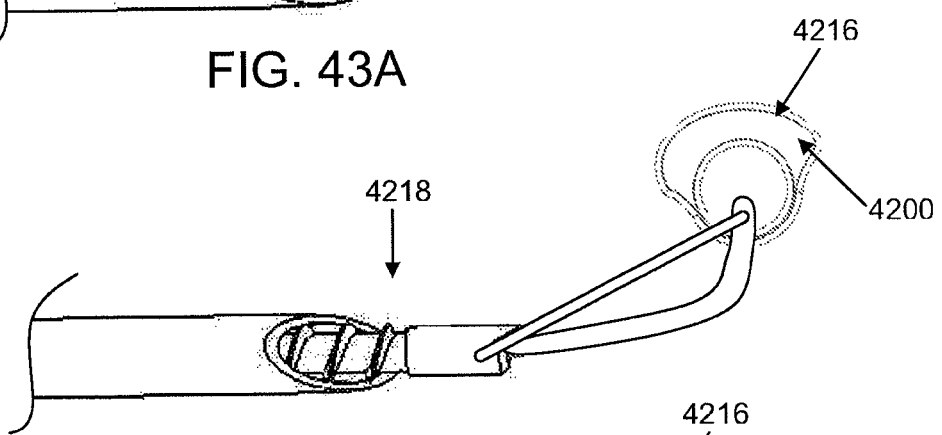
Figure 43C:
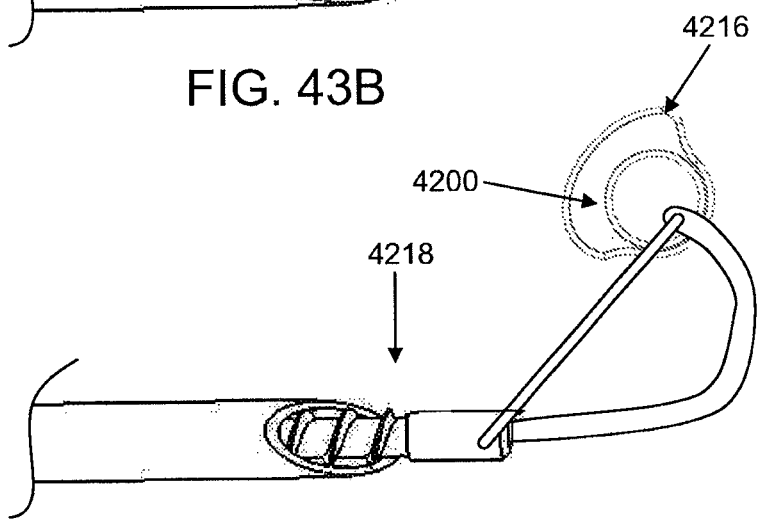
Figure 44A:
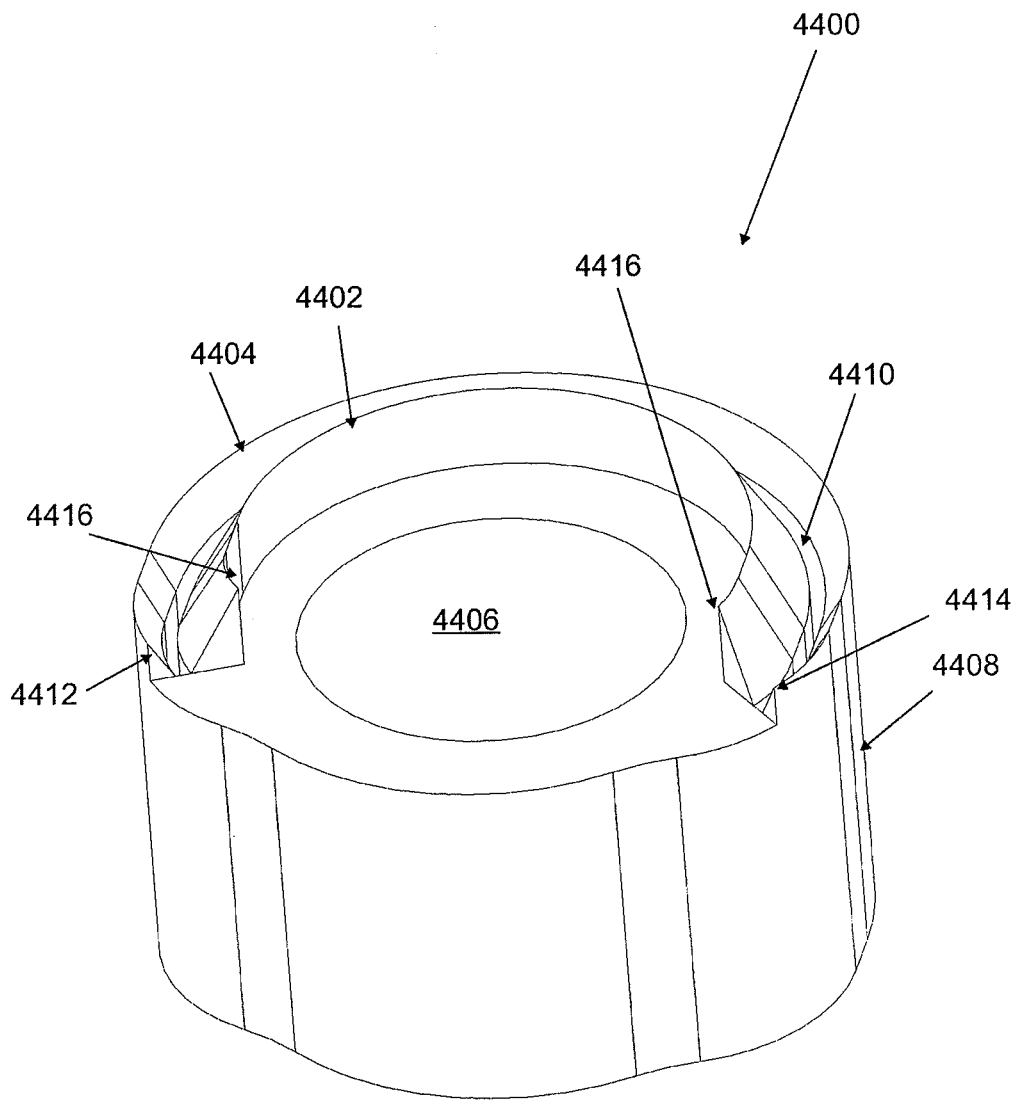
FIGS. 44A to 44C are various perspective views of another cutting element with multiple arcuate cutting edges.
Figure 44B:
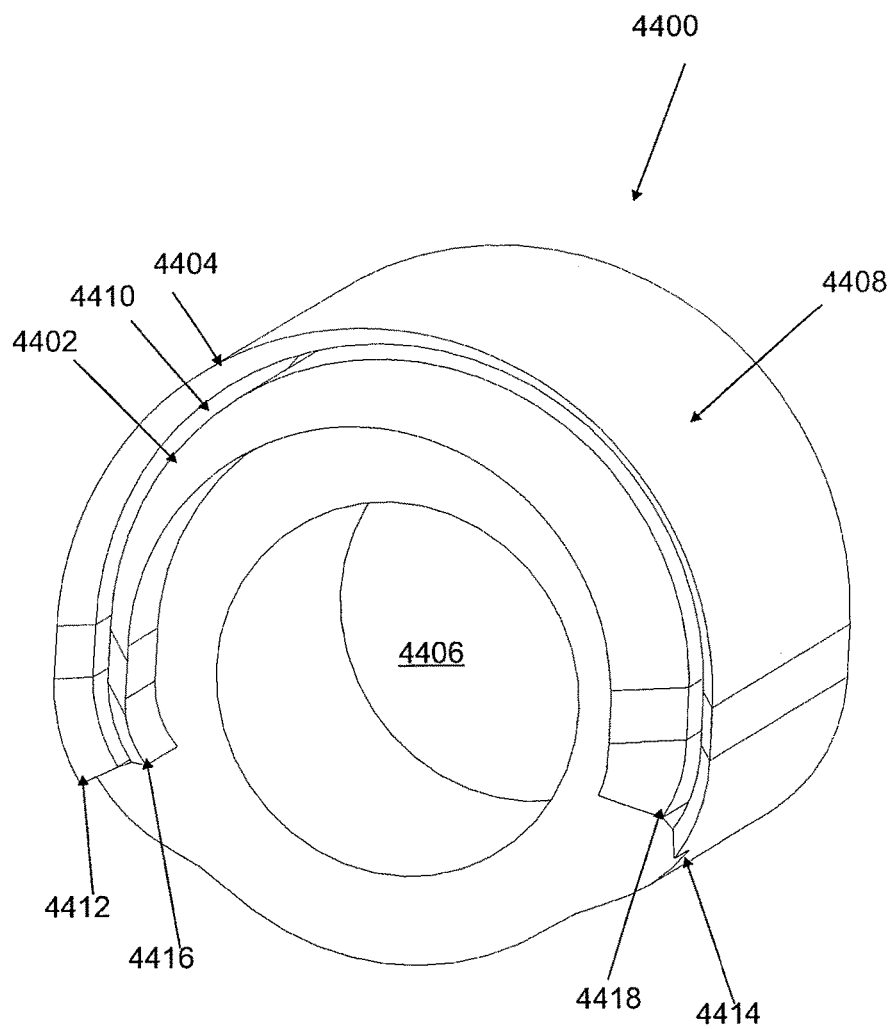
Figure 44C:
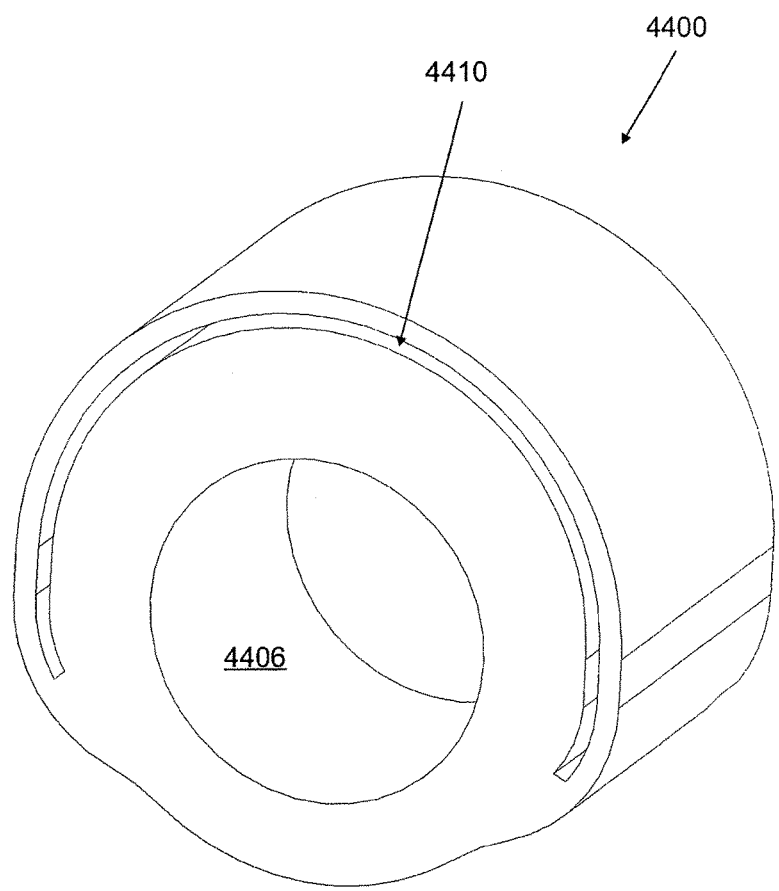

In some variations, the cutting edge 4202 may have a generally symmetrical configuration, but in other variations, as noted between FIGS. 42B and 42C, the ends 4212 and 4214 of the cutting edge 4202 may be asymmetrical. In the particular example illustrated in FIGS. 42B and 42C, when the cutting element 4200 is configured with respect to the cutting instrument to have a rounded distal end 4212 and an angled proximal end 4214. In other variations, the other configurations of the ends may be provided, or the angled/rounded relationship may be reversed. In some instances, a rounded distal end may reduce the risk or incidence of the edge 4212 catching on a tissue surface and stopping the rotational motion. The rounded or arched outer surface 4216 of the cutting element 4200 may facilitate maintaining a similar cutting behavior of the cutting element 4200 across a range of deployment positions, as depicted in FIGS. 43A.

FIGS. 46A to 46D depict another example of a cutting element 4600, comprising a cutting edge 4602 with a recessed sloped surface 4606 that leads into a cutting lumen 4604 which is also used to attach the cutting element 4600 to the flexible or support element of the tissue-removal device. The cutting edge 4602 protrudes from the cutting element 4600 while the recessed sloped surface 4606 is set towards the inside of the cutting element. The recessed sloped surface 4606 may allow the cutting element 4600 to penetrate more deeply into tissue and may increase the volume of tissue that is removed as the cutting element is rotated. The radius of curvature of the recessed sloped surface 4606 may from about 0.01 inch to about 0.02 inch, e.g., 0.016 inch. The flexible and/or support elements may be threaded through the cutting lumen 4604, or may be attached to a portion of the cutting lumen 4604 by soldering, gluing, brazing, welding, or the like. The cutting lumen 4604 may have a diameter of about 0.04 inch to about 0.05 inch, e.g., 0.0465 inch. The cutting element 4600 may have one or more curved surfaces, for example, a curved contour 4608, depicted in the side view of FIG. 46C. The curved contour 4608 may have a radius of about 0.025 inch to about 0.04 inch, e.g., 0.036 inch. The cutting element may have a dimension e.g., depth, D5, a dimension D6, e.g., height, and a dimension D7, e.g., width. The dimension D5 may be from about 0.05 inch to about 0.07 inch, e.g., 0.06 inch. The dimension D6 may be generally the same as the dimension D5, or somewhat larger, e.g., may be from about 0.051 inch to about 0.071 inch, or 0.062 inch. In some variations, the ratio between the dimension D5 and the dimension D6 may be about 0.9 to about 1.1, e.g., 0.97. The dimension D7 may be from about 0.060 inch to about 0.07 inch.

Another variation of a cutting element is depicted in FIGS. 47A to 47D. The cutting element 4700 may comprise a cutting edge 4702 that is bordered on the interior side by a rounded groove 4706 that at least partially circumscribes a cutting lumen 4704. The rounded groove 4706 may have a radius of curvature of about 0.01 inch to about 0.02 inch, e.g., 0.016 inch. As described previously, the cutting lumen 4704 may be sized and shaped to accommodate a flexible and/or support element therethrough. The cutting lumen 4704 may have a diameter from about 0.03 inch to about 0.05 inch, e.g., 0.046 inch. The cutting element 4700 may also have a curved contour 4708, illustrated in the side view in FIG. 47C. The curved contour 4708 may have a radius of curvature of about 0.016 inch. The cutting element may have a dimension D8, e.g., depth, a dimension D9, e.g., height, a dimension D10, e.g., width, and a dimension D11, e.g., depth of the curved contour 4708. The dimension D8 may be from about 0.03 inch to about 0.05 inch, e.g., 0.04 inch. The dimension D9 may be from about 0.05 inch to about 0.07 inch, e.g., 0.062 inch. The ratio of the dimension D8 to D9 may be about 0.6 to about 0.7, e.g., 0.65. Adjusting this ratio may affect the penetration depth of the cutting element 4700 as it is rotated The dimension D10 may be from about 0.055 inch to about 0.07 inch, e.g., 0.064 inch. The dimension D11 may be from about 0.01 inch to about 0.02 inch, e.g., 0.016 inch. The surface curvature, overall shape, and various dimensions of the cutting elements may be adjusted to accommodate the geometry and material properties of vertebral tissue and/or end plates.

Figure 48A:
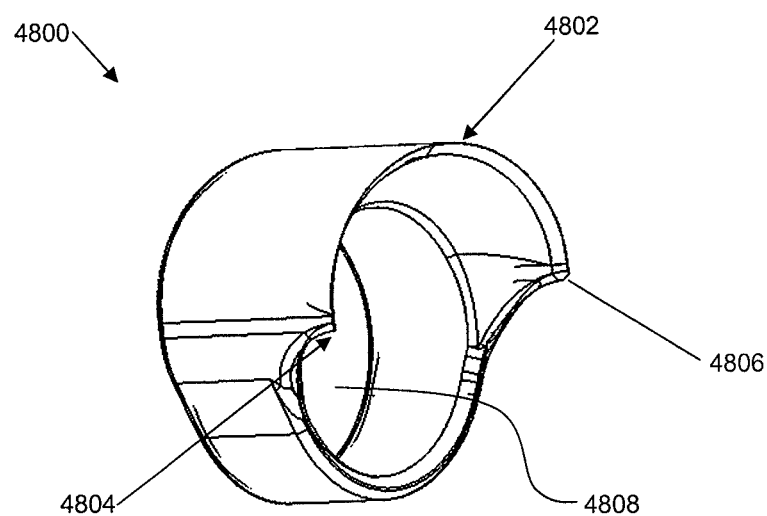
FIGS. 48A to 48B depict cutting elements with various cutting lumen geometries.

Another variation of a cutting element is depicted in FIG. 48A. The cutting element 4800 may comprise a cutting edge 4802 that has an angled distal end 4804 and an angled proximal end 4806 that at least partially circumscribes a cutting lumen 4808. For example, the cutting edge 4802 may be a rounded or arched shape that borders about 30% to about 50% of the perimeter of the cutting lumen 4808. The angled ends 4804 and 4806 of the cutting edge 4802 may meet at an angle from about 45 degrees to about 180 degrees, sometimes about 60 degrees to about 150 degrees, and other times about 75 degrees to about 120 degrees, and still other times about 90 degrees, as generally depicted in FIG. 48A. The angled ends 4804 and 4806 may also be angled towards the center of the cutting lumen 4808, which may help to direct pulverized tissue into the cutting lumen. Directing the pulverized tissue through the cutting lumen 4808 may help prevent the cutting element 4800 from becoming lodged and/or immobilized into a tissue mass. As described previously, the cutting lumen 4808 may be sized and shaped to accommodate the attachment of a flexible and/or support element therethrough. For example, the cutting lumen may have a circular or rounded geometry, a variable, tapered or uniform cross-sectional area, or any configuration that so that the cutting lumen may act as an attachment site for a extendable and/or support element.

Figure 48B:
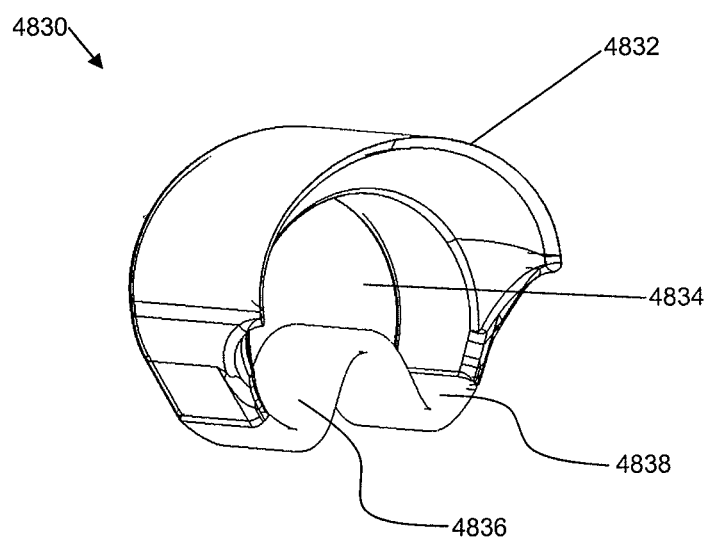

One example of a cutting element with a cutting lumen that is shaped for retaining an extendable element and a support element is illustrated in FIG. 48B. The cutting element 4830 may comprise a cutting edge 4832 that is substantially similar to the cutting edge 4802 described above. The cutting element 4830 may also comprise a cutting lumen 4834 that has a rounded lobed geometry. A cutting lumen may have one or more lobes that are suitable for accommodating and positioning flexible and/or support elements therethrough, so that the flexible and/or support elements retain their position within the cutting lumen. The cutting lumen 4834 may have a first distal lobe 4836 and a second proximal lobe 4838. The first distal lobe 4836 and the second distal lobe 4838 may be the same size, and symmetrically arranged in the cutting lumen 4834. In some variations, this non-circular configuration provides a greater surface area of the cutting element 4830 for fixation of the extendable and/or support elements. In other variations, the cutting lumen lobes may be sized differently and may be asymmetrically arranged, as appropriate for the size and arrangement of the extendable element and/or support element.

FIGS. 44A to 44G illustrate another embodiment of a cutting element 4400 comprising multiple cutting edges, including an inner cutting edge 4402 and an outer cutting edge 4404 located on the same side of a central cutting lumen 4406. In some variations, cutting elements with multiple cutting edges may redistribute forces acting along the cutting edges to reduce peak cutting forces that may reduce deep penetration of the cutting edges that may disrupt or stop the rotational motion of the cutting instrument. This cutting element 4400 also comprises a curved or arched outer surface 4408 that maintains a similar cutting edge orientation across a range of deployment positions. As depicted best in FIG. 44E, the inner cutting edge 4402 protrudes farther than the outer cutting edge 4404 with respect to the leading face of the cutting element 4400, but in other variations, the inner and outer cutting edges may have the same position, or the outer cutting edge may protrude farther than the inner cutting edge. In still other variations, the cutting edges may have a variable protrusion configuration along the arcuate length of one or more cutting edges. In addition to multiple cutting edges, the cutting element 4400 in FIGS. 44A to 44G further comprises a peripheral cutting lumen 4410 located between the inner and outer cutting edges 4402, 4404. Here, the peripheral cutting lumen 4410 comprises an arcuate, reduced height lumen, but in other examples, the peripheral cutting lumen may be tapered and/or flared, or have a greater height. In some instances, the outer cutting lumen 4410 permits passage of fluid that may reduce the resulting rotational resistance of the cutting element. In other examples, the outer cutting lumen 4410 may be configured with a cross-sectional shape and size that permits passage of tissue. In this particular embodiment, the ends 4412, 4414, 4416 4418 of the respective cutting edges 4402 and 4404 have similar relative configurations with respect to the central cutting lumen 4406, but in other variations, the cutting edges may have different lengths and/or different relative locations with respect to the central cutting lumen 4406. Although the cutting edges 4402 and 4404 are also shown with similar curvatures but with different radii, in other examples, the curvatures may be different and may also have a curvilinear or angled configuration. Although the outer cutting edge 4404 in FIGS. 44A to 44G is located along the arched outer surface 4408 of the cutting element 4400, in other variations the outer cutting edge may be spaced inwardly away from the arched outer surface 4408. Also, the angle of the inner and outer slope faces of each cutting edge may vary from about 0 degrees to about 90 degrees or more, including about 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115 or 120 degrees or greater, and may or may not be the same along the length of the cutting edge.

In other variations, a cutting element with multiple cutting edges may not comprise a cutting lumen between any two edges and instead, a groove or recess is provided. To facilitate separation of cut tissue from the cutting element, the cutting edges and/or grooves may be configured so that the cut tissue located between the cutting edges is swept out of the grooves. Such configurations may include cutting edges and/or grooves that sweep backwards from the leading face of the cutting element toward the trailing face of the cutting element. In some variations, both the cutting edges and the grooves have a sweep configuration, but in other variations, for example, only the grooves have a sweep configuration. The sweep configuration may also facilitate transport of cut tissue toward the auger element of the cutting instrument that transports the tissue out of the body.

Figure 35:
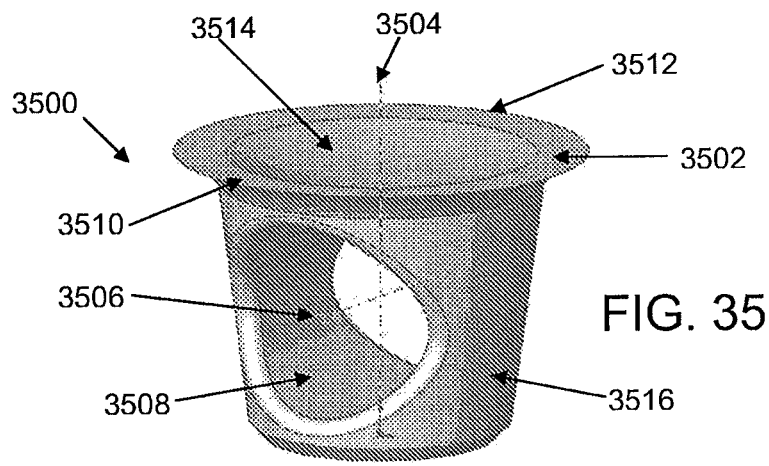
FIG. 35 depicts a low-profile cutting element with a circular cutting edge with a recessed outer surface.

FIG. 35 depicts another embodiment of a cutting element 3500, comprising a cutting blade 3502 having a planar configuration that is generally perpendicular to the radial axis 3504 of the device and facing the radially outward direction. In other examples, the blade 3502 may comprise a non-planar configuration, and/or may have a skewed angle with respect to radial axis 3504 or to the longitudinal axis 5900, if any, of the attachment lumen 3508. The non-planar configuration may comprise a cut cylindrical or ovoid shape, for example. The cutting blade 3502 may comprise a circular configuration as illustrated in FIG. 35, or may comprise any of a variety of other configurations, including an oval, square, rectangular, triangular, star, polygonal or other shape. The blade 3502 may be form a complete perimeter of the cutting element 3500 as depicted in FIG. 35, a partial perimeter of the cutting element or a plurality of blades around the cutting element. Rather than the zero degree angle with respect to the leading edge 3510 of the cutting element 3500, the cutting blade may alternatively have an angled orientation from the leading edge 3510 to the trailing edge 3512 that is about 5, 10, 15, 20, 25, 30, 35, 40, 45, 50, 55, 60, 65, 70, 75 degrees or greater, or in the range between any two of the angles. In still further examples, the cutting blade 3502 may also comprise an angled orientation with respect to the distal to proximal sections of the blade that is about 5, 10, 15, 20, 25, 30, 35, 40, 45, 50, 55, 60, 65, 70, 75 degrees or greater, or in the range between any two of the angles. As shown in FIG. 35, no cutting lumen is provided but the inner region of the cutting blade 3502 may comprise a recess 3514, which may reduce friction or drag as the cutting element 3500 is rotated or passed along tissue. In other examples, such as the cutting element 3700 in FIG. 37, the inner region of the cutting blade 3702 may comprise a planar surface 3704 or bulge surface in the radially outward direction. The attachment structure 3516 may have a generally frusto-conical shape as depicted, but in other variations may be cylindrical, rectangular block shaped, ring-shaped, or other suitable shapes.

Figure 36:
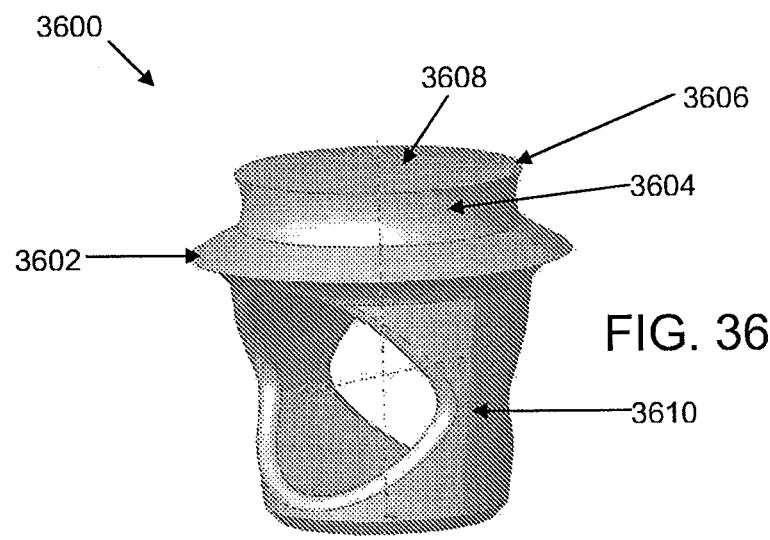
FIG. 36 depicts a low-profile cutting element with a circular cutting edge and an outer toroidal cutting head.
Figure 37:
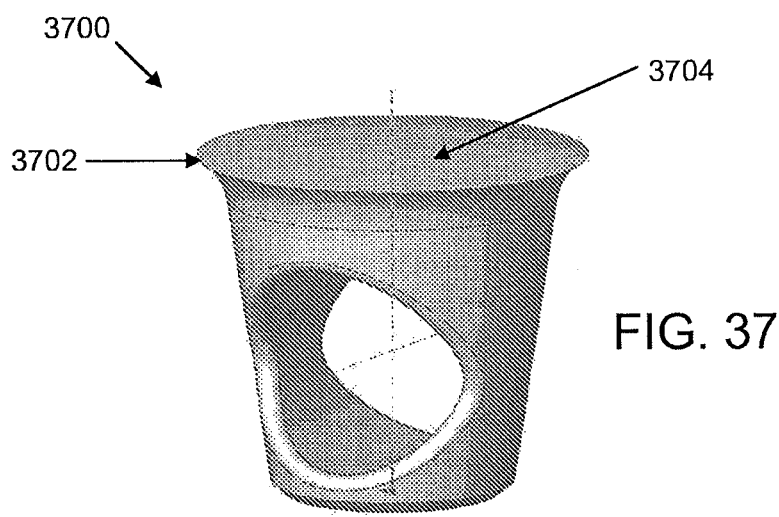
FIG. 37 depicts a low-profile cutting element with a circular cutting edge and a planar outer surface.
Figure 38:
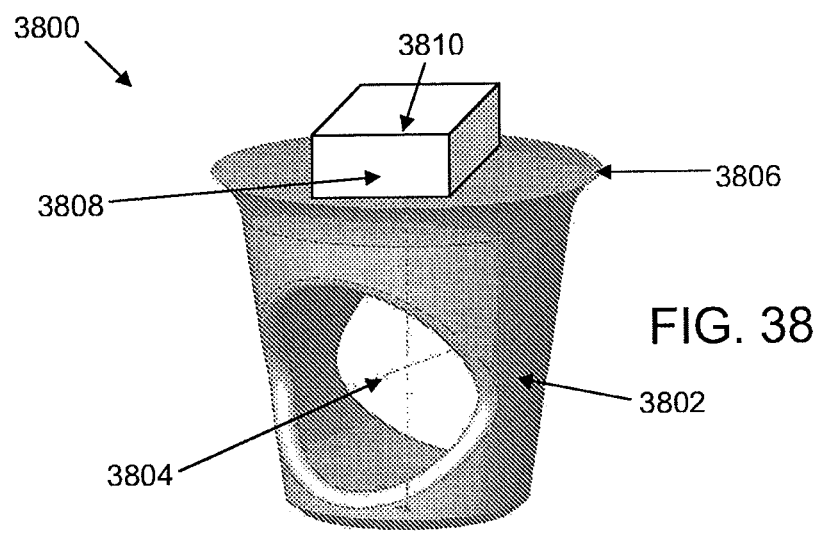
FIG. 38 depicts a low-profile spherical cutting element with a plurality of circular cutting edges.

FIG. 36 depicts another example wherein the cutting element 3600 comprises a circular cutting blade 3602 wherein the inner region of the blade 3602 comprises a radially outward structure or projection 3604 with a second cutting blade or edge 3606 along its radially outward surface 3608. Here, the projection 3604 has a smaller perimeter than the largest perimeter of the attachment structure 3608, but in other examples, the projection 3604 may have the same or a larger perimeter than the attachment structure 3610. The projection 3604 may comprise any of a variety of shapes, including but not limited the toroidal configuration depicted in FIG. 36, a cylindrical shape, a frusto-conical shape, a rectangular or square block, a triangular or other polygonal block, or other shape. The second cutting edge 3606 may have any of a variety of configurations, including but not limited to circular, oval, square, rectangular, triangular, star, polygonal or other configuration. The shape of the second cutting edge 3606 may be the same or different shape than the cross-sectional shape of the projection 3604. FIG. 38 depicts another example of a cutting element 3800 with generally frusto-conical attachment structure 3802 with an attachment lumen 3804, a circular cutting blade 3806, and a second structure 3808 with a square cross-sectional shape with non-projecting edges 3810 that act as additional cutting edges.

Figure 39:
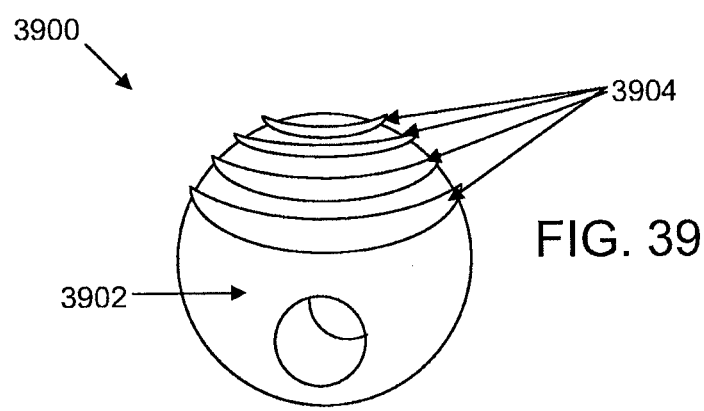
FIG. 39 depicts a low-profile cutting element with a circular cutting edge and a cutting block on the outer surface.

FIG. 39 depicts still another example of a cutting element 3900 comprising a generally spherical structure 3902 with a plurality of circular blades 3904 of different diameters along the radially outward portion of the cutting element 3900. As noted in other examples, although the blades depicted in FIG. 39 form a complete perimeter around the spherical structure, in other examples arcuate blades or other partial blade structures may be provided. Also, although the relative spacing and/or orientation of each blade 3904 may be constant and generally parallel as shown in FIG. 39, other examples, the spacing may vary and/or the orientations of the blades may be skewed or intersecting.

Figure 40:
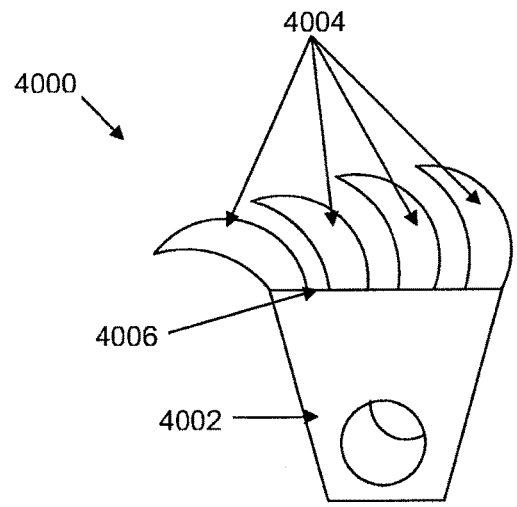
FIG. 40 depicts a cutting element with a multi-prong claw configuration.
Figure 48C:
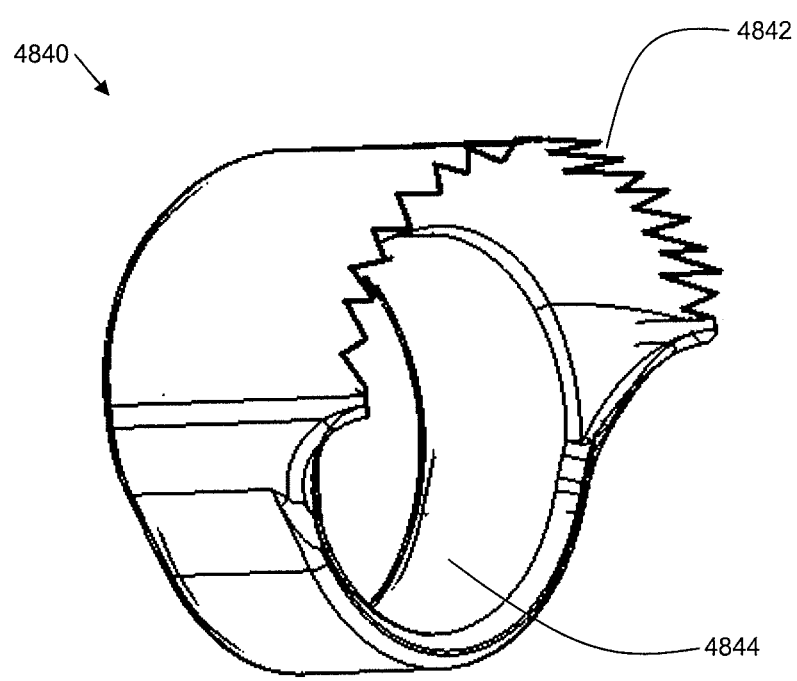
FIG. 48C is a perspective view of a cutting element with a serrated edge.

FIG. 40 depicts an example of a cutting element 4000 with an attachment structure 4002 with frusto-conical configuration and a plurality of curved cutting blades 4004 projecting from its radially outward surface 4006. Each blade 4004 may have the same or different size, orientation or configuration, including variable curvature. Cutting elements may also have one or more serrated cutting edges, such as the cutting element 4840 depicted in FIG. 48C. The cutting element 4840 comprises a serrated cutting edge 4842 located above a cutting lumen 4844. While the serrated cutting edge is shown to be on an upper edge of the cutting element 4840, it should be understood that any edge(s) of a cutting element may be serrated.

Figure 41:
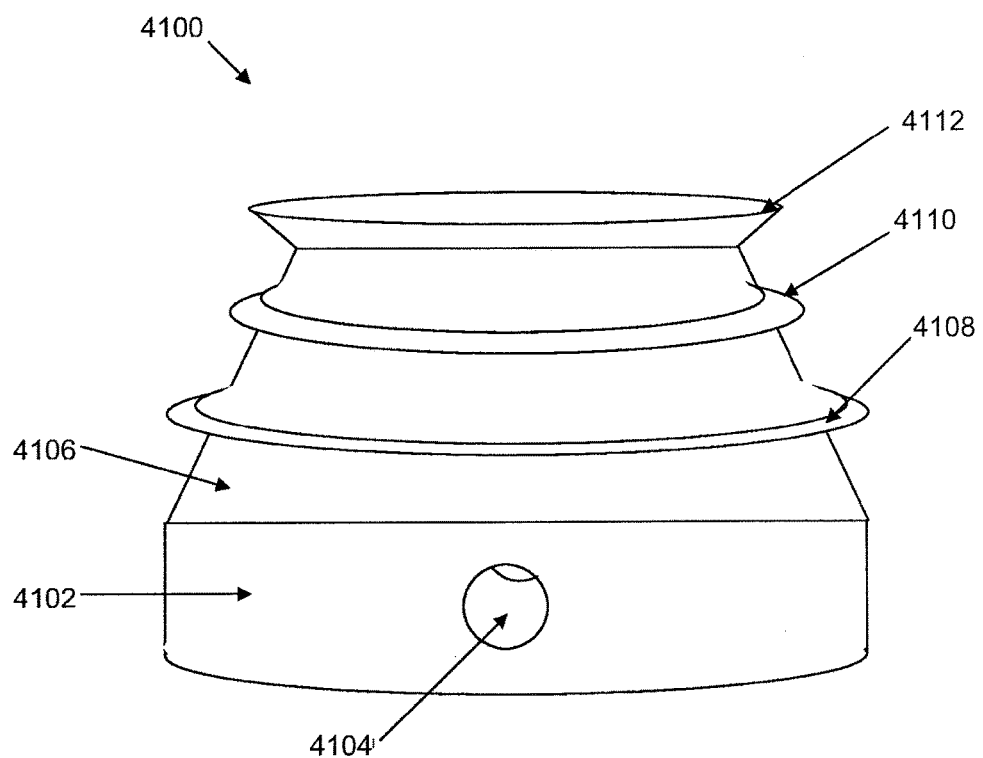
FIG. 41 depicts a multi-ring cutting element with an outwardly tapering configuration.

FIG. 41 depicts another example of a cutting element 4100 comprising a generally cylindrical attachment structure 4102 with an attachment lumen 4104, and further comprising a frusto-conical cutting structure 4106 with a plurality of circular cutting blades 4106, 4108 and 4110, wherein the cutting structure 4104 tapers in the radially outward direction and wherein the cutting blades 4108, 4110, and 4112 have a serially reduced diameter or perimeter in the radially outward direction, respectively. In other examples, however, either the cutting structure and/or the cutting blades may be configured with tapers or reduced diameters/perimeters in the radially inward direction.

Various embodiments of the tissue removal device with an extendable element may be used in a variety of medical procedures. As one specific example, a device with its extendable element made from a material that has lower flexural modulus than vertebral endplates, may be selected to be used in discectomy to remove herniated disc materials. Due to the difference in the flexural modulus, the extendable element may deform when in contact with rigid endplate tissues, therefore differentiating soft disc tissues from the bony endplates. In some embodiments, an extendable element tissue removal device whose maximum sweep diameter is about the same as the disc height may be used in discectomy to maximize the amount of herniated disc removed but minimize contact pressure on the endplates to avoid injury to the endplates.

In some embodiments, an extendable element tissue removal device may be used to remove cartilaginous endplates in interbody fusion. In such applications, the extendable element and/or the support element of the device may be made from multifilament cables with the filament comprised of metal, metal alloys or other high strength materials. Such a device may differentiate cartilaginous endplates from the harder vertebral bones underneath, therefore avoiding the impact forces and stresses imparted from the bone materials, which may cause breakage and undesired plastic deformation of the extendable element and/or the support element. In some embodiments, the surface of the entire or a portion of the extendable element may be gritted to enhance its cutting capacity. In other embodiments, a cutting mechanism may be attached to the intersection of the extendable element and the support element, as illustrated in FIG. 27 to facilitate cutting. When used in interbody fusion, a tissue removal device may comprise a maximum sweep diameter slighter larger than the disc height such that the distal most region of the device may reach out to the endplates. When an additional cutting structure, such as blades or serrations, is used to facilitate cutting, the dimension of the cutting structure's lateral projection may be similar the depth of the vertebral endplates to increase the amount of the endplates removed. In some examples, the lateral projection distance does not extend beyond endplate, which may reduce or avoid damage to the underlying bone.

Figure 51:
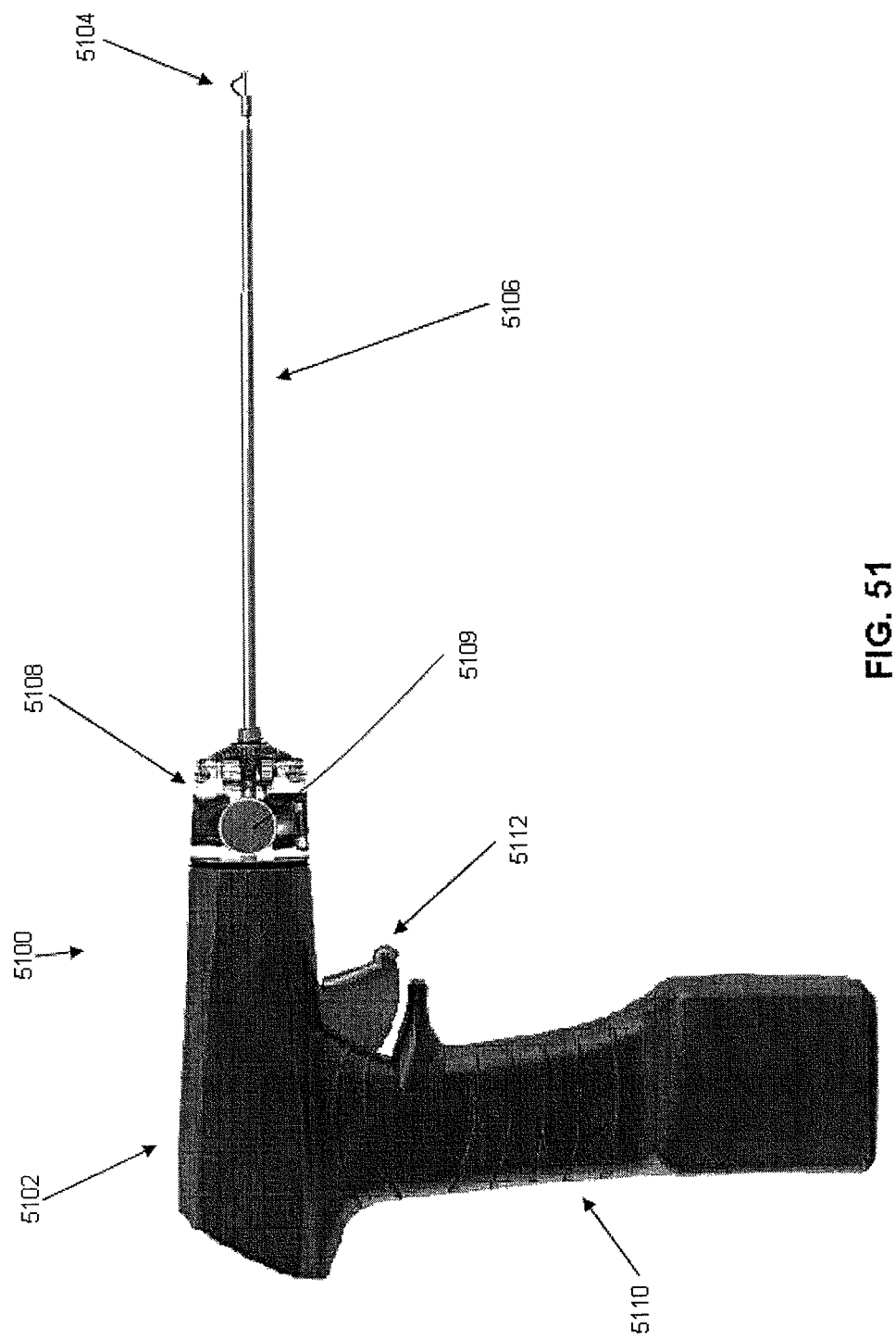
FIG. 51 illustrates one variation of a tissue-removal device comprising a handle portion, a shaft, and a tissue-removal assembly.

One variation of a device that may be used for surgical and/or percutaneous spinal procedures, e.g., interbody fusion procedures, is depicted in FIG. 51. The tissue-removal device 5100 may comprise a proximal handle portion 5102 and a distal tissue-removal assembly 5104 connected to the handle portion 5102 by a shaft 5106 with a longitudinal lumen therethrough. Optionally, the shaft 5106 may have an endoscope port or lumen for visualizing tissue during the procedure. In some variations, the shaft 5106 may be straight, or may have one or more pre-shaped curves or angles. The handle portion 5102 may comprise a gripping portion 5110 that has an ergonomic shape that is suitable for a one-handed grip. The handle portion 5102 may also comprise one or more control features, such as rocker-type switches, knobs, dials, levers, sliders, etc. that actuate, navigate, or otherwise regulate the use of the tissue-removal device. For example, the handle portion 5102 comprises a lever 5112 that may be used to actuate the components of the tissue-removal assembly 5104, and may additionally comprise a power switch, as well as a mechanism for navigating the tissue-removal assembly 5104. In some variations, the navigation and movement of the tissue-removal device 5100 may be constrained or restricted by a travel limiter. A travel limiter may be included with the tissue-removal device 5100, for example, at a location along the length of shaft 5106 distal to the collection chamber 5108. In certain variations, a travel limiter may be a separate device that is used in concert with the tissue-removal device 5100. Different variations of travel limiters will be described below.

The tissue removal device 3500 may also comprise an optically transparent chamber, as generally described previously for other embodiments. For example, as depicted in FIG. 51, the handle portion 5102 may comprise a collection chamber 5108 which may be in fluid connection with the tissue-removal assembly 5104 through a lumen of the shaft 5106. Tissue that is removed (e.g., pulverized, cut, scraped, dissected, etc.) and/or fluids by the tissue-removal assembly may be transported by a tissue transport assembly through the shaft 5106 to the collection chamber 5108, one variation of which has been described above, and additional variations will be described below. Alternatively or additionally, a vacuum source may be used to draw tissue and/or fluid from the target tissue site to the collector. Some tissue-removal devices may have a plurality of collection chambers, where some of the collection chambers may be used as a fluid reservoir for tissue infusion, and some of the collection chambers may be used to store tissue samples removed by the tissue-removal assembly. The one or more collection chambers may be located at a distal portion of the handle portion 5102, as illustrated in FIG. 51, or may be located within the housing of the handle portion 5102. The collection chamber 5108 may comprise one or more collection ports 5109 with a removable cap or plug. The collection port 5109 is shown to be circular, but may be rectangular, triangular, hexagonal, etc., as appropriate. The collection port 5109 may have a diameter from about 0.06 inch to about 0.28 inch, e.g., about 0.07 inch to about 0.25 inch. Optionally, a portion of the collection chamber 5108 may be a configured as a magnifying lens which may be used to visually inspect any collected samples. In some variations, the collection port plug or cap itself may be a magnifying lens. The collection chamber 5108 may be made of an optically transparent material, such as polycarbonate, acrylic and the like.

Figure 52A:
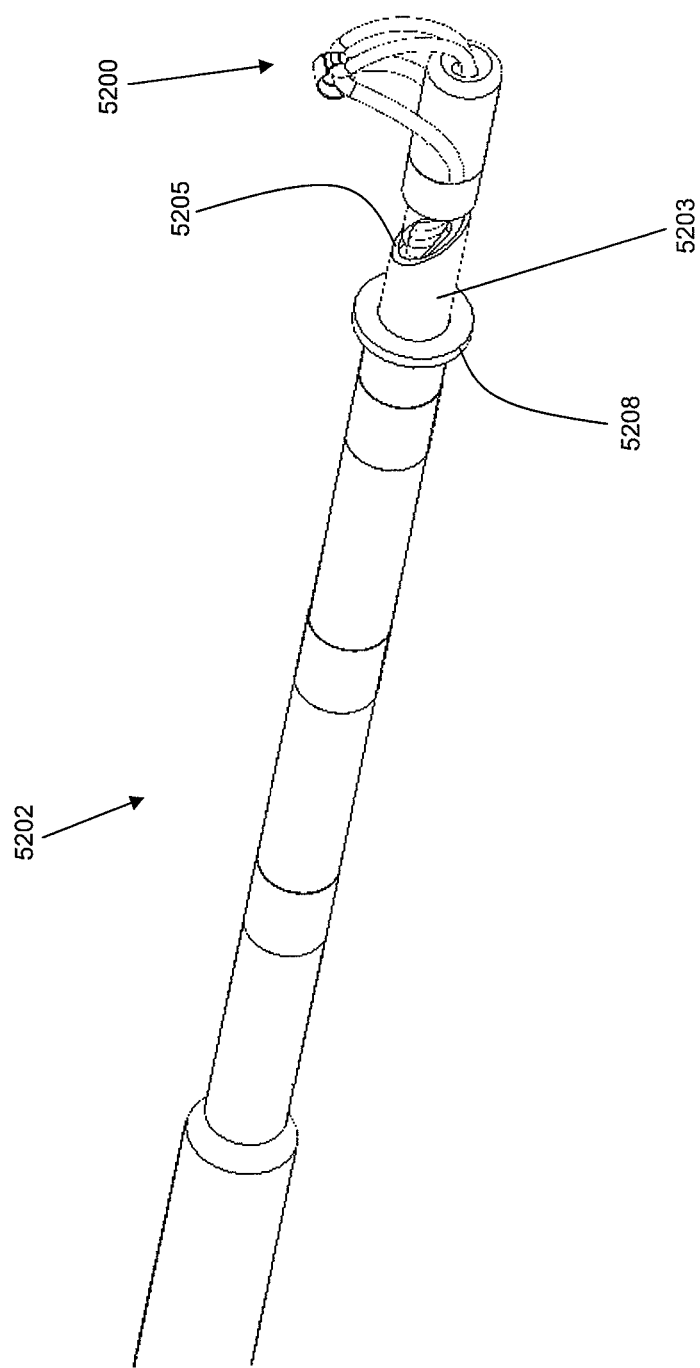
FIGS. 52A to 52F are various perspective views of one variation of a tissue-removal assembly that may be used with a tissue-removal device.

One example of a distal portion of a shaft and a tissue-removal assembly of a tissue-removal device is depicted in FIG. 52A. The distal portion of the shaft 5202 may a shaft tip 5203. In some variations, the distal portion of the shaft 5202 may comprise an insulating polymer sheath or tube that may prevent heat generated by the rotating mechanisms within the shaft to the outer portion of the shaft 5202, as such heat may thermally injure nerve tissue. The insulating sheath may be located at regions of the shaft 5202 that may have the greatest likelihood of contacting nerve tissue. For example, the insulating sheath may be located from the cutting edge 5205 of the shaft tip 5203 to about 0.5 inch to about 3 inches proximal to a shaft shoulder 5208.

The shaft tip 5203 may be similar to the distal tips of the outer tubular shafts that have been described above (e.g., FIGS. 49A to 50B). The shaft tip 5203 may have a cutting edge 5205 that may help to further break-up or cut tissue removed by the tissue-removal assembly 5200. The shaft tip 5203 may be welded, soldered, brazed, glued, and/or crimped to the distal portion 5216. Alternatively, the shaft tip 5203 may be integrally formed with the distal portion 5216. The shaft tip 5203 may be made of stainless steel (e.g., 440F SE stainless steel), and may be heat treated to RC 55-60, with a bright finish that may be passivated per ASTM-A967 standards. The outer tubular shaft may also be made of a variety of materials, such as other metallic materials (e.g., nickel titanium alloys, cobalt chromium, tungsten, etc.) and/or polymeric materials (e.g., PEEK, polyaramides, polyethylene, etc.), as appropriate.

Figure 52B:
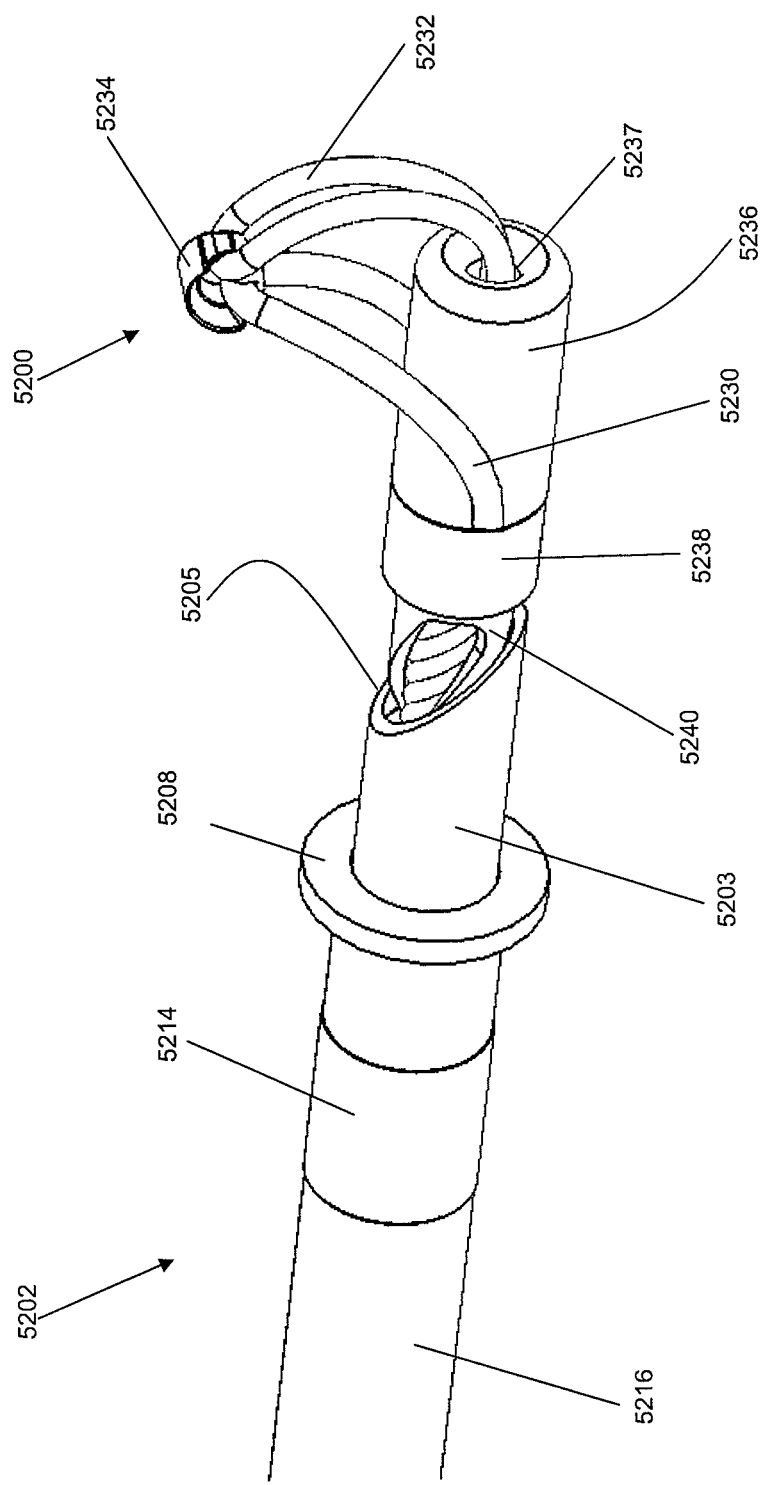

The tissue-removal assembly 5200 may extend distally from the shaft 5202 from the shaft tip 5203. The tissue-removal assembly 5200 may be any of the tissue-removal assemblies described above, as well as any of the tissue-removal assemblies described below. Another example of a tissue-removal assembly is shown in FIG. 52B. The tissue-removal assembly 5200 may comprise a looped extendable element 5232, a looped support element 5230, and a cutting element 5234 that joins the looped portions of the extendable element 5232 and the support element 5230. In this arrangement, adjusting the length and position of the extendable element 5232 adjusts the position and orientation of the cutting element 5234 and the support element 5230. In other variations, the support element 5230 may be independently adjustable from the length and position of the extendable element. There may be any number of extendable and support elements, and the extendable and/or support elements may or may not be looped through the cutting element. For example, the extendable element may not be looped through the cutting element (e.g., may be attached to the cutting element as a single strand), while the support elements are looped through the cutting element. The extendable and/or support elements may be slidably or fixedly coupled to the cutting element. The tissue-removal assembly 5200 may also comprise a distal cap 5236 from which the loops of extendable element 5232 and the support element 5230 extend, and a reinforcing ring 5238 located proximally to the distal cap 5236, configured to retain a proximal portion of the support element 5230. Optionally, a tissue transport assembly 5240 may be integrated with the tissue-removal assembly 5200 as described previously and further described below.

Figure 52C:
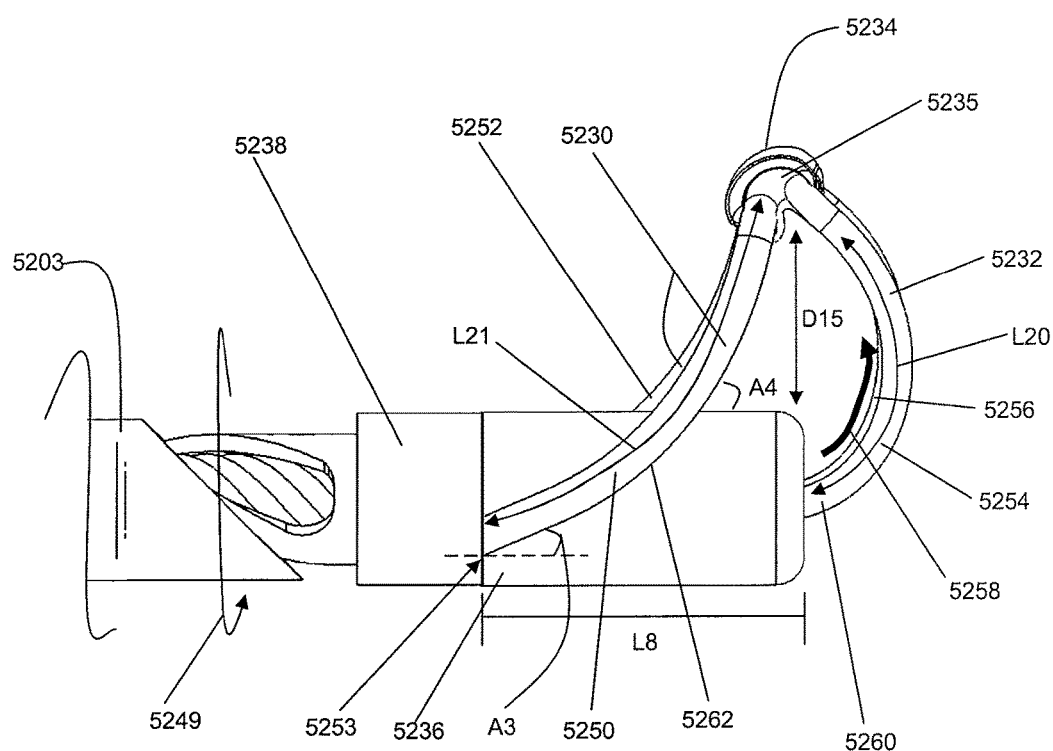
Figure 52D:
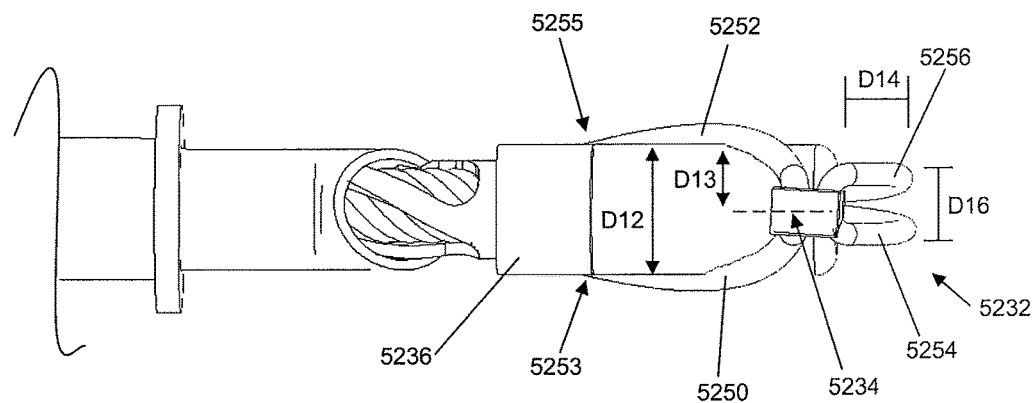
Figure 52E:
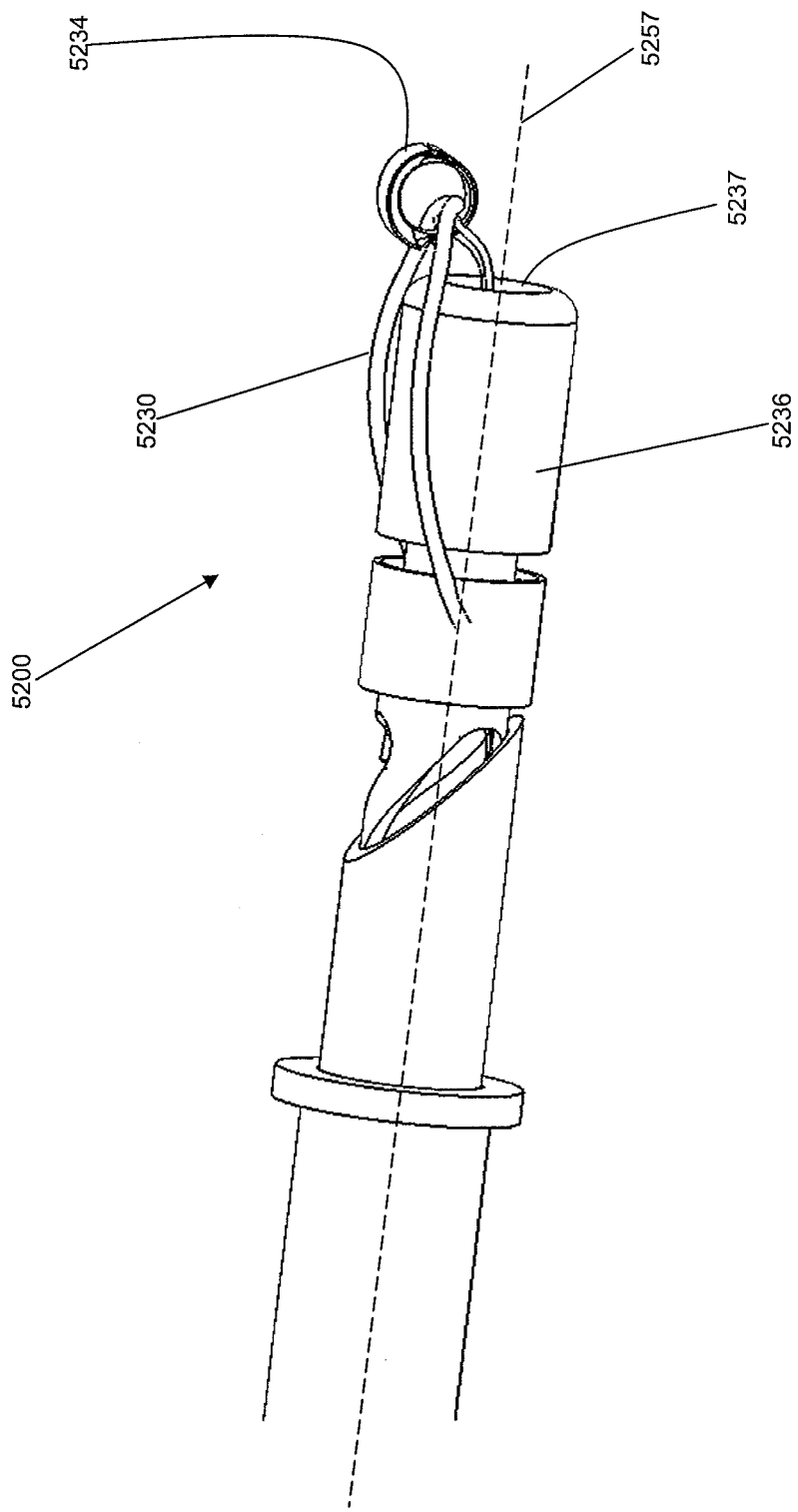

The tissue-removal assembly 5200 may have an expanded configuration, as depicted in FIGS. 52B to 52D, and a collapsed configuration depicted in FIG. 52E. In the expanded configuration, the cutting element 5234 may be displaced from the cap 5236, as illustrated in the side view of FIG. 52C. The shape and volume of the tissue region that is removed is at least partially determined by the displacement of the cutting element 5234 from the cap 5236. The location of the cutting element 5234 in the expanded configuration of the tissue-removal assembly 5200 may be determined by the length and compliance of the support element 5230 and the extendable element 5232, as well as attachment locations of the support element 5230 on the cap 5236, and the support and extendable element coupling locations on the cutting element 5234.

According to the direction of rotation 5249 that the tissue-removal assembly 5200 is configured to rotate during tissue removal, the looped support element 5230 and the looped extendable element 5232 may each have a leading segment and a trailing segment. A leading segment is the portion of the support or extendable element that first impacts tissue with respect to the direction of rotation 5249, and a trailing segment is the portion of the support or extendable element that impacts the tissue after the leading segment. While the leading segment 5250 and the trailing segment 5252 of the support element 5230 depicted in FIG. 52C are arranged such that they are substantially symmetric, in other variations, the leading and trailing segments may be arranged asymmetrically. Similarly, the leading segment 5254 and trailing segment 5256 of the extendable element 5232 may or may not be symmetrically arranged. In some variations, the looped support element 5230 may be configured so that the leading segment 5250 resist tilting or angulation of the cutting element from its desired cutting orientation. For example, the looped support element 5230 may comprise a structure with sufficient column strength to resist compressive loads and tension loads acting simultaneously on the support element 5230 as the support element 5230 is rotated. The leading segment may be configured to resist tension or elongation, while the trailing segment is configured to resist compression.

Figure 52F:
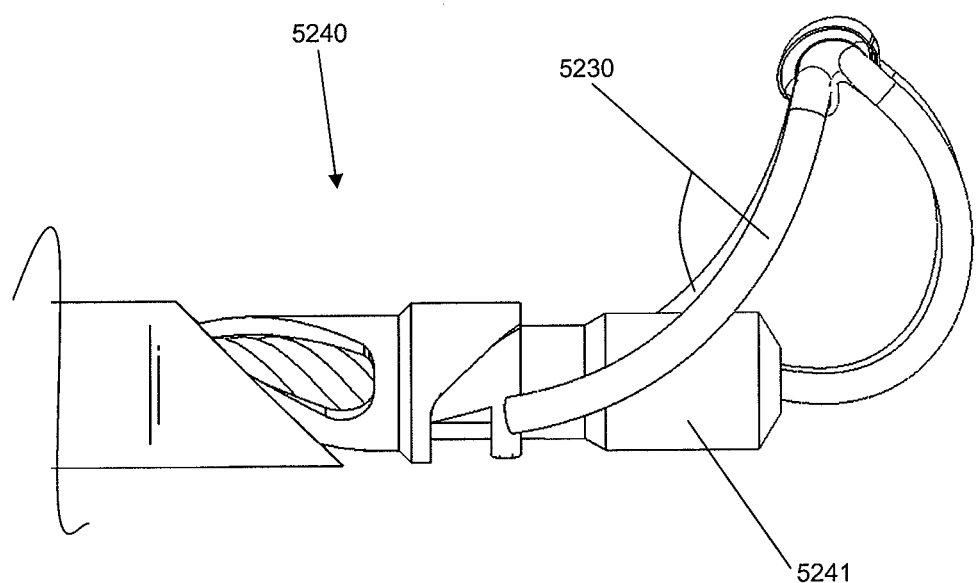

The support element 5230 and the extendable element 5232 may be metallic or polymeric multifilament cables as previously described. The proximal portion of a metal cable may be attached to a distal portion of a rotatable drive member, at the shaft base, and/or to components in the handle, e.g., the coupler 3626, the rotatable shaft 3620, the pin 3609, a slidable metal lug coupled to the pin 3609 disposed within the rotatable shaft, etc. A polymeric cable may be adhesive bonded, e.g., using epoxy, to the components described above, and may be optionally reinforced by a metallic and/or polymeric ring. A metallic support element may be attached to the cap 5236 and/or the tissue transport assembly 5240 by soldering, welding, etc. A polymeric support element may be attached to the cap and/or tissue transport assembly by gluing or any other suitable attachment method. FIG. 52F depicts the tissue-removal assembly 5200 without the cap 5236, revealing a portion of the tissue transport assembly 5240. The support element 5230 may be attached to an impeller 5241 of the tissue transport assembly 5240. The attachment of the looped support element to the cap and/or the tissue transport assembly may be further secured and reinforced by the reinforcement ring 523S. For example, as shown in FIGS. 52C and 52D, the proximal portion of the leading segment 5250 may be attached at a first attachment site 5253, and the proximal portion of the trailing segment 5252 may be attached at a second attachment site 5255, where the second attachment site is directly opposite the first attachment site. The first and second attachment sites 5253 and 5255 may be located at a length LS proximal to the distal end of the cap 5236, where LS may be from about 3 mm to about 10 mm, e.g., 5 mm.

As indicated previously, the looped support element 5230 and the looped extendable element 5232 may be joined at the cutting element 5234 by passing through a lumen 5235 of the cutting element. For example, the portion of the support or extendable element that is passed through the lumen of the cutting element may be restrained in a region of the lumen. For example, the lumen of the cutting element may have one or more lobes, as described previously and depicted in FIGS. 4SB and 52C, where the lobes are sized and shaped to prevent the support and/or extendable elements from shifting or sliding within the cutting element lumen. In other variations, the support and/or extendable elements may be bonded, glued, soldered, welded, etc to the cutting element 5234, according to the desired level of movement through and/or along the cutting element. The support and extendable elements may be attached to the cutting element such that they may be restricted from sliding along the plane of the lumen 5235, and/or may be restricted from sliding transversely through the plane of the lumen. For example, support and/or sliding elements retained in a cutting lumen lobe may be restricted from moving within the plane of the lumen, and soldering the support and/pr sliding elements may restrict both in-plane and transverse-plane movement.

The position of the cutting element 5234 and the angle of the support segment 5230 may be determined by adjusting the length of the extendable element 5232 that is external to the cap 5236. For example, the distance D15 between the cutting element 5234 and the surface of the cap 5236 may be increased by extending the extendable element 5232 along the arrow 5258, out through the distal aperture 5237. The length L20 of the extendable element 5232 that may protrude from the distal aperture 5237 may be from about 0 mm, e.g., in the retracted configuration, up to about 5 mm, about 10 mm or 15 mm or more in the extended configuration The distance D15 may be from 0 mm to about 10 mm, about 0 mm to about 8 mm, and about 0 mm to about 4 mm. The radius of curvature of the leading segment 5254 and/or the trailing segment 5256 of the extendable element 5232 may be from about 1 mm to about 4 mm. The orientation and position of the leading and trailing segments 5250, 5252 of the support element 5230 may vary according to the extension of the extendable element 5232 and the distance D15. For example, increasing the distance D15 may flex or bend the support element 5230, and may decrease the radius of curvature of the leading segment 5250. The angle A3 of the leading segment with respect to the longitudinal axis of the tissue-removal device at the first attachment site, and the angle A4 of the leading segment 5250 as it extends over the cap 5236 may vary as the radius of curvature of the leading segment. The angle A3 may be from about 0° to about 75°, e.g. 5° to 45°, and the angle A4 may be from about 0° to about 90°, e.g., 5° to 75°. The support element may be made of any materials as previously described, and may have a length L21 that does not substantially change as the extendable element 5232 is extended and/or retracted. For example, the length L21 may be from about 3 mm to about 10 mm.

The looped support element 5230 may be configured to stabilize and maintain the alignment of the cutting element 5234 with respect to the cap 5236. Referring to FIG. 52D, in the expanded configuration, the cutting element 5234 may be located a distance D13 away from an outer edge of the cap 5236. This alignment and position may be maintained and stabilized by the support element. For example, the distance D12 between the leading and trailing segments of the looped support element may be greater than the distance D16 between the leading and trailing segments of the looped extendable element. When the distance D12 is greater than the distance D16, the support element may act to maintain a certain cutting element alignment, and may help to prevent the cutting element from deviating from a desired cutting orientation as it is rotated. The distance D12 may be from about 1 mm to about 10 mm, e.g., about 2 mm to about 5 mm, the distance D13 may be from about 0.5 mm to about 5 mm, e.g. 1 mm to 3 mm, and the distance D16 may be from about 0.5 mm to about 5 mm, e.g., 1 mm to 3 mm. In the expanded configuration, the extendable element 5232 may be extended to a certain radius of curvature, where a portion of the extendable element may curve distally from the cap 5236. The distance D14 between the distal end of the cap 5236 and a distal curved portion of the extendable element 5232 may be from about 0.1 mm to about 10 mm, e.g., 1 mm to 5 mm.

In the collapsed configuration, the extendable element may be refracted, which may position the cutting element such that the tissue-removal assembly has a small profile, e.g., a profile that is substantially similar to the cross-sectional area of the cap. In some variations, the cutting element 5234 may be aligned along the central longitudinal axis of the tissue-removal assembly 5200 when the extendable element is retracted. For example, as shown in FIG. 52E, the cutting element 5234 is located along the central longitudinal axis 5257. Optionally, the cutting element 5234 may also be partially or entirely retracted into the cap 5236, e.g., via the cap distal aperture 5237. For example, the cutting element 5234 may be retracted such that its distal edge is flush with the distal edge of the cap 5236. Retraction of the extendable element and the cutting element 5234 into the cap 5236 may cause the support element 5230 to collapse towards the outer surface of the cap 5236, such that a substantial length of the support element 5230 contacts the cap 5236. The narrowed profile in the collapsed configuration may be suitable for advancing the tissue-removal assembly through small anatomical regions and within cracks and creases in tissue.

Figure 53A:
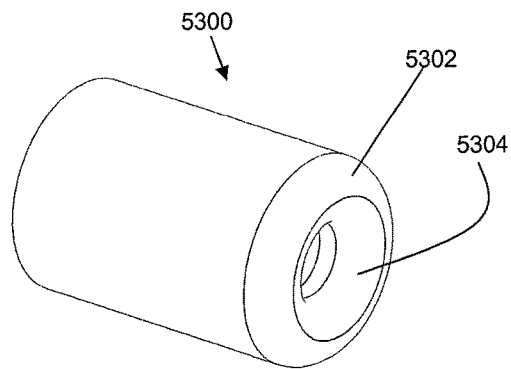
FIGS. 53A to 53D depict an anterior perspective view, a posterior perspective view, a posterior elevational view and a side cross-sectional view of one embodiment of a tissue-removal assembly cap.
Figure 53B:
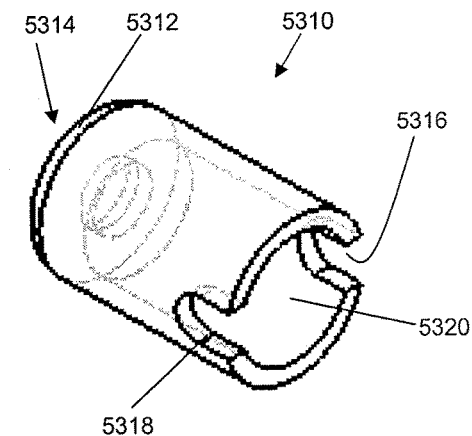
Figure 53C:
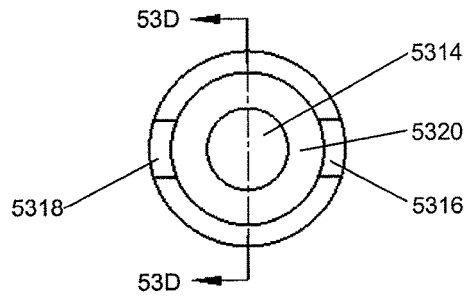
Figure 53D:
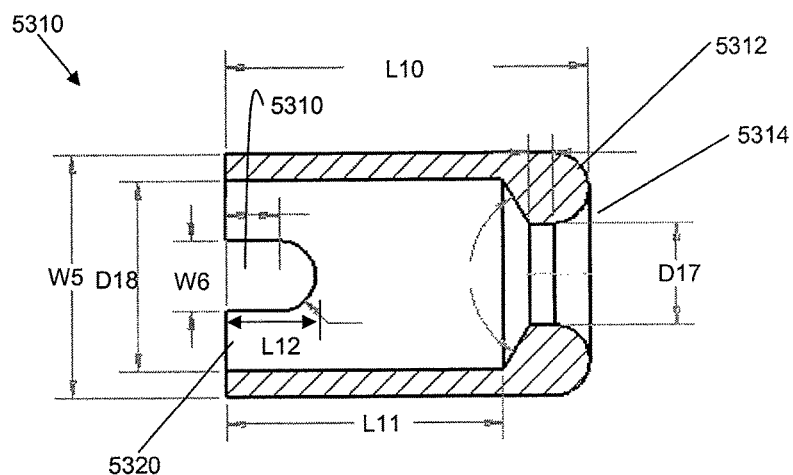

As described above, the support element may be attached at certain attachment sites along the outer surface of a cap, or may be additionally secured by a cap and/or reinforcement ring. The cap and/or the reinforcement ring may be metallic, e.g., stainless steel, nitinol, etc., and/or polymeric, e.g., PEEK, polyimide, Pebax, nylon, polyethylene, etc. The outer surface of the cap and/or reinforcement ring may be modified to help to reduce the coefficient of friction so that the tissue-removal device may pass smoothly through tissue. The cap may have a smooth, rounded geometry that may help reduce the risk of tissue trauma as the tissue-removal device is navigated towards the target tissue site. One variation of a cap 5300 is depicted in FIG. 53A. The cap 5300 has a rounded distal region 5302 and a distal aperture 5304. The aperture 5304 may be sized and shaped to accommodate one or more extendable and/or support elements. The cap may also have a lumen therethrough. For example, another variation of a cap 5310 comprises a rounded distal region 5312 and a distal aperture 5314 in connection with a lumen 5320 therethrough. The cap 5310 may also have a first slot 5316 in the wall of the lumen 5320, and a second slot 5318 opposite the first slot. The slots 5316, 5318 may extend along 10%, 20%, 40%, 50%, 70%, or 90% the length of the cap 5310. In some variations, a cap may comprise side apertures or windows. Slots, slits, windows, any closed or open shaped opening, and the like may provide a conduit for removed tissue to be extracted from the removal site to the collector, and may be any suitable size or shape, e.g., circular, ovoid, rectangular, etc. As depicted from a back view in FIG. 53C, the diameter of the distal aperture 5314 may be smaller than the diameter of the lumen 5320. FIG. 53D depicts a cross-sectional view taken along the lines 53D-53D. The distal aperture 5314 may have a diameter D1 7 from about 0.03 inch to about 0.05 inch, e.g., 0.046 inch, and the lumen 5320 may have a diameter D18 from about 0.06 inch to about 0.9 inch, e.g., 0.086 inch. The cap 5310 may have a length LIO from about 0.145 inch to about 0.17 inch, e.g., 0.164 inch, while the lumen 5320 may have a length L11 from about 0.11 inch to about 0.13 inch, e.g., 0.125 inch. The overall width W6 of the cap may be from about 0.09 inch to about 0.12 inch, and the width W6 of the slot 5318 may be from about 0.02 inch to about 0.04 inch, e.g., 0.032 inch. The length L12 of the slot 5318 may be about 0.04 inch. The rounded distal region 5312 may have a radius of curvature of about 0.016 inch. More generally, the dimensions and shapes of the cap 5310 may be varied according to the size of the tissue-removal assembly components, e.g., to match the diameter of the extendable or support elements.

Figure 55:
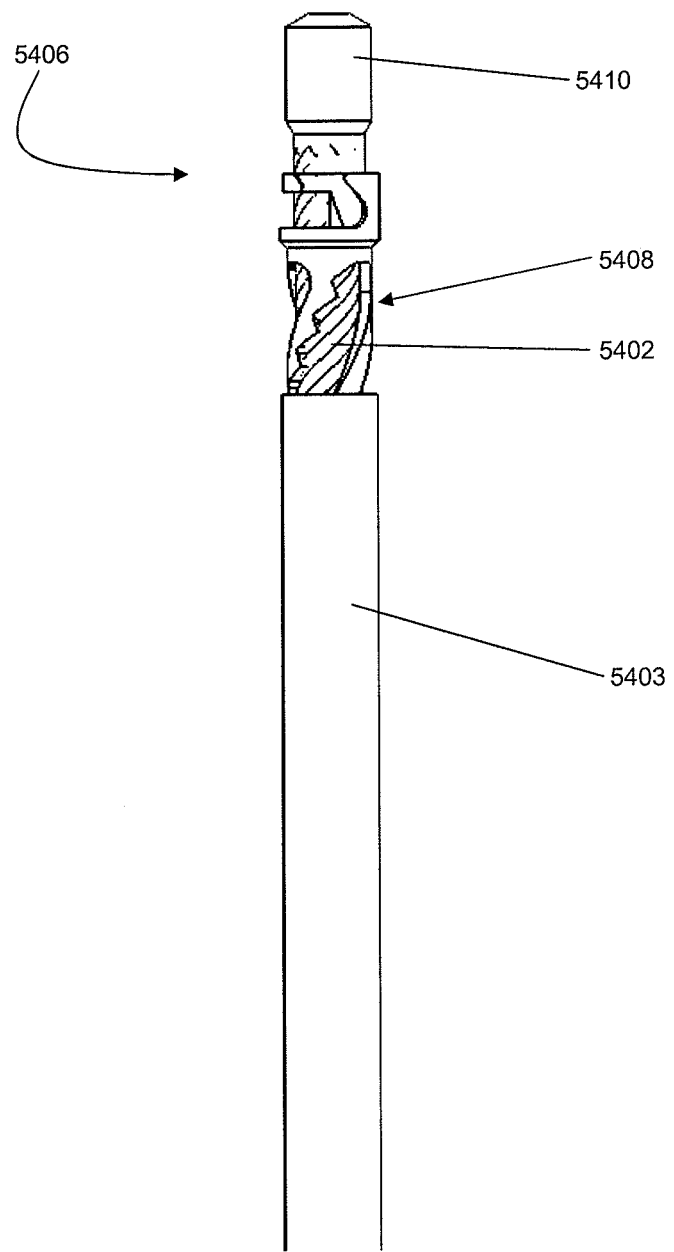
FIG. 55 depicts an example of a tissue transport assembly from FIG. 54A with a sheath.
Figure 56:
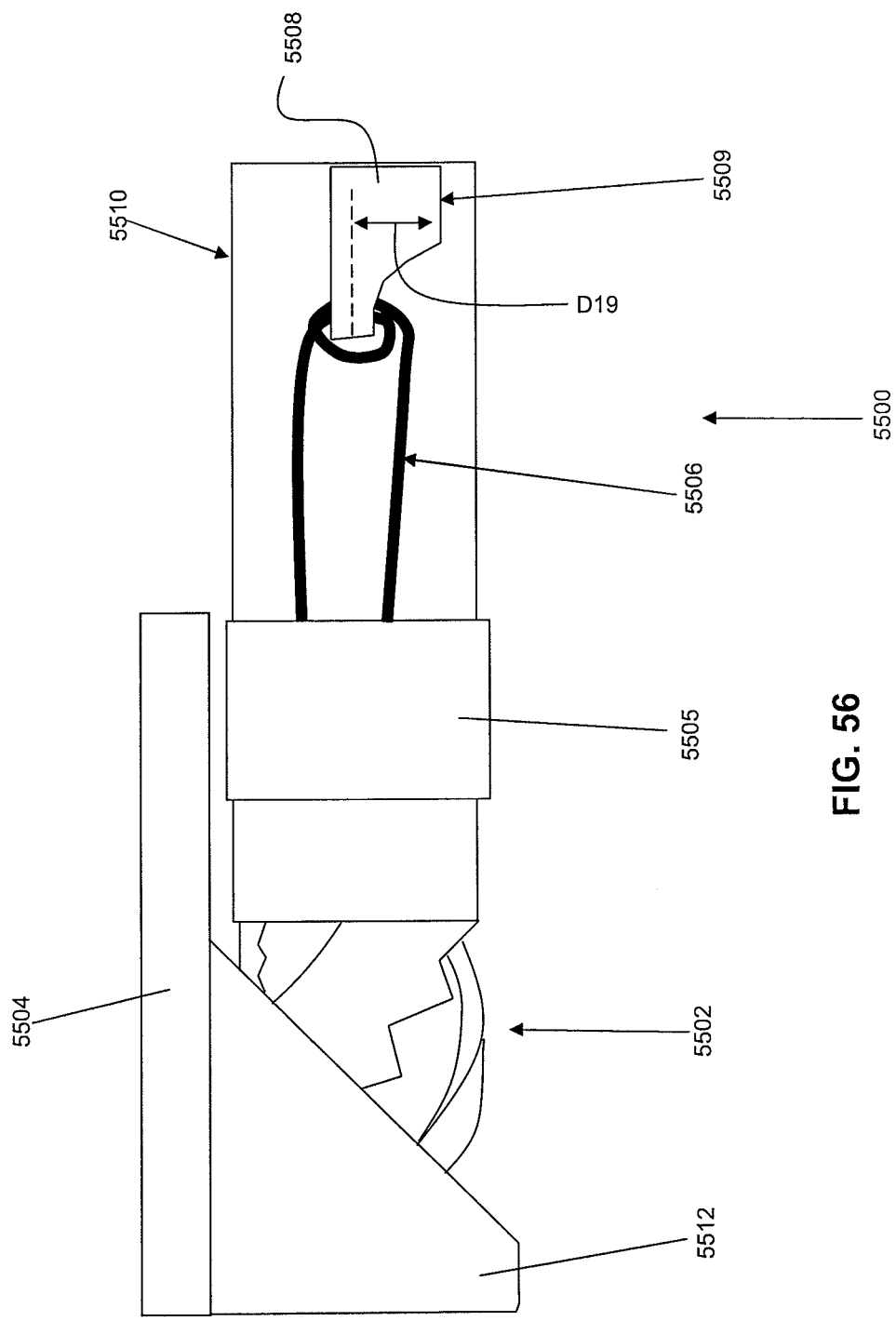
FIG. 56 schematically illustrates another variation of a tissue-removal assembly.

Another variation of a tissue-removal assembly 5500 is depicted in FIG. 55. The tissue-removal assembly 5500 may comprise a cutting element 5508, a extendable element 5506 looped through a lumen in the cutting element 5508. The extendable element 5506 may be double-looped through the cutting element 5508. The extendable element 5506 may be threaded through a distal shaft or a cap 5510, and may optionally be secured by a reinforcing ring 5505. The tissue-removal assembly 5500 is shown in its collapsed configuration, where the extendable element 5506 is retracted within the cap 5510. The extendable element 5506 may be retracted such that the distal edge of the cutting element 5508 is withdrawn within, or flush with, the distal edge of the cap 5510. The cutting element 5508 may be orientated such that the cutting edge lies in a plane parallel to the central longitudinal axis of the cap 5510, and is between the central longitudinal axis of the cap 5510 and the plane normal to the cap axis. The cutting edge 5509 may protrude a distance D19 beyond the extendable element attachment site on the cutting element 5508, where D19 may be from about 0.01 inch to about 0.1 inch, e.g., 0.036 inch. The tissue transport assembly 5502 may extend proximally from the tissue-removal assembly 5500 to transport tissue within the shaft 5512 to a proximal collector. Optionally, the shaft 5512 may comprise a visualization port, such as an endoscopic port 5504. In some variations, the visualization port may be configured for the injection of contrast agents, as well as for the insertion of other types of visualization instruments.

Figure 54A:
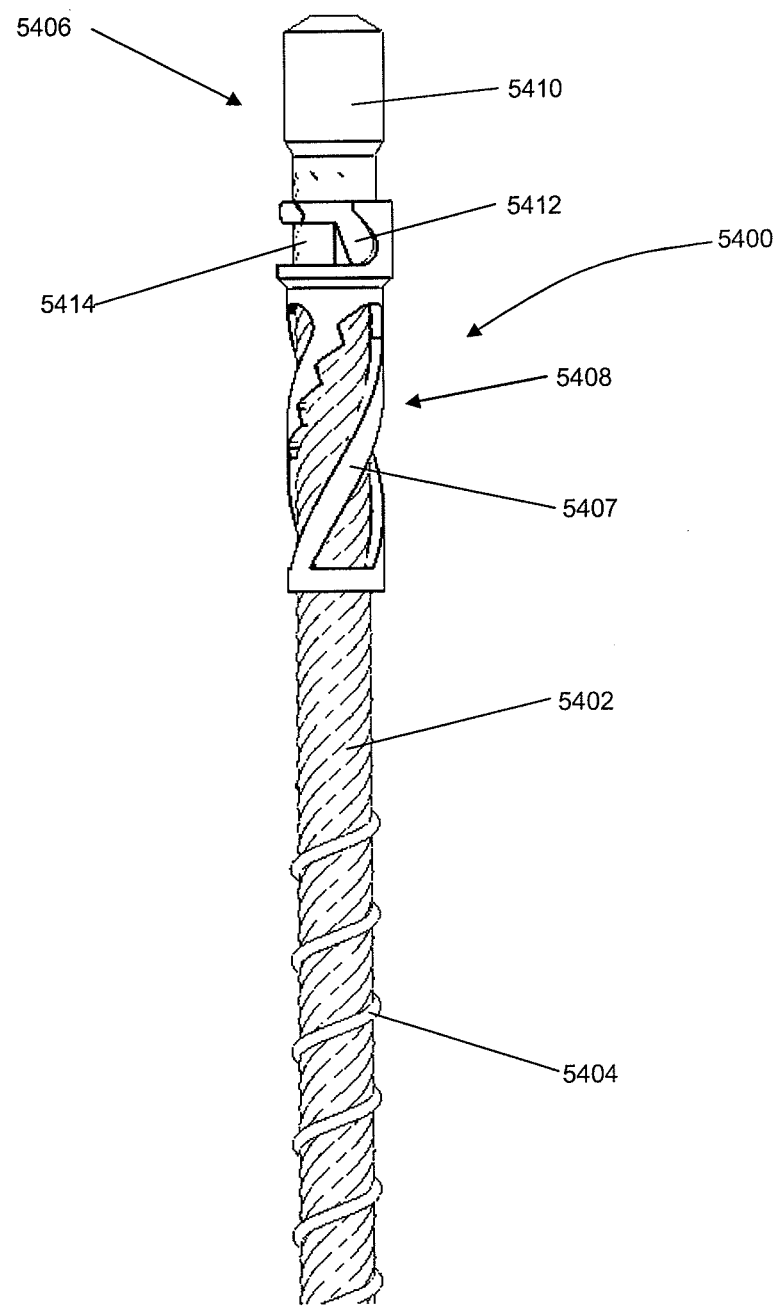
FIG. 54A illustrates an embodiment of tissue transport assembly that may be used with a tissue-removal assembly.

As indicated previously, a tissue-removal assembly may be provided with a tissue transport assembly, which may help draw the removed tissue away from the tissue site and into a collector. One example of a tissue transport assembly 5400 that may be used with the tissue-removal assembly 5200 is shown in FIG. 54A. As seen there, the tissue transport assembly 5400 comprises a drive member 5402 that is attached at its distal end to an impeller 5406, and a helical member 5404 mounted on at a least a portion of the drive member 5406. One variation of a tissue transport assembly that may be used with a tissue removal assembly is shown in FIG. 54A. The tissue transport assembly 5400 may comprise a rotatable drive member 5402, a helical member 5404 mounted on at least a portion of the rotatable drive member 5402, and an impeller 5406 attached at a distal portion of the drive member 5402. The rotatable drive member 5402 may be made of one or more polymeric and/or metallic materials that are suitable for drawing tissue up proximally from the tissue removal assembly to the collector. For example, the rotatable drive member 5402 may be made of stainless steel, nickel titanium alloy, carbon fiber, high density molecular weight polyethylene, and the like. The inner diameter of the rotatable drive member 5402 may be from about 0.010 inch to about 0.020 inch, e.g., 0.015 inch. The outer diameter of the rotatable drive member 5402 may be from about 0.0350 inch to about 0.0450 inch, e.g., 0.0407 inch. The helical member 5404 may be integrally formed with the rotatable drive member 5402, or may be separately formed and attached to the drive member. The pitch P1 of the helical member 5404 may be from about 0.010 inch to about 0.100 inch, e.g., 0.030 inch to about 0.25 inch, or about 0.060 inch to about 0.100 inch, or 0.030 inch, or 0.080 inch. The pitch P1 of the helical member may be adjusted according to the rotational speed driven by the motor, or according to the desired rate of tissue transport from the tissue removal assembly to the collector. The helical member 5404 may be made of materials similar to the rotatable drive member 5402, and may optionally include surface modifications such as friction-reducing coatings, fluid dynamic channels, etc., which may help to transport the removed tissue to the collector. The helical member 5404 may be right hand wound, or left hand wound, as appropriate for tissue transport. In some examples, the helical member 5404 may be wound in the same sense as the rotation of the drive member. In certain variations, a rotatable drive shaft may be an integrally formed tube, e.g., a tube formed from a solid sheet of material that is not woven or braided, with the helical member coiled along the outer surface of the tube. In other variations, the rotatable drive shaft may be made of multiple layers of tightly wound coiled members, where the inner layers of the coiled members may have a first pitch, the outer layers of the coiled members may have a second pitch. For example, the pitch of the coiled members may vary from the innermost layer to the outermost layer, e.g., the innermost coil layer may have the tightest pitch, and the outermost layer may have the highest pitch. In this variation, polymers or other adhesives, such as epoxy, parylene, polyurethane, and the like, may be applied in between coiled layers or as an outer coat, to secure the threads of the outermost coiled member to the next inner coiled layer. These adhesives coatings and layers may help prevent the coiled layers from separating and lifting off each other. In general, the tissue transport assembly 5400 may comprise one or more recesses, grooves, channels, protrusions, and the like which may expedite tissue transport as desired. Other characteristics of drive members and helical members have been described previously, and may also be used with the tissue transport assembly 5400.

Optionally, the tissue transport assembly may also comprise a sheath 5403, illustrated in FIG. 55, that encases at least a portion of the rotatable drive member 5402. The sheath may be included to help reduce the frictional forces between the drive member and the inner wall of shaft (e.g., wall of the longitudinal lumen of the shaft 5202), and may help dissipate any heat that is generated by the various moving parts of the tissue removal and/or transport assemblies. Reducing or dissipating any heat generated during use of the tissue-removal assembly may prevent the heat from being conducted to the shaft, which may thermally injure surrounding tissue, e.g., nerve tissue. In some variations, the sheath 5403 may be located around regions of the tissue transport assembly that have the greatest likelihood of contacting nerve tissue. The sheath 5403 may be made of polymeric and/or a metal materials, for example, polyimide with a stainless steel braid. The stainless steel braid may have a thickness of about 0.0005 inch by about 0.0025 inch, or 0.001 inch by 0.003 inch. The sheath may have an inner diameter for about 0.035 inch to about 0.050 inch, e.g., 0.0420 inch. The sheath may have an outer diameter of about 0.040 inch to about 0.055 inch, e.g., 0.048 inch. The wall thickness of the sheath may be about 0.0030 inch. In some variations, the sheath may have a length of about 10.00 inches to about 20.00 inches, e.g., 12.00 inches, or 12.25 inches.

Figure 54B:
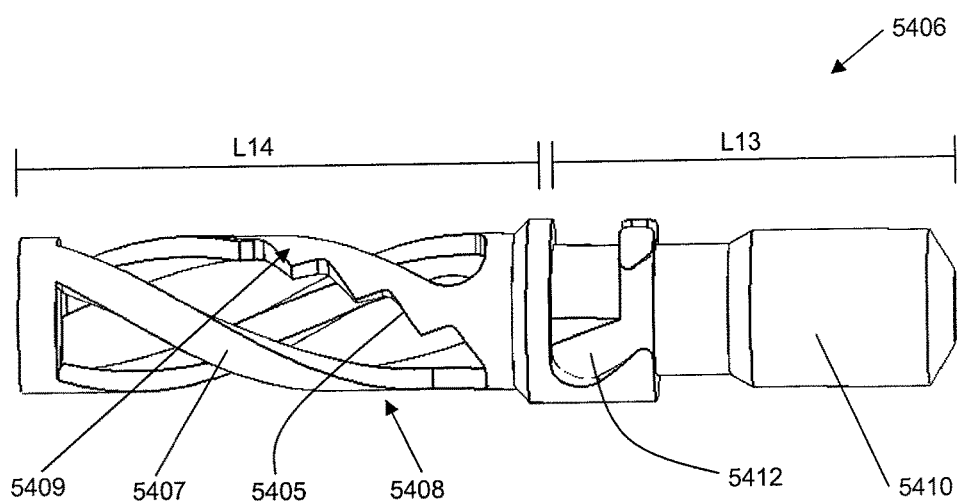
FIGS. 54B to 54I illustrate various examples of impellers that may be used in a tissue transport assembly.

The distal portion of the drive member 5402 may be coupled to the impeller 5406, which may have one or more recesses, grooves, channel, etc. which may help expedite tissue transport. An enlarged depiction of the impeller 5406 is shown in FIG. 54B. The proximal portion of the impeller 5406 may comprise a helical cage 5408, and the distal portion may comprise an impeller cap 5410. The impeller 5406 may also comprise one or more groves and/or cutout regions, for example, slanted groove 5412 and cutout region 5414 on the impeller cap 5410. The slanted groove 5412 and/or the cutout region 5414 may be sized and shaped for passing a cable (e.g., support or extendable element) over the surface of the impeller 5406, similar to the grooves and recesses that may be used with a rotatable shaft as previously described. The drive member 5402 may be inserted into the helical cage 5408, and/or may be attached by welding, gluing, soldering, and the like. The impeller cap 5410 may be made of a polymeric material such as PEEK, Pebax, nylon, polyethylene, polyimide, and the like, and may have a length L13 of about 0.150 inch to about 0.300 inch, e.g., 0.235 inch. In some variations, an insulating coating may be provided on a portion of the impeller to help reduce the risk of thermal nerve injury during the procedure.

Figure 54C:
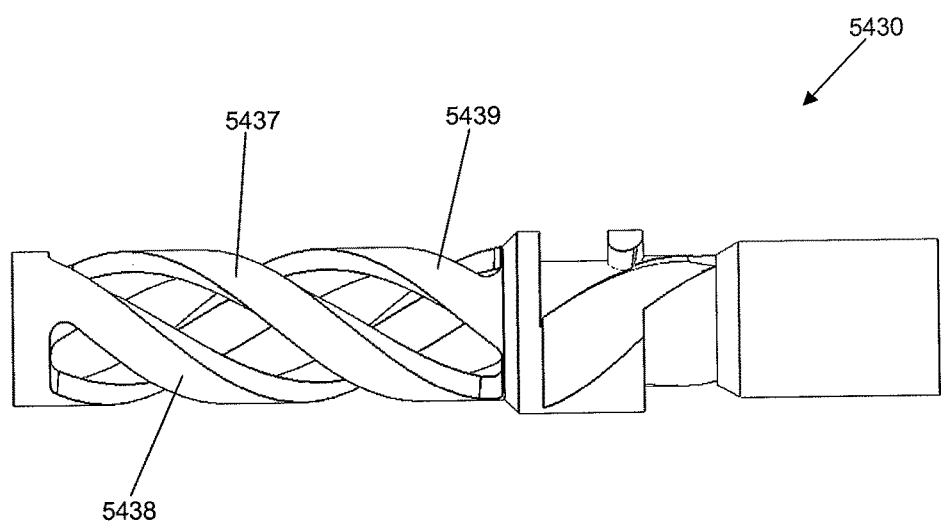
Figure 54D:
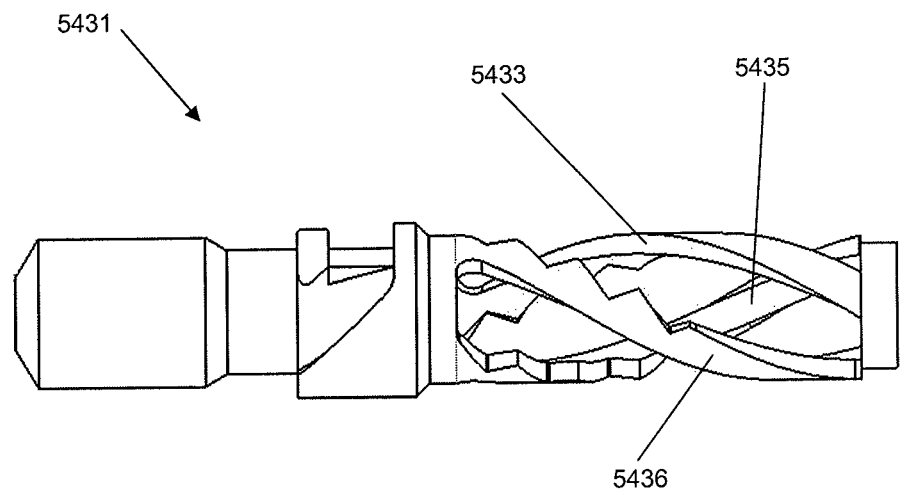
Figure 54E:
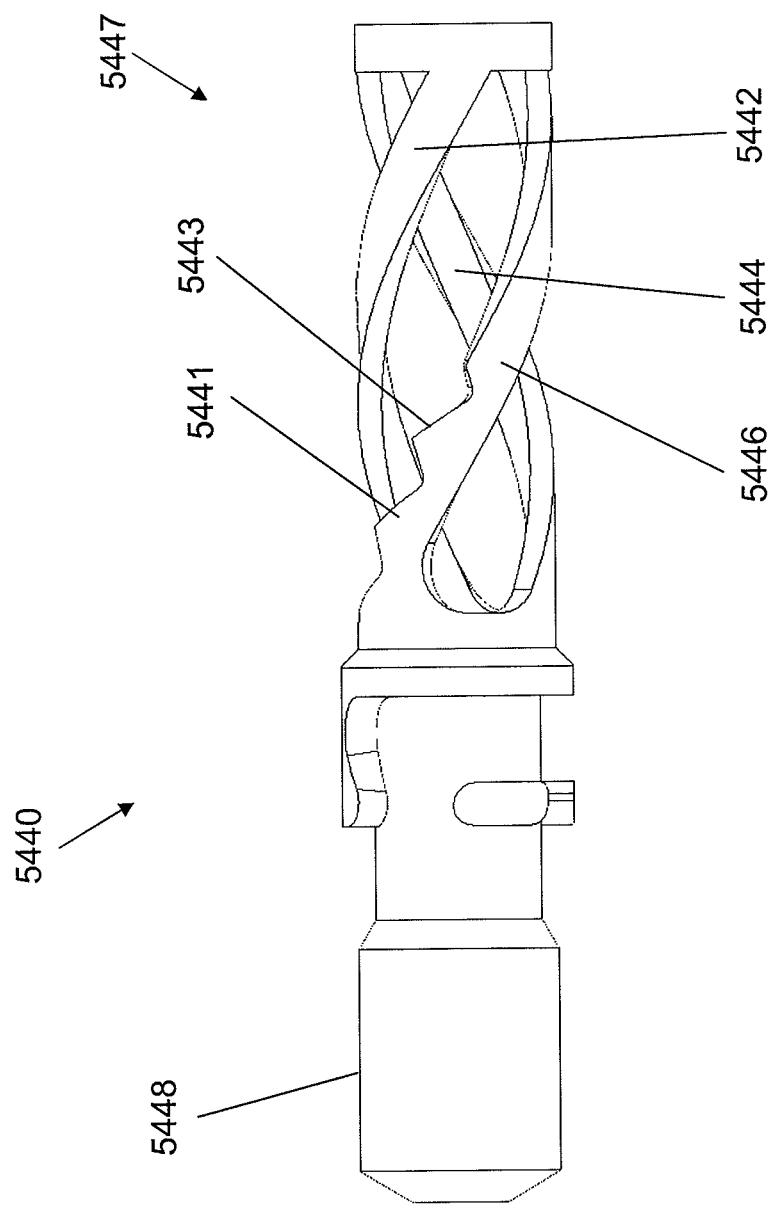
Figure 54F:
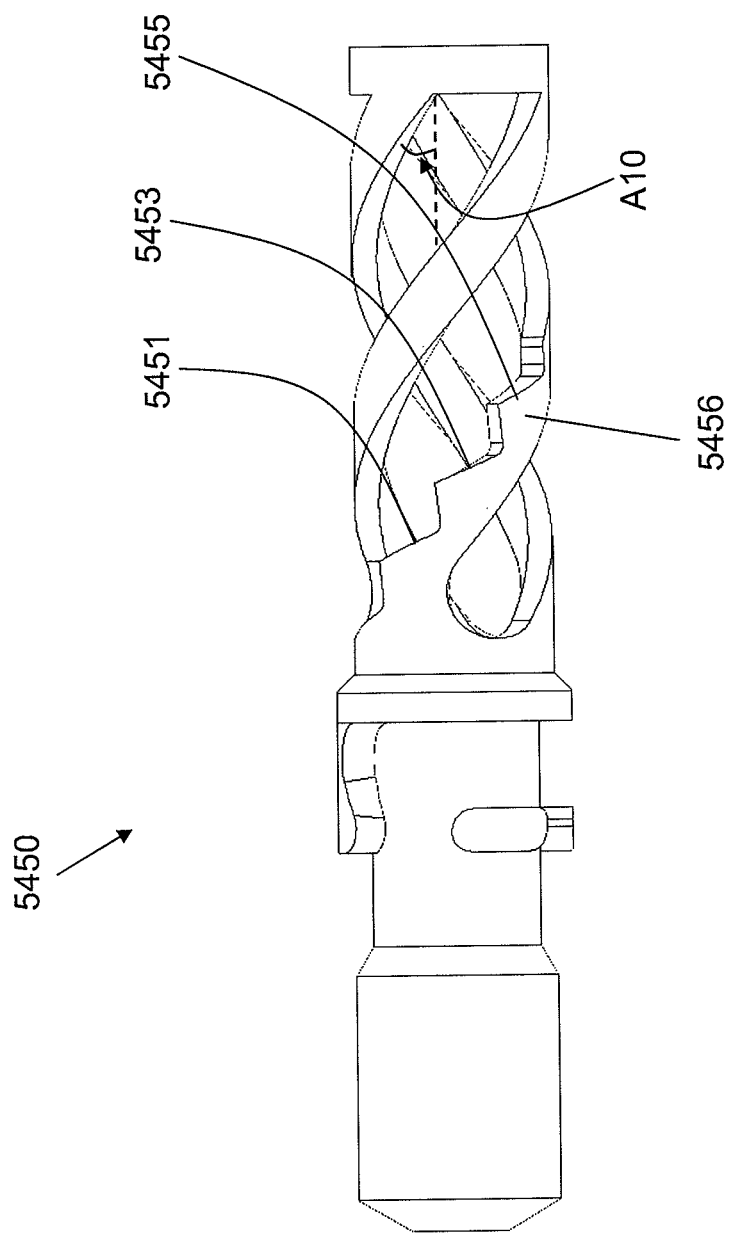

The helical cage 5408 may be made of a metallic material such as stainless steel or polymeric material such as PEEK. Certain variations of an impeller may comprise two more braids similar to braid 5407. As seen in FIG. 54B, the impeller 5406 may comprise three braids that have a clockwise pitch angle of about 30° to about 60°, e.g., 35°. The braids 5407 may have a rate of turning along the length L14 of the helical cage 4108 of about 3 turns/inch to about 5 turns/inch, e.g., 4.5 turns/inch. The length L14 of the helical cage 5408 may be from about 0.150 inch to about 0.300 inch, e.g., 0.230 inch. The braid 5407 may have a width from about 0.015 inch to about 0.030 inch, e.g., 0.028 inch. The helical cage 5408 may have any number of braids or surface structures such as serrations, ridges, etc., that may be useful for drawing tissue from the tissue removal assembly to the collector. For example, one braid 5409 may be serrated with one or more teeth 5405, while other braids 5407 and 5408 may not have any teeth. The cage teeth 5405 may be located on a leading edge of each braid as determined by the braid angle and direction of rotation. The sharpened edge of the cage teeth 5405 may be on the leading edge. The cage teeth 5405 may help to further break up the tissue as it is drawn proximally away from the target tissue site. The teeth 5405 may be slanted at an angle, for example, the slant angle may be between about 20° to about 40°, and/or about 60° to about 80°. The edges of teeth 5405 may be any length appropriate for cutting or pulverizing tissue, e.g., from about 0.001 inch to about 0.004 inch, e.g., 0.002 inch. Other variations of teeth may be larger, with edge lengths of about 0.01 inch to about 0.02 inch. The two edges of the cage teeth 5405 may have a first short edge, and a second long edge, while in other variations, the edges may be the same length. Some variations of cage teeth may be C-shaped, and/or may have other angular geometries with sharp turning edges. Other cutting features or edges may be provided along the impeller and/or drive shaft, such as sharpened helical members, enzymatic coatings, etc. that may break up tissue and expedite its transport to a collector. The serrations may help to further break up the tissue as it is drawn proximally away from the target tissue site. Alternatively, as depicted in FIG. 54C, the impeller 5430 may have braids 5437, 5438, and 5439 without any serrations. In another variation of an impeller 5431 shown in FIG. 54D, all of the braids 5433, 5435, and 5436 may be serrated or have one or more teeth.

Figure 54G:
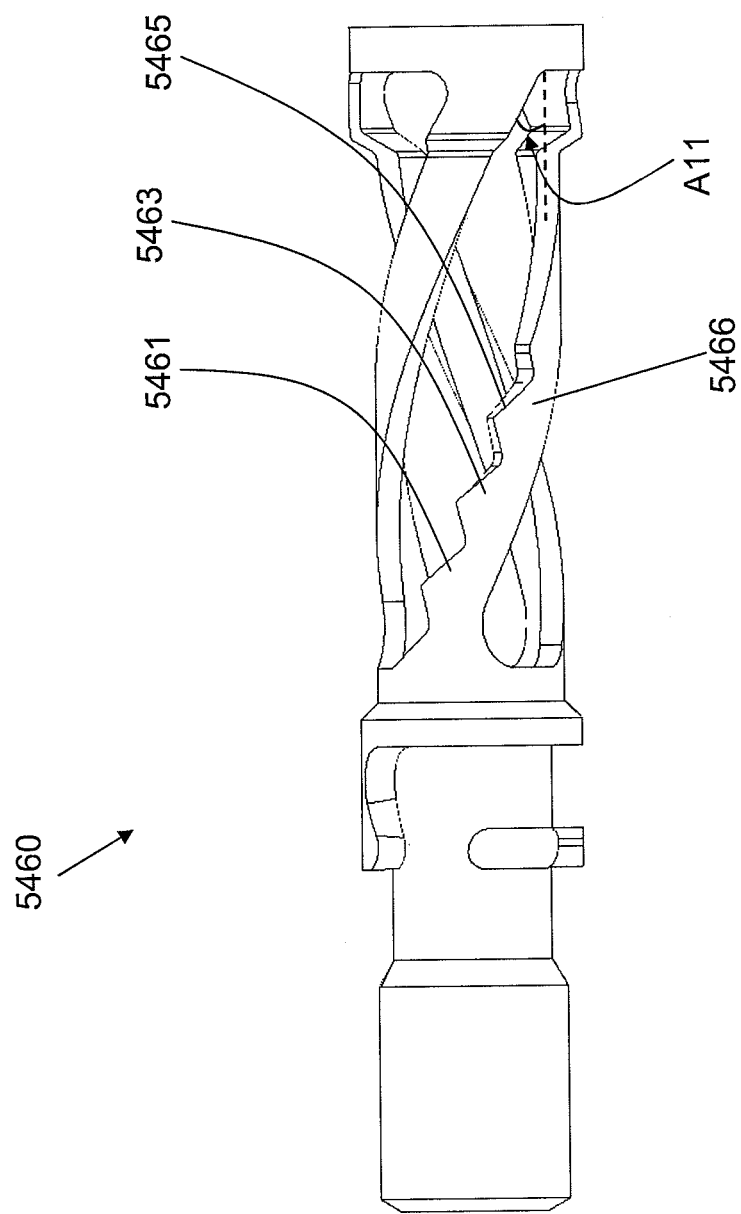
Figure 54H:
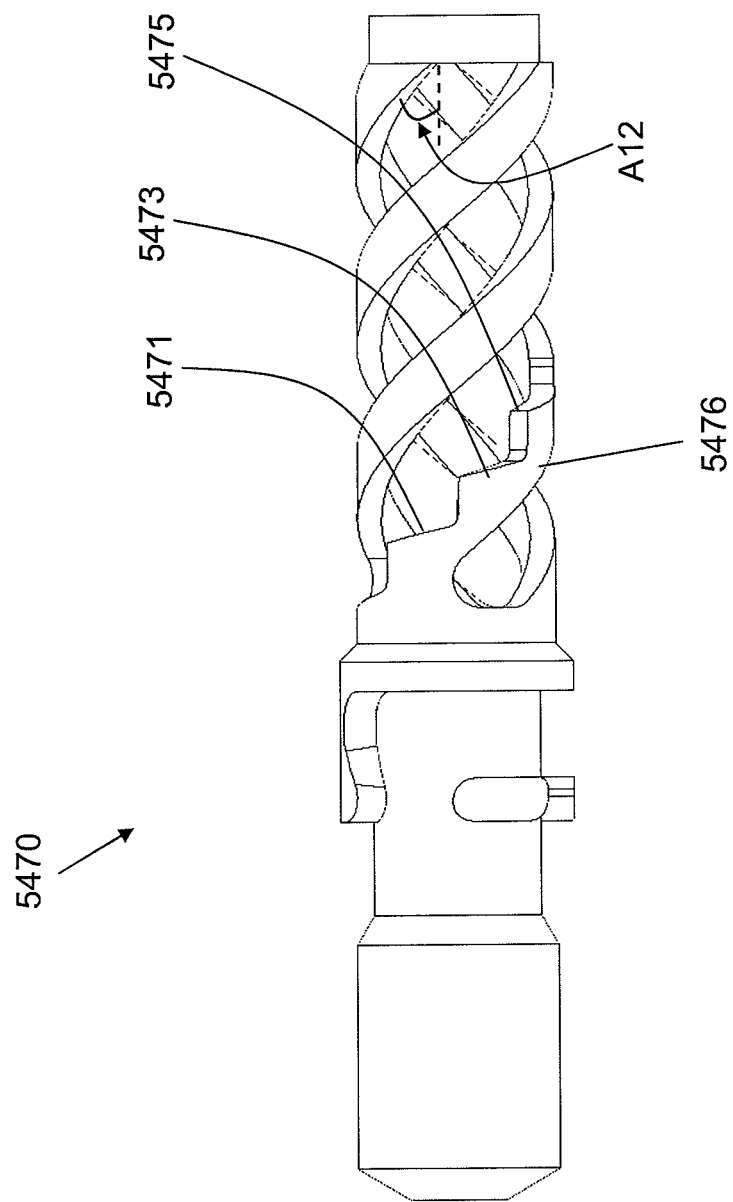
Figure 54I:
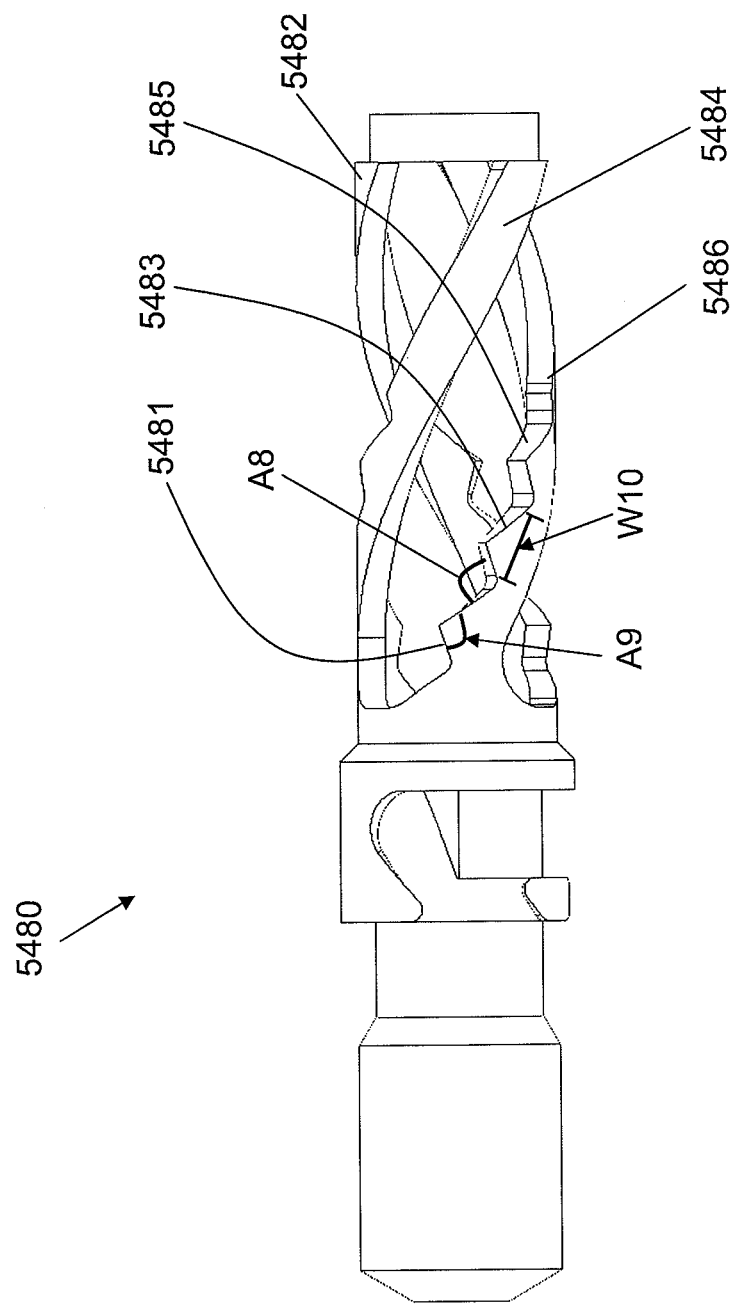

Additional variations of impellers are illustrated in FIGS. 54E-54I. For example, the variation of an impeller 5440 shown in FIG. 54E may comprise an impeller cap 5448 with an angled distal tip and helical cage 5447. The helical cage 5447 may have a first braid 5442, a second braid 5444, and a third braid 5446. One or more of the braids may have serrations, and there may be any number of serrations on a single braid. For example, the third braid 5446 may have two serrations 5441, 5443. In another variation of an impeller 5450 depicted in FIG. 54F, a braid 5456 may have three serrations 5451, 5453, and 5455. The braids of the impeller 5450 may have a braid twist angle A10 of about 40°. FIG. 54G depicts an impeller 5460 with three braids that have a twist angle A11 of about 30°. The braid 5466 may have three serrations 5461, 5463, and 5465. FIG. 54H depicts an impeller 5470 with three braids that have a twist angle A12 of about 50°. The braid 5476 may have three serrations 5471, 5473, and 5475. In other variations, such as impeller 5480 depicted in FIG. 54I, all the braids 5482, 5484, 5486 have one or more serrations on a leading edge of each braid, for example, three serrations 5481, 5483, 5485. Serrations may have a positive rake (e.g., from about 30° to 40°) or negative rake and/or may be slanted at an angle, as previously described. The angle A8 between the serrations 5481, 5483, 5485 may be from about 80° to 150°, e.g., 105°, or 104.6°. The sharpened or pointed portion of a serration may have an angle A9, where A9 may be from about 45° to 120°. The edges of the serrations 5481, 5483, 5485 may be from about 0.001 inch to about 0.004 inch, e.g., 0.002 inch. Other variations of serrations may be larger, with edge lengths of about 0.01 inch to about 0.02 inch. Serrations may have a width W10 that may be from about 0.01 inch to about 0.2 inch, e.g., 0.04 inch.

The movement, orientation, and stability of a tissue-removal device may be regulated by a travel limiter, which may help to prevent inadvertent movement and/or shifting that may result in tissue injury. A travel limiter may be used to constrain and/or define the range of axial, rotational, and/or transverse movement of a tissue removal device after it has been inserted into a patient. For example, a travel limiter may be configured to regulate and/or restrict the position and orientation of a distal tissue-removal assembly. Travel limiters may have a number of configurations that allow varying degrees of motion to the tissue removal device. Some variations of a travel limiter may be permanently coupled to an access cannula, while other travel limiters may be temporarily coupled to a shaft of a tissue-removal device during use. One variation of a travel limiter 5700 that may be temporarily coupled with the tissue-removal devices described above is depicted in FIGS. 57A and 57B. The travel limiter 5700 may comprise a guide opening 5704 located at the distal end of an elongate body 5706, where the guide opening 5704 may be configured receive a tissue-removal device therethrough. The guide opening may be sized and shaped to restrict the movement of a tissue-removal device along the plane of the guide opening 5704. The guide opening 5704 may have one or more curves, bends, and/or angles that may help to constrain the displacement of a tissue-removal device within the bounds of the guide opening.

Figure 57A:
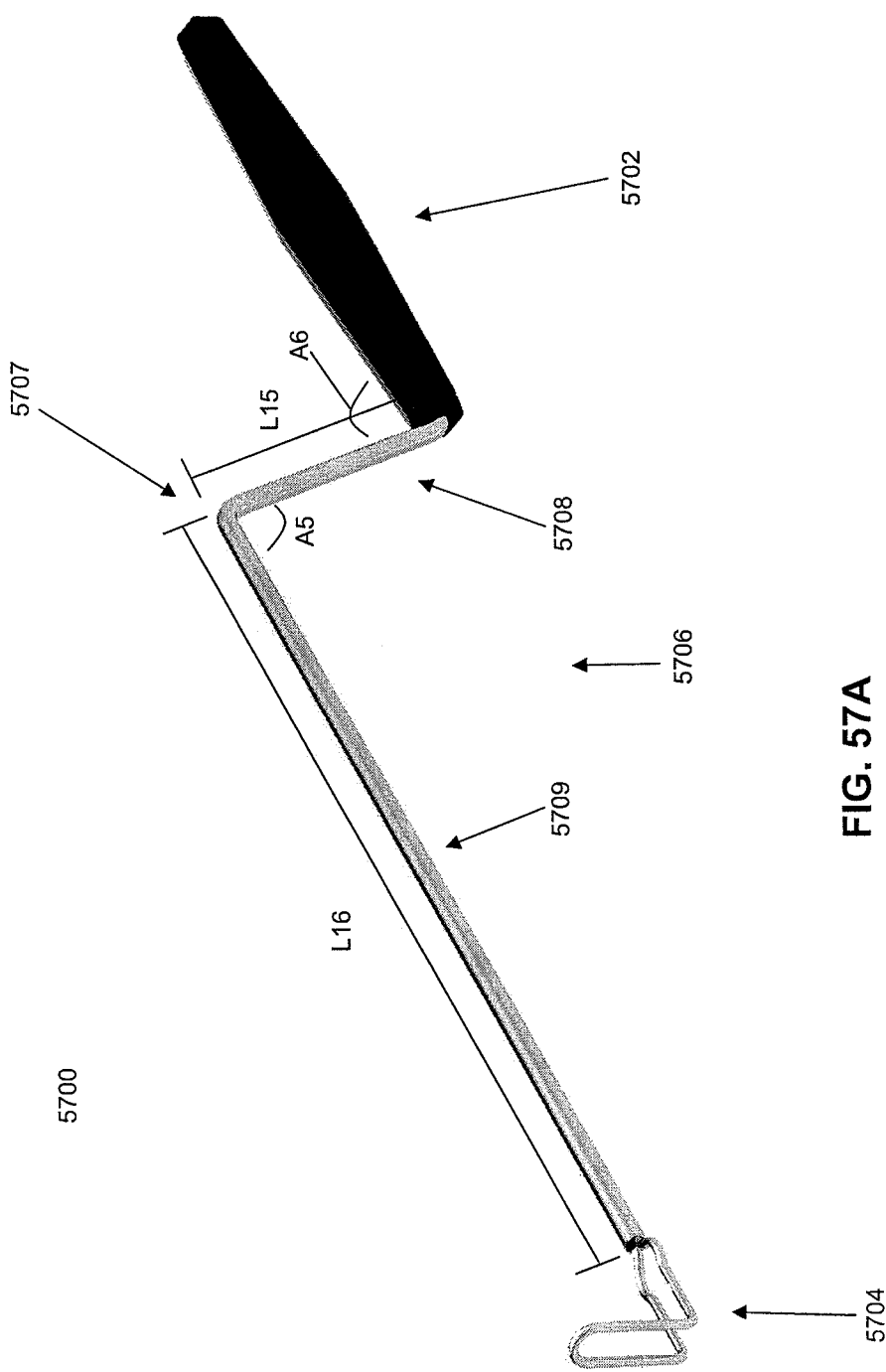
FIGS. 57A to 57F depict one variation of a travel limiter that may be used with a tissue-removal device.
Figure 57B:
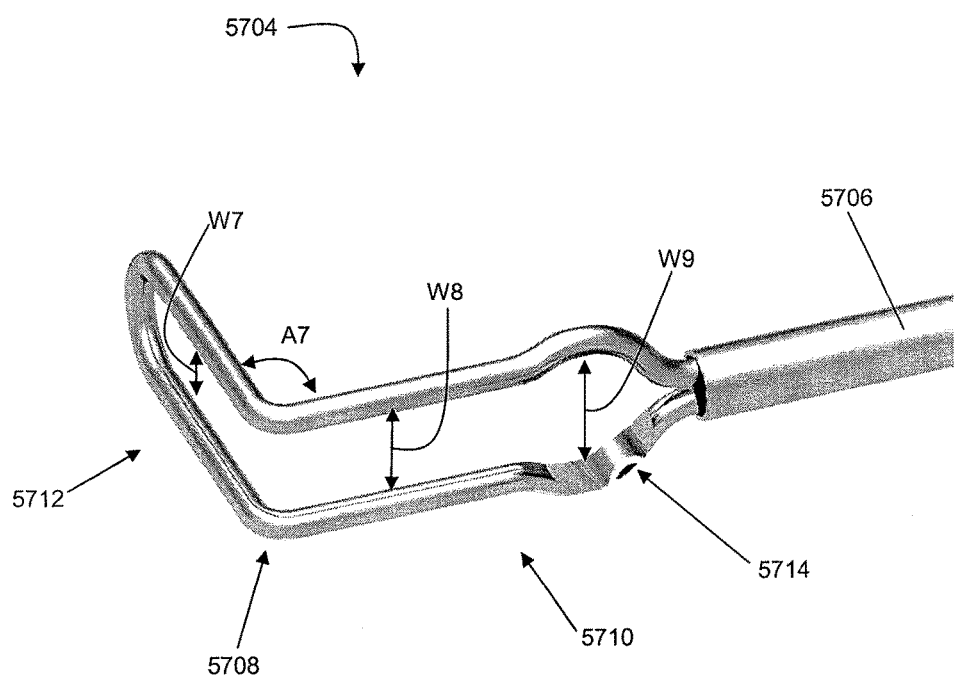

As depicted in FIG. 57B, the guide opening 5704 may comprise a loop of a metallic or polymeric material, where a first portion of the loop may be on a first plane, and the second portion of the loop may be on a second plane, where the first and second portions of the loop are separated by a bend 5708. In some variations, the first or second portion of the guide opening defined by the bend may be used to stabilize the travel limiter and/or the tissue-removal device against a tissue structure. Alternatively or additionally, the first and second portions of the guide opening defined by the bend may constrain the movement of a tissue-removal device in the guide opening along the first and second planes. For example, a tissue-removal device inserted through the first portion of the guide opening may be constrained to move along the first plane, within the boundaries of the first portion. The tissue-removal device may be translated across the bend to the second portion of the guide opening, where it may be constrained to move along the second plane, within the boundaries of the second portion. In some variations, the first and second portions may be co-planar, while in other variations, the first and second portions may be in unique planes. For example, the guide opening 5704 may have a first portion 5710 in a first plane, a second portion 5712 in a second plane that is joined to the first portion 5710 at the bend 5708. The bend 5708 may have a bend angle A7, where the bend angle A7 may be from about 30° to about 100°, e.g., 90°. The guide opening 5704 may optionally comprise an insertion region 5714 that may be sized and shaped to accommodate a tissue-removal device therethrough. The insertion region 5714 may be co-planar with the first portion 5710, and may be wider than the first and second portions 5710, 5712. For example, the widest portion of the second portion 5712 may have a width W7, the widest portion of the first portion 5710 may have a width W8, and the widest portion of the insertion region 5714 may have a width W9, where the width W7 may be similar to the width W8, and the width W9 may be wider than both widths W7 and W8. The width W7 of the second portion may be from about 0.1 inch to about 0.3 inch, e.g., 0.25 inch, the width W8 of the first portion may be from about 0.1 inch to about 0.3 inch, e.g., 0.25 inch, and the width W9 of the insertion region 5714 may be from about 0.4 inch to about 0.6 inch, e.g., 0.5 inch. In some variations, the width W9 of the insertion region may be greater than the largest diameter of a distal portion of a tissue-removal device.

Figure 57C:
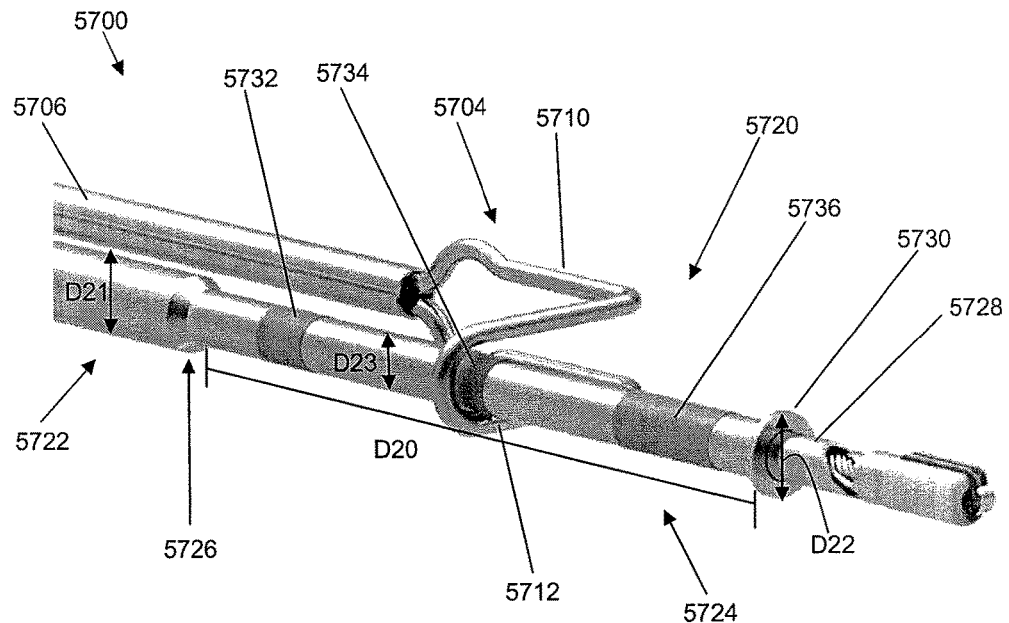

In some variations, the geometry of the guide opening 5704 in conjunction with the geometry of the distal portion of a tissue-removal device inserted in the guide opening may also restrict the axial movement of the tissue-removal device through the guide opening. For example, varying the widths W7, W8, and/or W9, as well as the width(s) of the distal portion of a tissue-removal device shaft, may control the axial movement of the device through different portions of the guide opening. For example, the various widths of the guide opening and the distal shaft of the tissue-removal device may constrain the depth to which the tissue-removal device may be inserted into a patient. As depicted in FIG. 57C, the distal portion of a tissue-removal device may have one or more features that interface with a travel limiter and/or access device to help advanced and/or position the tissue-removal assembly during a spinal procedure. For example, the distal portion of a shaft 5720 of a tissue-removal device may have a proximal portion 5722 that may be connected to a distal portion 5724 by a first shoulder 5726, and a shaft tip 5728 that may be distally connected to the distal portion 5724 by a second shoulder 5730. The diameter D21 of the proximal portion 5722 and the diameter D22 of the second shoulder 2730 may be larger than the diameter D23 of the distal portion 5724. The distance D20 between the first shoulder 5726 and the second shoulder 5730 may define a range of axial motion that the travel limiter or an access device may constrain the shaft to. In some variations, a travel limiter guide opening 5704 may be sized such that the width(s), e.g., W7 and W8, of the guide opening is greater than the diameter D23, but smaller than the diameters D21 and D22 of the first and second shoulders. Since the diameters of the first and second shoulders are greater than the width of the guide opening 5704, the shaft 5720 of the tissue-removal device may be axially translated along the narrowed distal portion 5724 between the first and second shoulders 5726 and 5730, but may not be axially translated past the first and second shoulders. Optionally, the distal portion 5724 of the shaft 5720 between the first shoulder 5726 and the second shoulder 5730 may comprise one or more length indicators that may indicate the distance that the shaft has been translated, e.g., insertion depth of the shaft during use. For example, the shaft 5202 may comprise a first marker 5732, a second marker 5734, and a third marker 5736 anywhere along the shaft length, e.g., the distal portion 5724. The markers may be equally spaced along the distal portion 5724, be equidistant from each other, or may be irregularly spaced. For example, the markers may be spaced 0.25 inch, 0.5 inch, 0.75 inch, 1 inch, etc. away from each other.

Figure 57D:
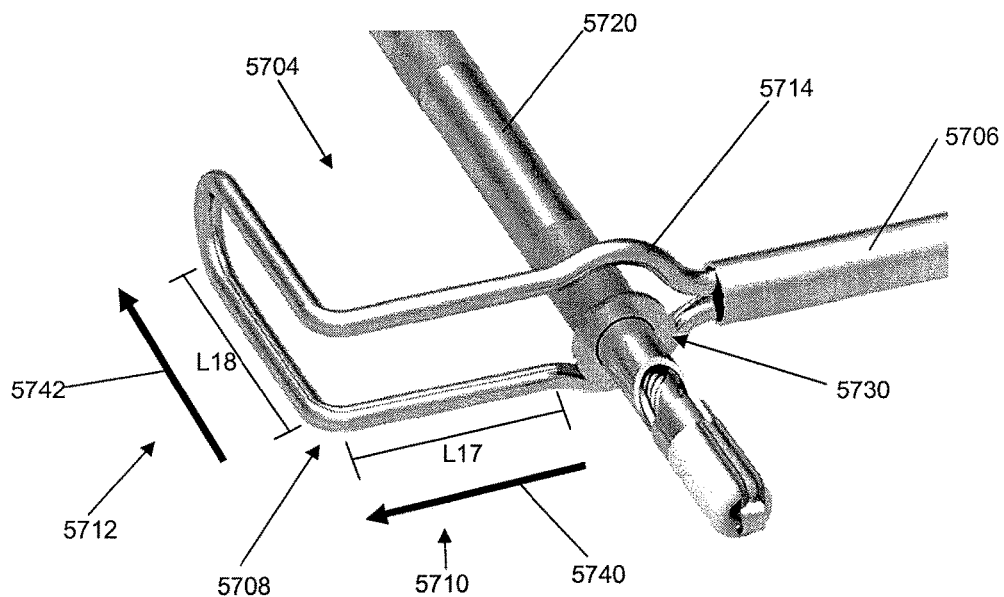

The shaft 5720 of the tissue-removal device may be engaged within the guide opening 5704 by inserting the shaft through the insertion region 5714, as illustrated in FIG. 57D. As described previously, the width W9 of the insertion region 5714 may be larger than the diameter of the shoulders of the shaft, e.g., the width W9 may be larger than the diameter D22 of the second shoulder 5730. Once inserted through the insertion region 5714, the shaft 5720 may be moved along the first portion 5710, e.g., in the direction of arrow 5740 towards the bend 5708. In this orientation, the shaft may be constrained to move a length L17 along the arrow 5740, where the length L17 may be from about 0.3 inch to about 0.8 inch, e.g., 0.4 inch. To traverse the bend 5708, the shaft 5720 may be axially twisted or rotated, for example, the shaft 5720 may be adjusted such that the longitudinal axis of the shaft is substantially parallel to the longitudinal axis of the elongate body 5706. In this orientation (depicted in FIG. 57C), the shaft 5720 may be moved along the second portion 5712, e.g., in the direction of arrow 5742, and the shaft may be constrained to move a length L18 along the arrow 5742, where the length L18 may be from about 0.25 inch to about 0.5 inch, e.g., 0.35 inch.

While the guide opening 5704 of the travel limiter 5700 has a single bend 5708, other variations of a guide opening may have a plurality of bends. In some variations, the plurality of bends may define a plurality of portions along which the tissue-removal device movement may be constrained. The different portions may be in a plurality of unique planes, or may be substantially co-planar. The guide opening may have rounded, tapered, and/or expanded regions, which may further guide and/or constrict the movement of a tissue-removal device inserted therethrough. For example, a looped guide opening may have two bends that define three portions. The three portions may be substantially co-planar, such that the movement of a shaft inserted therethrough is constrained only in that plane, by the boundaries of the guide opening. Alternatively, the three portions may occupy two or more unique planes, where the movement of a shaft in the guide opening may be constrained in multiple planes. The different planes of a guide opening may accommodate the geometry of the target tissue site, such that the tissue-removal device may be constrained in a fixed orientation regardless of the tissue geometry. In some variations, the first and third portion may occupy planes that are substantially parallel, such that a shaft may be inserted transversely through both the first and second portions. This may provide added stability as the tissue-removal device is used. The surface of the guide opening may be modified to increase or decrease the frictional forces between the shaft of the tissue-removal device and the guide opening, and in some variations, the surface may be coated with an anti-coagulant agent to reduce bleeding at the point of entry.

Another variation of a travel limiter may comprise an outer tube that is axially slidable relative to the impeller. The tube may have a flange from about 1 mm to about 5 mm from the distal end, which may help it to anchor onto the surface around the access hole such as the annulus of the disc. A proximal assembly may limit the travel of the tube to a specified distance of about 5 mm to 30 mm. Other variations of travel limiters are described below.

The orientation and position of the guide opening may be adjusted by a proximal handle 5702, one example of which is shown in FIG. 57A. The handle 5702 may be connected to the guide opening 5704 by the elongate body 5706, where the elongate body 5706 may have one or more angles to help a practitioner position the travel limiter 5700 during a spinal procedure. For example, the elongate body 5706 may have a first segment 5708 and a second segment 5709, where the first and second segments are separated by a first bend 5707. The first segment 5708 may have a length L15, where L15 may be from about 1 inch to about 2.5 inches, e.g., 1.5 inches. The second segment 5709 may have a length L16, where L16 may be from about 5 inches to about 8 inches, e.g., 6.25 inches. The first bend 5707 may have an angle A5, which may be from about 75° to about 100°, e.g., 90°. The first segment 5708 may also a second angle A6 with the handle 5702, where the angle A6 may be from about 75° to about 100°, e.g., 90°. Other variations of a travel limiter elongate body may have one or more pre-shaped bends or curves with various radii of curvature, e.g., rounded angles, helices, coils, quarter or half turns, etc., as appropriate for accommodating the anatomy of the patient, and the access path chosen by the practitioner.

Figure 57E:
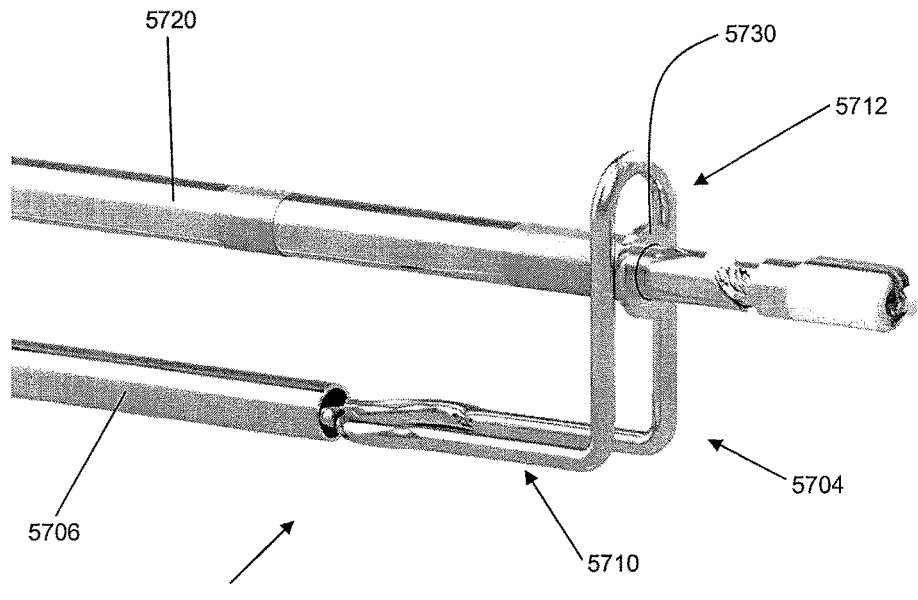
Figure 57F:
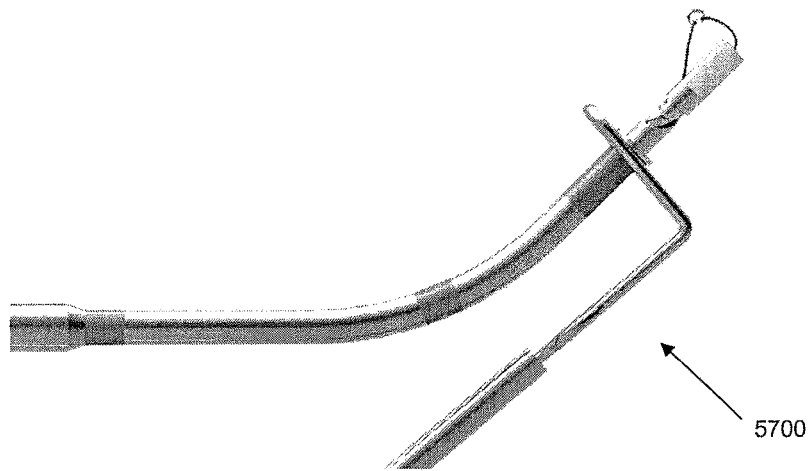

The travel limiter and the tissue-removal devices described above may be used in a surgical procedure, for example, to perform a discectomy in the course of an interbody fusion procedure. A practitioner may first test the tissue-removal device to ensure that it operates as desired, e.g., by powering the tissue-removal device on and off, expanding and collapsing the tissue removal assembly, etc. Once access is obtained to the target disc level, an annulotomy may be performed. About 1 cubic centimeter of saline may be injected into the middle of the disc. A tissue-removal device may be inserted through the guide opening of a travel limiter at the insertion region. For example, as shown in FIG. 57E, the tissue-removal device shaft 5720 may be inserted into the guide opening 5704 and moved to the distal part of the second portion 5712. FIG. 57F depicts how a tissue-removal device with a curved shaft may also be used with a travel limiter. The shaft 5720 may be pulled proximally so that the second shoulder 5730 is pressed against the guide opening 5704, which may limit further proximal movement. The tissue-removal device shaft 5720 and the travel limiter 5700 assembly may be advanced to the target disc. The travel limiter 5700 may be held stable against the outer annulus. The distal tip of the tissue-removal device may be positioned just inside the annulus. The tissue-removal device may be activated to rotate and may also be transitioned from a collapsed configuration to an expanded configuration. While the tissue-removal device is activated, the travel limiter may help to ensure that it is not removed from the patient during treatment. The tissue-removal device may be moved in small, expanding circular motions, which may gradually increase the size of the discectomy cavity and removed the target tissue. The quantity of tissue removed may be evaluated using Penfield or other metric. The tissue-removal device may be re-activated until the desired quantity of tissue has been removed. The tissue-removal device may be configured such that it should not be activated for more than 5 minutes to 10 minutes. Once a sufficient quantity of tissue has been removed, the tissue-removal device may be turned off and returned to a collapsed configuration. The tissue-removal device may then be withdrawn from the disc, and may be re-positioned at another disc level, or be withdrawn entirely. Devices for interbody fusion of vertebrae may be introduced as known by one of ordinary skill in the art.

Figure 58A:
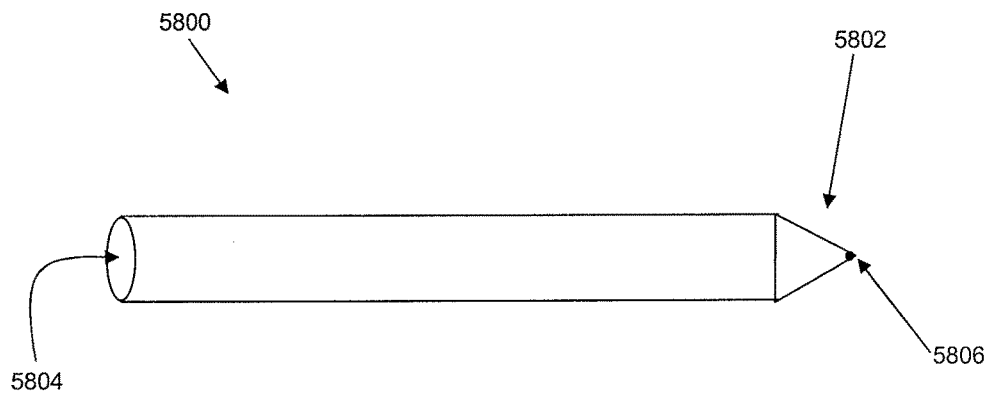
FIG. 58A depicts one variation of a dilator that may be used to enlarge an opening in a patient for the insertion of a tissue-removal device.

While the tissue-removal devices described above may be used in a surgical procedure, they may also be used in a percutaneous procedure. Access to the targeted disc level may be provided using a guidewire, a dilator, and an access cannula as briefly described above and further described here. One example of a dilator 5800 that may be used to enlarge the access pathway is depicted in FIG. 58A. The distal portion 5802 may be tapered such that the distal tip is the narrowest part of the dilator. The dilator 5800 may have a longitudinal lumen 5804 therethrough, which may terminate at an aperture 5806 at the distal tip of the dilator 5800. The dilator 5800 may be sized according to the size of the desired pathway, and may be determined in part by the size of the tissue-removal device shaft. The lumen 5804 may be sized to accommodate a guidewire or K-wire slidably therethrough. The outer diameter of the widest portion of the dilator 5800 may be from about 1.5 mm to about 10 mm, e.g., 7 mm, and the inner diameter, i.e., the diameter of the lumen 5804, of the widest portion may be from about 1 mm to about 9 mm, e.g., 6 mm. The diameter of the aperture 5806 may be about the diameter of a guide wire, for example, from about 1 mm to about 3 mm, e.g., 1.5 mm. The total length of the dilator 5800 may be from about 3 inches to about 12 inches, e.g., 8 inches. The taper angle of the distal portion 5802 may be from about 15° to about 75°, e.g., 60°. The dilator 5800 may be made of a metallic and/or polymeric material such as stainless steel, nickel titanium alloy, PEEK, polyethylene, etc.

Figure 58B:
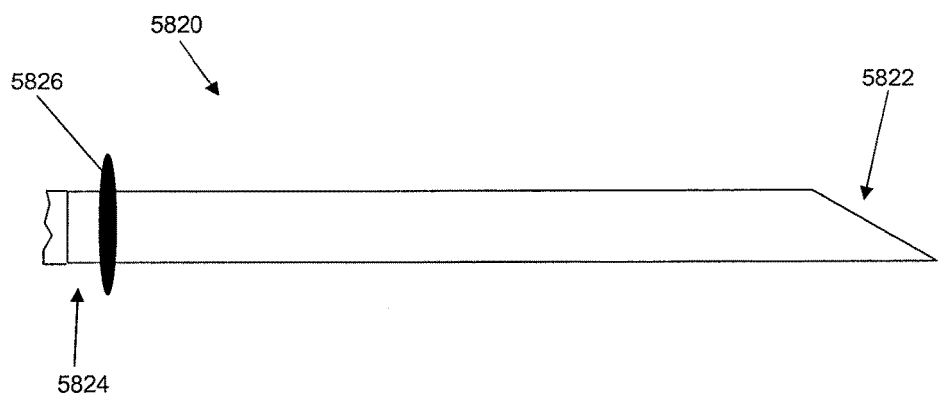
FIG. 58B depicts one example of an access cannula that may be used to provide an access path for a tissue-removal device to the target tissue.

Once a sufficiently large access pathway has been created using the dilator 5800, a cannula may be inserted and advanced to the target tissue site over the dilator 5800. One example of a cannula 5820 is depicted in FIG. 58B. The cannula 5820 may have an angled distal portion 5822, where the edges may be sharpened or rounded. Sharpened edges may be used to further cut away tissue as the cannula 5820 is advanced. The angle of the distal portion may be from about 20° to about 75°, e.g., 45°. The cannula 5820 may have a proximal connector 5804 configured to attach to stylets and/or portions of a tissue-removal device, e.g., a travel limiter. The proximal connector 5804 may be a standard connector type, e.g, Luer-lock, or may be a propriety connector. The proximal connector 5804 may have a shoulder 5806 that has a larger diameter than the cannula. This may help to prevent the cannula from being inserted entirely into a patient's body. The inner diameter of the cannula 5820 may be larger than the outer diameter of the dilator, so that the cannula may be advanced over the dilator. For example, the inner diameter of the cannula 5820 may be from about 1.5 mm to about 10 mm, e.g., 7 mm, and the outer diameter may be from about 2 mm to about 11 mm, e.g., 8 mm. The cannula 5820 may have a total length from about 3 inches to about 12 inches, e.g., 7.5 inches. The cannula 5820 may be made of any metallic and/or polymeric materials, such as stainless steel, nickel titanium alloy, PEEK, polyethylene, etc.

A tissue-removal device used in a percutaneous procedure may have a travel limiter that interfaces with the cannula 5820, and may use the cannula 5820 as a positional and orientation reference point. For example, a tissue-removal device may comprise a travel limiter may be permanently, but adjustably, coupled to the shaft of tissue-removal device, where the travel limiter may be connected to the proximal connector 5804 of the cannula 5820. One example of a travel limiter 5900 that may be suitable for use with an access cannula in a percutaneous procedure is shown in FIGS. 59A to 59G. The travel limiter 5900 may have a plurality of configurations, where each configuration constrains the movement of the tissue-removal device to a different degree. For example, in a first configuration, the distal portion of a tissue-removal device may be constrained to axial movement of up to 13.5 mm, and a second configuration where the tissue-removal device may be constrained to axial movement of up to 18.5 mm. In a third configuration, the tissue-removal device may be restrained from any axial movement. In certain configurations, the travel limiter may allow the position and/or orientation of the tissue-removal assembly to be adjusted along two or more degrees of freedom, e.g., adjusted axially and/or perpendicularly to the longitudinal axis of the device, and/or rotated around the longitudinal axis of the device. In other configurations, the travel limiter may immobilize the device so that it cannot be repositioned, or may constrain the movement of the device such that it may only be repositioned along one degree of freedom, e.g., perpendicular to the longitudinal axis of the device. Immobilizing or constraining the movement of the tissue-removal device after insertion into a patient may help prevent accidental withdrawal of the device, or unintentional shifts in location or orientation, which may damage peripheral tissue and neural structures. For example, restricting the movement of the tissue-removal device during a vertebral disc procedure may be a desirable safeguard against damage of nearby nerves by unintentionally twisting, rotating, pulling, or pushing the tissue removal assembly.

Figure 59A:
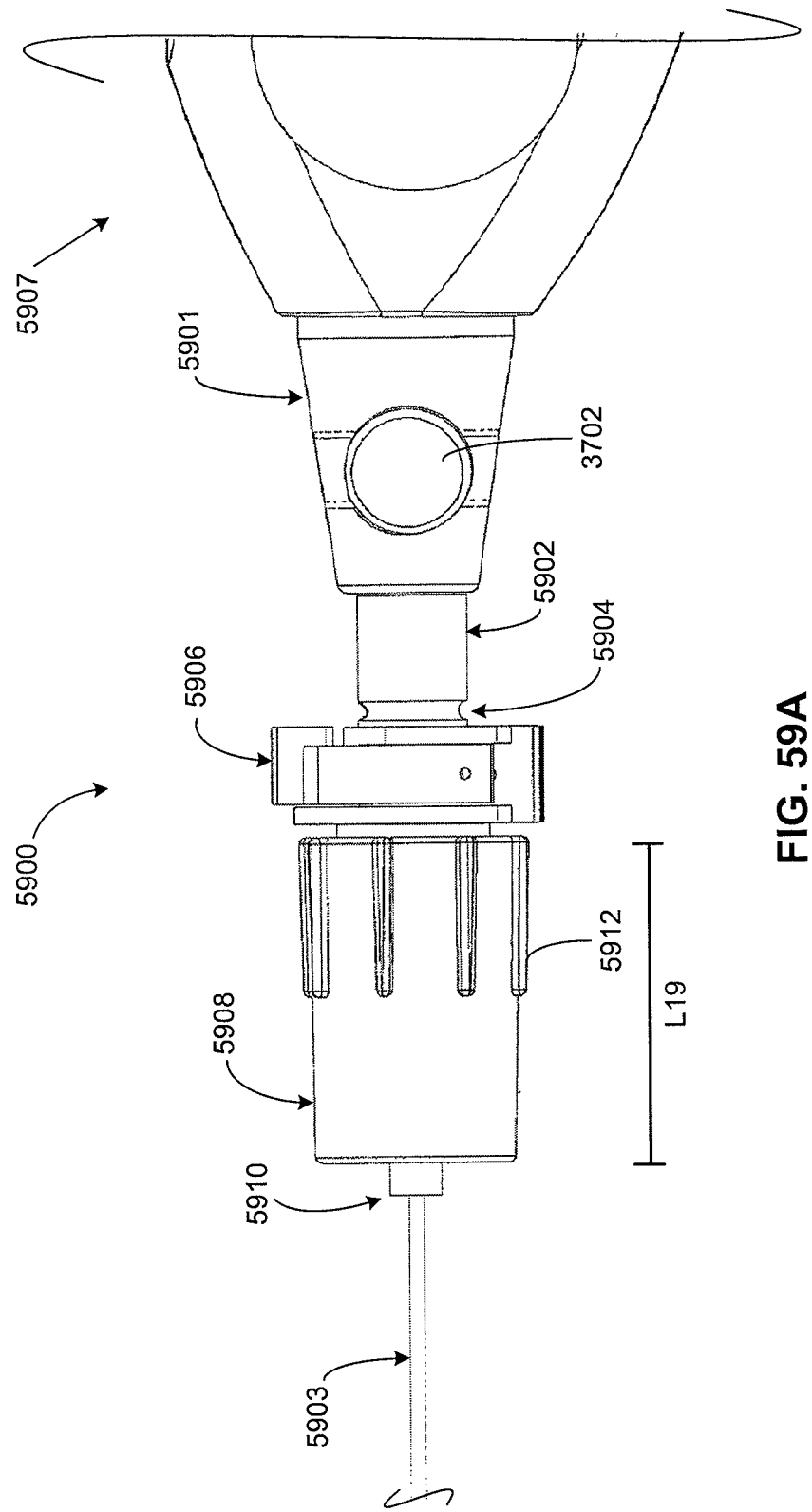
FIGS. 59A to 59G are various perspective views of another variation of a travel limiter that may be used with a tissue-removal device in a minimally invasive procedure.
Figure 59B:
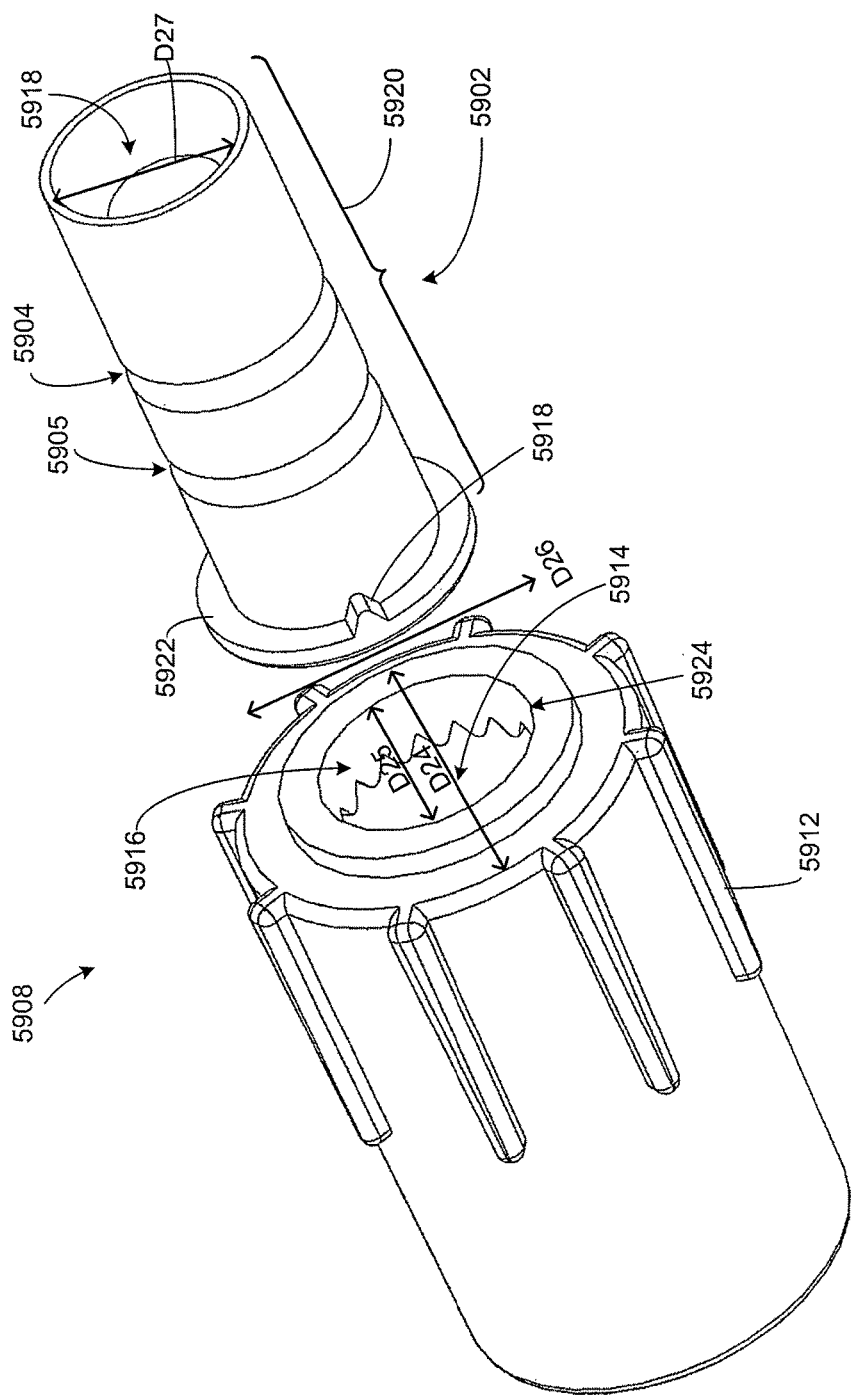

One variation of a travel limiter 5900 comprises a grooved tube 3802, a latch 5906 that is slidable over the grooved tube 5902, and a slide tube 5908 that is slidable over the body of the grooved tube 5902 as permitted by the latch 5906. The slide tube 5908 may also rotate around the grooved tube 5902. The slide tube 5908 may also comprise a connector 5910 that is configured for the attachment of cannula, stylets, tubes, etc. as desired. A cannula that is attached to the slide tube 5908 via the connector 5910 may move in conjunction with the slide tube 5908, e.g., sliding and/or rotating the slide tube 5908 may also slide and/or rotate the cannula. In other variations, the cannula may be in a fixed position, and engaging the travel limiter fixedly with the cannula may allow the tissue removal device to slide and rotate with respect to the cannula position. The connector 5910 may be a friction-fit, snap-fit, screw-fit, or Luer-Lok™ type connector. The slide tube 5908 comprises one or more grips 5912 around the perimeter to enable a user to translate the slide tube 5908 over the grooved tube 5902. The connector 5910 may have an aperture and/or channel configured to pass the outer tube 3508 through the slide tube 5908. The connector channel may extend partially or entirely across the length of the slide tube 5908, within the slide tube lumen 5914. A component perspective view of the slide tube 5908 is illustrated in FIG. 59B, which shows the slide tube lumen 5914, with inwardly pointing serrated locking features 5916 arranged around the circumference of the lumen 5914. There may be any suitable number of serrated locking features 5916, for example, 2, 3, 4, 5, 6, 8, 9, 10, 12, 15, 16, 20, etc., serrations that may be used to restrain relative motion between the slide tube 5908 and the grooved tube 5902.

The grooved tube 5902 comprises a tube body 5920 with a tube stop 5922 attached at the distal portion of the tube body 5920. The proximal portion of the grooved tube 5902 may be fixedly attached to the distal portion of a collector 5901 of a tissue-removal device 5907. In some variations, the grooved tube and the collector may be integrally formed. The grooved tube body 5920 may have one or more grooves, for example, a first groove 5904 and a second groove 5905, and a grooved tube lumen 5918 through the tube body. The tube lumen 5918 may be located and shaped to receive the shaft 5803 of the tissue-removal device 5907 that may be inserted through the slide tube 5908. The grooves may extend around the perimeter of the tube body, e.g., along the outer surface of the tube body 5920. The axial movement of the slide tube 5908 over the grooved tube 5902 may be determined in part by the spacing between the first and second grooves, as will be described in detail below. The spacing between the first groove 5904 and the second groove 5905 may be from about 5 mm to about 20 mm, for example, 10 mm. The tube stop 5922 may have one or more locking feature mates 5918 that are configured to engage the locking features 5916 of the slide tube 5908. While the tube stop 5922 has two locking feature mates 5918 (the first is shown in FIG. 59B, and the second is located directly opposite the first locking feature mate), other variations may have 1, 3, 5, 6, 8, 9, 10, 12, 15, 16, 20, etc., locking features mates. When the locking features 5916 are engaged with the locking feature mates 5918, the slide tube 5908 is restrained from rotating around the grooved tube 5902. For example, when the locking feature 5918 is engaged between the serrations of the locking feature 5916, the slide tube 5908 is rotatably locked with the grooved tube 5902, i.e., the slide tube is no longer rotatable around the grooved tube.

Figure 59C:
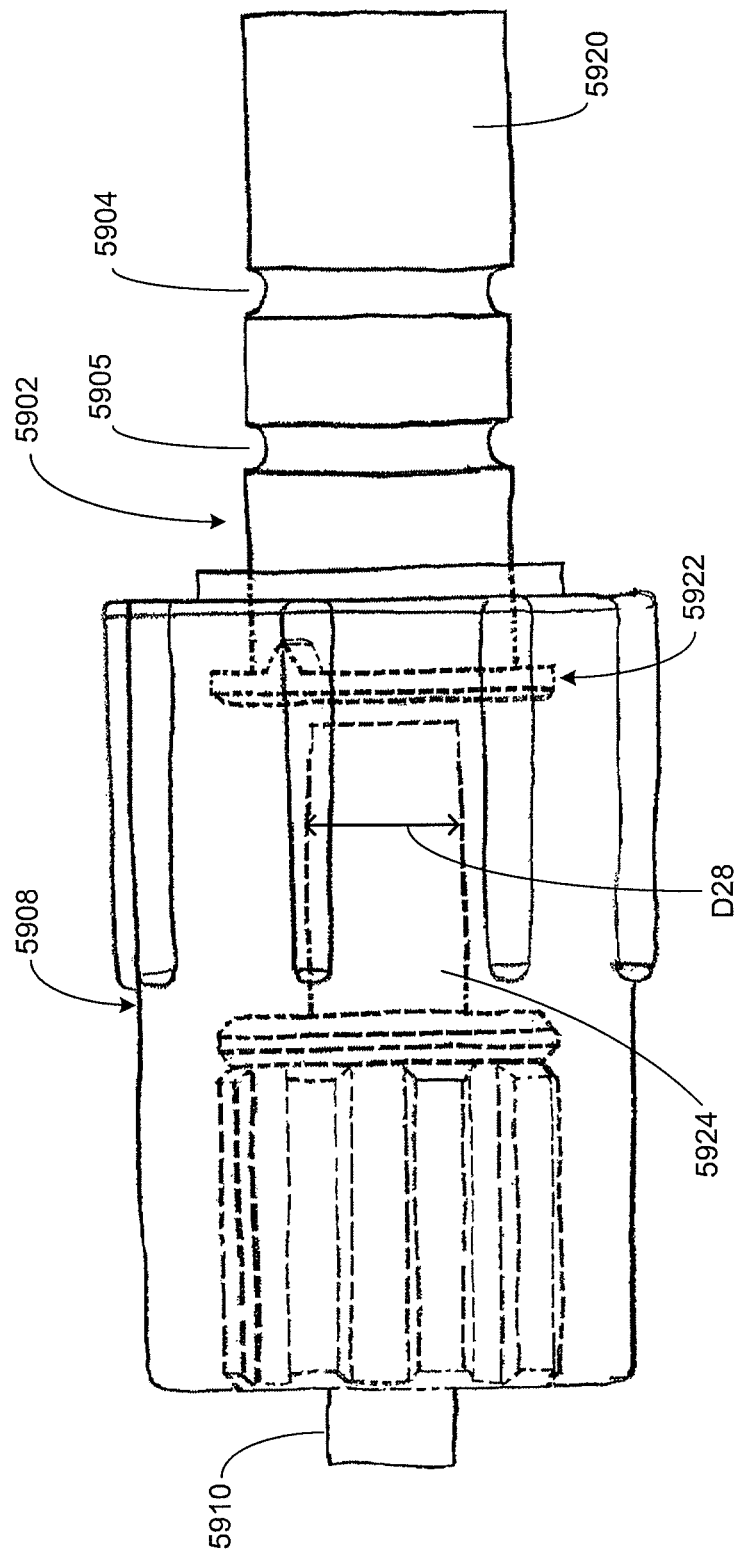

The slide tube 5908 and grooved tube 5902 may be sized and shaped such that the slide tube may slide along and/or rotate over the grooved tube. For example, the slide tube 5908 may have a length L19, where L19 may be from about 0.5 inch to about 1.5 inch, a first diameter D24, where D24 may be from about 0.5 inch to about 1.5 inch. The lumen 5914 may have a diameter that is the same as, or less than, D24. The opening 5924 to the lumen may have a second diameter D25, where D25 is less than D24, for example, 0.2 inch to about 1 inch. The tube stop 5922 has a diameter D26, where D26 may be less than or equal to the diameter D24 of the slide tube 5908, but greater than the diameter D25 of the opening 5924. The diameter D26 may be from about 0.3 inch to about 1.25 inch, for example, 0.44 inch. The tube body 5920 has a diameter D27, where D27 may be less than or equal to the diameter D25 of the opening 5924. The diameter D27 may be from about 0.1 inch to about 1 inch, for example, 0.34 inch. In the variation of the travel limiter 5900 depicted in FIG. 59A, the connector 5910, slide tube 5908, and the grooved tube 5902 may be configured as shown in FIG. 59C. The connector 5910 and collector channel 5924 may be affixed within the slide tube 5908. In this variation, the grooved tube body diameter D27 is less than the slide tube opening diameter D25, which may allow the slide tube 5908 to slide over the grooved tube 5902. The connector channel 5924 may have a diameter D28 that is smaller than grooved tube body diameter D27, so that it may be inserted into the grooved tube lumen 5918. However, the tube stop diameter D26 may be greater than the opening diameter D25, so that the grooved tube 5902 is retained within the lumen of the slide tube. Other arrangements may also be used where the slide tube may be moved with respect to the grooved tube, and limited by the tube stop.

While the slide tube 5908 and the grooved tube 5902 may comprise a rounded and cylindrical configuration, other variations of slide tubes and grooved tubes may have other suitable geometries, such as triangular, rectangular, hexagonal, octagonal, etc. In some variations, the slide tube 5908 may be made of an optically transparent material, such as nylon, polycarbonate, polyethylene, polyester, polypropylene, and the like, while in other variations, the slide tube may be optically opaque. Optionally, the surfaces of the slide tube and the grooved tube may be coated with a friction-modification agent, which may either increase or decrease the friction between the surfaces. It may be desirable in some variations to increase the frictional forces between the sliding surfaces to help prevent slippage, while in other variations, the frictional forces may be reduced to facilitate adjustment of the slide tube.

Figure 59D:
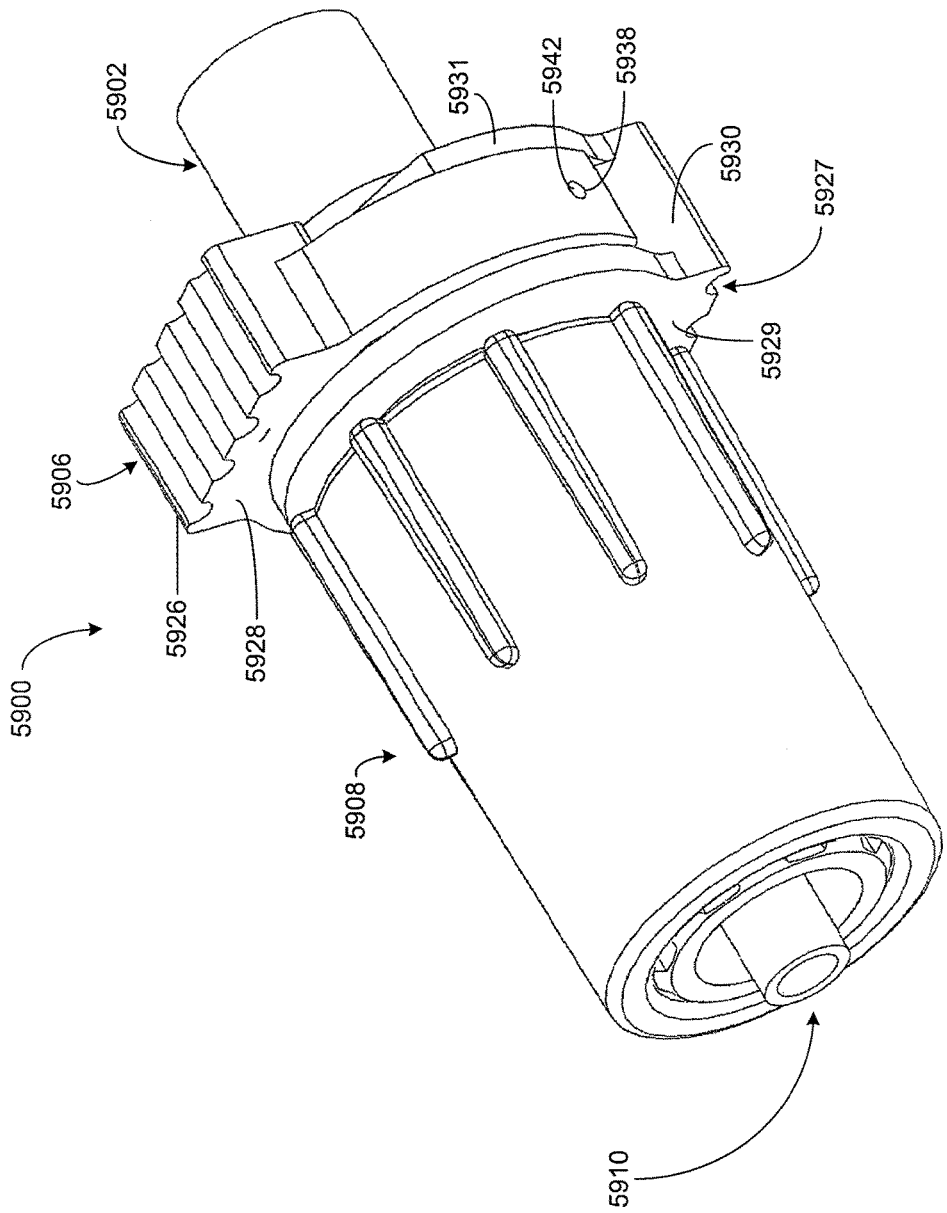
Figure 59E:
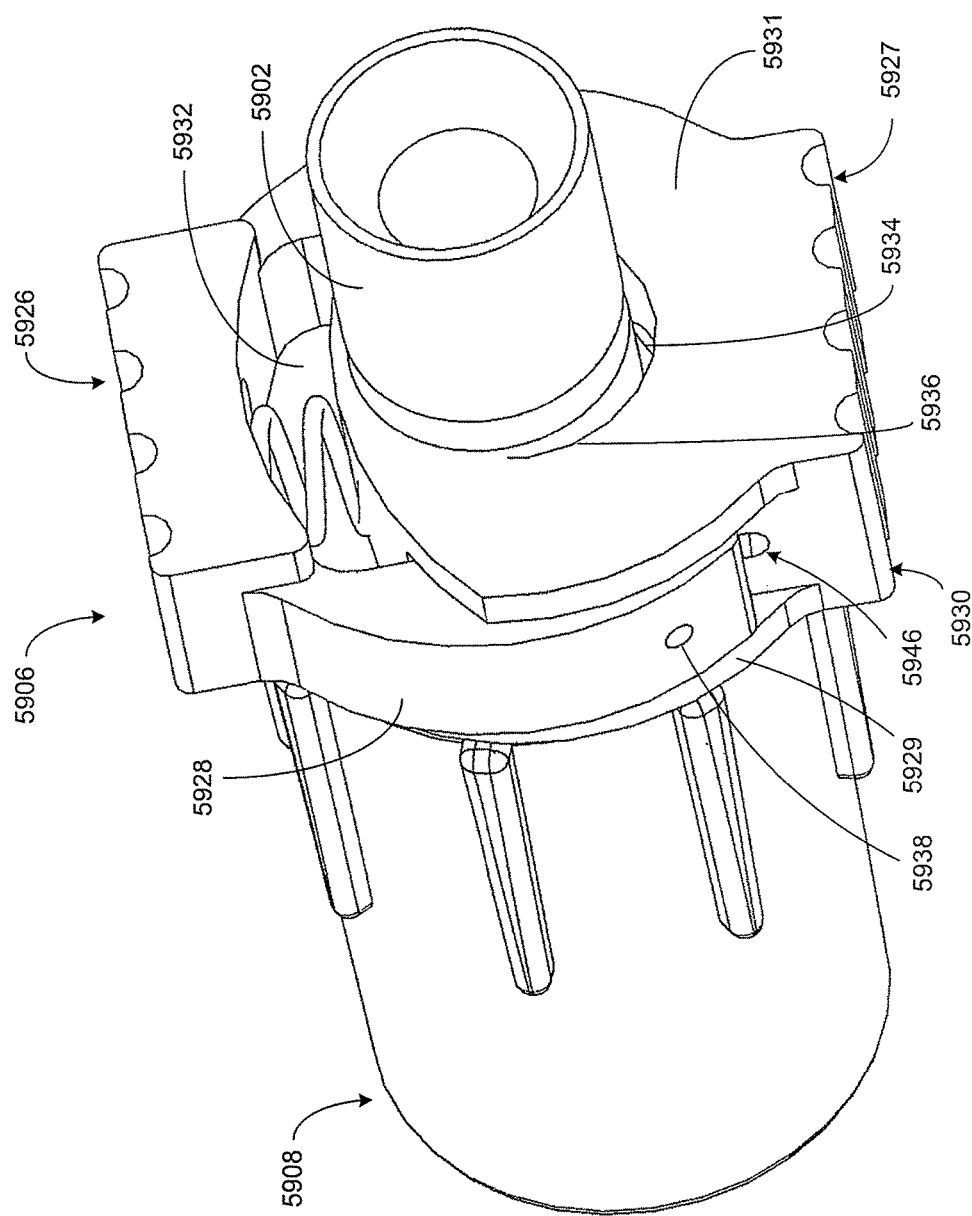

A perspective view of the travel limiter 5900 is shown in FIG. 59D, where the slide tube 5908 is slidably coupled over the grooved tube 5902 as previously described. Additionally, the latch 5906 is slidably coupled over the grooved tube 5902. The position of the latch 5906 along the length of the grooved tube 5902 may define the range of relative movement between the slide tube and the grooved tube. For example, the slide tube 5908 of the tissue-removal device 5907 may be fixedly attached to an access cannula that is inserted within a patient. The location of the latch 5906 along the grooved tube 5902 which may be fixedly attached to the handle defines the movement range of the tissue removal device with respect to the access cannula. The latch 5906 may comprise a circular bracket 5928 that is fitted between the two plates of a latch base 5930. The latch base 5930 may also comprise a latch base lumen 5936 that is sized and shaped to fit over the grooved tube 5902, as illustrated in FIG. 59E. The circular bracket 5928 and the latch base 5930 may be coupled by a pin 5942 that is inserted through a first aperture 5938 in the circular bracket, through a first pin-shift aperture in the latch base, through a pin channel, out a second aperture in the circular bracket. A portion of the first pin-shift aperture 5946 is depicted in the back perspective view of the travel limiter 5900 shown in FIG. 59E. The latch 5906 may have a first ridged region 5926 on the circular bracket 5928, and a second ridged region 5927 on the latch base 5930. Pressing the first ridged region 5926 and the second ridged region 5927 towards each other may adjust the position of the circular bracket 5928 and the pin 5942 within the pin-shift apertures and pin channel.

Some variations of a latch may comprise a mechanism that biases the latch to a locked configuration or an unlocked configuration. Such a bias mechanism enables the travel limiter to constrain the motion and/or position of the tissue removal device without the practitioner constantly applying pressure to the latch. One example of a bias mechanism may comprise a spring 5932 that may be located between the first ridged region 5926 of the circular bracket 5928 and the top portion of the latch base 5930. The spring 5932 may bias the position of the circular bracket 5928 and the pin 5942 with respect to the latch base 5930. For example, the spring 5932 may bias the travel limiter to a locked configuration by pressing against the circular bracket 5928 and the latch base 5930 such that the pin 5942 is urged to the top of the pin channel. Various latch configurations are described below.

Figure 59F:
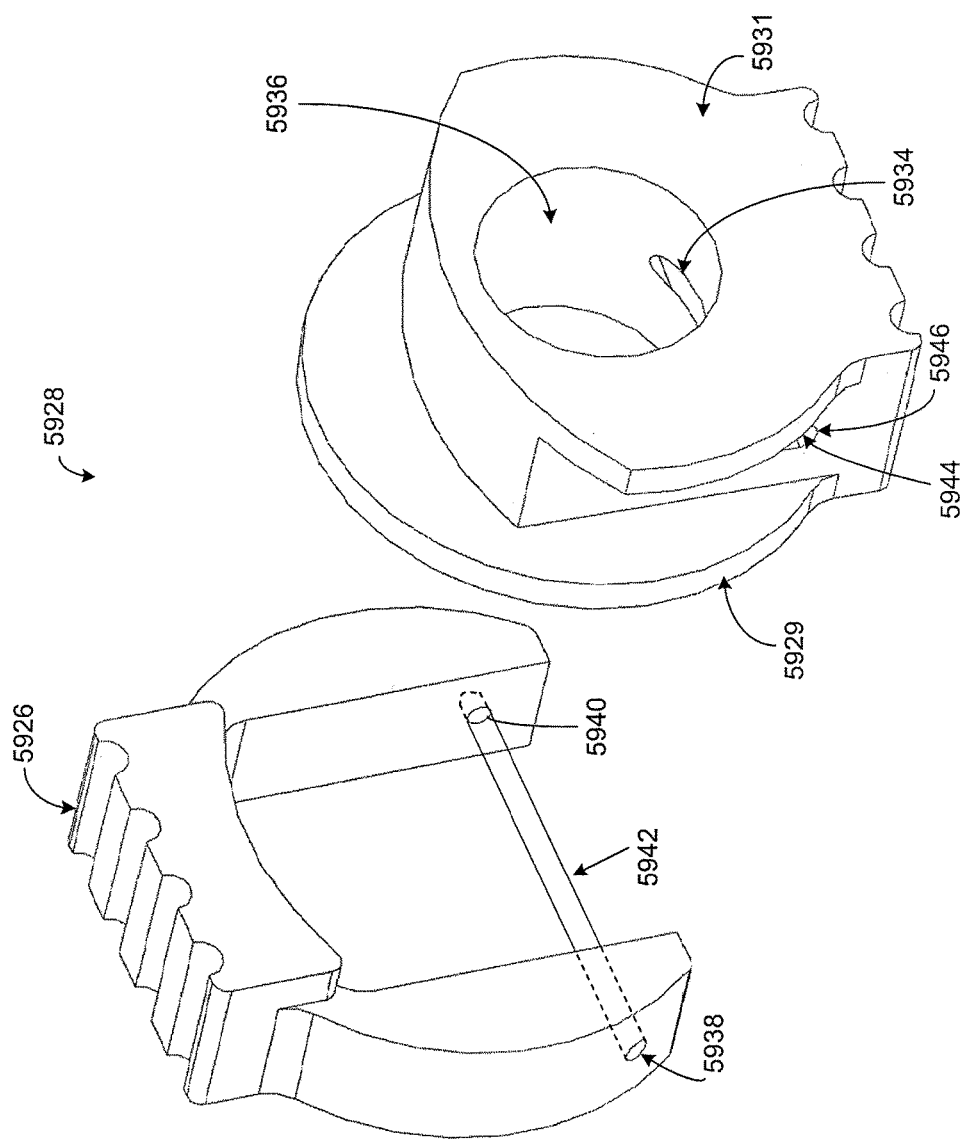
Figure 59G:
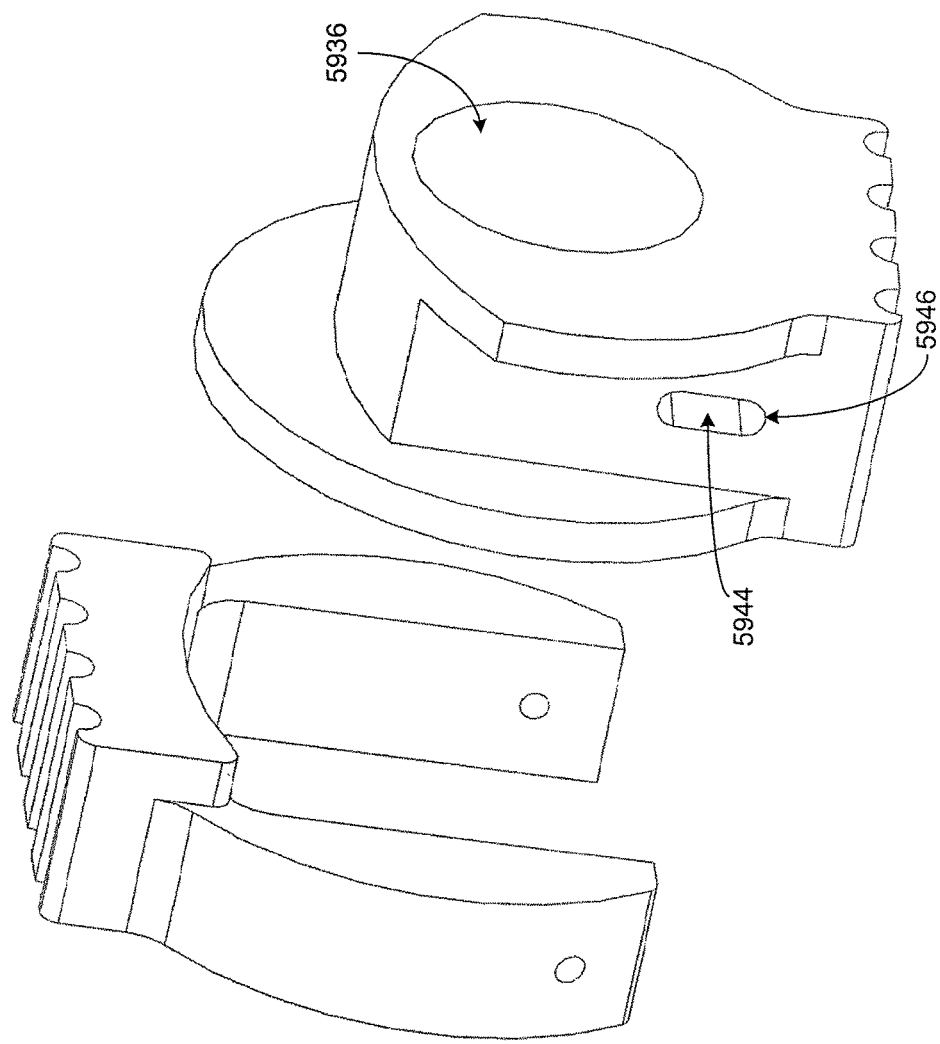

FIGS. 59F and 59G are perspective component views that illustrate one variation of a latch that has a locked configuration and an unlocked configuration. When the latch is fully assembled, the pin 5942 may be inserted from the first aperture 5938, through a first pin-shift aperture 5946 and pin channel 2844 in the latch base 5930, to the second aperture 5940. The circular bracket 5928 is coupled to the latch base 5930 via the pin 5942, and is also held in place by the distal base plate 5929 and the proximal base plate 5931. The latch base lumen 5936 may have a diameter that is equal to, or somewhat larger than, the diameter D27 of the grooved tube body 5920. There may be a pin channel cutout 5934 that allows a segment of a pin that is inserted through the pin channel 5944 to enter the latch base lumen 5936. FIG. 59G depicts a perspective side view of the circular bracket 5928 and the latch base 5930. The pin-shift aperture 5926 and the cross-section of the pin channel 5944 may have an elongated rounded shape. The pin-shift aperture and the pin channel cross-section may be any suitable shape such that the bottom portion of the shape is below the bottom of the latch base lumen 5936, and the top portion of the shape is above the bottom of the latch base lumen. For example, when the latch is in an unlocked configuration, a pin that is inserted through the pin channel 5944 is positioned at the bottom of the pin channel 5944, and may be entirely outside the latch base lumen 5936. In the unlocked configuration, the latch may slide freely over the grooved tube. In the locked position, the pin is positioned at the top of the pin channel, and a segment of the pin enters the latch base lumen 5936 via the pin channel cutout 5934, which may impede the sliding of the latch 5906 over a grooved tube. In the variation of the latch 5906 described here, when in the locked configuration, the pin may engage within one of the grooves of the grooved tube in the locked configuration, which may immobilize the position of the latch along the tube. In some variations, the latch may be biased to either the locked configuration or the unlocked configuration. For example, as shown in FIG. 59E, the spring 5932 biases the latch to the locked position by pushing upwardly on the circular bracket 5928. When the spring 5932 is compressed, the pin 5942 may be disengaged from the groove, and urged to the bottom of the pin channel 5944. This may unlock the latch 5906 and allow it to slide over the grooved tube.

The position of the latch 5906 along the grooved tube 5902 may limit the movement range of the slide tube 5908. Where a cannula, stylet, or other tool is attached to the connector 5910 over the shaft 5903, the movement of the slide tube determines the movement of the attached tool. Referring back to FIG. 59A, the latch 5906 is shown to be locked over the second groove 5905. In the configuration shown there, the serrated locking features 5916 on the slide tube are engaged with the locking feature mate 5918 on the grooved tube, which prevents the slide tube and the attached tube from rotating, and also restricts axial movement. When the latch 5906 is locked into the first groove 5904, the serrated locking features 5916 may be disengaged from the locking feature mate 5918, which allows the slide tube and the attached tool to rotate, as well as to move axially.

The components and configurations of one variation of a travel limiter for use with an access cannula in a percutaneous procedure have been described above. While the travel limiter 5900 has two evenly spaced grooves, other variations may have more than two grooves, where the spacing between the grooves may be varied. For example, grooves may be more closely spaced towards the distal portion of the travel limiter than at the proximal portion of the travel limiter. The travel limiter 5900 as shown has one latch 5906, however, other travel limiters may have two or more latches. For example, a first latch may be positioned proximal to the slide tube, while a second latch may be positioned distal to the slide tube. These optional features may allow the travel limiter to limit either or both the axial and rotational movement of the tissue-removal device with respect to slide tube. For example, when the slide tube is fixedly attached to an access cannula, the movement of the tissue removal device with respect to the slide tube may be constrained by the latch position on the grooved tube. Any combination of the above described travel limiter components may be used to control and regulate the position and/or orientation of the distal portion of the tissue-removal device.

The dilator, access cannula, and travel limiter described above may be used in a minimally-invasive interbody fusion procedure. The desired disc level may be accessed using any of the standard methods previously described. Once access to the target location is confirmed, e.g., via a guidewire or K-wire, a dilator such as the one depicted in FIG. 58A may be advanced over the guidewire to enlarge the insertion pathway. Then an introducer or cannula such as the cannula depicted in FIG. 58B may be inserted over the guidewire, followed by subsequent guidewire removal. The targeted tissue region may be visualized, e.g., using an endoscope and/or fluoroscopy, etc., to identify the relevant structures such as the disc, the nerve, or other adjacent structures and site(s) of tissue removal. Once the target region has been evaluated, a tissue-removal device may be inserted through the cannula, and may pierce through the annular wall of a herniated disc. In some variations, a tissue-removal device travel limiter may be attached to the proximal portion of the cannula, and adjusted to provide a desired degree of freedom and maneuverability. Once the travel limiter has been appropriately engaged and configured, the tissue-removal device may be manipulated such that the extendable member is extended, and the tissue removal assembly is in its expanded configuration. The tissue-removal device may be activated to emulsify or pulverize tissue of the nucleus fibrosus. Once a desired quantity of tissue has been removed, the tissue-removal device may be deactivated and withdrawn from the patient. In an interbody fusion procedure, a device may be delivered to occupy the space between two vertebrae. Examples of implantable interbody fusion devices may be used with the tissue removal devices herein include Medronic LT-CAGE® Device, and DePuy Concorde, or Stryker AVS TL PEEK Spacer Implant, for example. Further examples include the devices disclosed in U.S. Pat. Nos. 6,666,891, 6,127,597 and 7,621,950, which are hereby incorporated by reference in their entirety.

Kits for spinal tissue removal are also described herein. A kit for surgical discectomy may comprise a guidewire, one or more dilators, a cannula, a tissue-removal device with a straight shaft, and a travel limiter. Optionally, the kit may comprise a tissue-removal device with a curved shaft. The kit may also comprise additional travel limiters that constrain the motion of the tissue-removal devices in different planes and axes.

It is to be understood that this invention is not limited to particular exemplary embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a blade" includes a plurality of such blades and reference to "the energy source" includes reference to one or more sources of energy and equivalents thereof known to those skilled in the art, and so forth.

The publications discussed herein are provided solely for their disclosure. Nothing herein is to be construed as an admission that the present invention is not entitled to antedate such publication by virtue of prior invention. Further, the dates of publication provided, if any, may be different from the actual publication dates which may need to be independently confirmed.

What is claimed as new and desired to be protected by Letters Patent of the United States is:

1. A device, comprising:
   a rotatable shaft having a distal end and a distal opening about the distal end;
   a cutting mechanism;
   an extension mechanism having a distal end coupled to the cutting mechanism, the extension mechanism configured to extend and retract in the distal opening of the rotatable shaft;
   a support mechanism having a proximal portion coupled to the rotatable shaft and a distal portion coupled to the cutting mechanism, the support mechanism having a generally fixed length between the proximal portion and the distal portion, such that a portion of the distal end of the extension mechanism distal to the distal opening of the rotatable shaft deflects as the extension mechanism extends in the distal opening of the rotatable shaft.

2. The device of claim 1, wherein the extension mechanism comprises an elongate member with a resilient, non-linear extended configuration and a generally straightened retracted configuration.

3. The device of claim 2, wherein the elongate member is a looped elongate member.

4. The device of claim 3, wherein the looped elongate member is a fused looped elongate member.

5. The device of claim 1, wherein the proximal portion includes a first attachment to the rotatable shaft and a second attachment to the shaft.

6. The device of claim 5, wherein the first and second attachments to the rotatable shaft comprise pivot joint attachments.

7. The device of claim 5, wherein the distal portion of the support mechanism comprises a middle segment between the first attachment the second attachment.

8. The device of claim 1, wherein the cutting mechanism comprises a first cutting edge.

9. The device of claim 8, wherein the first cutting edge is an arcuate cutting edge.

10. The device of claim 8, wherein the cutting mechanism further comprises a second cutting edge located between the first cutting edge and the rotatable shaft.

11. The device of claim 8, wherein the cutting mechanism further comprises a second cutting edge located between the first cutting edge and the extension mechanism.

12. The device of claim 11, wherein the cutting mechanism further comprises a first lumen located between the first cutting edge and the second cutting edge.

13. The device of claim 12, wherein the cutting mechanism further comprises a second lumen in which at least one of the extension mechanism and the support mechanism resides.

14. The device of claim 8, wherein the cutting mechanism further comprises a retaining lumen in which at least one of the extension mechanism and the support mechanism resides.

15. The device of claim 8, wherein the first cutting edge is generally oriented in a first plane that is substantially transverse to a second plane that is transverse to a rotation axis of the rotatable shaft.

16. The device of claim 1, wherein the rotatable shaft further comprises a transport mechanism proximal to the proximal attachment of the support mechanism.

17. The device of claim 16, wherein the transport mechanism is a helical transport mechanism.

18. The device of claim 17, wherein the rotatable shaft comprises a multifilament cable.

19. The device of claim 17, wherein the rotatable shaft comprises a flexible rotatable cable.

20. The device of claim 1, further comprising a tube in which the rotatable shaft resides.

21. The device of claim 20, wherein the tube comprises a curved segment.

22. The device of claim 20, further comprising a travel limiter configured to slidably receive the tube.

23. The device of claim 1, further comprising a collection chamber in which a portion of the rotatable shaft resides.

* * * * *